US011440899B2

(12) United States Patent
Karra et al.

(10) Patent No.: US 11,440,899 B2
(45) Date of Patent: *Sep. 13, 2022

(54) PYRIMIDINE TBK/IKKE INHIBITOR COMPOUNDS AND USES THEREOF

(71) Applicants: Merck Patent GmbH, Darmstadt (DE); Srinivasa R. Karra, Pembroke, MA (US); Yufang Xiao, Lexington, MA (US); Brian Sherer, Nashua, NH (US); Eugene Checkler, Concord, MA (US)

(72) Inventors: Srinivasa R. Karra, Pembroke, MA (US); Yufang Xiao, Lexington, MA (US); Brian Sherer, Nashua, NH (US); Eugene Checkler, Concord, MA (US)

(73) Assignee: Merck Patent GmbH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/756,954

(22) PCT Filed: Oct. 17, 2018

(86) PCT No.: PCT/US2018/056192
§ 371 (c)(1),
(2) Date: Apr. 17, 2020

(87) PCT Pub. No.: WO2019/079375
PCT Pub. Date: Apr. 25, 2019

(65) Prior Publication Data
US 2021/0214339 A1    Jul. 15, 2021

Related U.S. Application Data

(60) Provisional application No. 62/573,255, filed on Oct. 17, 2017.

(51) Int. Cl.
| *C07D 401/14* | (2006.01) |
| *C07D 405/14* | (2006.01) |
| *C07D 419/14* | (2006.01) |
| *C07D 498/18* | (2006.01) |

(52) U.S. Cl.
CPC ......... *C07D 401/14* (2013.01); *C07D 405/14* (2013.01); *C07D 419/14* (2013.01); *C07D 498/18* (2013.01)

(58) Field of Classification Search
CPC .. C07D 401/14; C07D 405/14; C07D 419/14; C07D 498/18
See application file for complete search history.

(56) References Cited

U.S. PATENT DOCUMENTS

| 9,988,391 | B2 * | 6/2018 | Sherer | A61P 25/28 |
| 10,428,080 | B2 * | 10/2019 | Sherer | A61P 17/00 |
| 2005/0014753 | A1 * | 1/2005 | Ding | A61P 7/02 |
| | | | | 514/241 |
| 2005/0203092 | A1 | 9/2005 | Elfrida et al. | |
| 2010/0298312 | A1 * | 11/2010 | Kamenecka | C07D 403/12 |
| | | | | 544/122 |
| 2012/0238540 | A1 * | 9/2012 | Holcomb | A61K 31/52 |
| | | | | 514/210.18 |
| 2014/0228340 | A1 * | 8/2014 | Hoelzemann | C07D 401/12 |
| | | | | 514/210.2 |
| 2014/0288044 | A1 * | 9/2014 | Holcomb | C07D 413/14 |
| | | | | 514/210.18 |
| 2016/0000784 | A1 * | 1/2016 | Newton | A61P 31/04 |
| | | | | 544/70 |
| 2016/0096827 | A1 * | 4/2016 | Du | A61K 31/5377 |
| | | | | 514/210.18 |

FOREIGN PATENT DOCUMENTS

| RU | 2622034 C2 | 6/2017 | |
| WO | 2004089286 A2 | 10/2004 | |
| WO | 2006125616 A2 | 11/2006 | |
| WO | 2008099074 A1 | 8/2008 | |
| WO | 2009032861 A1 | 3/2009 | |
| WO | 2011046970 A1 | 4/2011 | |
| WO | 2012010826 A1 | 1/2012 | |
| WO | 2012142329 A1 | 10/2012 | |
| WO | 2013034238 A1 | 3/2013 | |
| WO | 2013175415 A1 | 11/2013 | |
| WO | 2017003995 A1 | 1/2017 | |
| WO | 2017114510 A1 | 7/2017 | |
| WO | WO-2019079373 A1 * | 4/2019 | C07D 401/14 |

OTHER PUBLICATIONS

Muvaffak; Molecular Cancer Research 2014, 12, 1055-1066. DOI:10.1158/1541-7786.MCR-13-0642 (Year: 2014).*
D.A.Barbie et al., Nature, 462:108-114, 2009.
S. M. Berge et al., J. Pharmaceutical Sciences, 66:1-19, 1977.
J.S. Boehm et al., Cell, 129:1065-1079, 2007.
Chien et al., Cell, 127:157-170, 2006.
Eddy et al., Cancer Res., 65:(24):11375-11383, 2005.
C.Korherr et al., PNAS, 103:4240-4245, 2006.
Weinstein-Oppenheimer et al., Pharma. &. Therap., 88:229-279, 2000.
Dyson G., May P. Chemistry of synthetic medicinal substances, translated from English, Moscow: Mir, 1964, pp. 12-19.
V.G.Belikov "Pharmaceutical chemistry", textbook, 2007, Moscow, MEDpress-Inform, pp. 27-29.
M.D. Mashkovsky "Medicines", Moscow, "Medicine", 1993, part I, p. 8.
I.G. Smirnova et al.: "Optical isomerism and biological activity of drugs", Bulletin of Moscow University, Series 2 Chemistry, 2012, 53(3), pp. 147-156.
Chemical Encyclopaedic Dictionary, Moscow, Sovetskaya Encyclopaedia, 1983, pp. 130-131.

(Continued)

*Primary Examiner* — Daniel R Carcanague
(74) *Attorney, Agent, or Firm* — Thomas W. Brown; EMD Serono Research and Development Institute, Inc.

(57) ABSTRACT

The present invention relates to compounds of Formula I and pharmaceutically acceptable compositions thereof, useful as TBK/IKKε inhibitors.

19 Claims, No Drawings

(56) References Cited

OTHER PUBLICATIONS

Richard J.Bastin et al.: "Salt selection and Optimisation Procedures for Pharmaceutical New Chemical Entities" Organic Process Research & Development, 2000, vol. 4, p. 427-435.
A.S. Trofimenko et al: "Extracorporal correction of nucleoprotein catabolism injuries on a model of systemic red lupus. Efficiency and safety assessment in the acute experiment", Biomedical Chemistry, 2015 vol 61, issue 5, pp. 622-627.
O. P. Kolesnikova et al.: "Early markers of phenotypic heterogeneity in systemic lupus erythematosus in an experimental model," Bulletin of Siberian Medicine. 2017;16(4):155-164.
P.V. Sergeev, "Short Course of Molecular Pharmacology", ed. Moscow, 1975, p. 10.
L.E. Kholodov, et al. "Clinical Pharmacokinetics" Moscow, Medicine, 1985, pp. 83-98, 134-138, 160, 378-380.
Zhulenko V.N., Gorshkov G.I. Pharmacology. Moscow: KolosS, 2008, pp. 34-35.
D.A. Harkiewicz, Pharmacology, 10th ed. Moscow: GEOTAR-Media, 2010, pp. 73-74.
"Little Medical Encyclopaedia", vol. 5, Moscow, Medicine, 1996, pp. 90-96.
Russian Office Action dated Oct. 22, 2021.

\* cited by examiner

PYRIMIDINE TBK/IKKE INHIBITOR COMPOUNDS AND USES THEREOF

RELATED APPLICATIONS

This application is a US national stage application of PCT international application PCT/US18/56192, filed on Oct. 17, 2018, which claims the benefit of U.S. Provisional Application 62/573,255, filed Oct. 17, 2017. The entire contents of the aforementioned applications are incorporated herein by reference.

TECHNICAL FIELD OF THE INVENTION

The present invention provides for compounds of Formula (I) as dual inhibitors of TBK and IKKε that can be used to treat immunological disorders, TBK and/or IKKε inhibitors and their use in the treatment of cancer, and other diseases related to TBK and/or IKKε overexpression, including rheumatoid arthritis, systemic lupus erythematosus or lupus nephritis.

BACKGROUND OF THE INVENTION

Protein kinases regulate nearly every cellular process, including metabolism, cell proliferation, cell differentiation, and cell survival, so they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

IKKε and TBK1 are serine/threonine kinases which are highly homologous to one another and other IkB kinases. The two kinases play an integral role in the innate immune system. Doublestranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene (J. S. Boehm et al., Cell 129, 1065-1079, 2007). 354 kinases were investigated with respect to their ability to recapitulate the Ras-transforming phenotype together with an activated form of the MAPK kinase Mek. IKKε was identified here as a cooperative oncogene. In addition, the authors were able to show that IKKε is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases (S. F. Eddy et al., Cancer Res. 2005; 65 (24), 11375-11383).

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defence as proangiogenic factors (C. Korherr et al., PNAS, 103, 4240-4245, 2006). In 2006, Chien et al. (Y. Chien et al., Cell 127, 157-170, 2006) published that TBK1−/− cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours (D. A. Barbie et al., Nature Letters 1-5, 2009).

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

IKKε and TBK1 are highly homologous Ser/Thr kinases critically involved in the innate immune response through induction of type 1 interferons and other cytokines. These kinases are stimulated in response to viral/bacterial infection. Immune response to viral and bacterial infection involves the binding of antigens such as bacterial lipopolysaccharide (LPS), viral doublestranded RNS (dsRNA) to Toll like receptors, then subsequent activation of TBK1 pathway. Activated TBK1 and IKKε phosphorylate IRF3 and IRF7, which triggers the dimerization and nuclear translocation of those interferon regulatory transcription factors, ultimately inducing a signaling cascades leading to IFN production.

SUMMARY OF THE INVENTION

In one aspect, the invention provides a compound of Formula (I):

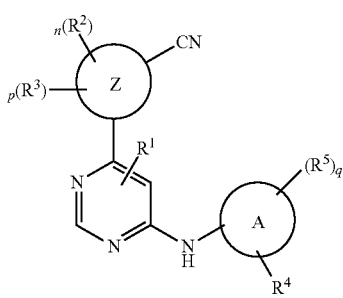

I or a pharmaceutically acceptable derivative, solvate, salt, hydrate or stereoisomer thereof.

In another aspect, the invention provides compounds of Formula (I) which are suitable as a dual inhibitor of TBK and IKKε. The compounds of the invention have high solubility and high bioavailability.

In another aspect, the invention provides methods for the treatment and/or prevention of immunological disorders related to TBK and IKKε comprising administering a compound of Formula (I). In another aspect, the invention provides compounds which are able to modulate, especially inhibit the activity or function of TBK and IKKε in disease states in mammals.

In certain embodiments, the present invention provides compounds of Formula (I) which are selective for TBK and/or IKKε. In certain embodiments, the present invention provides compounds of Formula (I) which are selective for TBK and IKKε.

DETAILED DESCRIPTION OF CERTAIN EMBODIMENTS

1. General Description of Compounds of the Invention

In certain aspects, the present invention provides for dual inhibitors of TBK and IKKε. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

According to the invention, bivalent groups include substitution in both directions, and when inserted between any two groups, (e.g., the group "—OC(O)—" or "CO$_2$" inserted between X and Y), includes both

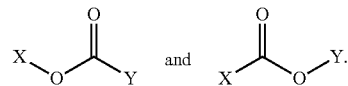

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

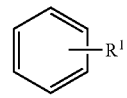

refers to at least

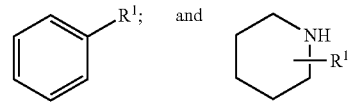

refers to at least

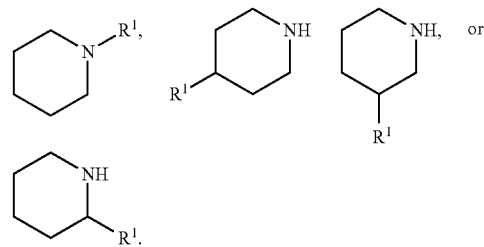

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with $R°$; —$(CH_2)_{0-4}O(CH_2)_{0-1}Ph$ which is optionally substituted with $R°$; —CH=CHPh, which is optionally substituted with $R°$; —$(CH_2)_{0-4}O(CH_2)_{0-1}$-pyridyl which is optionally substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ is optionally substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R°$ (or the ring formed by taking two independent occurrences of $R°$ together with their intervening atoms), are independently deuterium, halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =NNHC(O)$R^*$, =NNHC(O)O$R^*$, =NNHS(O)$_2R^*$, =$NR^*$, =NO$R^*$, =O(C($R^*_2$))$_{2-3}$O—, or =S(C($R^*_2$))$_{2-3}$S—, wherein each independent occurrence of $R^*$ is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C$R^*_2$)$_{2-3}$O—, wherein each independent occurrence of $R^*$ is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur. Suitable substituents on the aliphatic group of $R^*$ include halogen, —$R^\bullet$, -(halo$R^\bullet$), —OH, —O$R^\bullet$, —O(halo$R^\bullet$), —CN, —C(O)OH, —C(O)O$R^\bullet$, —$NH_2$, —NH$R^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)O$R^\dagger$, —C(O)C(O)$R^\dagger$, —C(O)CH$_2$C(O)$R^\dagger$, —S(O)$_2R^\dagger$, —S(O)$_2NR^\dagger_2$, —C(S)$NR^\dagger_2$, —C(NH)$NR^\dagger_2$, or —N($R^\dagger$)S(O)$_2R^\dagger$; wherein each $R^\dagger$ is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —O$R^\bullet$, —O(halo$R^\bullet$), —CN, —C(O)OH, —C(O)O$R^\bullet$, —$NH_2$, —NH$R^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,
—OH, protected hydroxy, alkoxy, oxo, thiooxo,
—$NO_2$, —CN, $CF_3$, $N_3$,
—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino,
—O-alkyl, —O-alkenyl, —O-alkynyl, —O-cycloalkyl, —O-aryl, —O-heteroaryl, —O-heterocyclic,
—C(O)-alkyl, —C(O)-alkenyl, —C(O)-alkynyl, —C(O)-carbocyclyl, —C(O)-aryl, —C(O)-heteroaryl, —C(O)-heterocyclyl, —CONH$_2$, —CONH-alkyl, —CONH-alkenyl, —CONH-alkynyl, —CONH-carbocyclyl, —CONH-aryl, —CONH-heteroaryl, —CONH-heterocyclyl, —OCO$_2$-alkyl, —OCO$_2$-alkenyl, —OCO$_2$-alkynyl, —OCO$_2$-carbocyclyl, —OCO$_2$-aryl, —OCO$_2$-heteroaryl, —OCO$_2$-heterocyclyl, —OCONH$_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —NHCO$_2$-alkyl, —NHCO$_2$-alkenyl, —NHCO$_2$-alkynyl, —NHCO$_2$-carbocyclyl, —NHCO$_2$-aryl, —NHCO$_2$-heteroaryl, —NHCO$_2$-heterocyclyl, —NHC(O)NH$_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in TBK and/or IKKε activity between a sample comprising a compound of the present invention, or composition thereof, and TBK and/or IKKε, and an equivalent sample comprising TBK and/or IKKε, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

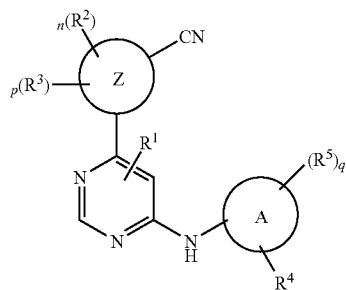

I or pharmaceutically acceptable derivatives, solvates, salts, hydrates, or stereoisomers thereof, wherein:

$R^1$ is hydrogen, optionally substituted $C_{1-6}$ aliphatic, —OR, or halogen;

ring Z is phenyl or a 5-6-membered heteroaryl having 1, 2, or 3 nitrogens;

each $R^2$ is independently —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;

each $R^3$ is independently —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;

ring A is phenyl or a 5-6-membered heteroaryl having 1, 2, or 3 nitrogens;

$R^4$ is —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;

each $R^5$ is independently —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur; or a 6-12 membered spiro, fused, or bridged bicyclic carbocyclic or heterocyclic ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

n is 1 or 2;

p is 0, 1, or 2; and q is 0, 1, or 2.

In certain embodiments, $R^1$ is H.

In certain embodiments, ring Z is phenyl or a 5-6-membered heteroaryl having 1, 2, or 3 nitrogens.

In certain embodiments, ring Z is phenyl, pyridine, or pyrimidine.

In certain embodiments, ring Z is phenyl.

In certain embodiments, ring Z is pyridine.

In certain embodiments, ring Z is

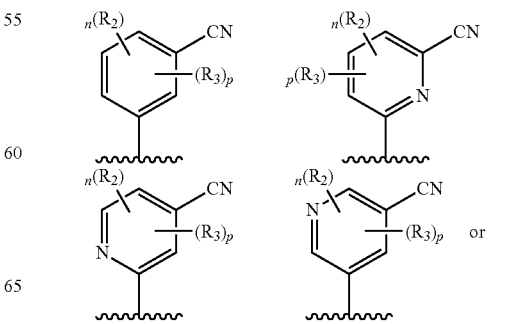

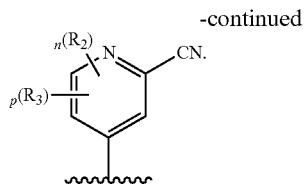

In certain embodiments, ring Z is

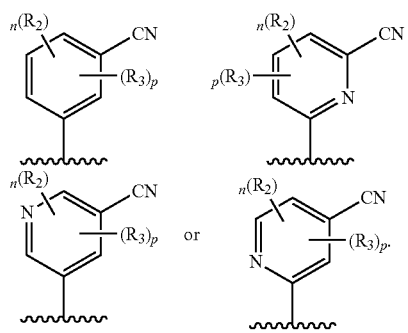

In certain embodiments, each R² is independently —R, halogen, —OR, or —N(R)₂.

In certain embodiments, each R² is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or R² is halogen, —OR, or —N(R)₂.

In certain embodiments, each R² is independently methyl, ethyl, propyl, i-propyl, butyl, s-butyl, t-butyl, straight chain or branched pentyl, or straight chain or branched hexyl; each of which is optionally substituted.

In certain embodiments, each R² is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each R² is independently F, Cl, Br, or I.

In certain embodiments, each R² is independently —OR, or —N(R)₂.

In certain embodiments, each R² is independently

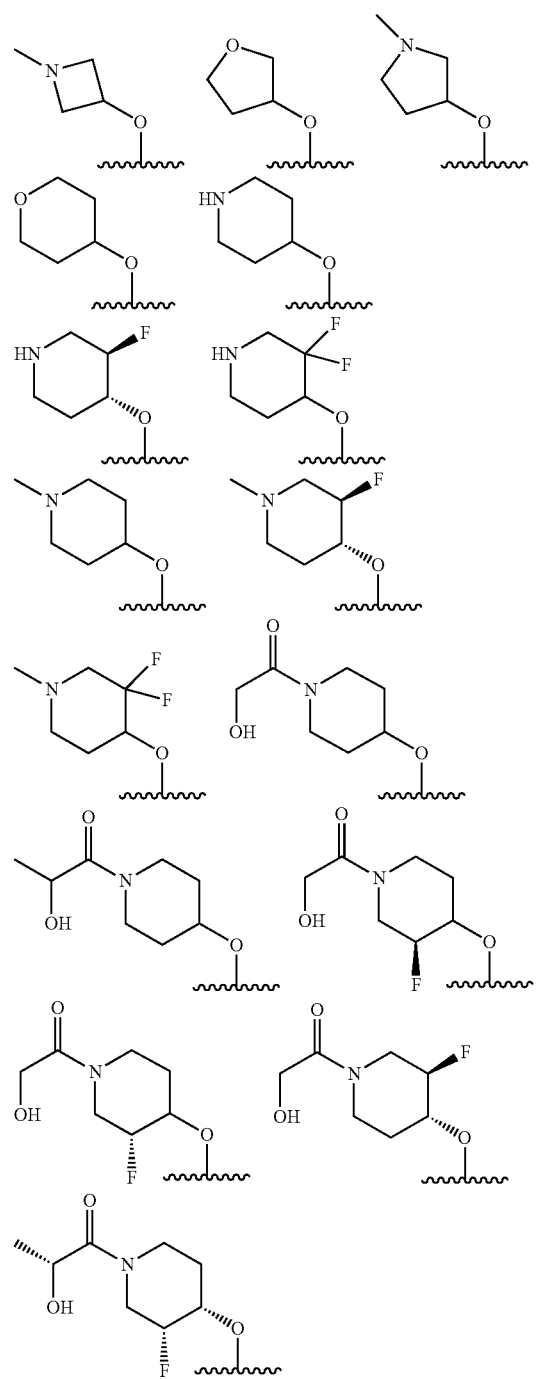

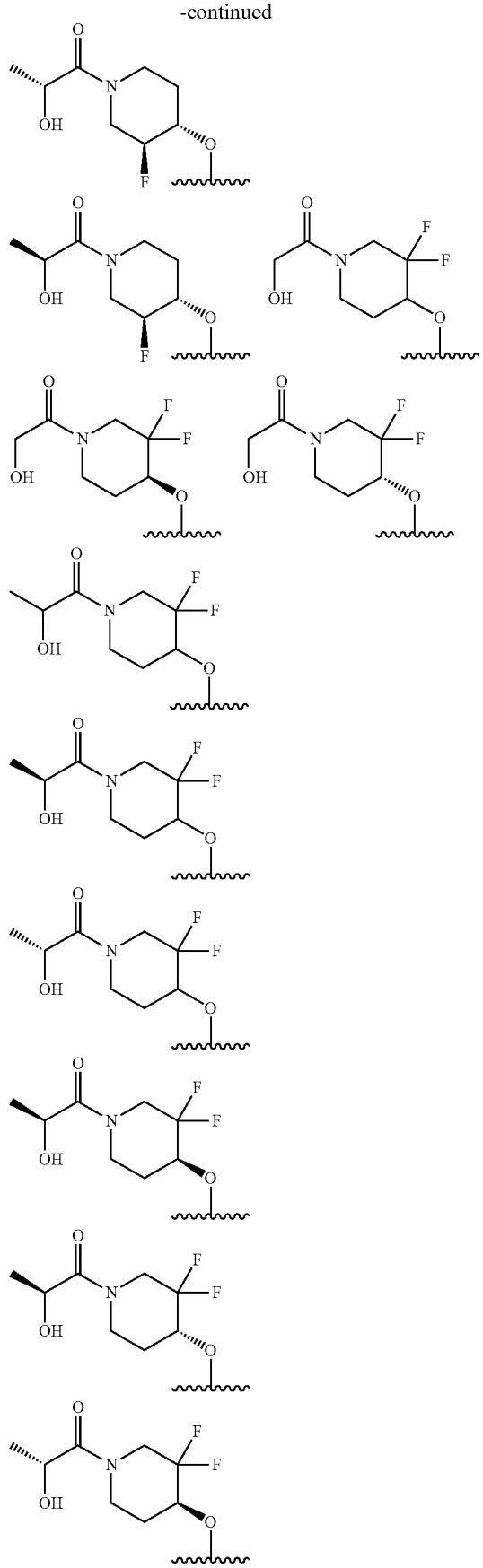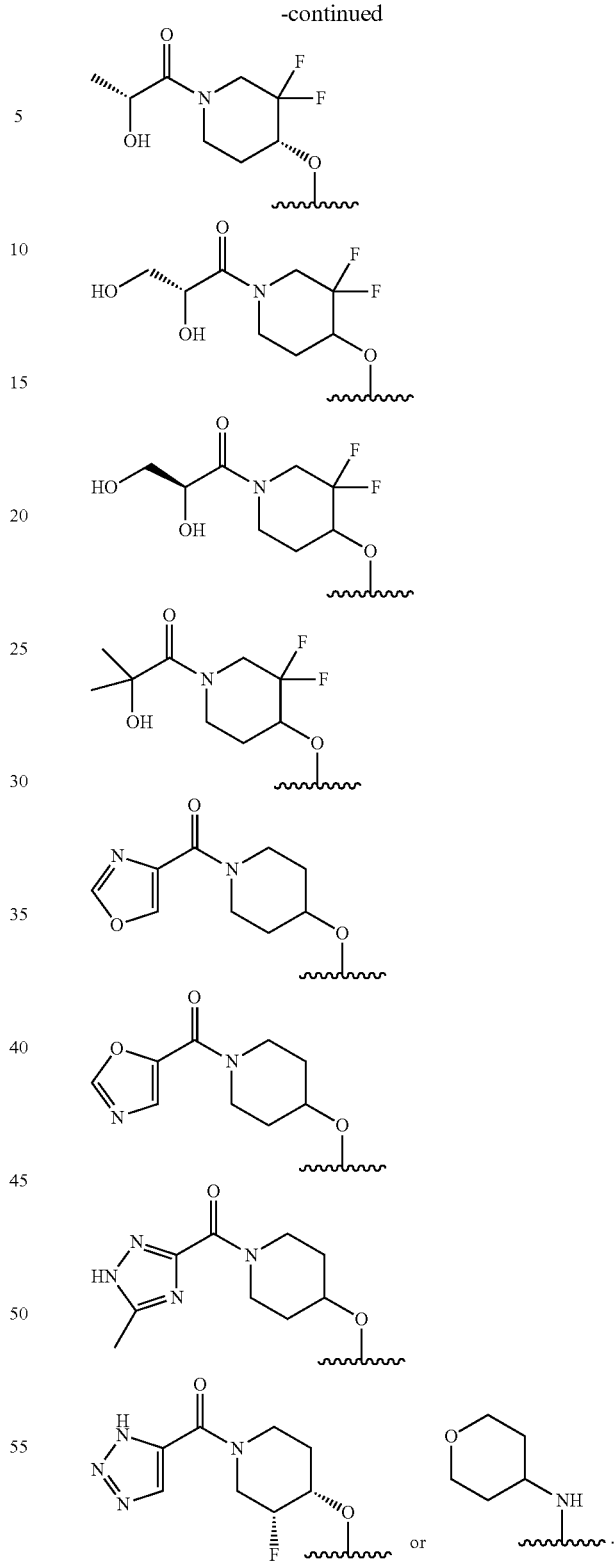
In certain embodiments, each $R^3$ is independently —R, halogen, —OR, or —N(R)$_2$.
In certain embodiments, each $R^3$ is independently H.
In certain embodiments, ring A is phenyl or pyridyl.
In certain embodiments, ring A is pyridyl.

In certain embodiments, ring A is

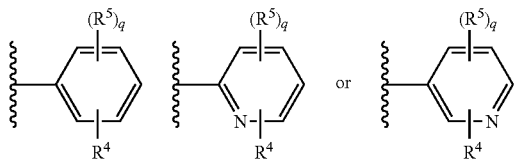

In certain embodiments, ring A is

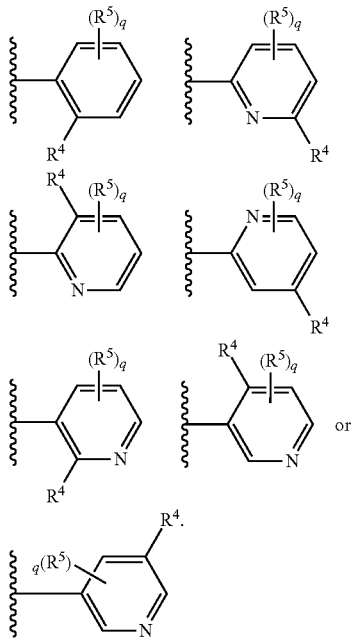

In certain embodiments, ring A is

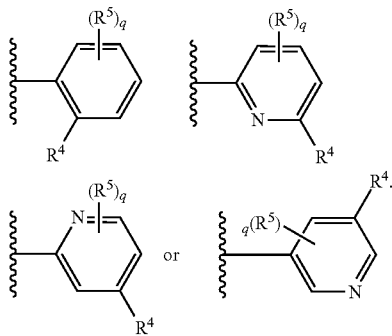

In certain embodiments, $R^4$ is —R, halogen, —OR, —NRC(O)R, —NRC(O)N(R)$_2$, —NRSO$_2$R, or —N(R)$_2$. In certain embodiments, $R^4$ is —R or —OR.

In certain embodiments, $R^4$ is H.

In certain embodiments, $R^4$ is —OR, wherein R is H, C$_{1-6}$ aliphatic, C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^4$ is —H or —OCH$_3$.

In certain embodiments, each $R^5$ is independently —R, —OR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^5$ is independently —R, —C(O)R, —CO$_2$R, —C(O)N(R)$_2$, —NRC(O)R, or —N(R)$_2$.

In certain embodiments, each $R^5$ is independently C$_{1-6}$ aliphatic, C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or $R^2$ is halogen, —OR, or —N(R)$_2$.

In certain embodiments, each $R^5$ is independently methyl, ethyl, propyl, i-propyl, butyl, s-butyl, t-butyl, straight chain or branched pentyl, or straight chain or branched hexyl; each of which is optionally substituted.

In certain embodiments, each $R^5$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^5$ is independently —R, —C(O)R, —CO$_2$R, —C(O)N(R)$_2$, —NRC(O)R, or —N(R)$_2$.

In certain embodiments, each $R^5$ is independently

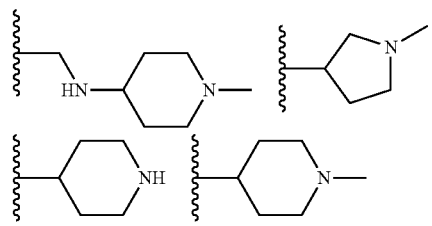

-continued

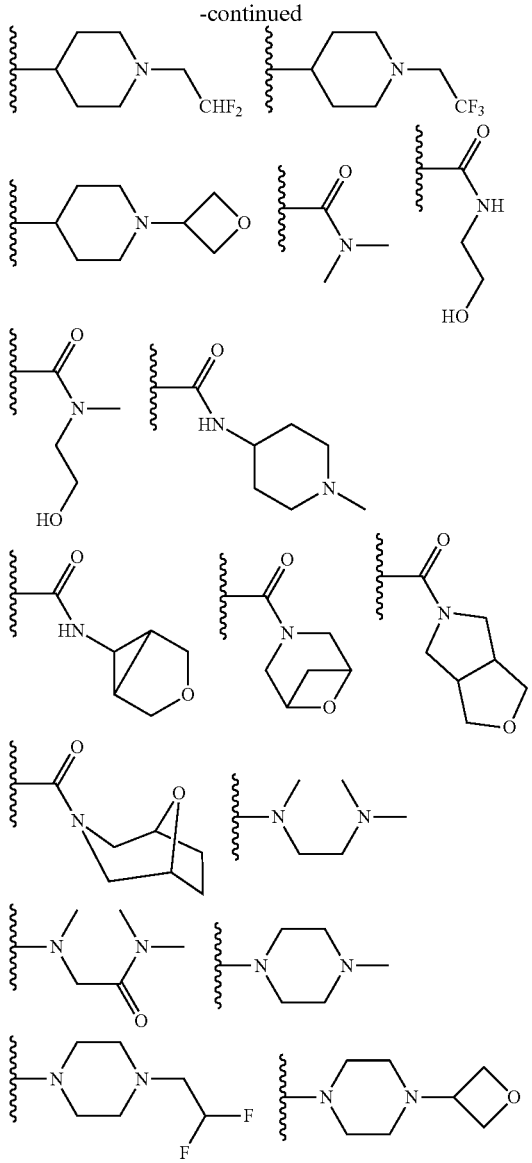
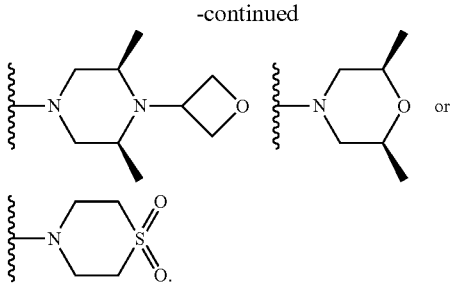

-continued

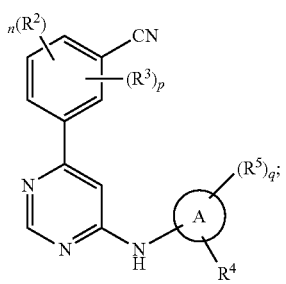

In certain embodiments, each of Ring A, Ring Z, R, $R^1$, $R^2$, $R^3$, $R^4$, $R^5$, n, p, and q, is as defined above and described in embodiments, classes and subclasses above and herein, singly or in combination.

In certain embodiments, the present invention provides a compound of formula II,

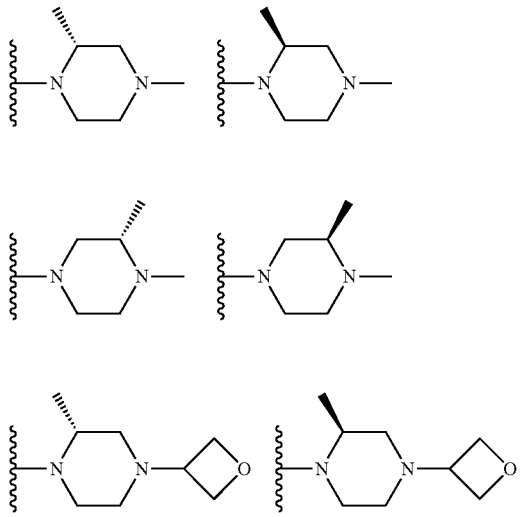

II or a pharmaceutically acceptable salt thereof, wherein each of ring A, $R^2$, $R^3$, $R^4$, $R^5$, n, p, and q, is as defined above and described in embodiments, classes and subclasses above and herein, singly or in combination.

In certain embodiments, the present invention provides a compound of formula III,

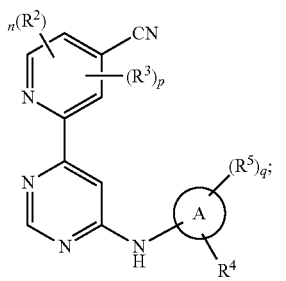

III or a pharmaceutically acceptable salt thereof, wherein each of ring A, $R^2$, $R^3$, $R^4$, $R^5$, n, p, and q, is as defined above and described in embodiments, classes and subclasses above and herein, singly or in combination.

In certain embodiments, the present invention provides a compound of formula IV,

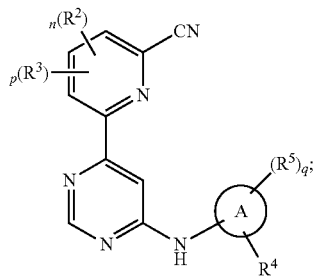

IV or a pharmaceutically acceptable salt thereof, wherein each of ring A, $R^2$, $R^3$, $R^4$, $R^5$, n, p, and q, is as defined above and described in embodiments, classes and subclasses above and herein, singly or in combination.

In certain embodiments, the present invention provides a compound of formula V,

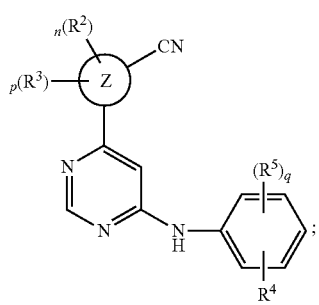

V or a pharmaceutically acceptable salt thereof, wherein each of ring Z, $R^2$, $R^3$, $R^4$, $R^5$, n, p, and q, is as defined above and described in embodiments, classes and subclasses above and herein, singly or in combination.

In certain embodiments, the present invention provides a compound of formula VI,

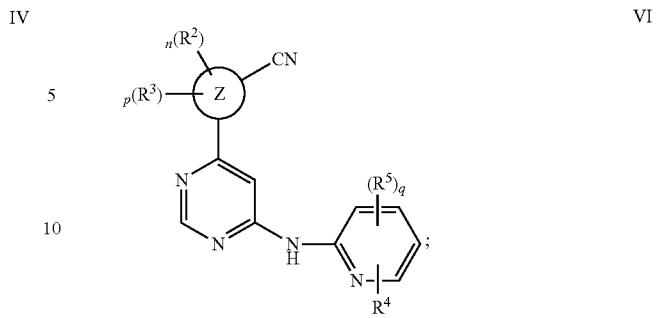

VI or a pharmaceutically acceptable salt thereof, wherein each of ring Z, $R^2$, $R^3$, $R^4$, $R^5$, n, p, and q, is as defined above and described in embodiments, classes and subclasses above and herein, singly or in combination.

In certain embodiments, the present invention provides a compound of formula VII,

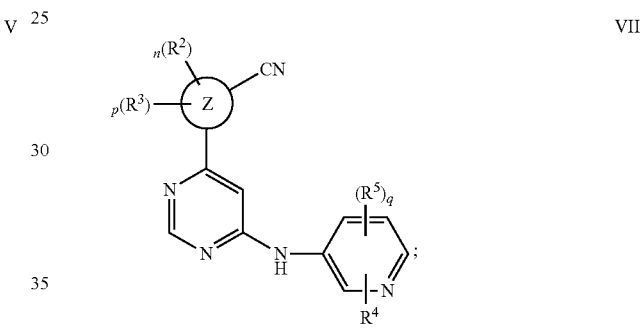

VII or a pharmaceutically acceptable salt thereof, wherein each of ring Z, $R^2$, $R^3$, $R^4$, $R^5$, n, p, and q, is as defined above and described in embodiments, classes and subclasses above and herein, singly or in combination.

In certain embodiments, the invention provides a compound selected from Table 1:

TABLE 1

1

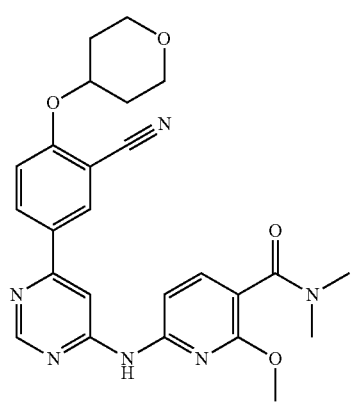 [SMILES: COc1nc(Nc2cc(-c3ccc(OC4CCOCC4)c(C#N)c3)ncn2)ccc1C(=O)N(C)C]

TABLE 1-continued
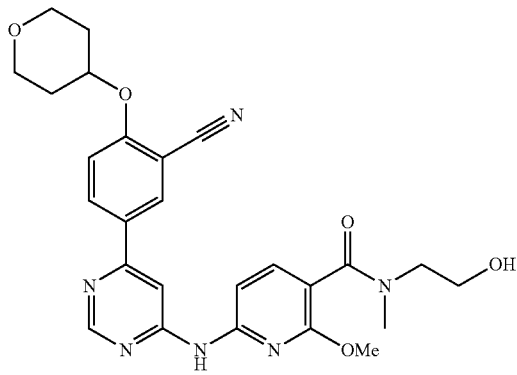 [SMILES: COc1nc(Nc2cc(-c3ccc(OC4CCOCC4)c(C#N)c3)ncn2)ccc1C(=O)N(C)CCO]
2
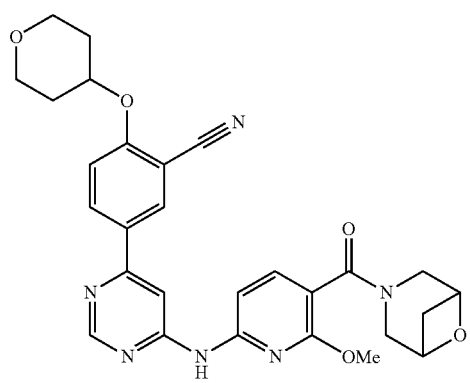 [SMILES: COc1nc(Nc2cc(-c3ccc(OC4CCOCC4)c(C#N)c3)ncn2)ccc1C(=O)N1CC2CC(C1)O2]
3
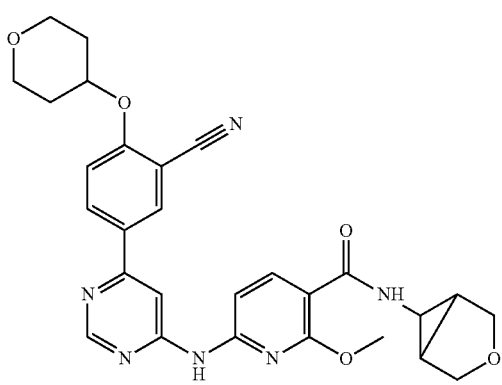 [SMILES: COc1nc(Nc2cc(-c3ccc(OC4CCOCC4)c(C#N)c3)ncn2)ccc1C(=O)NC1C2COCC21]
4
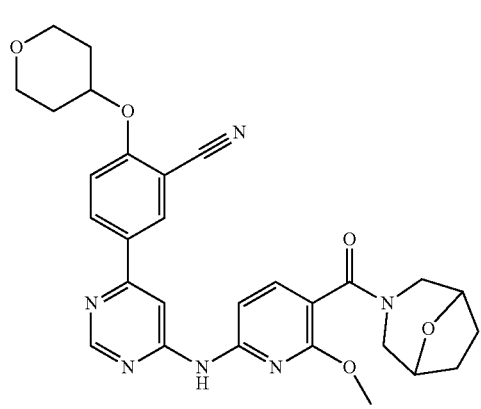 [SMILES: COc1nc(Nc2cc(-c3ccc(OC4CCOCC4)c(C#N)c3)ncn2)ccc1C(=O)N1CC2CCC(C1)O2]
5

TABLE 1-continued
| | |
|---|---|
| 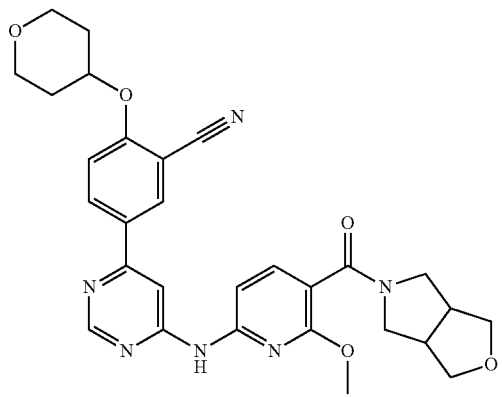 [SMILES: COc1nc(Nc2cc(-c3ccc(OC4CCOCC4)c(C#N)c3)ncn2)ccc1C(=O)N1CC2COCC2C1] | 6 |
| 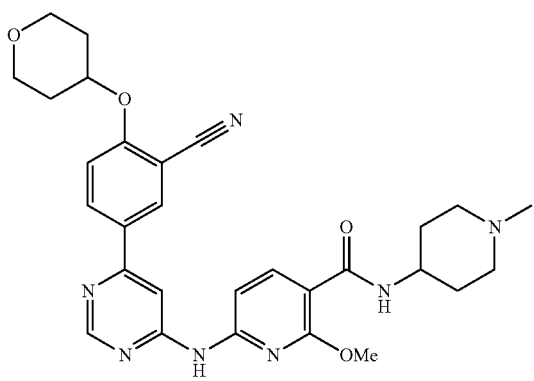 [SMILES: COc1nc(Nc2cc(-c3ccc(OC4CCOCC4)c(C#N)c3)ncn2)ccc1C(=O)NC1CCN(C)CC1] | 7 |
| 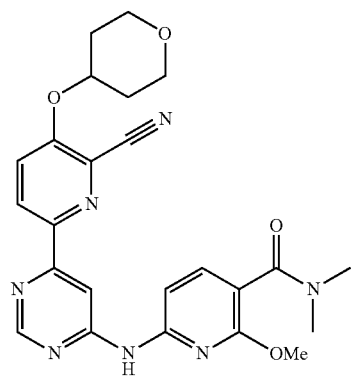 [SMILES: COc1nc(Nc2cc(-c3ccc(OC4CCOCC4)c(C#N)n3)ncn2)ccc1C(=O)N(C)C] | 8 |
| 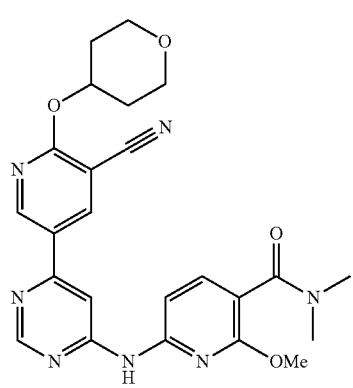 [SMILES: COc1nc(Nc2cc(-c3cnc(OC4CCOCC4)c(C#N)c3)ncn2)ccc1C(=O)N(C)C] | 9 |

TABLE 1-continued
| | |
|---|---|
| 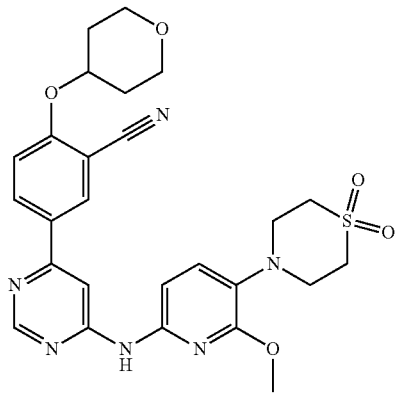 [SMILES: COc1nc(Nc2cc(-c3ccc(OC4CCOCC4)c(C#N)c3)ncn2)ccc1N1CCS(=O)(=O)CC1] | 10 |
| 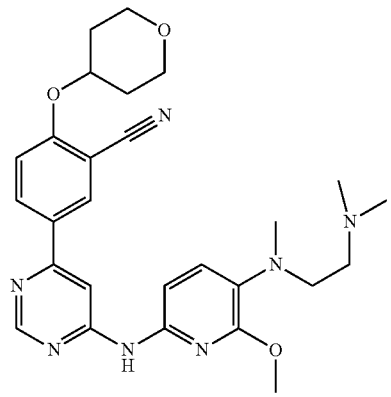 [SMILES: COc1nc(Nc2cc(-c3ccc(OC4CCOCC4)c(C#N)c3)ncn2)ccc1N(C)CCN(C)C] | 11 |
| 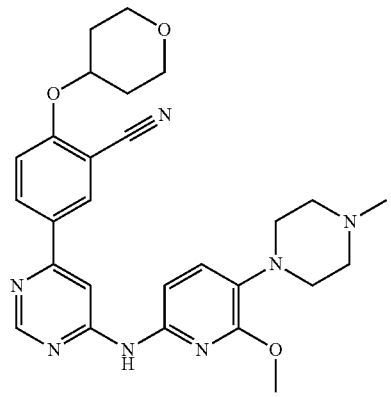 [SMILES: COc1nc(Nc2cc(-c3ccc(OC4CCOCC4)c(C#N)c3)ncn2)ccc1N1CCN(C)CC1] | 12 |
| 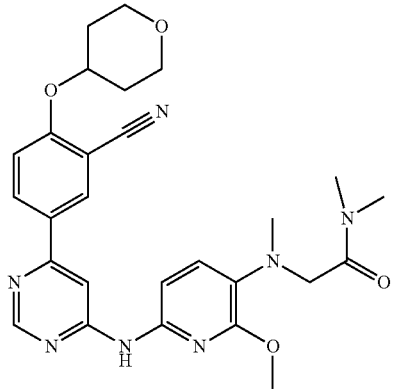 [SMILES: COc1nc(Nc2cc(-c3ccc(OC4CCOCC4)c(C#N)c3)ncn2)ccc1N(C)CC(=O)N(C)C] | 13 |

TABLE 1-continued
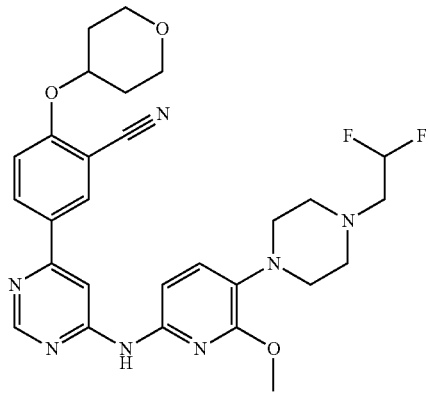 [SMILES: COc1nc(Nc2cc(-c3ccc(OC4CCOCC4)c(C#N)c3)ncn2)ccc1N1CCN(CC(F)F)CC1]
14
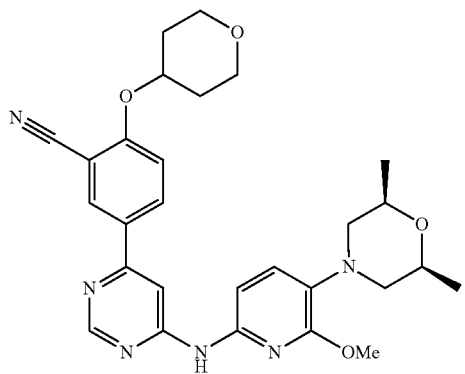 [SMILES: COc1nc(Nc2cc(-c3ccc(OC4CCOCC4)c(C#N)c3)ncn2)ccc1N1C[C@@H](C)O[C@@H](C)C1]
15
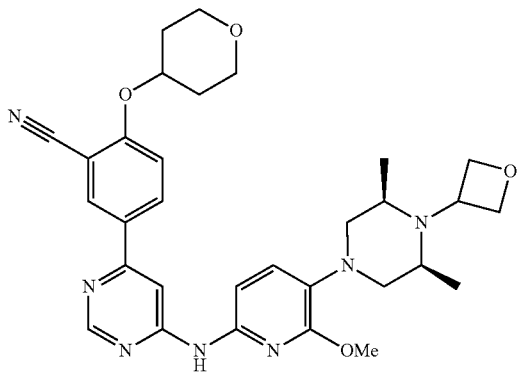 [SMILES: COc1nc(Nc2cc(-c3ccc(OC4CCOCC4)c(C#N)c3)ncn2)ccc1N1C[C@@H](C)N(C2COC2)[C@@H](C)C1]
16
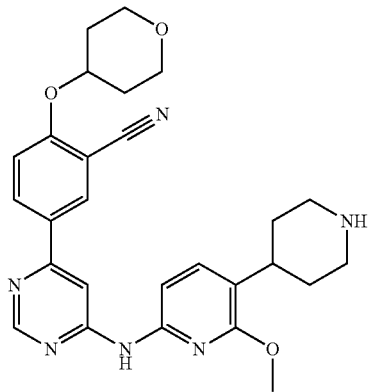 [SMILES: COc1nc(Nc2cc(-c3ccc(OC4CCOCC4)c(C#N)c3)ncn2)ccc1C1CCNCC1]
17

TABLE 1-continued
| | |
|---|---|
| 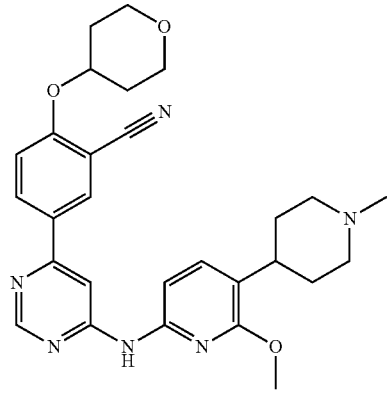 [SMILES: COc1nc(Nc2cc(-c3ccc(OC4CCOCC4)c(C#N)c3)ncn2)ccc1C1CCN(C)CC1] | 18 |
| 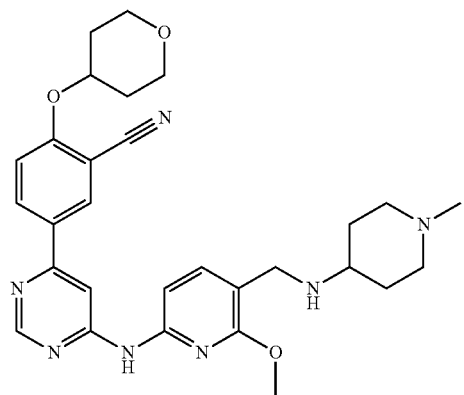 [SMILES: COc1nc(Nc2cc(-c3ccc(OC4CCOCC4)c(C#N)c3)ncn2)ccc1CNC1CCN(C)CC1] | 19 |
| 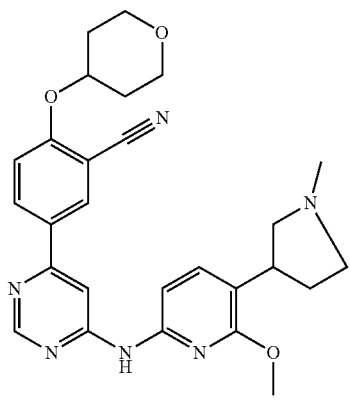 [SMILES: COc1nc(Nc2cc(-c3ccc(OC4CCOCC4)c(C#N)c3)ncn2)ccc1C1CCN(C)C1] | 20 |
| 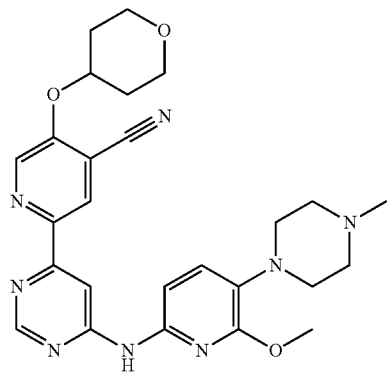 [SMILES: COc1nc(Nc2cc(-c3cc(C#N)c(OC4CCOCC4)cn3)ncn2)ccc1N1CCN(C)CC1] | 21 |

TABLE 1-continued
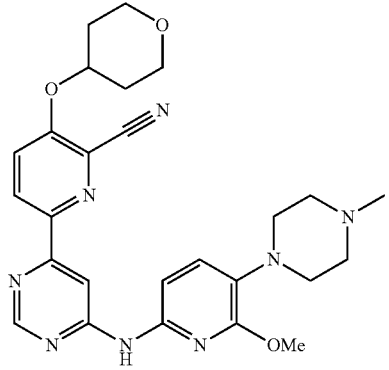 [SMILES: COc1nc(Nc2cc(-c3ccc(OC4CCOCC4)c(C#N)n3)ncn2)ccc1N1CCN(C)CC1]
22
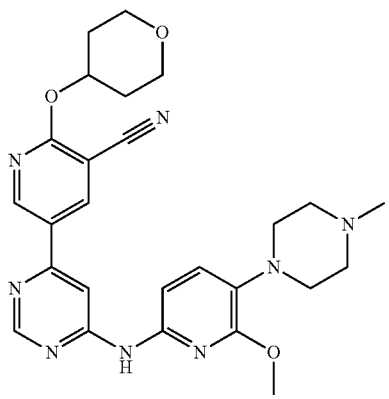 [SMILES: COc1nc(Nc2cc(-c3cnc(OC4CCOCC4)c(C#N)c3)ncn2)ccc1N1CCN(C)CC1]
23
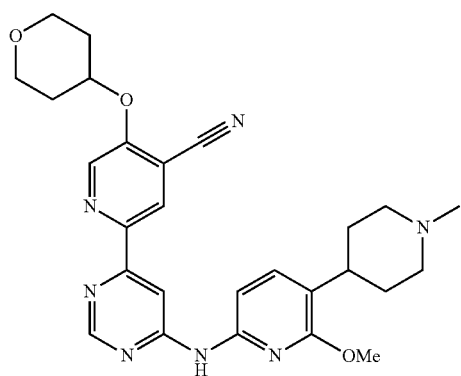 [SMILES: COc1nc(Nc2cc(-c3cc(C#N)c(OC4CCOCC4)cn3)ncn2)ccc1C1CCN(C)CC1]
24
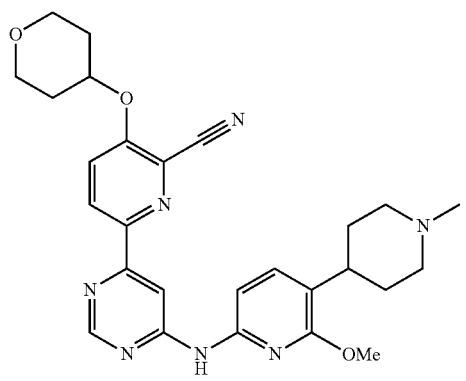 [SMILES: COc1nc(Nc2cc(-c3ccc(OC4CCOCC4)c(C#N)n3)ncn2)ccc1C1CCN(C)CC1]
25

TABLE 1-continued
| | |
|---|---|
| 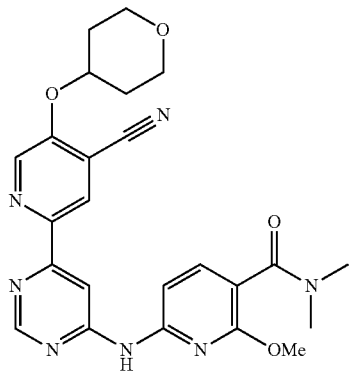 | 26 |
| 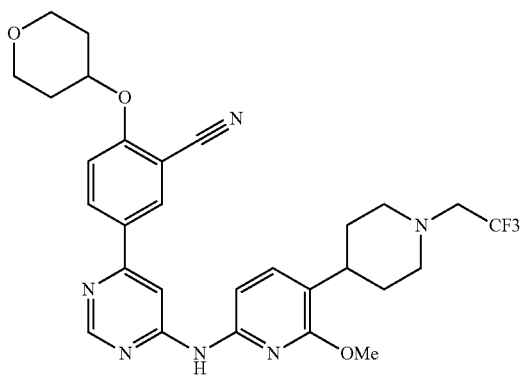 [SMILES: COc1nc(Nc2cc(-c3ccc(OC4CCOCC4)c(C#N)c3)ncn2)ccc1C1CCN(CC(F)(F)F)CC1] | 27 |
| 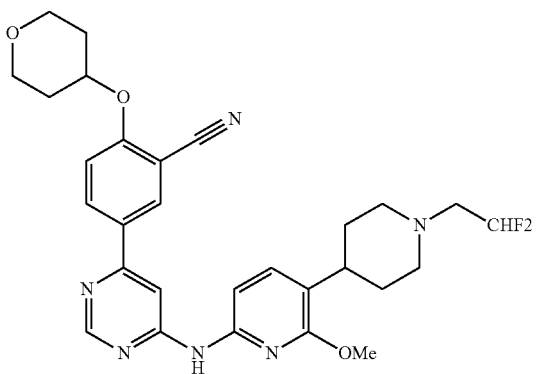 [SMILES: COc1nc(Nc2cc(-c3ccc(OC4CCOCC4)c(C#N)c3)ncn2)ccc1C1CCN(CC(F)F)CC1] | 28 |
| 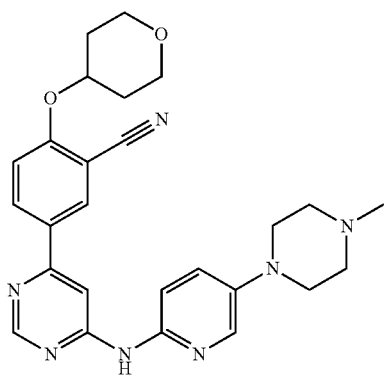 [SMILES: CN1CCN(c2ccc(Nc3cc(-c4ccc(OC5CCOCC5)c(C#N)c4)ncn3)nc2)CC1] | 29 |

TABLE 1-continued
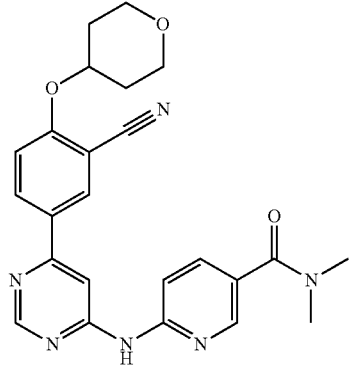 [SMILES: CN(C)C(=O)c1ccc(Nc2cc(-c3ccc(OC4CCOCC4)c(C#N)c3)ncn2)nc1]
30
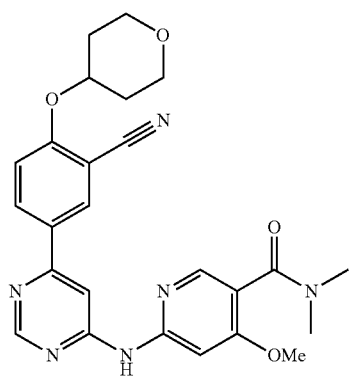
31
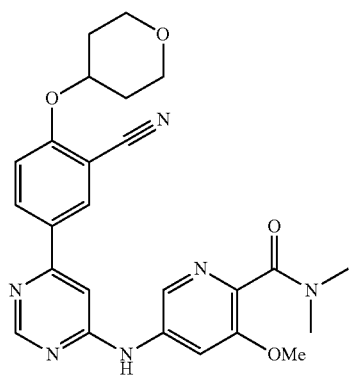
32
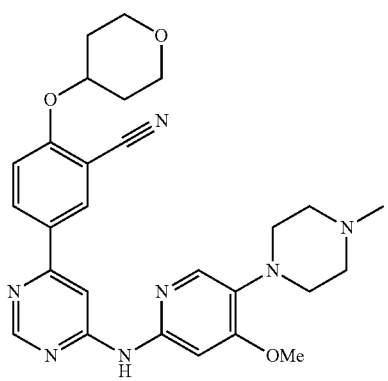 [SMILES: COc1cc(Nc2cc(-c3ccc(OC4CCOCC4)c(C#N)c3)ncn2)ncc1N1CCN(C)CC1]
33

TABLE 1-continued
| | |
|---|---|
| 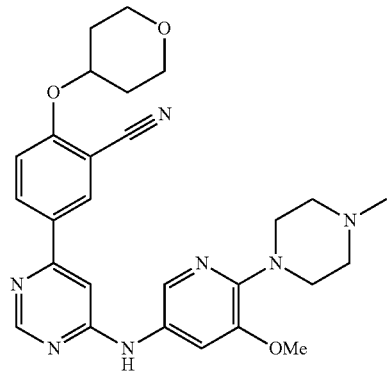 [SMILES: COc1cc(Nc2cc(-c3ccc(OC4CCOCC4)c(C#N)c3)ncn2)cnc1N1CCN(C)CC1] | 34 |
| 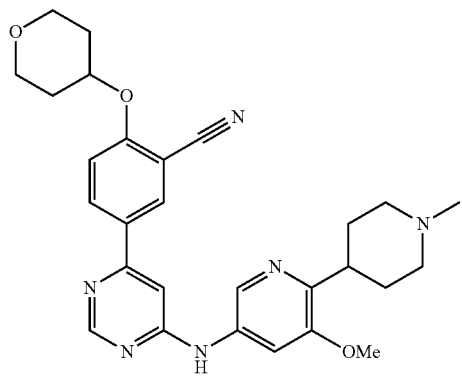 [SMILES: COc1cc(Nc2cc(-c3ccc(OC4CCOCC4)c(C#N)c3)ncn2)cnc1C1CCN(C)CC1] | 35 |
| 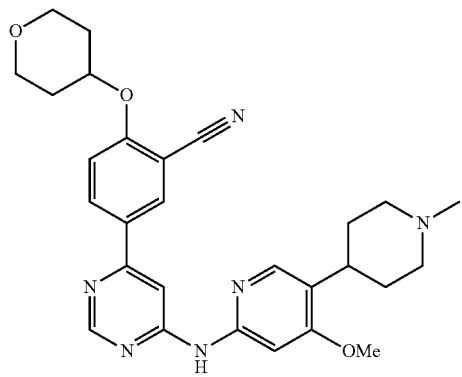 [SMILES: COc1cc(Nc2cc(-c3ccc(OC4CCOCC4)c(C#N)c3)ncn2)ncc1C1CCN(C)CC1] | 36 |
| 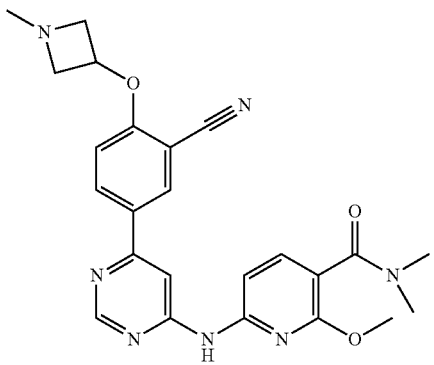 | 37 |

TABLE 1-continued
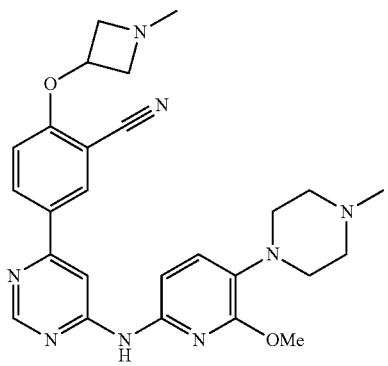 [SMILES: COc1nc(Nc2cc(-c3ccc(OC4CN(C)C4)c(C#N)c3)ncn2)ccc1N1CCN(C)CC1]
38
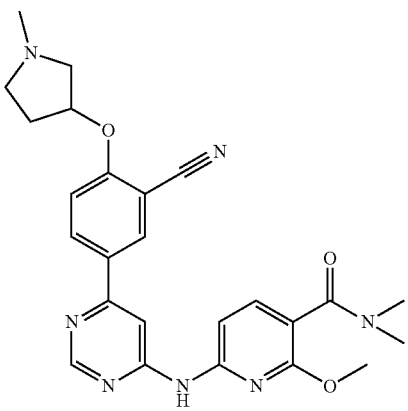 [SMILES: COc1nc(Nc2cc(-c3ccc(OC4CCN(C)C4)c(C#N)c3)ncn2)ccc1C(=O)N(C)C]
39
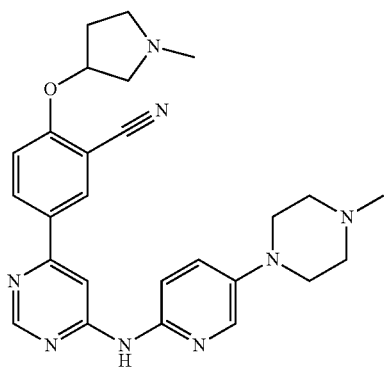 [SMILES: CN1CCN(c2ccc(Nc3cc(-c4ccc(OC5CCN(C)C5)c(C#N)c4)ncn3)nc2)CC1]
40
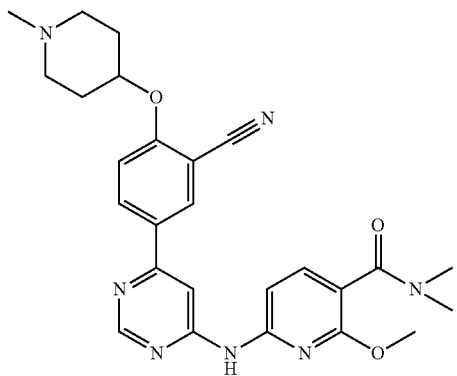
41

TABLE 1-continued
42
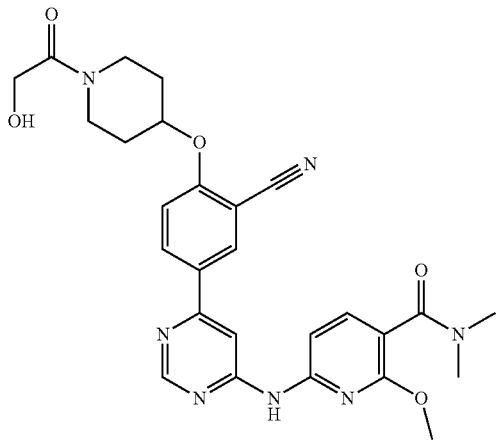 [SMILES: COc1nc(Nc2cc(-c3ccc(OC4CCN(C(=O)CO)CC4)c(C#N)c3)ncn2)ccc1C(=O)N(C)C]
43
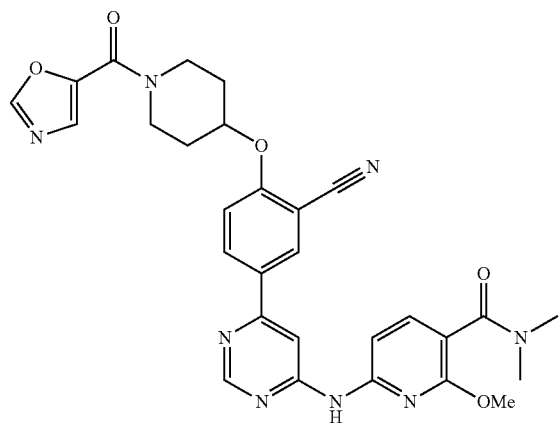 [SMILES: COc1nc(Nc2cc(-c3ccc(OC4CCN(C(=O)c5cnco5)CC4)c(C#N)c3)ncn2)ccc1C(=O)N(C)C]
44
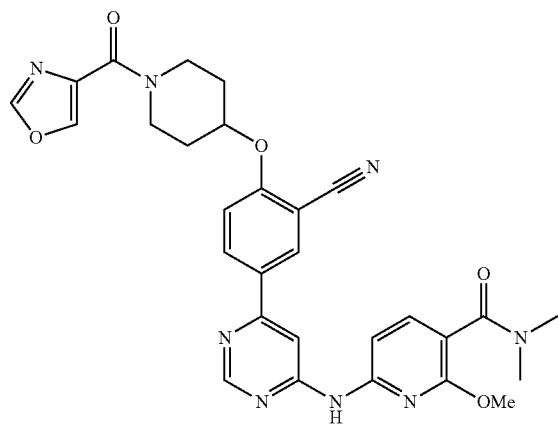 [SMILES: COc1nc(Nc2cc(-c3ccc(OC4CCN(C(=O)c5cocn5)CC4)c(C#N)c3)ncn2)ccc1C(=O)N(C)C]

TABLE 1-continued
| | |
|---|---|
| 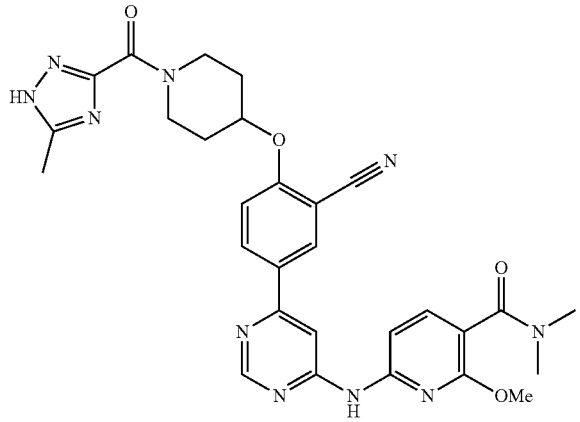 [SMILES: COc1nc(Nc2cc(-c3ccc(OC4CCN(C(=O)c5n[nH]c(C)n5)CC4)c(C#N)c3)ncn2)ccc1C(=O)N(C)C] | 45 |
| 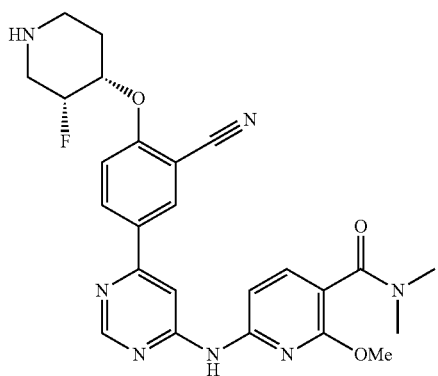 [SMILES: COc1nc(Nc2cc(-c3ccc(O[C@H]4CCNC[C@H]4F)c(C#N)c3)ncn2)ccc1C(=O)N(C)C] | 46 |
| 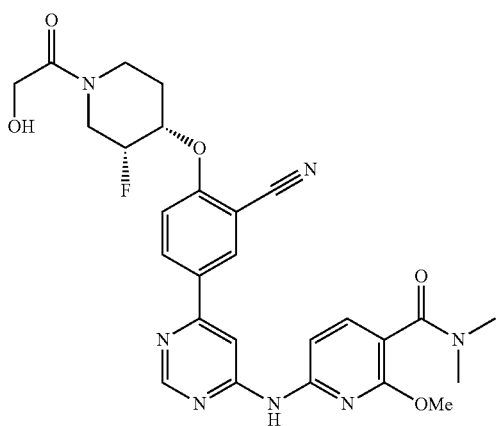 [SMILES: COc1nc(Nc2cc(-c3ccc(O[C@H]4CCN(C(=O)CO)C[C@H]4F)c(C#N)c3)ncn2)ccc1C(=O)N(C)C] | 47 |
| 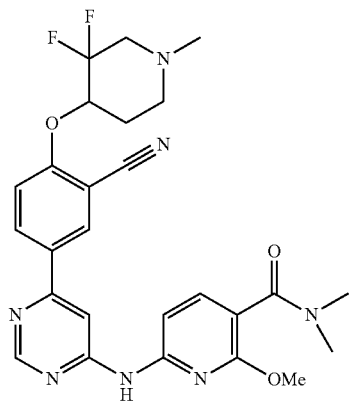 [SMILES: COc1nc(Nc2cc(-c3ccc(OC4CCN(C)CC4(F)F)c(C#N)c3)ncn2)ccc1C(=O)N(C)C] | 48 |

TABLE 1-continued
| | |
|---|---|
| 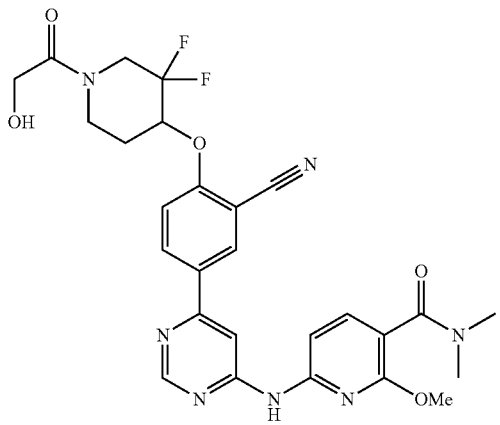 [SMILES: COc1nc(Nc2cc(-c3ccc(OC4CCN(C(=O)CO)CC4(F)F)c(C#N)c3)ncn2)ccc1C(=O)N(C)C] | 49 |
| 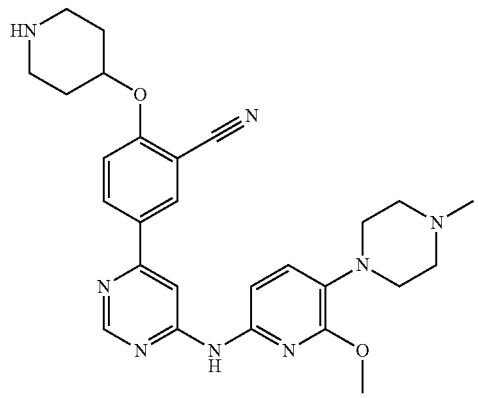 [SMILES: COc1nc(Nc2cc(-c3ccc(OC4CCNCC4)c(C#N)c3)ncn2)ccc1N1CCN(C)CC1] | 50 |
| 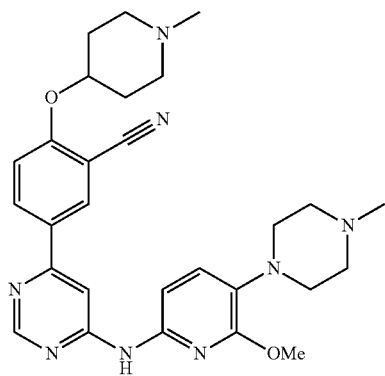 [SMILES: COc1nc(Nc2cc(-c3ccc(OC4CCN(C)CC4)c(C#N)c3)ncn2)ccc1N1CCN(C)CC1] | 51 |
| 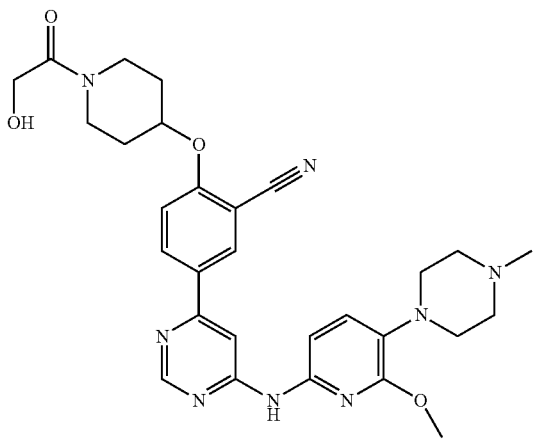 [SMILES: COc1nc(Nc2cc(-c3ccc(OC4CCN(C(=O)CO)CC4)c(C#N)c3)ncn2)ccc1N1CCN(C)CC1] | 52 |

TABLE 1-continued
53
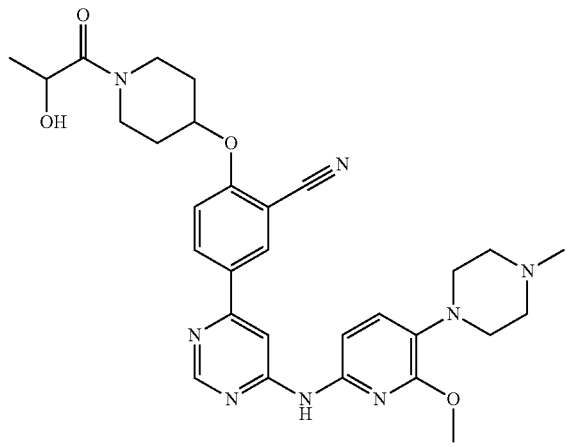 [SMILES: COc1nc(Nc2cc(-c3ccc(OC4CCN(C(=O)C(C)O)CC4)c(C#N)c3)ncn2)ccc1N1CCN(C)CC1]
54
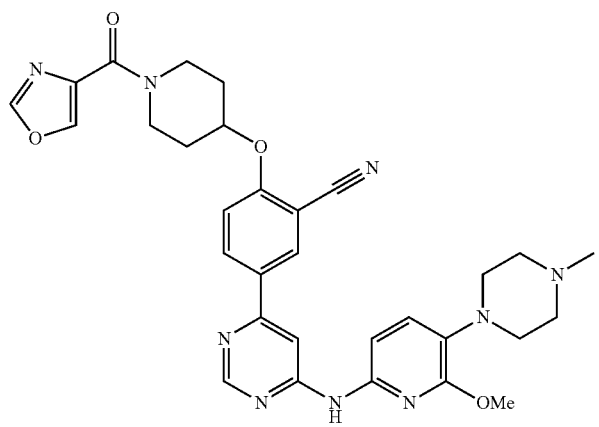 [SMILES: COc1nc(Nc2cc(-c3ccc(OC4CCN(C(=O)c5cocn5)CC4)c(C#N)c3)ncn2)ccc1N1CCN(C)CC1]
55
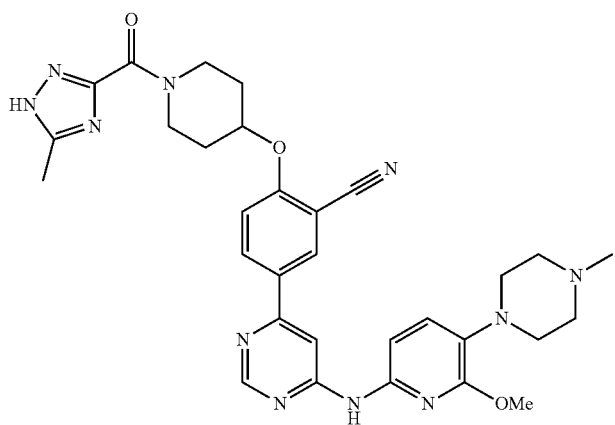 [SMILES: COc1nc(Nc2cc(-c3ccc(OC4CCN(C(=O)c5n[nH]c(C)n5)CC4)c(C#N)c3)ncn2)ccc1N1CCN(C)CC1]

TABLE 1-continued
56
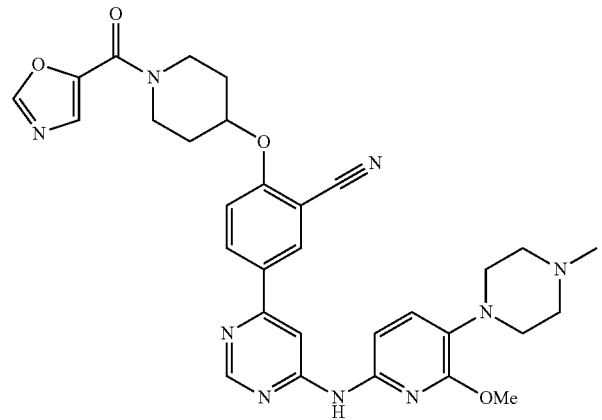 [SMILES: COc1nc(Nc2cc(-c3ccc(OC4CCN(C(=O)c5cnco5)CC4)c(C#N)c3)ncn2)ccc1N1CCN(C)CC1]
57
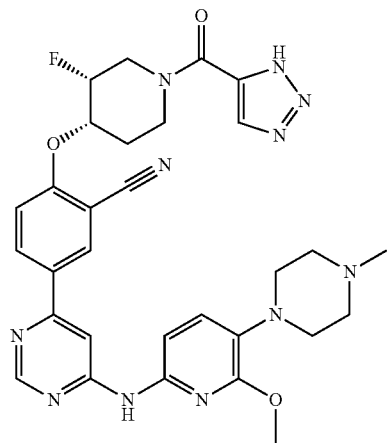 [SMILES: COc1nc(Nc2cc(-c3ccc(O[C@H]4CCN(C(=O)c5cnn[nH]5)C[C@H]4F)c(C#N)c3)ncn2)ccc1N1CCN(C)CC1]
58
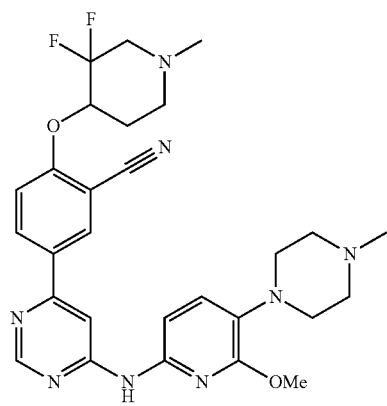 [SMILES: COc1nc(Nc2cc(-c3ccc(OC4CCN(C)CC4(F)F)c(C#N)c3)ncn2)ccc1N1CCN(C)CC1]

TABLE 1-continued
59
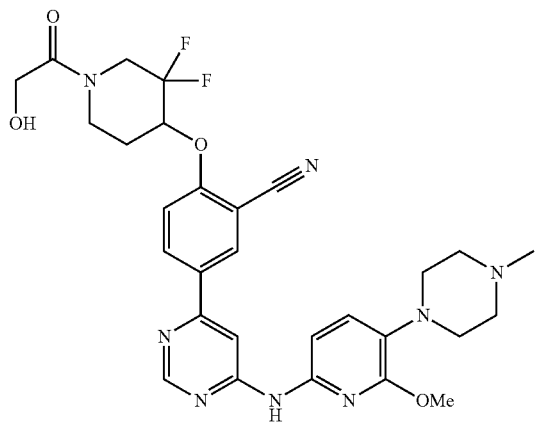 [SMILES: COc1nc(Nc2cc(-c3ccc(OC4CCN(C(=O)CO)CC4(F)F)c(C#N)c3)ncn2)ccc1N1CCN(C)CC1]
60
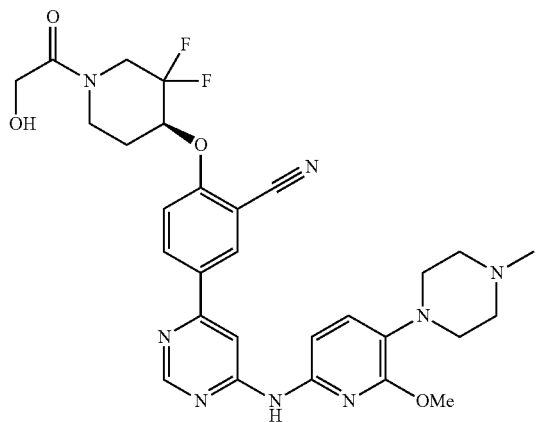 [SMILES: COc1nc(Nc2cc(-c3ccc(O[C@H]4CCN(C(=O)CO)CC4(F)F)c(C#N)c3)ncn2)ccc1N1CCN(C)CC1]
61
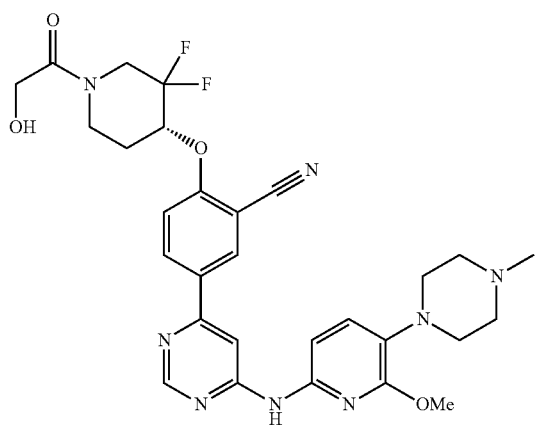 [SMILES: COc1nc(Nc2cc(-c3ccc(O[C@@H]4CCN(C(=O)CO)CC4(F)F)c(C#N)c3)ncn2)ccc1N1CCN(C)CC1]

TABLE 1-continued
62
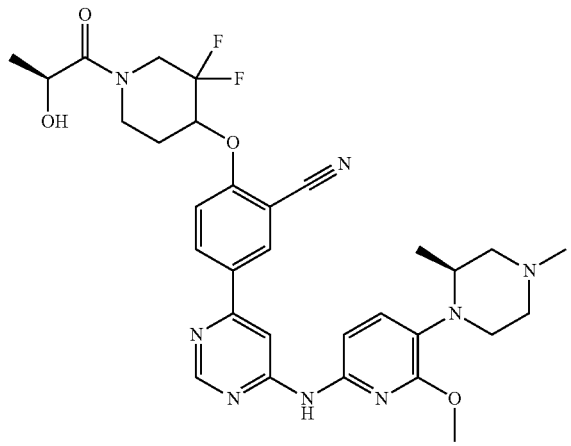 [SMILES: COc1nc(Nc2cc(-c3ccc(OC4CCN(C(=O)[C@H](C)O)CC4(F)F)c(C#N)c3)ncn2)ccc1N1CCN(C)C[C@@H]1C]
63
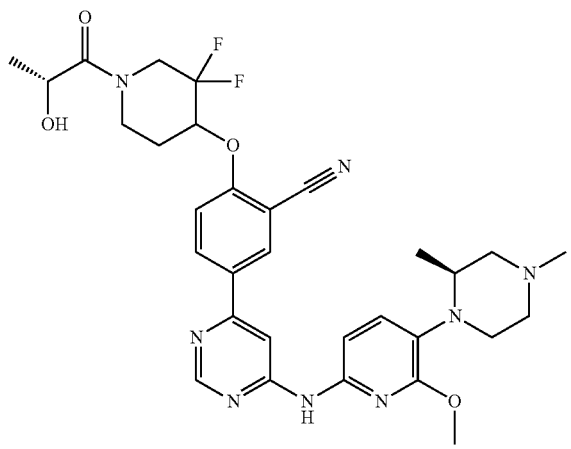 [SMILES: COc1nc(Nc2cc(-c3ccc(OC4CCN(C(=O)[C@@H](C)O)CC4(F)F)c(C#N)c3)ncn2)ccc1N1CCN(C)C[C@@H]1C]
64
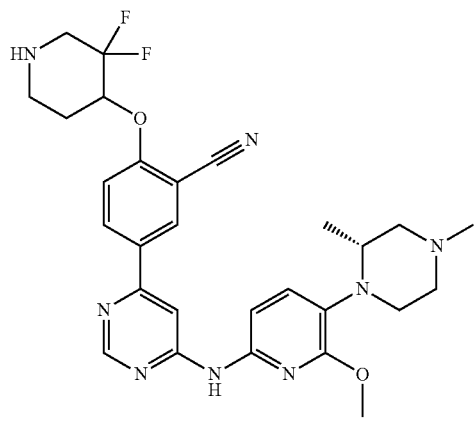 [SMILES: COc1nc(Nc2cc(-c3ccc(OC4CCNCC4(F)F)c(C#N)c3)ncn2)ccc1N1CCN(C)C[C@H]1C]

TABLE 1-continued
65
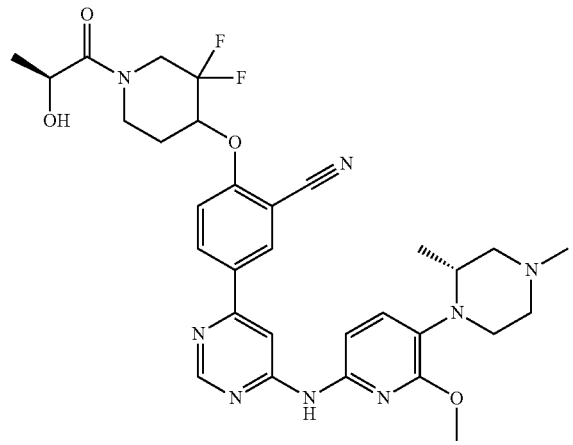 [SMILES: COc1nc(Nc2cc(-c3ccc(OC4CCN(C(=O)[C@H](C)O)CC4(F)F)c(C#N)c3)ncn2)ccc1N1CCN(C)C[C@H]1C]
66
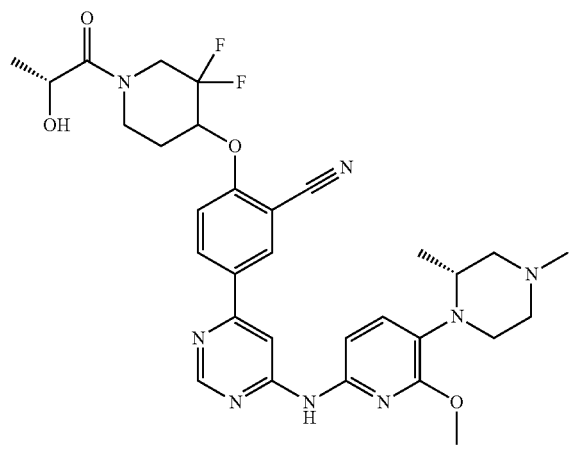 [SMILES: COc1nc(Nc2cc(-c3ccc(OC4CCN(C(=O)[C@@H](C)O)CC4(F)F)c(C#N)c3)ncn2)ccc1N1CCN(C)C[C@H]1C]
67
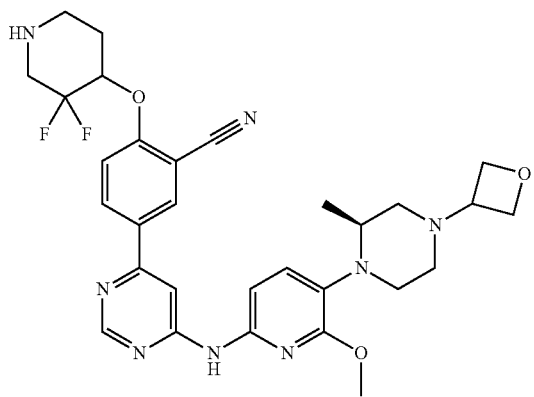 [SMILES: COc1nc(Nc2cc(-c3ccc(OC4CCNCC4(F)F)c(C#N)c3)ncn2)ccc1N1CCN(C2COC2)C[C@@H]1C]

TABLE 1-continued
68
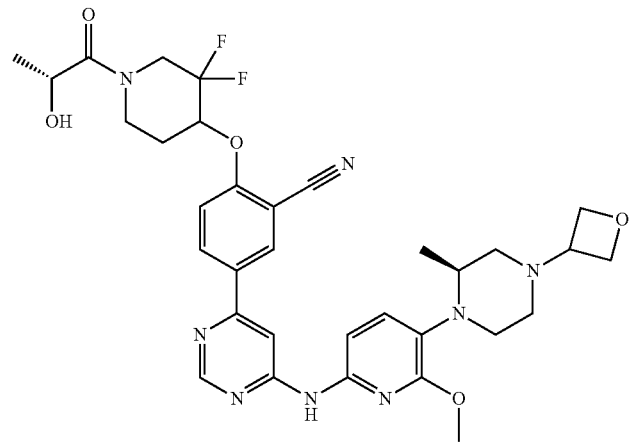 [SMILES: COc1nc(Nc2cc(-c3ccc(OC4CCN(C(=O)[C@@H](C)O)CC4(F)F)c(C#N)c3)ncn2)ccc1N1CCN(C2COC2)C[C@@H]1C]
69
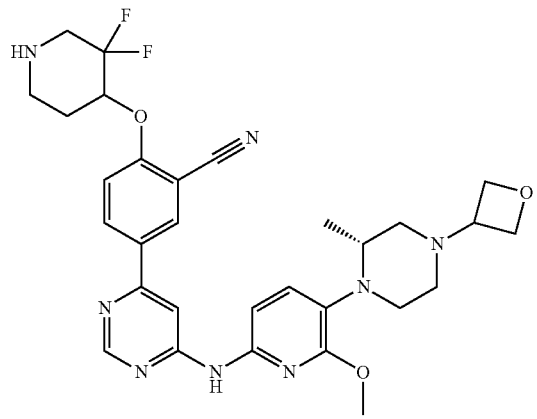 [SMILES: COc1nc(Nc2cc(-c3ccc(OC4CCNCC4(F)F)c(C#N)c3)ncn2)ccc1N1CCN(C2COC2)C[C@H]1C]
70
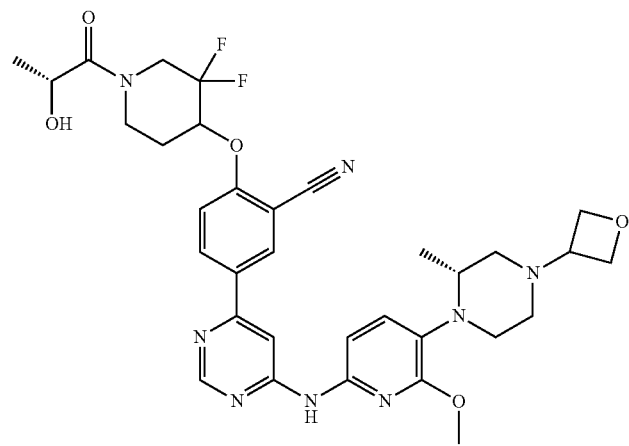 [SMILES: COc1nc(Nc2cc(-c3ccc(OC4CCN(C(=O)[C@@H](C)O)CC4(F)F)c(C#N)c3)ncn2)ccc1N1CCN(C2COC2)C[C@H]1C]

TABLE 1-continued
71
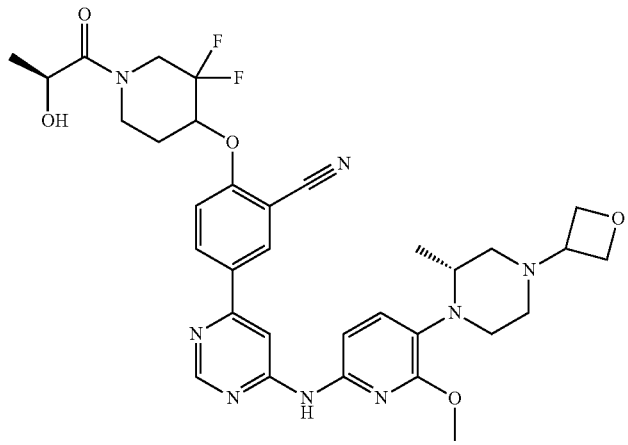 [SMILES: COc1nc(Nc2cc(-c3ccc(OC4CCN(C(=O)[C@H](C)O)CC4(F)F)c(C#N)c3)ncn2)ccc1N1CCN(C2COC2)C[C@H]1C]
72
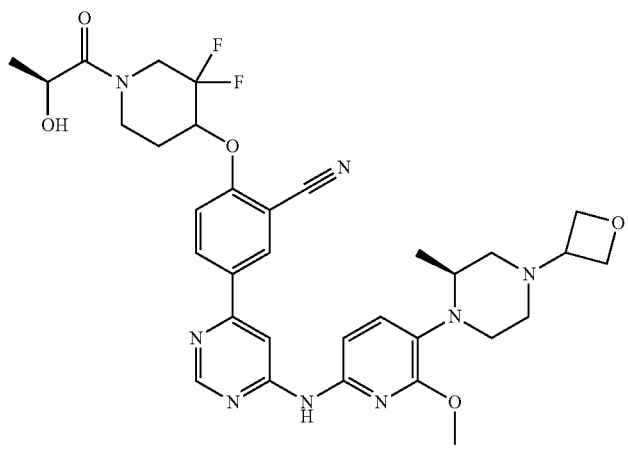 [SMILES: COc1nc(Nc2cc(-c3ccc(OC4CCN(C(=O)[C@H](C)O)CC4(F)F)c(C#N)c3)ncn2)ccc1N1CCN(C2COC2)C[C@@H]1C]
73
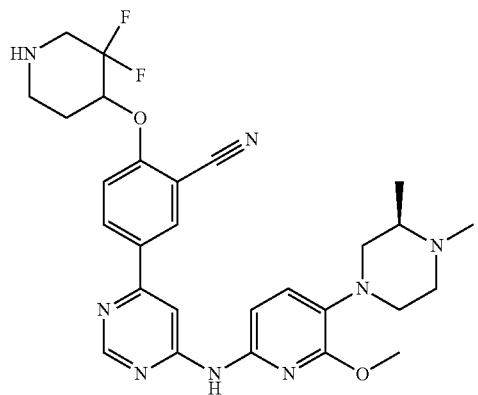 [SMILES: COc1nc(Nc2cc(-c3ccc(OC4CCNCC4(F)F)c(C#N)c3)ncn2)ccc1N1CCN(C)[C@H](C)C1]

TABLE 1-continued
74
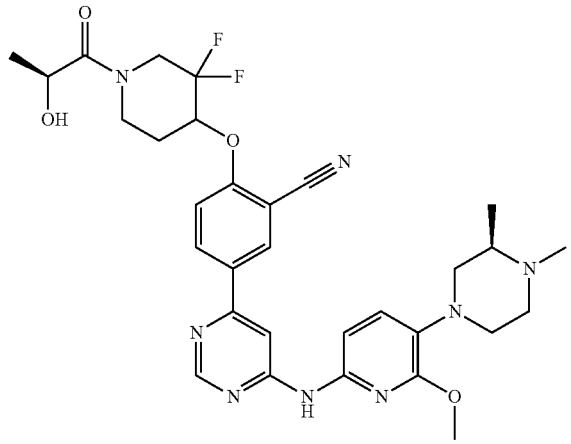 [SMILES: COc1nc(Nc2cc(-c3ccc(OC4CCN(C(=O)[C@H](C)O)CC4(F)F)c(C#N)c3)ncn2)ccc1N1CCN(C)[C@H](C)C1]
75
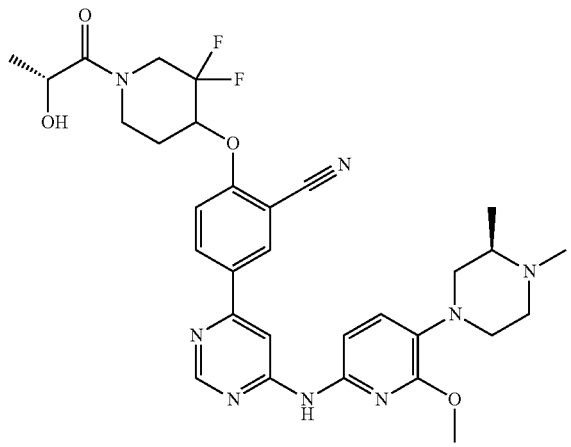 [SMILES: COc1nc(Nc2cc(-c3ccc(OC4CCN(C(=O)[C@@H](C)O)CC4(F)F)c(C#N)c3)ncn2)ccc1N1CCN(C)[C@H](C)C1]
76
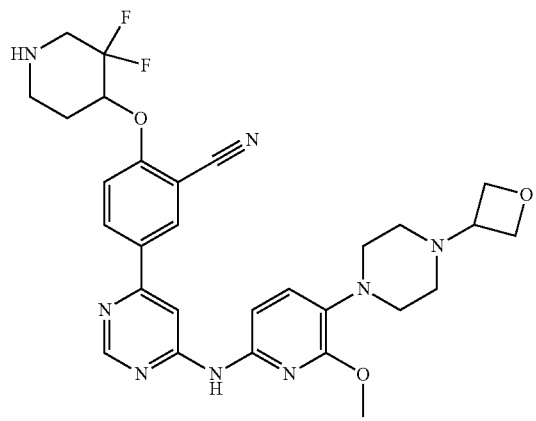 [SMILES: COc1nc(Nc2cc(-c3ccc(OC4CCNCC4(F)F)c(C#N)c3)ncn2)ccc1N1CCN(C2COC2)CC1]

TABLE 1-continued
77
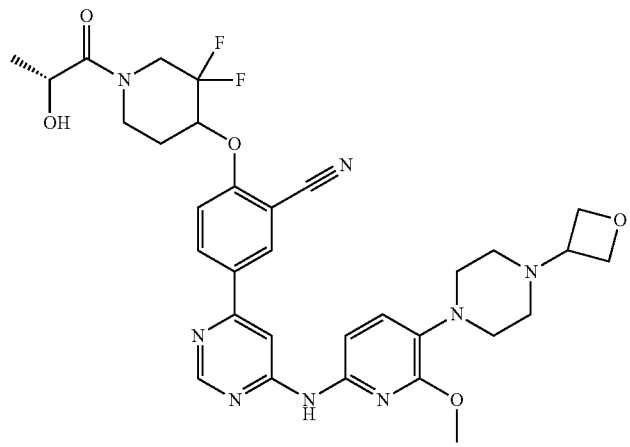 [SMILES: COc1nc(Nc2cc(-c3ccc(OC4CCN(C(=O)[C@@H](C)O)CC4(F)F)c(C#N)c3)ncn2)ccc1N1CCN(C2COC2)CC1]
78
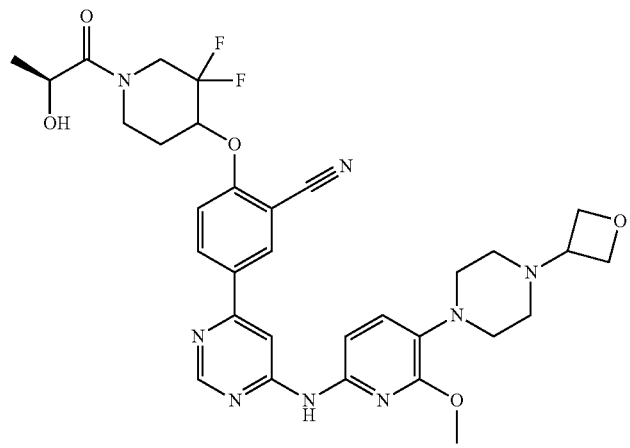 [SMILES: COc1nc(Nc2cc(-c3ccc(OC4CCN(C(=O)[C@H](C)O)CC4(F)F)c(C#N)c3)ncn2)ccc1N1CCN(C2COC2)CC1]
79
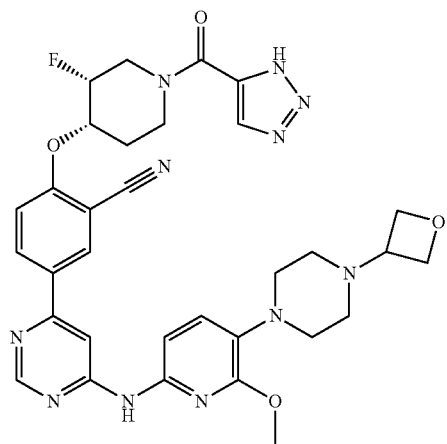

TABLE 1-continued
80
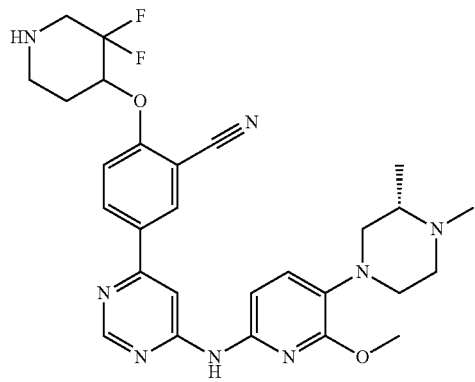 [SMILES: COc1nc(Nc2cc(-c3ccc(OC4CCNCC4(F)F)c(C#N)c3)ncn2)ccc1N1CCN(C)[C@@H](C)C1]
81
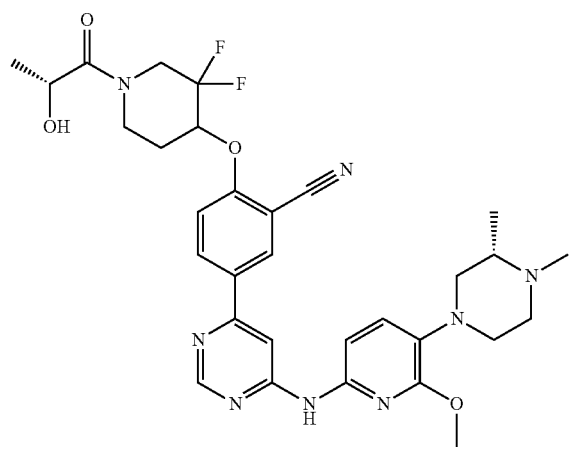 [SMILES: COc1nc(Nc2cc(-c3ccc(OC4CCN(C(=O)[C@@H](C)O)CC4(F)F)c(C#N)c3)ncn2)ccc1N1CCN(C)[C@@H](C)C1]
82
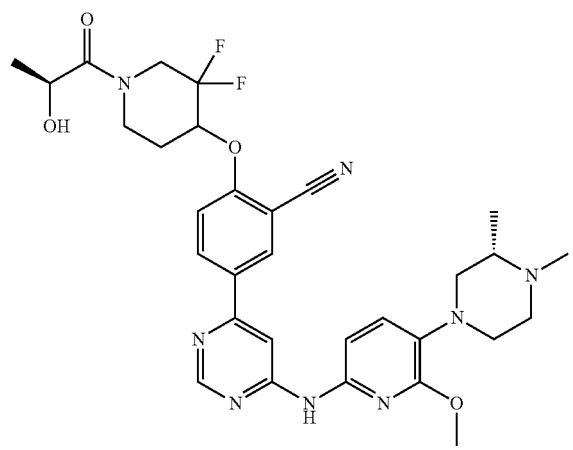 [SMILES: COc1nc(Nc2cc(-c3ccc(OC4CCN(C(=O)[C@H](C)O)CC4(F)F)c(C#N)c3)ncn2)ccc1N1CCN(C)[C@@H](C)C1]

TABLE 1-continued
83
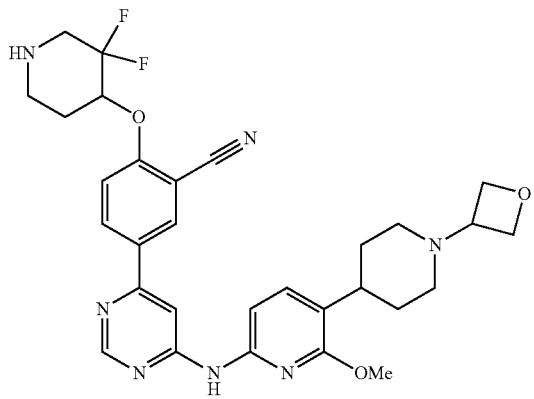 [SMILES: COc1nc(Nc2cc(-c3ccc(OC4CCNCC4(F)F)c(C#N)c3)ncn2)ccc1C1CCN(C2COC2)CC1]
84
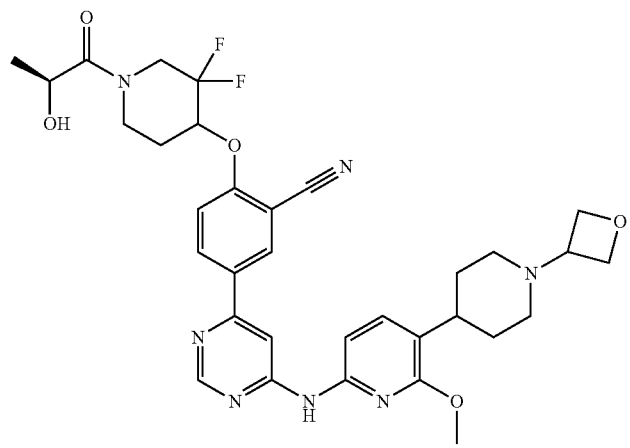 [SMILES: COc1nc(Nc2cc(-c3ccc(OC4CCN(C(=O)[C@H](C)O)CC4(F)F)c(C#N)c3)ncn2)ccc1C1CCN(C2COC2)CC1]
85
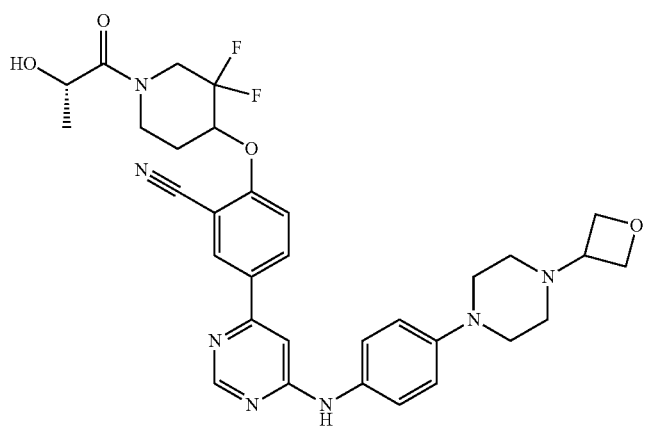 [SMILES: C[C@H](O)C(=O)N1CCC(Oc2ccc(-c3cc(Nc4ccc(N5CCN(C6COC6)CC5)cc4)ncn3)cc2C#N)C(F)(F)C1]

TABLE 1-continued

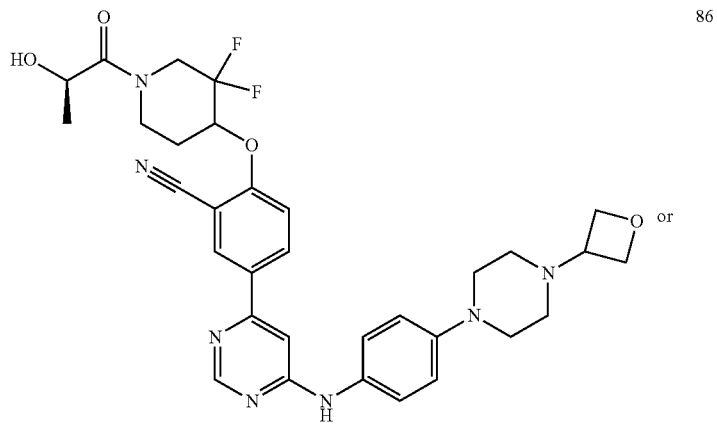

86

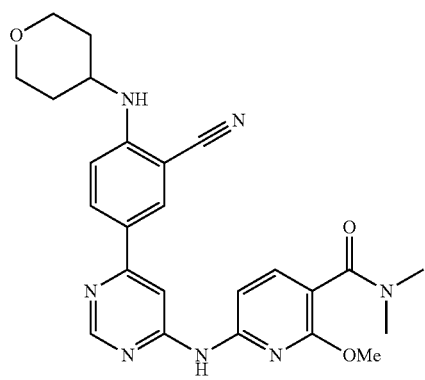 [SMILES: COc1nc(Nc2cc(-c3ccc(NC4CCOCC4)c(C#N)c3)ncn2)ccc1C(=O)N(C)C]

87 and compounds 88 to 105.

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

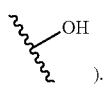
).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TBK and IKKε, or a mutant thereof, in a biological sample or in a patient. In certain embodiments, the amount of compound in compositions of this invention is such that is effective to measurably inhibit TBK and IKKε, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from a TBK or IKKε related disorder, comprising administering to said subject an effective amount of a compound of formula I or any formulae presented herein.

The present invention preferably relates to a method, wherein the TBK or IKKε associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis *nodosa*, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkinson diseases, trauma, and chronic bacterial infection.

In certain embodiments, disorders associated with TBK or IKKε are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinaemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, disorders associated with TBK or IKKε are selected from cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In certain aspects, the invention relates to the compounds of the invention for the use for the treatment of a disease or disorder described herein.

In certain aspects, the invention relates to the use of compounds of formula I, or any formulae presented herein, for the preparation of a medicament for the treatment or a disease or disorder described herein.

In various embodiments, compounds of formula (I), and related formulae exhibit a IC50 for the binding to TBK and/or IKKε of less than about 5 µM, preferably less than about 1 µM, preferably less than about 100 nM, preferably less than about 10 nM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit TBK and/or IKKε activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TBK and/or IKKε-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of TBK and/or IKKε activity if expedient.

The invention also relates to the use of compounds according to formula (I) and/or physiologically acceptable salts thereof for the prophylactic or therapeutic treatment and/or monitoring of diseases that are caused, mediated and/or propagated by TBK and/or IKKε activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by TBK and/or IKKε activity. In certain embodiments, the invention provides the use of a compound according to formula I or physiologically acceptable salts thereof, for the production of a medicament for the prophylactic or therapeutic treatment of a TBK and/or IKKε-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TBK and/or IKKε activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with TBK and/or IKKε activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib. In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil. The disclosed compounds of the formula I can be administered in combination with other known therapeutic agents, including anticancer agents. As used here, the term "anticancer agent" relates to any agent which is administered to a patient with cancer for the purposes of treating the cancer. The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloridel[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2] Rec. INN (Recommended International Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. According to one embodiment, the invention relates to a method of inhibiting TBK and/or IKKε activity in a biological sample comprising the step of contacting said biological sample with a compound of this invention, or a composition comprising said compound.

According to another embodiment, the invention relates to a method of inhibiting TBK and/or IKKε, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TBK and/or IKKε, including the evaluation of the many factors thought to influence, and be influenced by, the production of TBK and/or IKKε and the interaction of TBK and/or IKKε. The present compounds are also useful in the development of other compounds that interact with TBK and/or IKKε since the present compounds provide important structure-activity relationship (SAR) information that facilitate that development. Compounds of the present invention that bind to TBK and/or IKKε can be used as reagents for detecting TBK and/or IKKε in living cells, fixed cells, in biological fluids, in tissue homogenates, in purified, natural biological materials, etc. For example, by labeling such compounds, one can identify cells expressing TBK and/or IKKε. In addition, based on their ability to bind TBK and/or IKKε, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TBK and/or IKKε inside permeabilized cells. The compounds of the invention can also be utilized as commercial research reagents for various medical research and diagnostic uses. Such uses can include but are not limited to: use as a calibration standard for quantifying the activities of candidate TBK and/or IKKε inhibitors in a variety of functional assays; use as blocking reagents in random compound screening, i.e. in looking for new families of TBK and/or IKKε ligands, the compounds can be used to block recovery of the presently claimed TBK and/or IKKε compounds; use in the co-crystallization with TBK and/or IKKε enzyme, i.e. the compounds of the present invention will allow formation of crystals of the compound bound to TBK and/or IKKε, enabling the determination of enzyme/compound structure by x-ray crystallography; other research and diagnostic applications, wherein TBK and/or IKKε is preferably activated or such activation is conveniently calibrated against a known quantity of an TBK and/or IKKε inhibitor, etc.; use in assays as probes for determining the expression of TBK and/or IKKε in cells; and developing assays for detecting compounds which bind to the same site as the TBK and/or IKKε binding ligands.

The compounds of the invention can be applied either themselves and/or in combination with physical measurements for diagnostics of treatment effectiveness. Pharmaceutical compositions containing said compounds and the use of said compounds to treat TBK and/or IKKε-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TBK and/or IKKε, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

General Conditions and Analytical Methods

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesized by processes developed by the inventors.

Compound numbers utilized in the Examples below correspond to compound numbers set forth supra.

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at δ 0.00 for both $^1$H and $^{13}$C).

LC-MS analyses were performed on a SHIMADZU LC-MS machine consisting of an UFLC 20-AD system and LCMS 2020 MS detector. The column used was a Shimpack XR-ODS, 2.2 µm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

BPD is the abbreviation for 4,4,5,5-tetramethyl-2-(tetramethyl-1,3,2-dioxaborolan-2-yl)-1,3,2-dioxaborolane.

Example 1: 6-([6-[3-cyano-4-(oxan-4-yloxy)phenyl]pyrimidin-4-yl]amino)-2-methoxy-N,N-dimethylpyridine-3-carboxamide

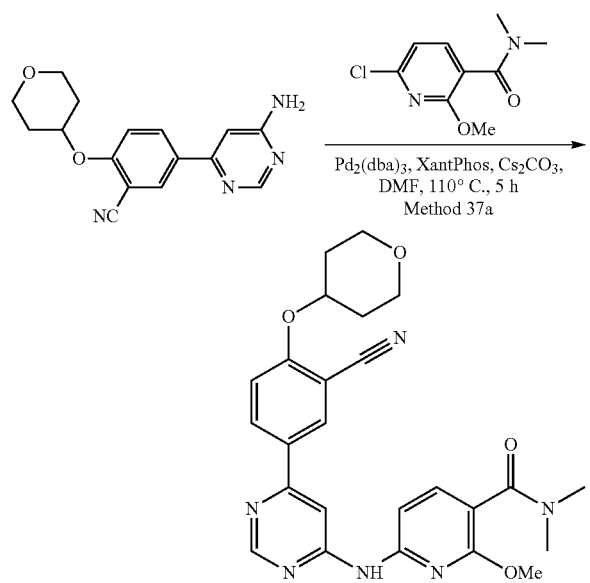

Method 37a 6-([6-[3-cyano-4-(oxan-4-yloxy)phenyl]pyrimidin-4-yl]amino)-2-methoxy-N,N-dimethylpyridine-3-carboxamide: To a solution of 5-(6-aminopyrimidin-4-yl)-2-(oxan-4-yloxy)benzonitrile (91 mg, 0.31 mmol) in N,N-dimethylformamide (10 mL) was added 6-chloro-2-methoxy-N,N-dimethylpyridine-3-carboxamide (81 mg, 0.38 mmol), Pd$_2$(dba)$_3$ (29 mg, 0.03 mmol), Xantphos (38 mg, 0.07 mmol) and Cs$_2$CO$_3$ (209 mg, 0.64 mmol) at room temperature. The resulting mixture was stirred for 5 h at 110° C. When the reaction was done, the reaction mixture was concentrated under reduced pressure and the residue was purified by prep-HPLC under the following conditions: column, XBridge Prep C18 OBD Column, 150×19 mm, 5 um; mobile phase, acetonitrile in water (with 0.05% NH$_3$.H$_2$O), 30% to 55% gradient in 8 min; detector, UV 254 nm. 6-([6-[3-cyano-4-(oxan-4-yloxy)phenyl]pyrimidin-4-yl]amino)-2-methoxy-N,N-dimethylpyridine-3-carboxamide was obtained as yellow solid (24 mg, 17%). HPLC: 97.8% purity, RT=1.38 min. MS: m/z=475.2 [M+H]$^+$. $^1$H NMR (300 MHz, Methanol-d$_4$) δ 8.71 (s, 1H), 8.32-8.17 (m, 3H), 7.65-7.56 (m, 1H), 7.41-7.26 (m, 2H), 4.92-4.84 (m, 1H), 4.05 (s, 3H), 4.02-3.92 (m, 2H), 3.71-3.57 (m, 2H), 3.07 (s, 3H), 2.94 (s, 3H), 2.15-2.03 (m, 2H), 1.90-1.72 (m, 2H).

Example 2: 6-([6-[3-cyano-4-(oxan-4-yloxy)phenyl]pyrimidin-4-yl]amino)-N-(2-hydroxyethyl)-2-methoxy-N-methylpyridine-3-carboxamide

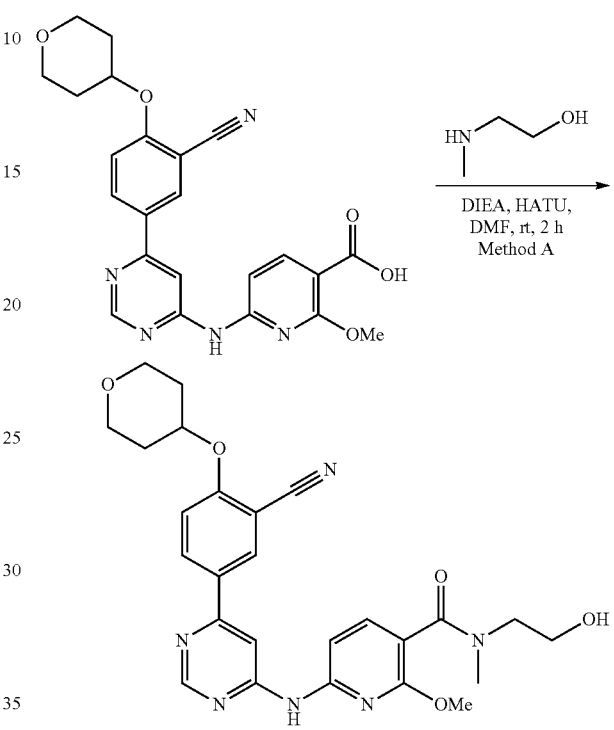

Method A 6-([6-[3-cyano-4-(oxan-4-yloxy)phenyl]pyrimidin-4-yl]amino)-N-(2-hydroxyethyl)-2-methoxy-N-methylpyridine-3-carboxamide: To a solution of 6-([6-[3-cyano-4-(oxan-4-yloxy)phenyl]pyrimidin-4-yl]amino)-2-methoxypyridine-3-carboxylic acid (88 mg, 0.20 mmol) in N,N-dimethylformamide (10 mL) were added 2-(methylamino)ethan-1-ol (29 mg, 0.38 mmol), HATU (161 mg, 0.40 mmol) and DIEA (261 mg, 2.02 mmol) at room temperature. The resulting mixture was stirred for 2 h at room temperature. When the reaction was done, it was quenched by the addition of water (20 mL). The resulting mixture was extracted with ethyl acetate (35 mL×3). The organic phases were combined, washed with brine and dried over Na$_2$SO$_4$. The solvent was removed under reduced pressure and the residue was purified by prep-HPLC under the following conditions: column, XBridge BEH C18 OBD Column, 150× 19 mm, 5 um; mobile phase, acetonitrile in water (with 10 mmol/L NH$_4$HCO$_3$ and 0.1% NH$_3$.H$_2$O), 34% to 40% gradient in 10 min; detector, UV 254 nm. 6-([6-[3-cyano-4-(oxan-4-yloxy)phenyl]pyrimidin-4-yl]amino)-N-(2-hydroxyethyl)-2-methoxy-N-methylpyridine-3-carboxamide was obtained as white solid (14 mg, 14%). HPLC: 97.4% purity, RT=7.94 min. MS: m/z=505.2 [M+H]$^+$. $^1$H NMR (400 MHz, DMSO-d$_6$) δ 10.37 (s, 1H), 8.81 (s, 1H), 8.45-8.36 (m, 2H), 8.35-8.27 (m, 1H), 7.67-7.52 (m, 2H), 7.28-7.19 (m, 1H), 4.99-4.88 (m, 1H), 4.78-4.64 (m, 1H), 4.02 (s, 1.5H) 4.01 (s, 1.5H), 3.93-3.83 (m, 2H), 3.64-3.38 (m, 5H), 3.25-3.20 (m, 1H), 2.99 (s, 1.5H), 2.89 (s, 1.5H), 2.10-2.00 (m, 2H), 1.76-1.63 (m, 2H).

Example 3: 5-(6-[[6-methoxy-5-([6-oxa-3-azabicyclo[3.1.1]heptan-3-yl]carbonyl)pyridin-2-yl]amino]pyrimidin-4-yl)-2-(oxan-4-yloxy)benzonitrile

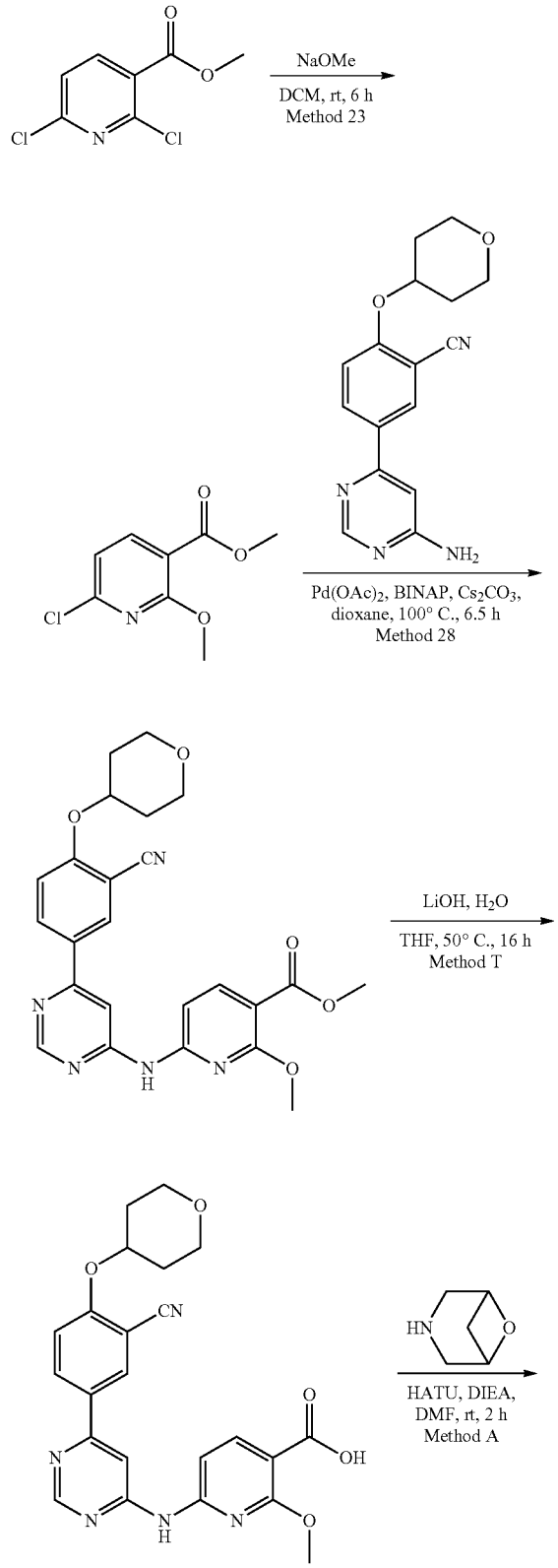

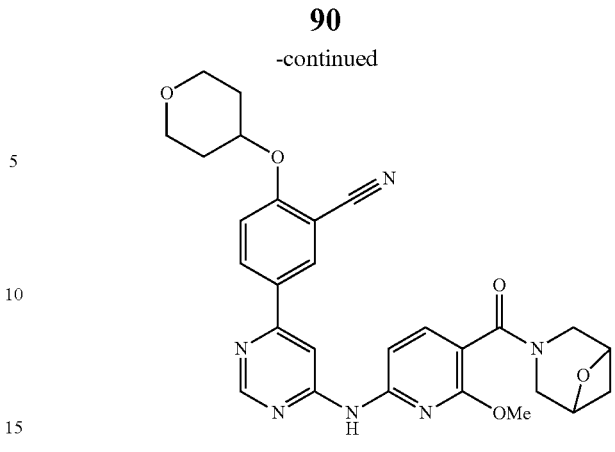

Method 23

5-(6-[[6-methoxy-5-([6-oxa-3-azabicyclo[3.1.1]heptan-3-yl]carbonyl)pyridin-2-yl]amino]pyrimidin-4-yl)-2-(oxan-4-yloxy)benzonitrile: To a solution of methyl 2,6-dichloropyridine-3-carboxylate (10.4 g, 50.35 mmol) in dichloromethane (110 mL) was added NaOMe (4.05 g, 74.97 mmol) at room temperature. The resulting mixture was stirred for 6 h at room temperature. When the reaction was done, the reaction mixture pH was adjusted to 6~7 by HCl (3 M). The resulting solution was extracted with dichloromethane (200 mL×3). The organic phases were combined, washed with brine and dried over $Na_2SO_4$. The solution was concentrated under reduced pressure to yield methyl 6-chloro-2-methoxypyridine-3-carboxylate as a white solid (9.47 g, 93%). MS: m/z=202.1 [M+H]$^+$.

Method 28

Methyl 6-([6-[3-cyano-4-(oxan-4-yloxy)phenyl]pyrimidin-4-yl]amino)-2-methoxypyridine-3-carboxylate: To a solution of 5-(6-aminopyrimidin-4-yl)-2-(oxan-4-yloxy)benzonitrile (1.88 g, 6.36 mmol) in 1,4-dioxane (80 mL) were added methyl 6-chloro-2-methoxypyridine-3-carboxylate (1.07 g, 5.29 mmol), Pd(OAc)$_2$ (248 mg, 1.11 mmol), BINAP (2.07 g, 3.32 mmol) and Cs$_2$CO$_3$ (2.97 g, 9.12 mmol) at room temperature. The resulting mixture was stirred for 6.5 h at 100° C. When the reaction was done, the reaction mixture was concentrated under reduced pressure and the residue was purified by flash chromatography eluting with MeOH in EtOAc (0% to 25% gradient) to yield methyl 6-([6-[3-cyano-4-(oxan-4-yloxy)phenyl]pyrimidin-4-yl]amino)-2-methoxypyridine-3-carboxylate as brown solid (4.50 g, crude). MS: m/z=462.1 [M+H]$^+$.

Method T 6-([6-[3-cyano-4-(oxan-4-yloxy)phenyl]pyrimidin-4-yl]amino)-2-methoxypyridine-3-carboxylic acid: To a solution of methyl 6-([6-[3-cyano-4-(oxan-4-yloxy)phenyl]pyrimidin-4-yl]amino)-2-methoxypyridine-3-carboxylate (4.5 g, crude) in tetrahydrofuran (100 mL) was added a solution of LiOH in H$_2$O (0.92 M, 100 mL, 92 mmol) at room temperature. The resulting mixture was stirred for 16 h at 50° C. When the reaction was done, the pH value of the mixture was adjusted to 9 with HCl (1 M) and the resulting mixture was extracted with diethyl ether (100 mL×3). The aqueous phase was adjusted to pH 3 with HCl solution (1 M) and precipitation happened. The solids were collected by filtration and washed with H$_2$O (20 mL×2). The solids were dried under reduced pressure to yield 6-([6-[3-cyano-4-(oxan-4-yloxy)phenyl]pyrimidin-4-yl]amino)-2-methoxypyridine-3-carboxylic acid as yellow solid (1.14 g, 80% for 2 steps). MS: m/z=448.1 [M+H]$^+$.

5-(6-[[6-methoxy-5-([6-oxa-3-azabicyclo[3.1.1]heptan-3-yl]carbonyl)pyridin-2-yl]amino]pyrimidin-4-yl)-2-(oxan-4-yloxy)benzonitrile: 5-(6-[[6-methoxy-5-([6-oxa-3-azabicyclo[3.1.1]heptan-3-yl]carbonyl)pyridin-2-yl]amino]pyrimidin-4-yl)-2-(oxan-4-yloxy)benzonitrile was prepared from 6-([6-[3-cyano-4-(oxan-4-yloxy)phenyl]pyrimidin-4-yl]amino)-2-methoxypyridine-3-carboxylic acid and 6-oxa-3-aza-bicyclo[3.1.1]heptane using Method A. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 33% to 35% gradient in 10 min; detector, UV 254 nm. 5-(6-[[6-methoxy-5-([6-oxa-3-azabicyclo[3.1.1]heptan-3-yl]carbonyl)pyridin-2-yl]amino]pyrimidin-4-yl)-2-(oxan-4-yloxy)benzonitrile was obtained as white solid (11 mg, 5.1%). HPLC: 98.2% purity, RT=5.03 min. MS: m/z=529.2 [M+H]$^+$. $^1$H NMR (400 MHz, DMSO-d$_6$) δ 10.41 (s, 1H), 8.82 (s, 1H), 8.46-8.36 (m, 2H), 8.35-8.28 (m, 1H), 7.75-7.68 (m, 1H), 7.59-7.52 (m, 1H), 7.30-7.23 (m, 1H), 4.99-4.88 (m, 1H), 4.65 (br s, 1H), 4.50 (br s, 1H), 4.04 (s, 3H), 3.94-3.84 (m, 3H), 3.66-3.52 (m, 4H), 3.43-3.35 (m, 1H), 3.15-3.05 (m, 1H), 2.10-2.01 (m, 2H), 1.82 (d, J=8.9 Hz, 1H), 1.77-1.63 (m, 2H).

Example 4: 6-([6-[3-cyano-4-(oxan-4-yloxy)phenyl]pyrimidin-4-yl]amino)-2-methoxy-N-[3-oxabicyclo[3.1.0]hexan-6-yl]pyridine-3-carboxamide

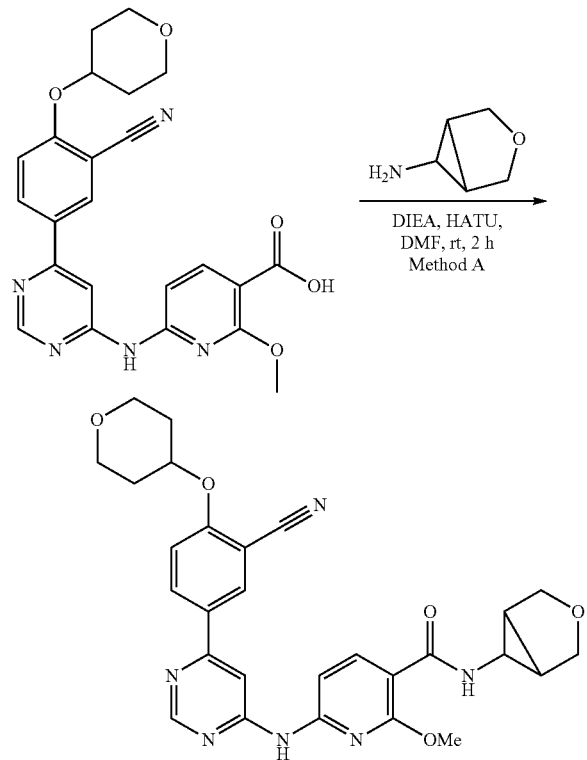

The title compound was prepared from 6-([6-[3-cyano-4-(oxan-4-yloxy)phenyl]pyrimidin-4-yl]amino)-2-methoxypyridine-3-carboxylic acid and 3-oxabicyclo[3.1.0]hexan-6-amine using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 33% to 40% gradient in 10 min; detector, UV 254 nm. 6-([6-[3-cyano-4-(oxan-4-yloxy)phenyl]pyrimidin-4-yl]amino)-2-methoxy-N-[3-oxabicyclo[3.1.0]hexan-6-yl]pyridine-3-carboxamide was obtained as light yellow solid (33 mg, 32%). HPLC: 98.8% purity, RT=5.05 min. MS: m/z=529.2 [M+H]$^+$. $^1$H NMR (400 MHz, DMSO-d$_6$) δ 10.52 (s, 1H), 8.82 (s, 1H), 8.45 (s, 1H), 8.39-8.27 (m, 2H), 8.17-8.10 (m, 1H), 8.02-7.96 (m, 1H), 7.57-7.50 (m, 1H), 7.23 (d, J=8.3 Hz, 1H), 4.98-4.87 (m, 1H), 4.10 (s, 3H), 3.93-3.83 (m, 4H), 3.68-3.61 (m, 2H), 3.61-3.50 (m, 2H), 2.61-2.54 (m, 1H), 2.10-2.00 (m, 2H), 1.95-1.89 (m, 2H), 1.76-1.62 (m, 2H).

Example 5: 5-(6-((5-(8-oxa-3-azabicyclo[3.2.1]octane-3-carbonyl)-6-methoxypyridin-2-yl)amino)pyrimidin-4-yl)-2-((tetrahydro-2H-pyran-4-yl)oxy)benzonitrile

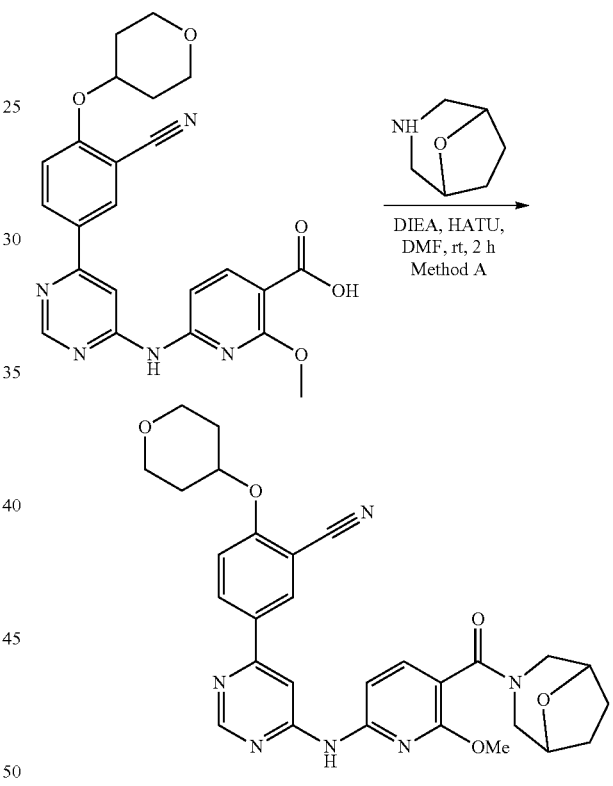

The title compound was prepared from 6-([6-[3-cyano-4-(oxan-4-yloxy)phenyl]pyrimidin-4-yl]amino)-2-methoxypyridine-3-carboxylic acid and 8-oxa-3-azabicyclo[3.2.1]octane using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 32% to 39% gradient in 10 min; detector, UV 254 nm. 5-(6-((5-(8-oxa-3-azabicyclo[3.2.1]octane-3-carbonyl)-6-methoxypyridin-2-yl)amino)pyrimidin-4-yl)-2-((tetrahydro-2H-pyran-4-yl)oxy)benzonitrile was obtained as light yellow solid (31 mg, 29%). HPLC: 98.1% purity, RT=4.71 min. MS: m/z=543.2 [M+H]$^+$. $^1$H NMR (400 MHz, DMSO-d$_6$) δ 10.41 (s, 1H), 8.82 (s, 1H), 8.45-8.36 (m, 2H), 8.35-8.27 (m, 1H), 7.67 (br s, 1H), 7.59-7.52 (m, 1H), 7.29-7.21 (m, 1H), 4.99-4.88 (m, 1H), 4.39 (br s, 1H), 4.21 (br s, 1H), 4.14 (br s, 1H), 4.03 (s, 3H), 3.94-3.84 (m, 2H), 3.62-3.51 (m, 2H), 3.33-3.17 (m, 1H), 3.13-3.05 (m, 1H), 3.00-2.92 (m, 1H), 2.11-2.00 (m, 2H), 1.83-1.63 (m, 6H).

Example 6: 5-(6-[[5-([hexahydro-1H-furo[3,4-c]pyrrol-5-yl]carbonyl)-6-methoxypyridin-2-yl]amino]pyrimidin-4-yl)-2-(oxan-4-yloxy)benzonitrile

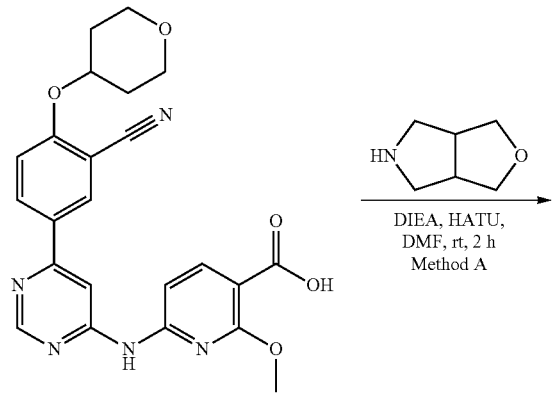

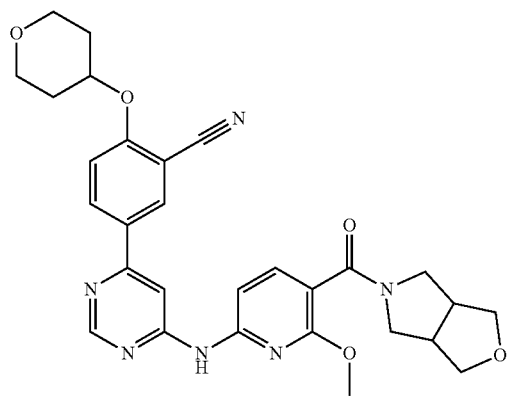

The title compound was prepared from 6-([6-[3-cyano-4-(oxan-4-yloxy)phenyl]pyrimidin-4-yl]amino)-2-methoxy-pyridine-3-carboxylic acid and hexahydro-1H-furo[3,4-c]pyrrole using Method A. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$·H$_2$O), 28% to 40% gradient in 10 min; detector, UV 254 nm. 5-(6-[[5-([hexahydro-1H-furo[3,4-c]pyrrol-5-yl]carbonyl)-6-methoxypyridin-2-yl]amino]pyrimidin-4-yl)-2-(oxan-4-yloxy)benzonitrile was obtained as off-white solid (28 mg, 26%). HPLC: 98.2% purity, RT=3.59 min. MS: m/z=543.3 [M+H]$^+$. $^1$H NMR (400 MHz, DMSO-d$_6$) δ 10.41 (s, 1H), 8.85-8.79 (m, 1H), 8.44 (s, 1H), 8.4-8.37 (m, 1H), 8.35-8.27 (m, 1H), 7.71-7.64 (m, 1H), 7.59-7.52 (m, 1H), 7.23 (d, J=8.1 Hz, 1H), 4.99-4.88 (m, 1H), 4.04 (s, 3H), 3.94-3.63 (m, 5H), 3.63-3.39 (m, 6H), 3.32 (s, 3H), 3.18-3.09 (m, 1H), 3.01-2.82 (m, 2H), 2.10-2.01 (m, 2H), 1.77-1.63 (m, 2H).

Example 7: 6-([6-[3-cyano-4-(oxan-4-yloxy)phenyl]pyrimidin-4-yl]amino)-2-methoxy-N-(1-methylpiperidin-4-yl)pyridine-3-carboxamide hydrochloride

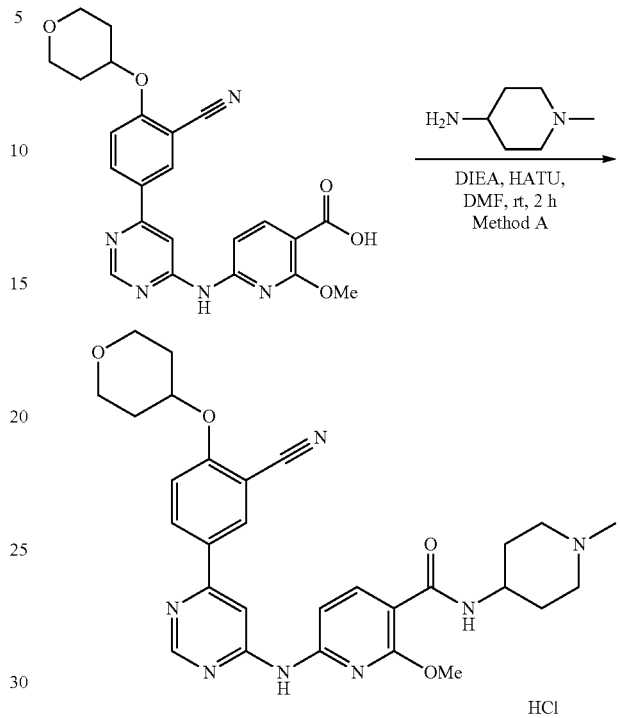

The title compound was prepared from 6-([6-[3-cyano-4-(oxan-4-yloxy)phenyl]pyrimidin-4-yl]amino)-2-methoxy-pyridine-3-carboxylic acid and 1-methylpiperidin-4-amine using Method A. The final product was purified by prep-HPLC under the following conditions: column, XBridge BEH C18 OBD Column, 150×19 mm, 5 um; mobile phase, acetonitrile in water (with 0.05% HCl), 33% to 40% gradient in 10 min; detector, UV 254 nm. 6-([6-[3-cyano-4-(oxan-4-yloxy)phenyl]pyrimidin-4-yl]amino)-2-methoxy-N-(1-methylpiperidin-4-yl)pyridine-3-carboxamide hydrochloride was obtained as yellow solid (17 mg, 16%). HPLC: 93.7% purity, RT=6.66 min. MS: m/z=544.1 [M+H]$^+$. $^1$H NMR (300 MHz, Methanol-d$_4$) δ 8.99 (s, 1H), 8.50 (s, 1H), 8.39-8.12 (m, 3H), 7.62-7.53 (m, 1H), 7.36 (d, J=8.2 Hz, 1H), 5.02-4.96 (m, 1H), 4.34-4.11 (m, 4H), 4.07-3.93 (m, 2H), 3.75-3.55 (m, 4H), 3.30-3.11 (m, 2H), 2.90 (s, 3H), 2.37-1.76 (m, 8H).

Example 8: 6-([6-[6-cyano-5-(oxan-4-yloxy)pyridin-2-yl]pyrimidin-4-yl]amino)-2-methoxy-N,N-dimethylpyridine-3-carboxamide

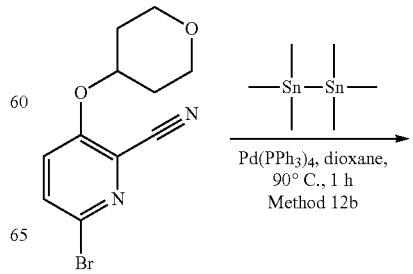

-continued

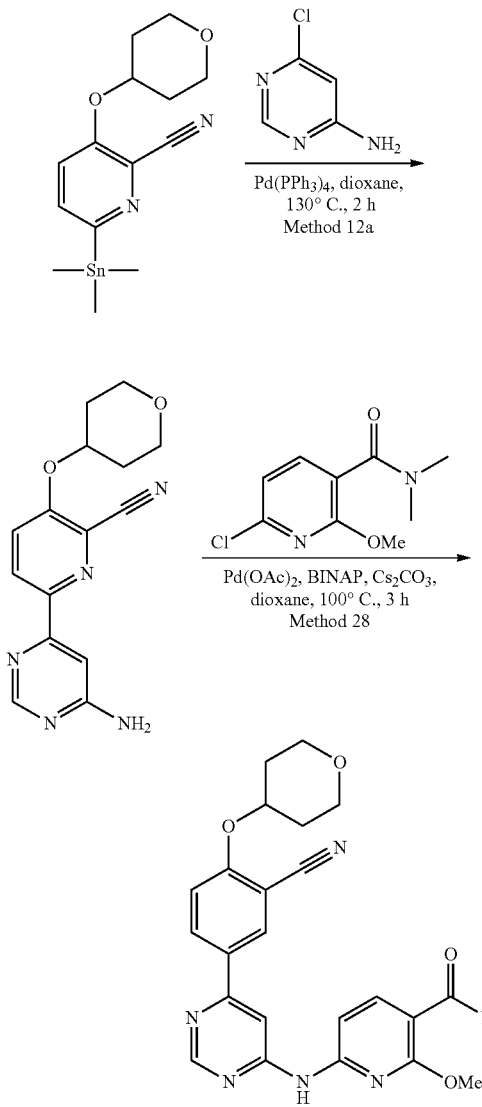

Method 12b 3-(oxan-4-yloxy)-6-(trimethylstannyl)pyridine-2-carbonitrile: To a solution of 6-bromo-3-(oxan-4-yloxy)pyridine-2-carbonitrile (493 mg, 1.74 mmol) in dioxane (10 mL) was added Pd(PPh₃)₄ (64 mg, 0.06 mmol), hexamethyldistannane (1.10 g, 3.35 mmol) at room temperature. The resulting mixture was stirred for 1 h at 90° C. When the reaction was done, the solvent was concentrated under reduced pressure and the residue was purified by flash chromatography eluting with EtOAc in hexane (0% to 30% gradient) to yield 3-(oxan-4-yloxy)-6-(trimethylstannyl)pyridine-2-carbonitrile as a brown solid (198 mg, 31%). MS: m/z=368.9 [M+H]⁺.

Method 12a 6-(6-aminopyrimidin-4-yl)-3-(oxan-4-yloxy)pyridine-2-carbonitrile: To a solution of 3-(oxan-4-yloxy)-6-(trimethylstannyl)pyridine-2-carbonitrile (260 mg, 0.71 mmol) in dioxane (7 mL) were added 6-chloropyrimidin-4-amine (90 mg, 0.70 mmol) and Pd(PPh₃)₄ (77 mg, 0.07 mmol) at temperature. The resulting mixture was stirred for 3 h at 130° C. When the reaction was done, the reaction mixture was concentrated under reduced pressure and the residue was purified by flash chromatography eluting with MeOH in EtOAc (0% to 100% gradient) to yield 6-(6-aminopyrimidin-4-yl)-3-(oxan-4-yloxy)pyridine-2-carbonitrile as off-white solid (166 mg, 79%). MS: m/z=298.0 [M+H]⁺.

6-([6-[6-cyano-5-(oxan-4-yloxy)pyridin-2-yl]pyrimidin-4-yl]amino)-2-methoxy-N,N-dimethylpyridine-3-carboxamide: 6-([6-[6-cyano-5-(oxan-4-yloxy)pyridin-2-yl]pyrimidin-4-yl]amino)-2-methoxy-N,N-dimethylpyridine-3-carboxamide was prepared from 6-(6-aminopyrimidin-4-yl)-3-(oxan-4-yloxy)pyridine-2-carbonitrile and 6-chloro-2-methoxy-N,N-dimethylnicotinamide using Method 28. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 30% to 45% gradient in 7 min; detector, UV 254 nm. 6-([6-[6-cyano-5-(oxan-4-yloxy)pyridin-2-yl]pyrimidin-4-yl]amino)-2-methoxy-N,N-dimethylpyridine-3-carboxamide was obtained as white solid (54 mg, 29%). HPLC: 98.4% purity, RT=2.43 min. MS: m/z=476.3 [M+H]⁺. ¹H NMR (400 MHz, DMSO-d₆) δ 10.56 (s, 1H), 9.21 (s, 1H), 8.82 (s, 1H), 8.62-8.53 (m, 1H), 8.11-8.03 (m, 1H), 7.67-7.60 (m, 1H), 7.09-7.02 (m, 1H), 5.02-4.92 (m, 1H), 4.14 (s, 3H), 3.93-3.83 (m, 2H), 3.61-3.50 (m, 2H), 2.98 (s, 3H), 2.85 (s, 3H), 2.11-1.99 (m, 2H), 1.77-1.64 (m, 2H).

Example 9: 6-([6-[5-cyano-6-(oxan-4-yloxy)pyridin-3-yl]pyrimidin-4-yl]amino)-2-methoxy-N,N-dimethylpyridine-3-carboxamide hydrochloride

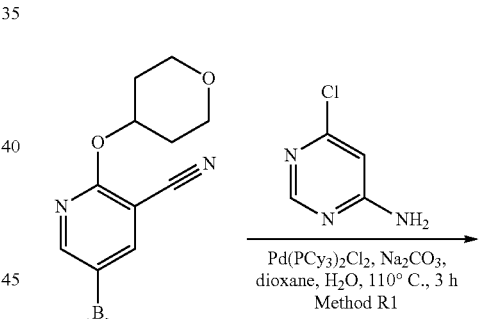

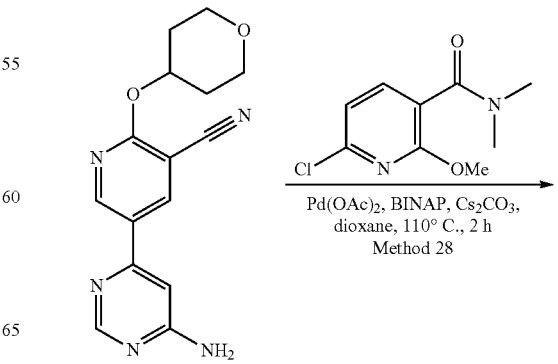

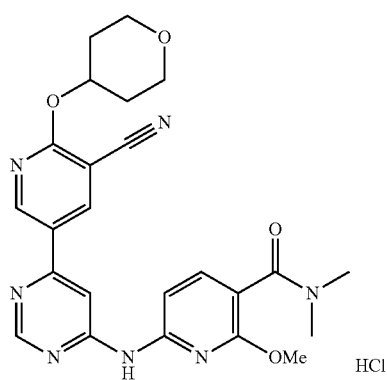

The title compound was prepared from 2-(tetrahydro-2H-pyran-4-yloxy)-5-(4,4,5,5-tetramethyl-1,3,2-dioxaborolan-2-yl)nicotinonitrile, 6-chloropyrimidin-4-amine, and 6-chloro-2-methoxy-N,N-dimethylnicotinamide using Method R1 and 28. The final product was purified by prep-HPLC under the following conditions: column, XBridge Prep C18 OBD Column, 150×19 mm, 5 um; mobile phase, acetonitrile in water (with 0.05% HCl), 29% to 38% gradient in 12 min; detector, UV 254 nm. 6-([6-[5-cyano-6-(oxan-4-yloxy)pyridin-3-yl]pyrimidin-4-yl]amino)-2-methoxy-N,N-dimethylpyridine-3-carboxamide hydrochloride was obtained as yellow solid (20 mg, 4.6% for 2 steps). HPLC: 97.7% purity, RT=1.89 min. MS: m/z=476.3 [M+H]$^+$. $^1$H NMR (400 MHz, DMSO-d$_6$) δ 10.62 (s, 1H), 9.10-9.05 (m, 1H), 8.87 (s, 1H), 8.85-8.81 (m, 1H), 8.44 (s, 1H), 7.69-7.62 (m, 1H), 7.27-7.18 (m, 1H), 5.51-5.40 (m, 1H), 4.00 (s, 3H), 3.93-3.83 (m, 2H), 3.63-3.52 (m, 2H), 2.98 (s, 3H), 2.84 (s, 3H), 2.13-2.01 (m, 2H), 1.81-1.68 (m, 2H).

Example 10: 5-(6-[[5-(1,1-dioxo-1λ,4-thiomorpholin-4-yl)-6-methoxypyridin-2-yl]amino]pyrimidin-4-yl)-2-(oxan-4-yloxy)benzonitrile

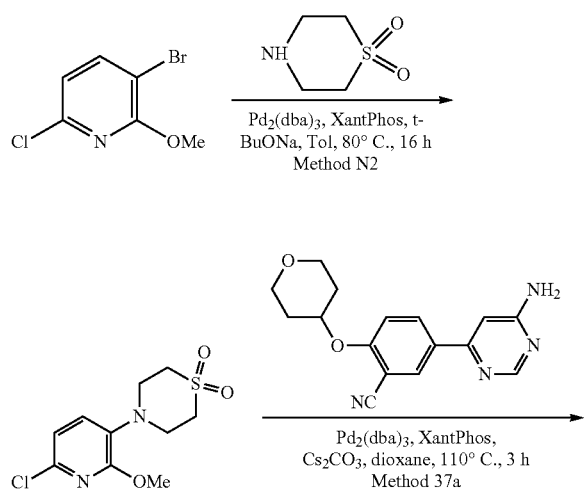

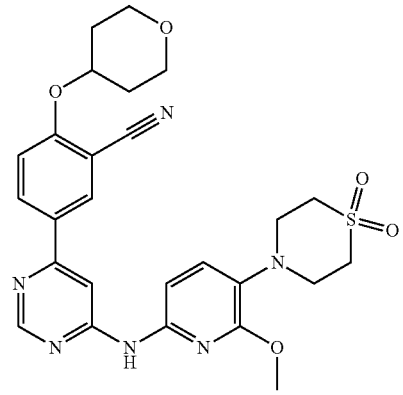

Method N2

5-(6-[[5-(1,1-dioxo-1lambda6,4-thiomorpholin-4-yl)-6-methoxypyridin-2-yl]amino]pyrimidin-4-yl)-2-(oxan-4-yloxy)benzonitrile: To a solution of 3-bromo-6-chloro-2-methoxypyridine (950 mg, 4.27 mmol) in toluene (80 mL) was added thiomorpholine 1,1-dioxide (579 mg, 4.28 mmol), Pd$_2$(dba)$_3$ (94 mg, 0.10 mmol), t-BuONa (1263 mg, 13.2 mmol) and XantPhos (208 mg, 0.36 mmol). The resulting mixture was stirred for 16 h at 80° C. When the reaction was done, the reaction mixture was concentrated under reduced pressure and the residue was purified by flash chromatography eluting with EtOAc in hexane (0% to 100% gradient) to yield 4-(6-chloro-2-methoxypyridin-3-yl)-1lambda6,4-thiomorpholine-1,1-dione as yellow solid (896 mg, 76%). MS: m/z=276.9 [M+H]$^+$.

5-(6-[[5-(1,1-dioxo-1lambda6,4-thiomorpholin-4-yl)-6-methoxypyridin-2-yl]amino]pyrimidin-4-yl)-2-(oxan-4-yloxy)benzonitrile: 5-(6-[[5-(1,1-dioxo-1lambda6,4-thiomorpholin-4-yl)-6-methoxypyridin-2-yl]amino]pyrimidin-4-yl)-2-(oxan-4-yloxy)benzonitrile was prepared from 5-(6-aminopyrimidin-4-yl)-2-(oxan-4-yloxy)benzonitrile and 4-(6-chloro-2-methoxypyridin-3-yl)-1lambda6,4-thiomorpholine-1,1-dione using Method 37a. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 32% to 51% gradient in 8 min; detector, UV 254 nm. 5-(6-[[5-(1,1-dioxo-1lambda6,4-thiomorpholin-4-yl)-6-methoxypyridin-2-yl]amino]pyrimidin-4-yl)-2-(oxan-4-yloxy)benzonitrile was obtained as yellow solid (29 mg, 14%). HPLC: 99.2% purity, RT=5.69 min. MS: m/z=537.1 [M+H]$^+$. $^1$H NMR (300 MHz, DMSO-d$_6$) δ 10.05 (s, 1H), 8.73 (s, 1H), 8.38-8.19 (m, 3H), 7.60-7.37 (m, 2H), 7.24-7.14 (m, 1H), 4.96-4.87 (m, 1H), 4.01 (s, 3H), 3.95-3.81 (m, 2H), 3.62-3.48 (m, 2H), 3.48-3.37 (m, 4H), 3.35-3.20 (m, 4H), 2.09-1.99 (m, 2H), 1.77-1.61 (m, 2H).

Example 11: 5-[6-[(5-[[2-(dimethylamino)ethyl](methyl)amino]-6-methoxypyridin-2-yl)amino]pyrimidin-4-yl]-2-(oxan-4-yloxy)benzonitrile

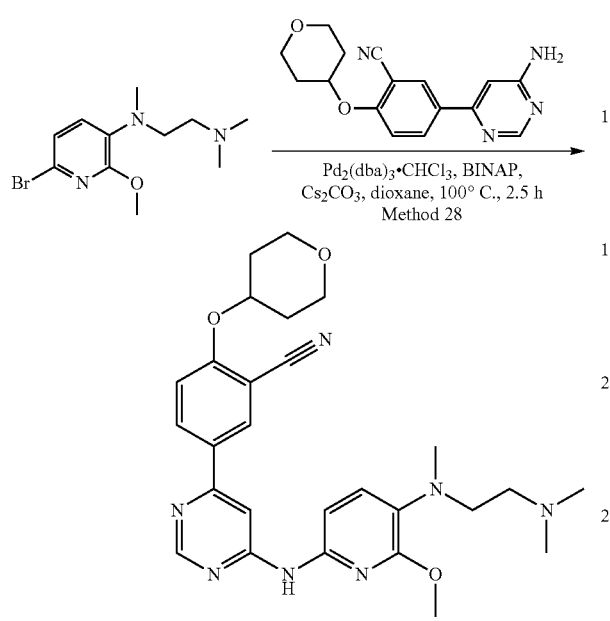

The title compound was prepared from 6-bromo-N-[2-(dimethylamino)ethyl]-2-methoxy-N-methylpyridin-3-amine and 5-(6-aminopyrimidin-4-yl)-2-(oxan-4-yloxy)benzonitrile using Method 28. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 50% to 80% gradient in 8 min; detector, UV 254 nm. 5-[6-[(5-[[2-(dimethylamino)ethyl](methyl)amino]-6-methoxypyridin-2-yl)amino]pyrimidin-4-yl]-2-(oxan-4-yloxy)benzonitrile was obtained as off-white solid (39 mg, 59%). HPLC: 95.0% purity, RT=4.88 min. MS: m/z=504.2 [M+H]$^+$. $^1$H NMR (300 MHz, DMSO-d$_6$) δ 9.93 (s, 1H), 8.70 (s, 1H), 8.38-8.15 (m, 3H), 7.57-7.47 (m, 1H), 7.28-7.19 (m, 1H), 7.18-7.09 (m, 1H), 4.97-4.85 (m, 1H), 3.98 (s, 3H), 3.94-3.80 (m, 2H), 3.62-3.47 (m, 2H), 3.15-3.04 (m, 2H), 2.70 (s, 3H), 2.40-2.28 (m, 2H), 2.12 (s, 6H), 2.09-1.97 (m, 2H), 1.77-1.59 (m, 2H).

Example 12: 5-(6-[[6-methoxy-5-(4-methylpiperazin-1-yl)pyridin-2-yl]amino]pyrimidin-4-yl)-2-(oxan-4-yloxy)benzonitrile

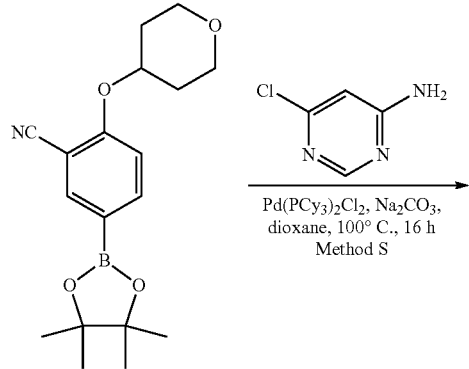

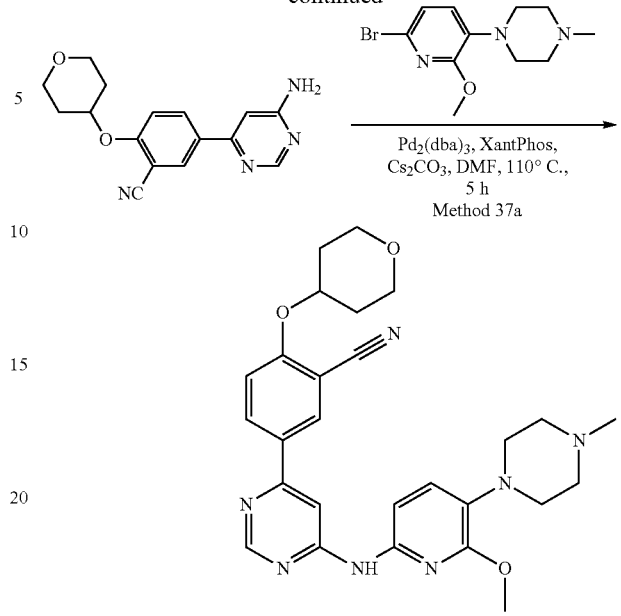

Method S 5-(6-aminopyrimidin-4-yl)-2-(oxan-4-yloxy)benzonitrile: To a solution of 2-(oxan-4-yloxy)-5-(tetramethyl-1,3,2-dioxaborolan-2-yl)benzonitrile (525 mg, 1.59 mmol) in 1,4-dioxane (16 mL) was added 6-chloropyrimidin-4-amine (1.64 g, 12.63 mmol), Pd(pcy$_3$)$_2$Cl$_2$ (324 mg, 0.44 mmol) and a solution of sodium carbonate in H$_2$O (1.9 M, 4 mL, 7.60 mmol) at room temperature. The resulting mixture was stirred for 16 h at 100° C. When the reaction was done, the solids in the reaction mixture were filtered out and the filtrate was concentrated under reduced pressure. The residue was purified by flash chromatography eluting with MeOH in EtOAc (0% to 50% gradient) to yield 5-(6-aminopyrimidin-4-yl)-2-(oxan-4-yloxy)benzonitrile as light yellow solid (448 mg, 95%).

Method 37

5-(6-[[6-methoxy-5-(4-methylpiperazin-1-yl)pyridin-2-yl]amino]pyrimidin-4-yl)-2-(oxan-4-yloxy)benzonitrile: To a solution of 5-(6-aminopyrimidin-4-yl)-2-(oxan-4-yloxy)benzonitrile (448 mg, 1.48 mmol) in N,N-dimethylformamide (20 mL) were added 1-(6-bromo-2-methoxypyridin-3-yl)-4-methylpiperazine (464 mg, 1.62 mmol), Xantphos (175 mg, 0.30 mmol), Cs$_2$CO$_3$ (961 mg, 2.95 mmol) and Pd$_2$(dba)$_3$ (136 mg, 0.15 mmol) at room temperature. The resulting mixture was stirred for 5 h at 110° C. When the reaction was done, The reaction mixture was concentrated under reduced pressure and the residue was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 35% to 47% gradient in 8 min; detector, UV 254 nm. 5-(6-[[6-methoxy-5-(4-methylpiperazin-1-yl)pyridin-2-yl]amino]pyrimidin-4-yl)-2-(oxan-4-yloxy)benzonitrile was obtained as yellow solid (206 mg, 27%). HPLC: 99.8% purity, RT=8.23 min. MS: m/z=502.1 [M+H]$^+$. $^1$H NMR (300 MHz, Methanol-d$_4$) δ 8.64-8.57 (m, 1H), 8.25-8.13 (m, 2H), 8.00 (s, 1H), 7.37-7.21 (m, 2H), 7.19-7.10 (m, 1H), 4.91-4.81 (m, 1H), 4.02 (s, 3H), 3.99-3.91 (m, 2H), 3.70-3.56 (m, 2H), 3.07-3.00 (m, 4H), 2.63-2.57 (m, 4H), 2.32 (s, 3H), 2.14-2.01 (m, 2H), 1.89-1.71 (m, 2H).

Example 13: 2-[[6-([6-[3-cyano-4-(oxan-4-yloxy) phenyl]pyrimidin-4-yl]amino)-2-methoxypyridin-3-yl](methyl)amino]-N,N-dimethylacetamide

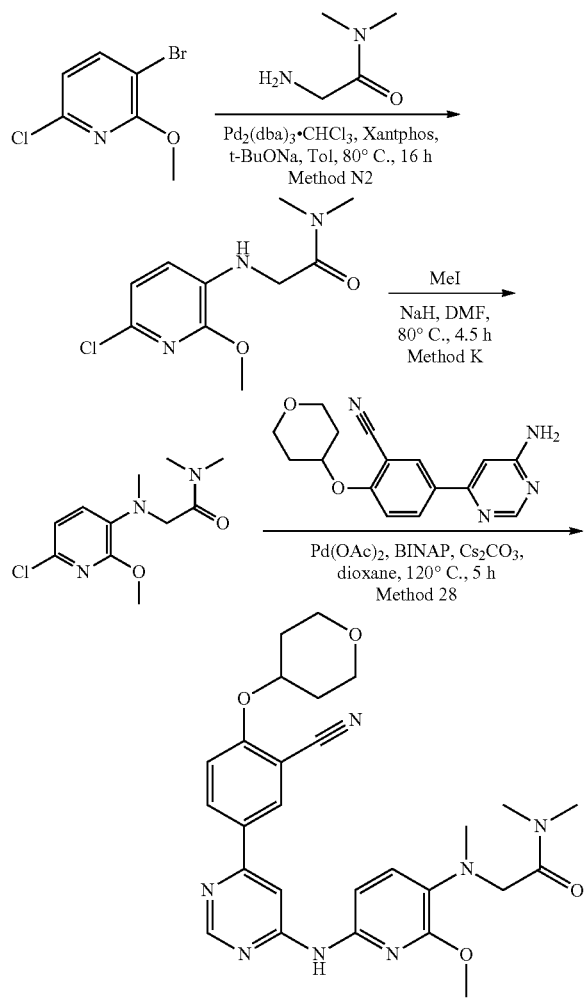

2-[(6-chloro-2-methoxypyridin-3-yl)amino]-N,N-dimethylacetamide: 2-[(6-chloro-2-methoxypyridin-3-yl)amino]-N,N-dimethylacetamide was prepared from 3-bromo-6-chloro-2-methoxypyridine and 2-amino-N,N-dimethylacetamide using Method N2 to yield 2-[(6-chloro-2-methoxypyridin-3-yl)amino]-N,N-dimethylacetamide as brown oil (146 mg, 64%). MS: m/z=244.2 [M+H]$^+$.

Method K

2-[(6-chloro-2-methoxypyridin-3-yl)(methyl)amino]-N,N-dimethylacetamide: To a solution of 2-[(6-chloro-2-methoxypyridin-3-yl)amino]-N,N-dimethylacetamide (127 mg, 0.52 mmol) in N,N-dimethylformamide (13 mL) was added sodium hydride (28 mg, 1.18 mmol) at 0° C. The resulting mixture was stirred for 20 min and then was added by iodomethane (93 mg, 0.66 mmol) slowly at 0° C. The reaction mixture was stirred for 4.5 h at 80° C. When the reaction was done, it was quenched by aqueous NH$_4$Cl solution (30 mL). The resulting mixture was extracted with ethyl acetate (50 mL×3). The organic phases were combined, washed with brine and dried over Na$_2$SO$_4$. The solvent was removed under reduced pressure to yield 2-[(6-chloro-2-methoxypyridin-3-yl)(methyl)amino]-N,N-dimethylacetamide as brown syrup (140 mg, crude). MS: m/z=258.2 [M+H]$^+$.

2-[[6-([6-[3-cyano-4-(oxan-4-yloxy)phenyl]pyrimidin-4-yl]amino)-2-methoxypyridin-3-yl](methyl)amino]-N,N-dimethylacetamide: 2-[[6-([6-[3-cyano-4-(oxan-4-yloxy)phenyl]pyrimidin-4-yl]amino)-2-methoxypyridin-3-yl](methyl)amino]-N,N-dimethylacetamide was prepared from 5-(6-aminopyrimidin-4-yl)-2-(oxan-4-yloxy)benzonitrile and 2-[(6-chloro-2-methoxypyridin-3-yl)(methyl)amino]-N,N-dimethylacetamide using Method 28. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 30% to 42% gradient in 10 min; detector, UV 254 nm. 2-[[6-([6-[3-cyano-4-(oxan-4-yloxy)phenyl]pyrimidin-4-yl]amino)-2-methoxypyridin-3-yl](methyl)amino]-N,N-dimethylacetamide was obtained as yellow solid (17 mg, 8% for 2 steps). HPLC: 94.1% purity, RT=3.23 min. MS: m/z=518.2 [M+H]$^+$. $^1$H NMR (300 MHz, DMSO-d$_6$) δ 9.92 (s, 1H), 8.70 (s, 1H), 8.45-8.17 (m, 3H), 7.58-7.48 (m, 1H), 7.31-7.21 (m, 1H), 7.16-7.06 (m, 1H), 4.98-4.86 (m, 1H), 4.04 (s, 2H), 3.98 (s, 3H), 3.95-3.81 (m, 2H), 3.62-3.48 (m, 2H), 2.97 (s, 3H), 2.81 (s, 3H), 2.78 (s, 3H), 2.11-1.99 (m, 2H), 1.78-1.60 (m, 2H).

Example 14: 5-[6-([5-[4-(2,2-difluoroethyl)piperazin-1-yl]-6-methoxypyridin-2-yl]amino)pyrimidin-4-yl]-2-(oxan-4-yloxy)benzonitrile

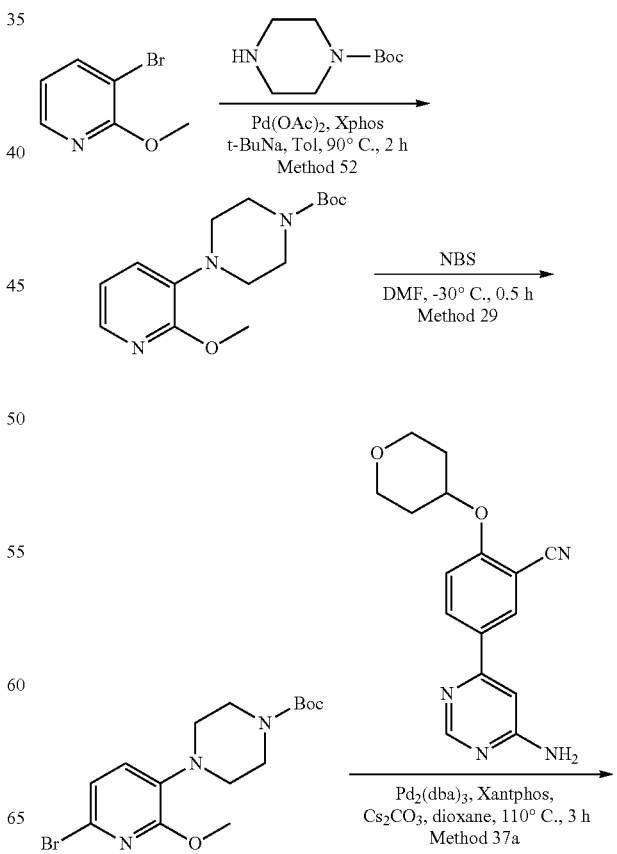

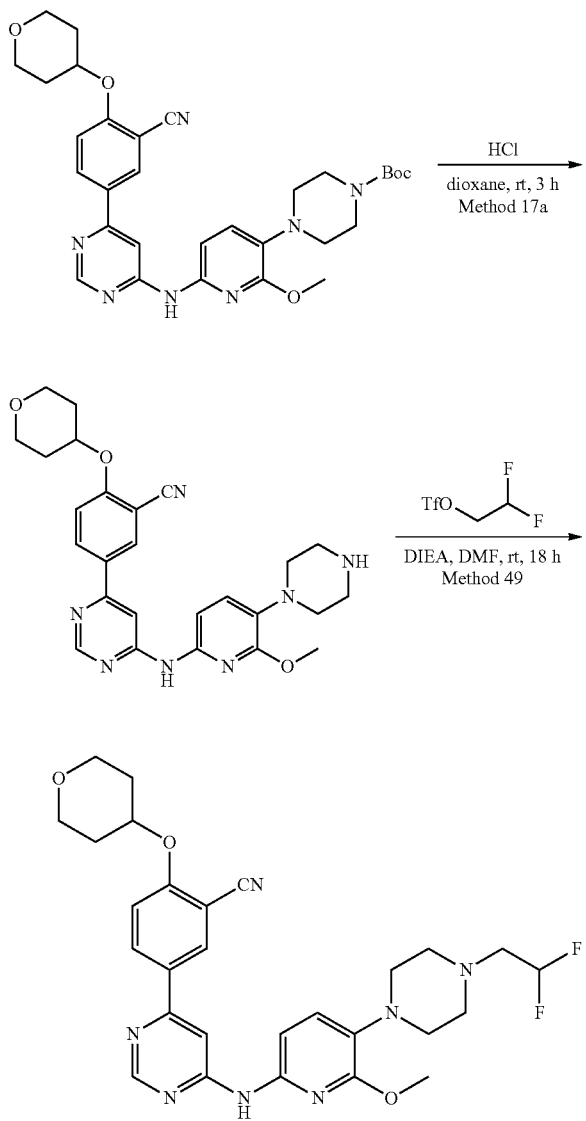

Method 52

5-[6-([5-[4-(2,2-difluoroethyl)piperazin-1-yl]-6-methoxypyridin-2-yl]amino)pyrimidin-4-yl]-2-(oxan-4-yloxy)benzonitrile: To a solution of 3-bromo-2-methoxypyridine (475 mg, 2.53 mmol) in toluene (10 mL) were added tert-butyl piperazine-1-carboxylate (594 mg, 3.19 mmol), Pd(OAc)2 (114 mg, 0.51 mmol), XPhos (234 mg, 0.50 mmol) and t-BuONa (485 mg, 5.04 mmol) at room temperature. The resulting mixture was stirred for 2 h at 90° C. When the reaction was done, the solids in the reaction mixture were filtered out and the filtrate was concentrated under reduced pressure. The residue was purified by flash chromatography eluting with EtOAc in hexane (0% to 30% gradient) to yield tert-butyl 4-(2-methoxypyridin-3-yl)piperazine-1-carboxylate as brown oil (595 mg, 80%). MS: m/z=294.0 [M+H]$^+$.

Method 29

5-(6-[[6-methoxy-5-(piperazin-1-yl)pyridin-2-yl]amino]pyrimidin-4-yl)-2-(oxan-4-yloxy)benzonitrile: At −30° C., to a solution of tert-butyl 4-(2-methoxypyridin-3-yl)piperazine-1-carboxylate (547 mg, 1.87 mmol) in N,N-dimethylformamide (8 ml) was added a solution of NBS in DMF (5 mL, 2.0 mmol, 0.4 M) slowly. The resulting mixture was stirred for 30 min at −30° C. When the reaction was done, the reaction mixture was diluted with H$_2$O (50 mL) and extracted with ethyl acetate (30 mL×3). The organic phases were combined, washed with brine and dried over Na$_2$SO$_4$. The solvent was removed under reduced pressure to yield tert-butyl 4-(6-bromo-2-methoxypyridin-3-yl)piperazine-1-carboxylate as brown oil (830 mg, crude). MS: m/z=372.0 [M+H]$^+$.

tert-butyl 4-[6-([6-[3-cyano-4-(oxan-4-yloxy)phenyl]pyrimidin-4-yl]amino)-2-methoxypyridin-3-yl]piperazine-1-carboxylate: tert-butyl 4-[6-([6-[3-cyano-4-(oxan-4-yloxy)phenyl]pyrimidin-4-yl]amino)-2-methoxypyridin-3-yl]piperazine-1-carboxylate was prepared from 5-(6-aminopyrimidin-4-yl)-2-(oxan-4-yloxy)benzonitrile and tert-butyl 4-(6-bromo-2-methoxypyridin-3-yl)piperazine-1-carboxylate using Method 37a to yield tert-butyl 4-[6-([6-[3-cyano-4-(oxan-4-yloxy)phenyl]pyrimidin-4-yl]amino)-2-methoxypyridin-3-yl]piperazine-1-carboxylate as yellow solid (528 mg, 60%). MS: m/z=588.3 [M+H]$^+$.

Method 17a 5-(6-[[6-methoxy-5-(piperazin-1-yl)pyridin-2-yl]amino]pyrimidin-4-yl)-2-(oxan-4-yloxy)benzonitrile: To a solution of tert-butyl 4-[6-([6-[3-cyano-4-(oxan-4-yloxy)phenyl]pyrimidin-4-yl]amino)-2-methoxypyridin-3-yl]piperazine-1-carboxylate (519 mg, 0.88 mmol) in 1,4-dioxane (15 mL) was added hydrogen chloride solution (12 M, 1.5 mL, 18 mmol). The resulting mixture was stirred for 2 h at room temperature. When the reaction was done, the reaction mixture was concentrated under reduced pressure to yield 5-(6-[[6-methoxy-5-(piperazin-1-yl)pyridin-2-yl]amino]pyrimidin-4-yl)-2-(oxan-4-yloxy)benzonitrile as yellow solid (700 mg, crude). MS: m/z=488.2 [M+H]$^+$.

Method 49

5-[6-([5-[4-(2,2-difluoroethyl)piperazin-1-yl]-6-methoxypyridin-2-yl]amino)pyrimidin-4-yl]-2-(oxan-4-yloxy)benzonitrile: To a solution of 5-(6-[[6-methoxy-5-(piperazin-1-yl)pyridin-2-yl]amino]pyrimidin-4-yl)-2-(oxan-4-yloxy)benzonitrile (95 mg, 0.19 mmol) in DMF (10 mL) was added 2,2-difluoroethyl trifluoromethanesulfonate (108 mg, 0.51 mmol) and DIEA (256 mg, 1.98 mmol) at room temperature. The resulting mixture was stirred for 18 h at room temperature. When the reaction was done, the reaction mixture was diluted with H$_2$O (20 mL) and extracted with ethyl acetate (30 mL×3). The organic phases were combined, washed with brine and dried over Na$_2$SO$_4$. The solvent was removed under reduced pressure and the residue was purified by prep-HPLC under the following conditions: column, XBridge Prep C18 OBD Column, 150× 19 mm, 5 um; mobile phase, acetonitrile in water (with 10 mmol/L NH$_4$HCO$_3$ and 0.1% NH$_3$.H$_2$O), 40% to 63% gradient in 8 min; detector, UV 254 nm. 5-[6-([5-[4-(2,2-difluoroethyl)piperazin-1-yl]-6-methoxypyridin-2-yl]amino)pyrimidin-4-yl]-2-(oxan-4-yloxy)benzonitrile was obtained as yellow solid (29 mg, 16% for 4 steps). HPLC: 99.1% purity, RT=4.62 min. MS: m/z=552.2 [M+H]$^+$. $^1$H NMR (300 MHz, DMSO-d$_6$) δ 9.97 (s, 1H), 8.72 (s, 1H), 8.38-8.22 (m, 2H), 8.20 (s, 1H), 7.58-7.48 (m, 1H), 7.33-7.24 (m, 1H), 7.22-7.13 (m, 1H), 6.42-5.92 (m, 1H), 4.98-4.86 (m, 1H), 3.98 (s, 3H), 3.94-3.81 (m, 2H), 3.62-3.48 (m, 2H), 2.99-2.91 (m, 4H), 2.88-2.62 (m, 6H), 2.09-1.99 (m, 2H), 1.77-1.60 (m, 2H).

Example 15: 5-[6-([5-[(2R,6S)-2,6-dimethylmorpholin-4-yl]-6-methoxypyridin-2-yl]amino)pyrimidin-4-yl]-2-(oxan-4-yloxy)benzonitrile

Example 16: 5-[6-([5-[(3R,5S)-3,5-dimethyl-4-(oxetan-3-yl)piperazin-1-yl]-6-methoxypyridin-2-yl]amino)pyrimidin-4-yl]-2-(oxan-4-yloxy)benzonitrile

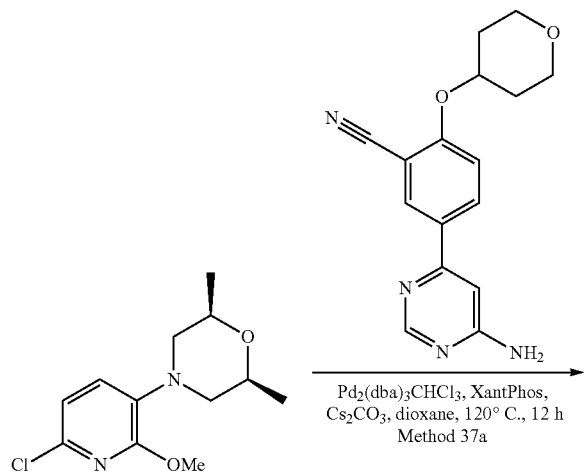
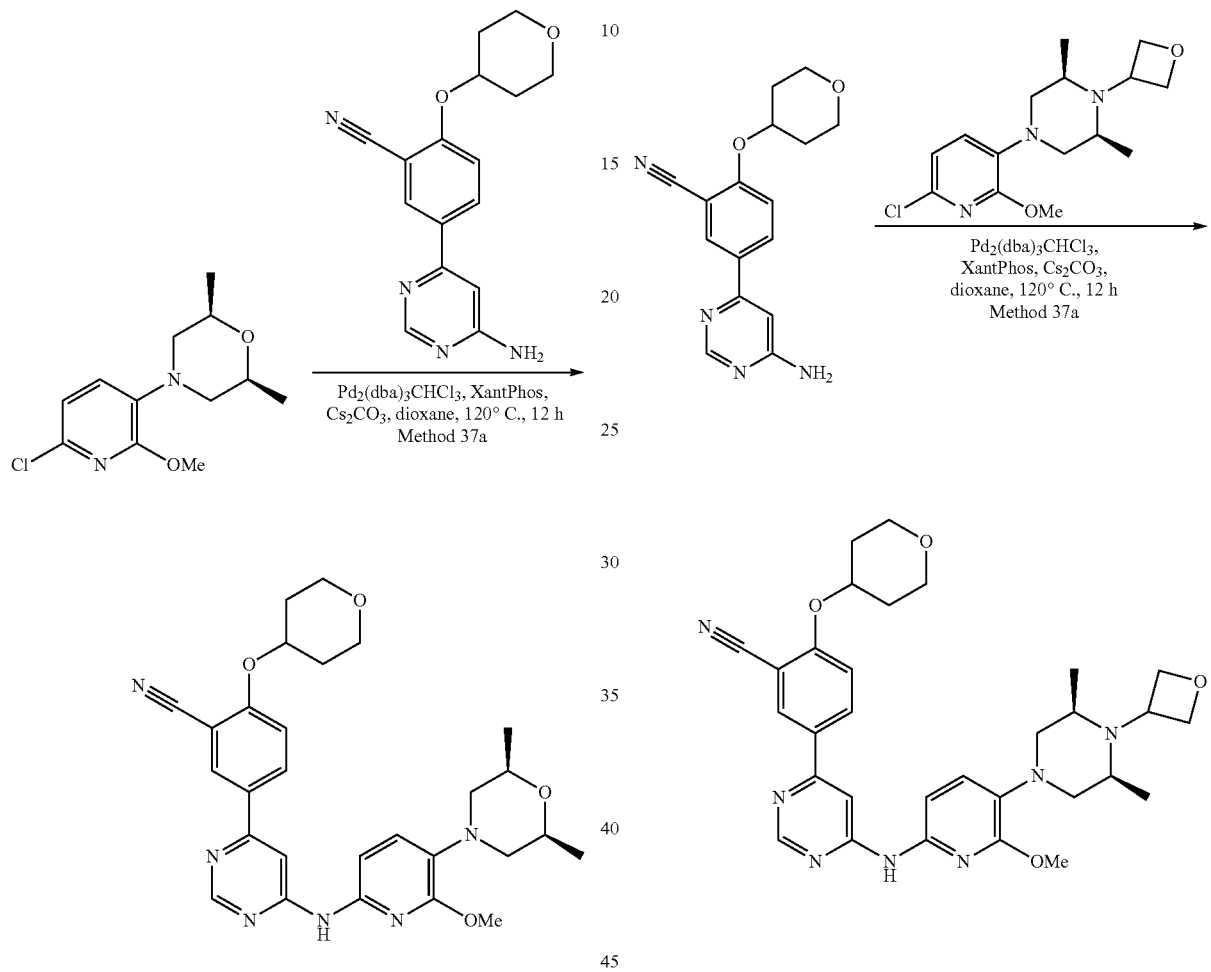

The title compound was prepared from 5-(6-aminopyrimidin-4-yl)-2-(oxan-4-yloxy)benzonitrile and (2S,6R)-4-(6-chloro-2-methoxypyridin-3-yl)-2,6-dimethylmorpholine using Method 37a.

The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 48% to 55% gradient in 8 min; detector, UV 254 nm. 5-[6-([5-[(2R,6S)-2,6-dimethylmorpholin-4-yl]-6-methoxypyridin-2-yl]amino)pyrimidin-4-yl]-2-(oxan-4-yloxy)benzonitrile was obtained as off-white solid (25 mg, 15%). HPLC: 99.4% purity, RT=5.53 min. MS: m/z=517.0 [M+H]$^+$. $^1$H NMR (300 MHz, DMSO-$d_6$) δ 9.93 (s, 1H), 8.68 (s, 1H), 8.34-8.20 (m, 2H), 8.15 (s, 1H), 7.54-7.44 (m, 1H), 7.28-7.19 (m, 1H), 7.19-7.10 (m, 1H), 4.94-4.82 (m, 1H), 3.95 (s, 3H), 3.91-3.77 (m, 2H), 3.76-3.63 (m, 2H), 3.59-3.44 (m, 2H), 3.25-3.16 (m, 2H), 2.27-2.13 (m, 2H), 2.06-1.95 (m, 2H), 1.74-1.56 (m, 2H), 1.09 (s, 3H), 1.07 (s, 3H).

The title compound was prepared from 5-(6-aminopyrimidin-4-yl)-2-(oxan-4-yloxy)benzonitrile and (2R,6S)-4-(6-chloro-2-methoxypyridin-3-yl)-2,6-dimethyl-1-(oxetan-3-yl)piperazine using Method 37a. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 55% to 85% gradient in 8 min; detector, UV 254 nm. 5-[6-([5-[(3R,5S)-3,5-dimethyl-4-(oxetan-3-yl)piperazin-1-yl]-6-methoxypyridin-2-yl]amino)pyrimidin-4-yl]-2-(oxan-4-yloxy)benzonitrile was obtained as light yellow solid (17 mg, 9%). HPLC: 98.7% purity, RT=4.34 min. MS: m/z=572.3 [M+H]$^+$. $^1$H NMR (300 MHz, DMSO-$d_6$) δ 9.96 (s, 1H), 8.71 (s, 1H), 8.38-8.23 (m, 2H), 8.22 (s, 1H), 7.57-7.47 (m, 1H), 7.29-7.19 (m, 1H), 7.19-7.10 (m, 1H), 4.97-4.85 (m, 1H), 4.57-4.48 (m, 4H), 4.13-4.00 (m, 1H), 3.98 (s, 3H), 3.94-3.81 (m, 2H), 3.62-3.48 (m, 2H), 2.98-2.87 (m, 2H), 2.85-2.61 (m, 4H), 2.09-1.99 (m, 2H), 1.77-1.60 (m, 2H), 1.05 (s, 3H), 1.03 (s, 3H).

Example 17: 5-(6-[[6-methoxy-5-(piperidin-4-yl)pyridin-2-yl]amino]pyrimidin-4-yl)-2-(oxan-4-yloxy)benzonitrile

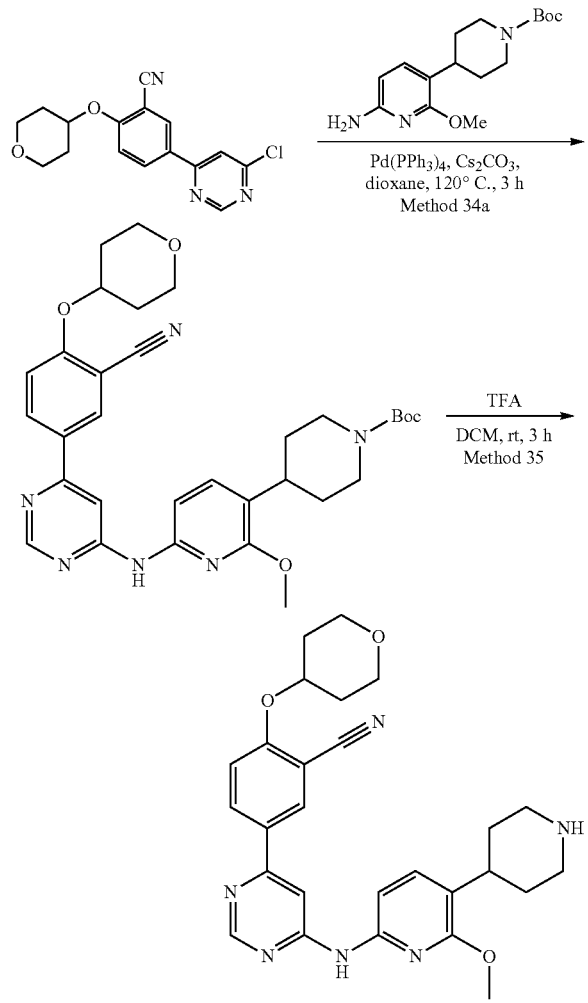

Method 34a tert-butyl 4-[6-([6-[3-cyano-4-(oxan-4-yloxy)phenyl]pyrimidin-4-yl]amino)-2-methoxypyridin-3-yl]piperidine-1-carboxylate: To a solution of 5-(6-chloropyrimidin-4-yl)-2-(oxan-4-yloxy)benzonitrile (91 mg, 0.29 mmol) in dioxane (10 mL) was added tert-butyl 4-(6-amino-2-methoxypyridin-3-yl)piperidine-1-carboxylate (87 mg, 0.28 mmol), Pd(PPh$_3$)$_4$ (70 mg, 0.06 mmol) and Cs$_2$CO$_3$ (245 mg, 0.75 mmol) at room temperature. The resulting mixture was stirred for 3 h at 120° C. When the reaction was done, the solids in the reaction mixture were filtered out and the filtrate was concentrated under reduced pressure. The residue was purified by flash chromatography eluting with MeOH in EtOAc (0% to 50% gradient) to yield tert-butyl 4-[6-([6-[3-cyano-4-(oxan-4-yloxy)phenyl]pyrimidin-4-yl]amino)-2-methoxypyridin-3-yl]piperidine-1-carboxylate as yellow solid (59 mg, 35%). MS: m/z=587.3 [M+H]$^+$.

Method 35

5-(6-[[6-methoxy-5-(piperidin-4-yl)pyridin-2-yl]amino]pyrimidin-4-yl)-2-(oxan-4-yloxy)benzonitrile: To a solution of tert-butyl 4-[6-([6-[3-cyano-4-(oxan-4-yloxy)phenyl]pyrimidin-4-yl]amino)-2-methoxypyridin-3-yl]piperidine-1-carboxylate (81 mg, 0.14 mmol) in dichloromethane (5 mL) was added trifluoroacetic acid (2 mL, 25.58 mmol) at room temperature. The resulting mixture was stirred for 3 h at room temperature. When the reaction was done, the pH value of the reaction mixture was adjusted to 8-9 with NaOH solution (2 M). The resulting mixture was extracted with dichloromethane (20 mL×3). The organic phases were combined, washed with brine and dried over Na$_2$SO$_4$. The solvent was removed under reduced pressure and the residue was purified prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 42% gradient in 7 min; detector, UV 254 nm. 5-(6-[[6-methoxy-5-(piperidin-4-yl)pyridin-2-yl]amino]pyrimidin-4-yl)-2-(oxan-4-yloxy)benzonitrile was obtained as white solid (15 mg, 22%). HPLC: 95.3% purity, RT=5.80 min. MS: m/z=487.2 [M+H]$^+$. $^1$H NMR (300 MHz, DMSO-d$_6$) δ 10.09 (s, 1H), 8.74 (s, 1H), 8.48-8.21 (m, 3H), 7.58-7.48 (m, 2H), 7.19-7.10 (m, 1H), 4.98-4.85 (m, 1H), 3.98 (s, 3H), 3.94-3.77 (m, 2H), 3.62-3.48 (m, 2H), 3.06-2.95 (m, 2H), 2.86-2.72 (m, 1H), 2.64-2.52 (m, 2H), 2.09-1.98 (m, 2H), 1.78-1.59 (m, 4H), 1.55-1.37 (m, 2H).

Example 18: 5-(6-[[6-methoxy-5-(1-methylpiperidin-4-yl)pyridin-2-yl]amino]pyrimidin-4-yl)-2-(oxan-4-yloxy)benzonitrile

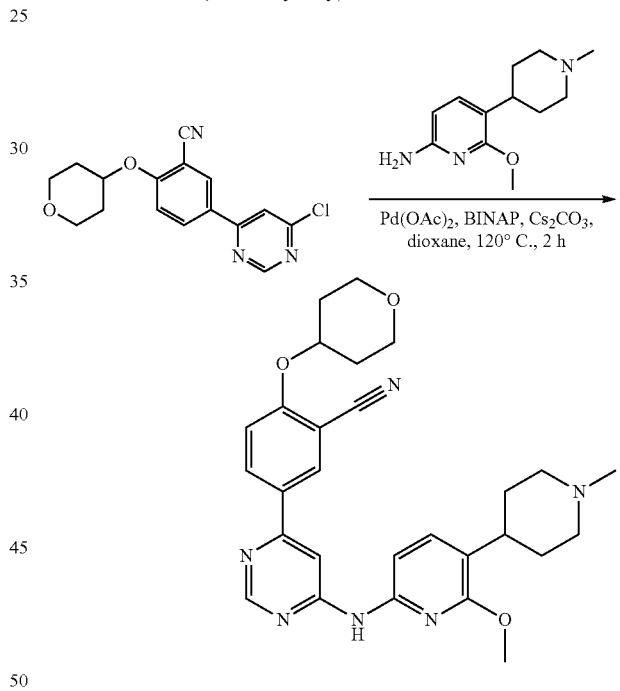

The title compound was prepared from 5-(6-chloropyrimidin-4-yl)-2-(oxan-4-yloxy)benzonitrile and 6-methoxy-5-(1-methylpiperidin-4-yl)pyridin-2-amine using Method 28. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 40% to 55% gradient in 7 min; detector, UV 254 nm. 5-(6-[[6-methoxy-5-(1-methylpiperidin-4-yl)pyridin-2-yl]amino]pyrimidin-4-yl)-2-(oxan-4-yloxy)benzonitrile was obtained as white solid (11 mg, 8%). HPLC: 97.1% purity, RT=3.02 min. MS: m/z=501.5 [M+H]$^+$. $^1$H NMR (400 MHz, Methanol-d$_4$) δ 8.71 (s, 1H), 8.35-8.24 (m, 3H), 7.58-7.51 (m, 1H), 7.45-7.38 (m, 1H), 7.21-7.14 (m, 1H), 4.94-4.86 (m, 1H), 4.07 (s, 3H), 4.06-3.99 (m, 2H), 3.74-3.64 (m, 2H), 3.19-3.06 (m, 2H), 2.93-2.82 (m, 1H), 2.44 (s, 3H), 2.39-2.28 (m, 2H), 2.18-2.09 (m, 2H), 1.9-1.75 (m, 6H).

Example 19: 5-[6-[(6-methoxy-5-[[(1-methylpiperidin-4-yl)amino]methyl]pyridin-2-yl)amino]pyrimidin-4-yl]-2-(oxan-4-yloxy)benzonitrile

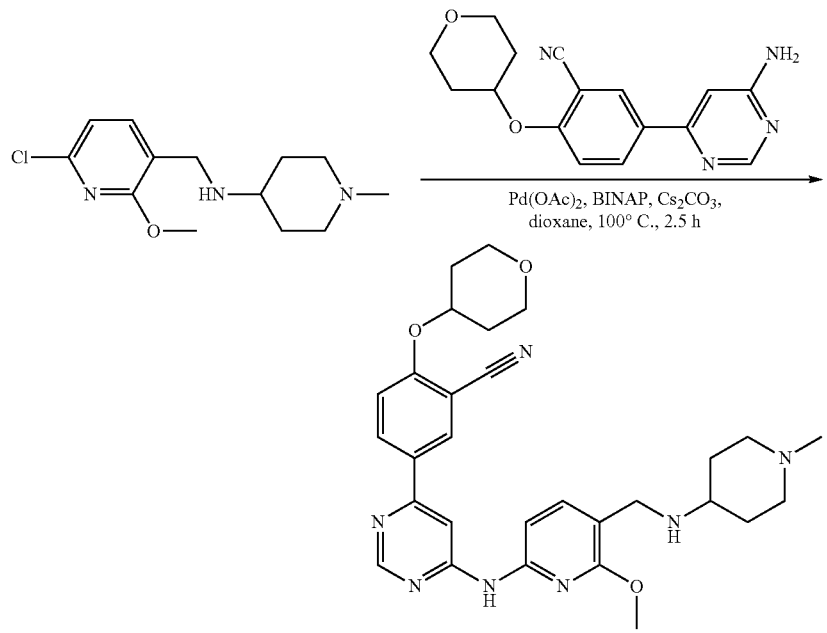

The title compound was prepared from 5-(6-aminopyrimidin-4-yl)-2-(oxan-4-yloxy)benzonitrile and N-[(6-chloro-2-methoxypyridin-3-yl)methyl]-1-methylpiperidin-4-amine using Method 28. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 55% to 80% gradient in 8 min; detector, UV 254 nm. 5-[6-[(6-methoxy-5-[[(1-methylpiperidin-4-yl)amino]methyl]pyridin-2-yl)amino]pyrimidin-4-yl]-2-(oxan-4-yloxy)benzonitrile was obtained as off-white solid (33 mg, 45%). HPLC: 90.8% purity, RT=2.07 min. MS: m/z=530.3 [M+H]$^+$. $^1$H NMR (300 MHz, DMSO-d$_6$) δ 10.13 (s, 1H), 8.75 (s, 1H), 8.41-8.23 (m, 3H), 7.71-7.61 (m, 1H), 7.57-7.48 (m, 1H), 7.17-7.08 (m, 1H), 4.97-4.85 (m, 1H), 3.98 (s, 3H), 3.94-3.80 (m, 2H), 3.71-3.47 (m, 4H), 2.72-2.62 (m, 2H), 2.34-2.27 (m, 1H), 2.11 (s, 3H), 2.08-1.96 (m, 2H), 1.91-1.57 (m, 7H), 1.35-1.16 (m, 2H).

Example 20: 5-(6-[[6-methoxy-5-(1-methylpyrrolidin-3-yl)pyridin-2-yl]amino]pyrimidin-4-yl)-2-(oxan-4-yloxy)benzonitrile

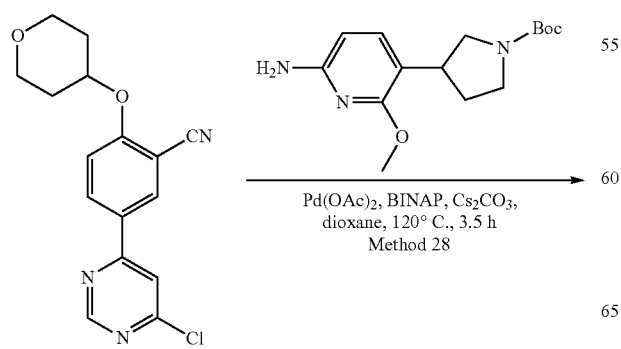

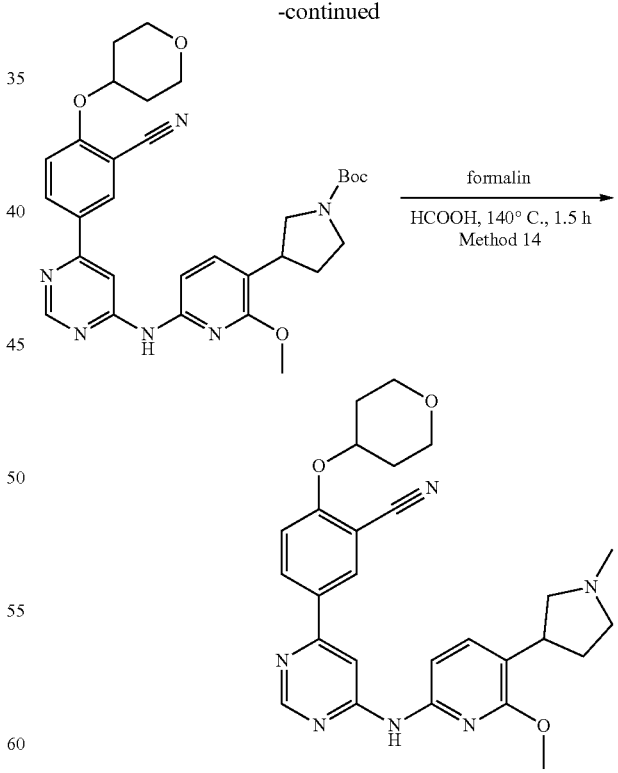

5-(6-[[6-methoxy-5-(1-methylpyrrolidin-3-yl)pyridin-2-yl]amino]pyrimidin-4-yl)-2-(oxan-4-yloxy)benzonitrile: tert-butyl 3-[6-([6-[3-cyano-4-(oxan-4-yloxy)phenyl]pyrimidin-4-yl]amino)-2-methoxypyridin-3-yl]pyrrolidine-1-carboxylate was prepared from 5-(6-chloropyrimidin-4-yl)-

2-(oxan-4-yloxy)benzonitrile and tert-butyl 3-(6-amino-2-methoxypyridin-3-yl)pyrrolidine-1-carboxylate using Method 28 to yield tert-butyl 3-[6-([6-[3-cyano-4-(oxan-4-yloxy)phenyl]pyrimidin-4-yl]amino)-2-methoxypyridin-3-yl]pyrrolidine-1-carboxylate as brown solid (150 mg, crude). MS: m/z=573.3 [M+H]$^+$.

Method 14

5-(6-[[6-methoxy-5-(1-methylpyrrolidin-3-yl)pyridin-2-yl]amino]pyrimidin-4-yl)-2-(oxan-4-yloxy)benzonitrile: To a solution of tert-butyl 3-[6-([6-[3-cyano-4-(oxan-4-yloxy)phenyl]pyrimidin-4-yl]amino)-2-methoxypyridin-3-yl]pyrrolidine-1-carboxylate (80 mg, crude) in HCOOH (8 mL) was added formalin (5 mL, 72 mmol, 14.4 M) at room temperature. The resulting mixture was stirred for 1.5 h at 140° C. When the reaction was done, the reaction mixture was concentrated under reduced pressure and the residue was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 35% to 50% gradient in 8 min; detector, UV 254 nm. 5-(6-[[6-methoxy-5-(1-methylpyrrolidin-3-yl)pyridin-2-yl]amino]pyrimidin-4-yl)-2-(oxan-4-yloxy)benzonitrile was obtained as off-white solid (12 mg, 7.3% for 2 steps). HPLC: 96.5% purity, RT=2.92 min. MS: m/z=530.3 [M+H]$^+$.

$^1$H NMR (300 MHz, DMSO-d$_6$) δ 10.10 (s, 1H), 8.75 (s, 1H), 8.47-8.24 (m, 3H), 7.69-7.59 (m, 1H), 7.62-7.48 (m, 1H), 7.17-7.08 (m, 1H), 4.98-4.85 (m, 1H), 3.98 (s, 3H), 3.94-3.78 (m, 2H), 3.62-3.39 (m, 3H), 2.83-2.71 (m, 1H), 2.65-2.53 (m, 2H), 2.45-2.33 (m, 1H), 2.28 (s, 3H), 2.26-2.07 (m, 1H), 2.09-1.99 (m, 2H), 1.82-1.60 (m, 3H).

Example 21: 2-(6-[[6-methoxy-5-(4-methylpiperazin-1-yl)pyridin-2-yl]amino]pyrimidin-4-yl)-5-(oxan-4-yloxy)pyridine-4-carbonitrile

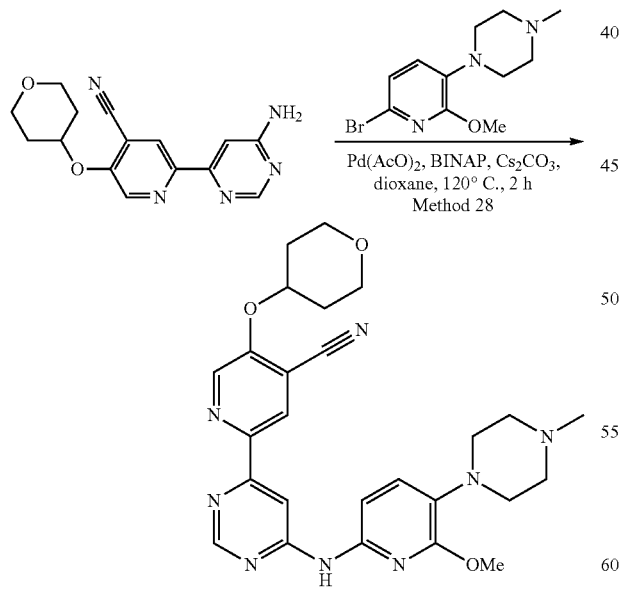

The title compound was prepared from 2-(6-aminopyrimidin-4-yl)-5-(oxan-4-yloxy)pyridine-4-carbonitrile and 1-(6-bromo-2-methoxypyridin-3-yl)-4-methylpiperazine using Method 28. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 32% gradient in 7 min; detector, UV 254 nm. 2-(6-[[6-methoxy-5-(4-methylpiperazin-1-yl)pyridin-2-yl]amino]pyrimidin-4-yl)-5-(oxan-4-yloxy)pyridine-4-carbonitrile was obtained as yellow solid (19 mg, 15%). HPLC: 99.1% purity, RT=5.45 min. MS: m/z=503.2 [M+H]$^+$. $^1$H NMR (300 MHz, Methanol-d$_4$) δ 8.76-8.60 (m, 3H), 8.47 (s, 1H), 7.36-7.27 (m, 1H), 7.11-7.01 (m, 1H), 5.11-4.96 (m, 1H), 4.08 (s, 3H), 4.04-3.90 (m, 2H), 3.72-3.57 (m, 2H), 3.43-3.36 (m, 6H), 3.19-3.12 (m, 2H), 2.93 (s, 3H), 2.20-2.06 (m, 2H), 1.93-1.75 (m, 2H).

Example 22: 6-(6-[[6-methoxy-5-(4-methylpiperazin-1-yl)pyridin-2-yl]amino]pyrimidin-4-yl)-3-(oxan-4-yloxy)pyridine-2-carbonitrile

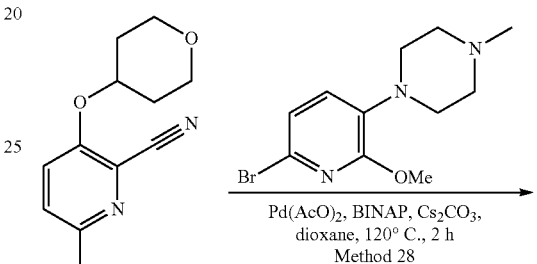

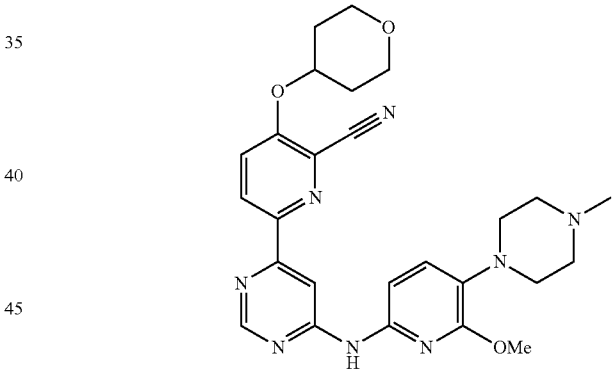

The title compound was prepared from 6-(6-aminopyrimidin-4-yl)-3-(oxan-4-yloxy)pyridine-2-carbonitrile and 1-(6-bromo-2-methoxypyridin-3-yl)-4-methylpiperazine using Method 28. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 32% to 41% gradient in 7 min; detector, UV 254 nm. 6-(6-[[6-methoxy-5-(4-methylpiperazin-1-yl)pyridin-2-yl]amino]pyrimidin-4-yl)-3-(oxan-4-yloxy)pyridine-2-carbonitrile was obtained as light yellow solid (57 mg, 28%). HPLC: 98.2% purity, RT=1.40 min. MS: m/z=503.4 [M+H]$^+$. $^1$H NMR (400 MHz, DMSO-d$_6$) δ 10.17 (s, 1H), 9.05 (s, 1H), 8.74 (s, 1H), 8.62-8.54 (m, 1H), 8.11-8.03 (m, 1H), 7.31-7.24 (m, 1H), 6.99 (s, 1H), 5.03-4.92 (m, 1H), 4.11 (s, 3H), 3.94-3.81 (m, 2H), 3.61-3.50 (m, 2H), 3.00-2.93 (m, 4H), 2.49-2.44 (m, 4H), 2.23 (s, 3H), 2.11-2.00 (m, 2H), 1.78-1.64 (m, 2H).

Example 23: 5-(6-[[6-methoxy-5-(4-methylpiperazin-1-yl)pyridin-2-yl]amino]pyrimidin-4-yl)-2-(oxan-4-yloxy)pyridine-3-carbonitrile

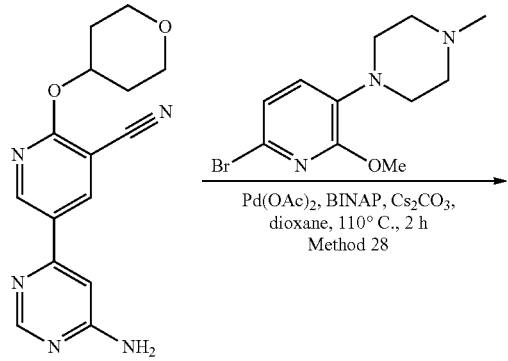

Example 24: 2-(6-[[6-methoxy-5-(1-methylpiperidin-4-yl)pyridin-2-yl]amino]pyrimidin-4-yl)-5-(oxan-4-yloxy)pyridine-4-carbonitrile

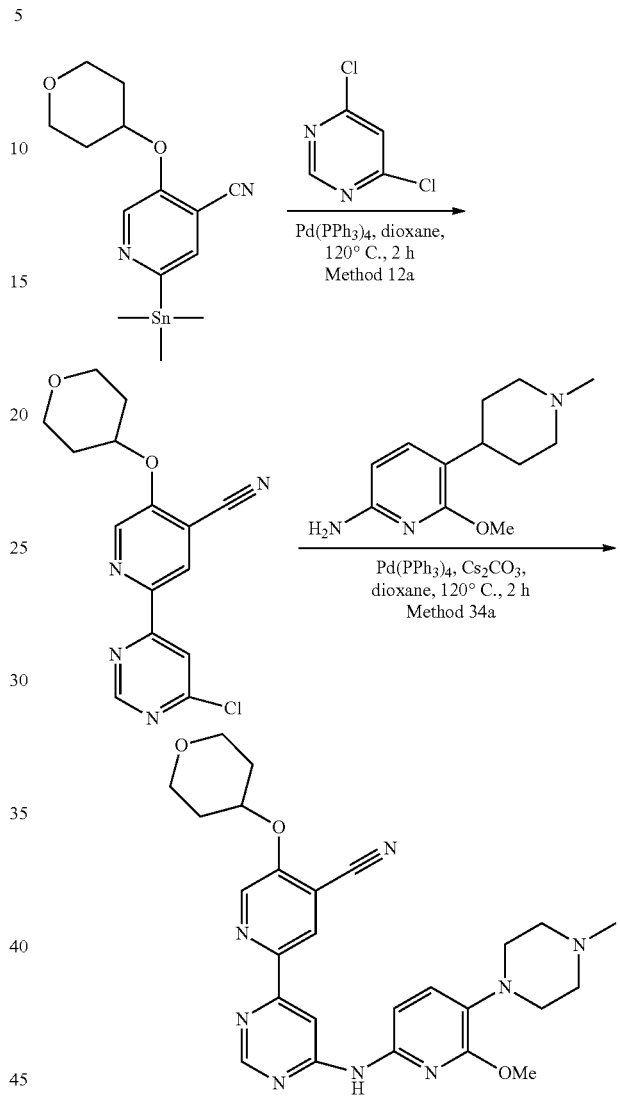

5-(6-[[6-methoxy-5-(4-methylpiperazin-1-yl)pyridin-2-yl]amino]pyrimidin-4-yl)-2-(oxan-4-yloxy)pyridine-3-carbonitrile: 5-(6-[[6-methoxy-5-(4-methylpiperazin-1-yl)pyridin-2-yl]amino]pyrimidin-4-yl)-2-(oxan-4-yloxy)pyridine-3-carbonitrile was prepared from 5-(6-aminopyrimidin-4-yl)-2-(tetrahydro-2H-pyran-4-yloxy)nicotinonitrile and 1-(6-bromo-2-methoxypyridin-3-yl)-4-methylpiperazine using Method 28. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 40% to 45% gradient in 7 min; detector, UV 254 nm. 5-(6-[[6-methoxy-5-(4-methylpiperazin-1-yl)pyridin-2-yl]amino]pyrimidin-4-yl)-2-(oxan-4-yloxy)pyridine-3-carbonitrile was obtained as light yellow solid (31 mg, 21%). HPLC: 98.1% purity, RT=1.15 min. MS: m/z=503.2 [M+H]$^+$. $^1$H NMR (400 MHz, DMSO-$d_6$) δ 10.04 (s, 1H), 9.07-9.02 (m, 1H), 8.80-8.77 (m, 1H), 8.74 (s, 1H), 8.18 (br s, 1H), 7.32-7.24 (m, 1H), 7.19-7.12 (m, 1H), 5.50-5.39 (m, 1H), 3.97 (s, 3H), 3.94-3.84 (m, 2H), 3.63-3.52 (m, 2H), 2.99-2.94 (m, 4H), 2.49-2.42 (m, 4H), 2.23 (s, 3H), 2.12-2.03 (m, 2H), 1.81-1.68 (m, 2H).

The title compound was prepared from 5-(tetrahydro-2H-pyran-4-yloxy)-2-(trimethylstannyl)isonicotinonitrile, 4,6-dichloropyrimidine, and 6-methoxy-5-(1-methylpiperidin-4-yl)pyridin-2-amine using Method 12a and 34a. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 35% to 45% gradient in 13 min; detector, UV 254 nm. 2-(6-[[6-methoxy-5-(1-methylpiperidin-4-yl)pyridin-2-yl]amino]pyrimidin-4-yl)-5-(oxan-4-yloxy)pyridine-4-carbonitrile was obtained as off-white solid (9 mg, 4.7% for 2 steps). HPLC: 95.5% purity, RT=3.14 min. MS: m/z=502.2 [M+H]$^+$. $^1$H NMR (400 MHz, DMSO-$d_6$) δ 10.25 (s, 1H), 8.89 (s, 2H), 8.77 (s, 1H), 8.56 (s, 1H), 7.56 (d, J=8.0 Hz, 1H), 7.12 (br s, 1H), 5.18-5.09 (m, 1H), 4.02 (s, 3H), 3.93-3.83 (m, 2H), 3.61-3.51 (m, 2H), 2.89-2.81 (m, 2H), 2.67-2.60 (m, 1H), 2.18 (s, 3H), 2.13-2.03 (m, 2H), 1.99-1.88 (m, 2H), 1.79-1.54 (m, 6H).

Example 25: 6-(6-[[6-methoxy-5-(1-methylpiperidin-4-yl)pyridin-2-yl]amino]pyrimidin-4-yl)-3-(oxan-4-yloxy)pyridine-2-carbonitrile Example 26: 6-([6-[4-cyano-5-(oxan-4-yloxy)pyridin-2-yl]pyrimidin-4-yl]amino)-2-methoxy-N,N-dimethylpyridine-3-carboxamide

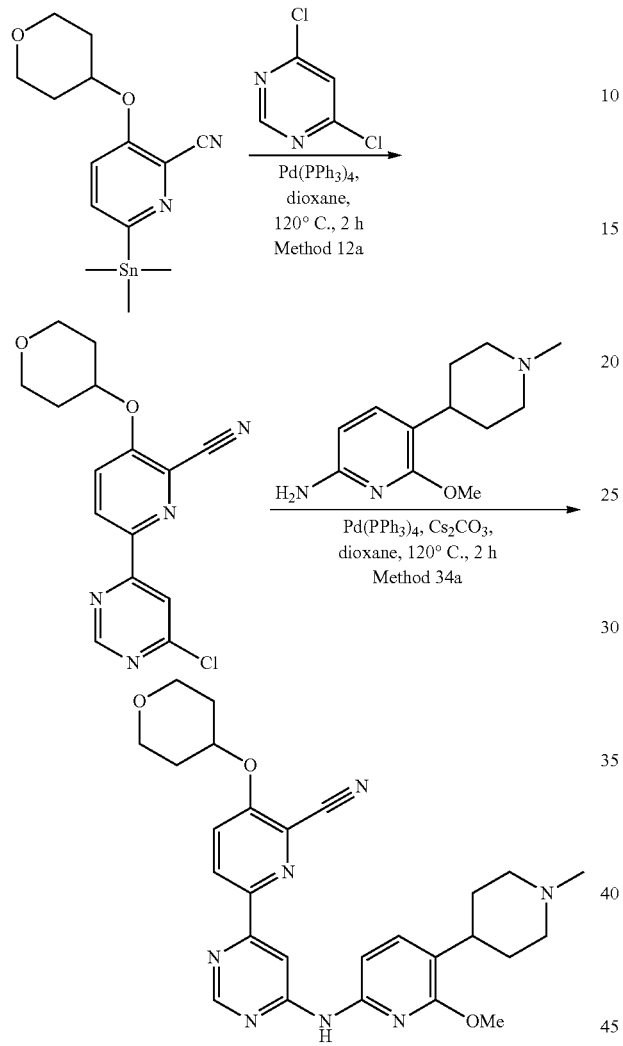

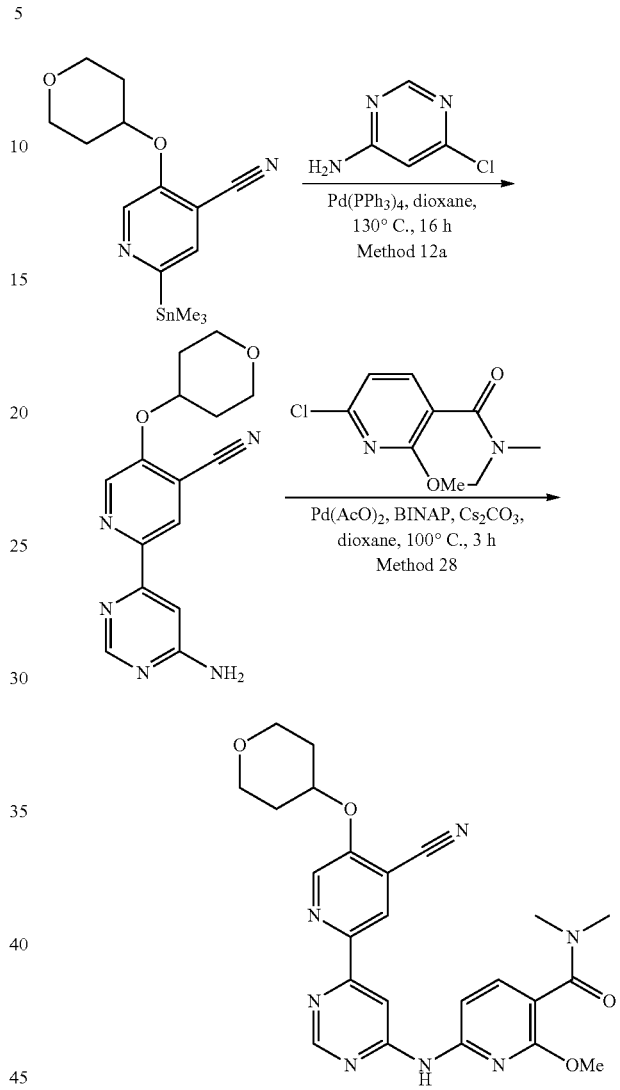

The title compound was prepared from 3-(oxan-4-yloxy)-6-(trimethylstannyl)pyridine-2-carbonitrile, 4,6-dichloropyrimidine, and 6-methoxy-5-(1-methylpiperidin-4-yl)pyridin-2-amine using Method 12a and 34a. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 35% to 45% gradient in 7 min; detector, UV 254 nm. 6-(6-[[6-methoxy-5-(1-methylpiperidin-4-yl)pyridin-2-yl]amino]pyrimidin-4-yl)-3-(oxan-4-yloxy)pyridine-2-carbonitrile was obtained as white solid (23 mg, 7.7% for 2 steps). HPLC: 98.7% purity, RT=3.08 min. MS: m/z=502.5 [M+H]$^+$. $^1$H NMR (400 MHz, DMSO-$d_6$) δ 10.30 (s, 1H), 9.19 (s, 1H), 8.79 (d, J=1.2 Hz, 1H), 8.63-8.56 (m, 1H), 8.12-8.05 (m, 1H), 7.56 (d, J=8.0 Hz, 1H), 6.98 (s, 1H), 5.04-4.93 (m, 1H), 4.12 (s, 3H), 3.94-3.84 (m, 2H), 3.62-3.51 (m, 2H), 2.86 (d, J=11.2 Hz, 2H), 2.73-2.61 (m, 1H), 2.20 (s, 3H), 2.10-1.90 (m, 4H), 1.80-1.54 (m, 6H).

The title compound was prepared from 5-(tetrahydro-2H-pyran-4-yloxy)-2-(trimethylstannyl)isonicotinonitrile, 6-chloropyrimidin-4-amine, and 6-chloro-2-methoxy-N,N-dimethylnicotinamide using Method 12a and 28. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 20% to 37% gradient in 8 min; detector, UV 254 nm. 6-([6-[4-cyano-5-(oxan-4-yloxy)pyridin-2-yl]pyrimidin-4-yl]amino)-2-methoxy-N,N-dimethylpyridine-3-carboxamide was obtained as white solid (9 mg, 2.9% for 2 steps). HPLC: 92.3% purity, RT=1.41 min. MS: m/z=476.1 [M+H]$^+$. $^1$H NMR (300 MHz, DMSO-$d_6$) δ 10.56 (s, 1H), 8.99 (s, 1H), 8.92 (s, 1H), 8.85 (s, 1H), 8.60 (s, 1H), 7.70-7.61 (m, 1H), 7.27-7.17 (m, 1H), 5.19-5.13 (m, 1H), 4.08 (s, 3H), 3.95-3.84 (m, 2H), 3.61-3.55 (m, 2H), 2.98 (s, 3H), 2.85 (s, 3H), 2.16-2.05 (m, 2H), 1.78-1.69 (m, 2H).

Example 27: 5-[6-([6-methoxy-5-[1-(2,2,2-trifluoroethyl)piperidin-4-yl]pyridin-2-yl]amino)pyrimidin-4-yl]-2-(oxan-4-yloxy)benzonitrile

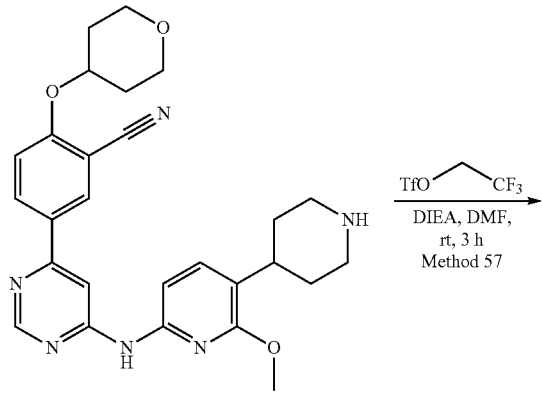

Method 57

To a solution of 5-(6-[[6-methoxy-5-(piperidin-4-yl)pyridin-2-yl]amino]pyrimidin-4-yl)-2-(oxan-4-yloxy)benzonitrile (77 mg, 0.16 mmol) in N,N-dimethylformamide (10 mL) was added 2,2,2-trifluoroethyl trifluoromethanesulfonate (114 mg, 0.49 mmol) and DIEA (257 mg, 1.98 mmol) at room temperature. The resulting mixture was stirred for 3 h at room temperature. When the reaction was done, the reaction mixture was diluted with water (25 mL) and extracted with ethyl acetate (40 mL×3). The organic phases were combined, washed with brine and dried over Na₂SO₄. The solvent was removed under reduced pressure and the residue was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 55% to 80% gradient in 8 min; detector, UV 254 nm. 5-[6-([6-methoxy-5-[1-(2,2,2-trifluoroethyl)piperidin-4-yl]pyridin-2-yl]amino)pyrimidin-4-yl]-2-(oxan-4-yloxy)benzonitrile was obtained as white solid (29 mg, 33%). HPLC: 98.3% purity, RT=3.19 min. MS: m/z=569.3 [M+H]⁺. ¹H NMR (400 MHz, Methanol-d₄) δ 8.69 (s, 1H), 8.32-8.22 (m, 3H), 7.57-7.49 (m, 1H), 7.44-7.36 (m, 1H), 7.17-7.10 (m, 1H), 4.97-4.88 (m, 1H), 4.05 (s, 3H), 4.04-3.98 (m, 2H), 3.74-3.63 (m, 2H), 3.17-3.05 (m, 4H), 2.88-2.75 (m, 1H), 2.57-2.45 (m, 2H), 2.19-2.07 (m, 2H), 1.93-1.70 (m, 6H).

Example 28: 5-[6-([5-[1-(2,2-difluoroethyl)piperidin-4-yl]-6-methoxypyridin-2-yl]amino)pyrimidin-4-yl]-2-(oxan-4-yloxy)benzonitrile

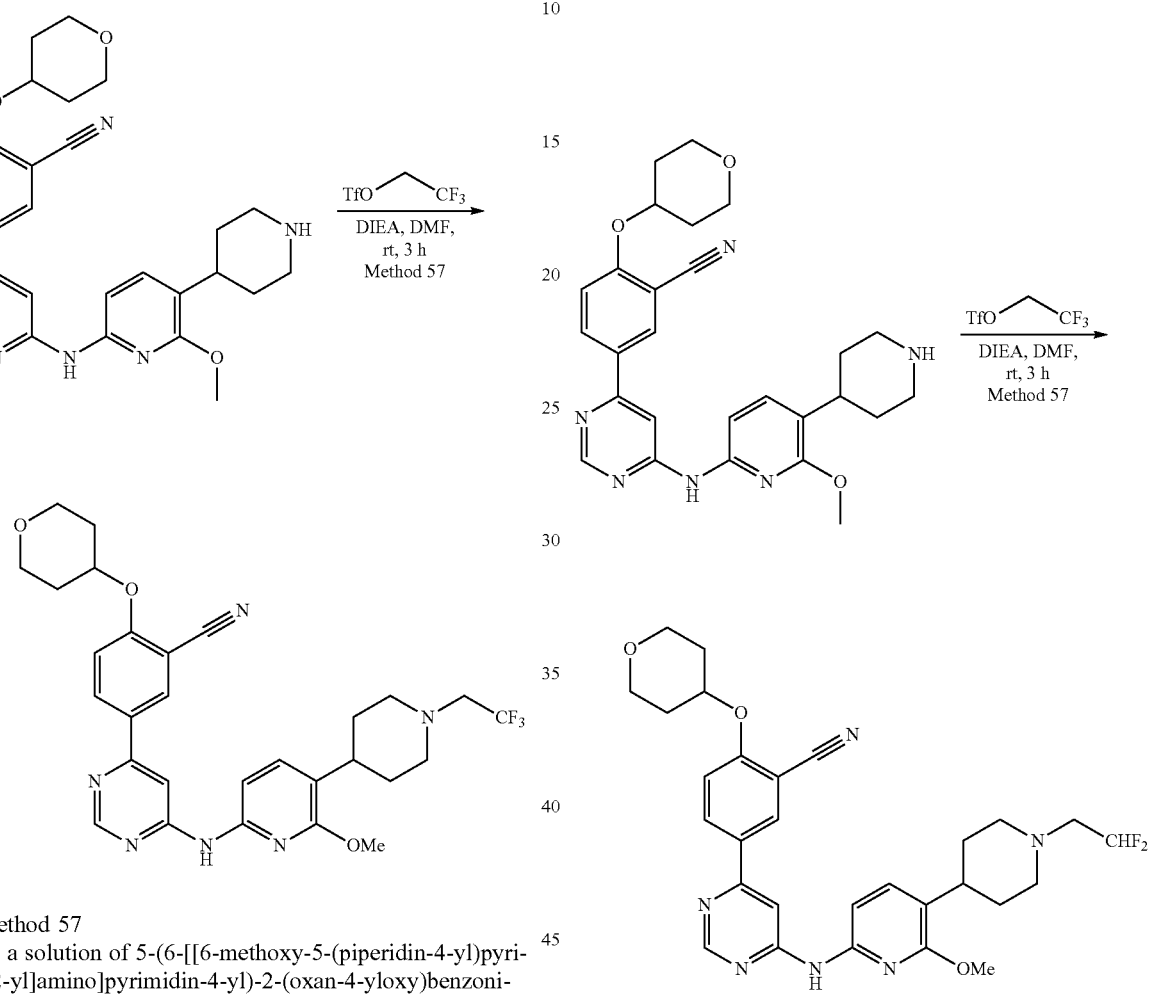

The title compound was prepared from 5-(6-[[6-methoxy-5-(piperidin-4-yl)pyridin-2-yl]amino]pyrimidin-4-yl)-2-(oxan-4-yloxy)benzonitrile and 2,2-difluoroethyl trifluoromethanesulfonate using Method 57. The final product was purified by prep-HPLC under the following conditions: column, XBridge Shield RP18 OBD Column, 150×19 mm, 5 um; mobile phase, acetonitrile in water (with 10 mmol/L NH₄HCO₃ and 0.1% NH₃.H₂O), 55% to 80% gradient in 8 min; detector, UV 254 nm. 5-[6-([5-[1-(2,2-difluoroethyl)piperidin-4-yl]-6-methoxypyridin-2-yl]amino)pyrimidin-4-yl]-2-(oxan-4-yloxy)benzonitrile was obtained as white solid (27 mg, 31%). HPLC: 90.0% purity, RT=3.16 min. MS: m/z=551.3 [M+H]⁺. ¹H NMR (400 MHz, Methanol-d₄) δ 8.70 (s, 1H), 8.34-8.23 (m, 3H), 7.57-7.50 (m, 1H), 7.44-7.37 (m, 1H), 7.18-7.11 (m, 1H), 6.22-5.86 (m, 1H), 4.96-4.89 (m, 1H), 4.06 (s, 3H), 4.05-3.97 (m, 2H), 3.74-3.63 (m, 2H), 3.15-3.07 (m, 2H), 2.88-2.75 (m, 2H), 2.43-2.32 (m, 2H), 2.18-2.08 (m, 2H), 1.93-1.71 (m, 6H).

Example 29: 5-(6-[[5-(4-methylpiperazin-1-yl)pyridin-2-yl]amino]pyrimidin-4-yl)-2-(oxan-4-yloxy)benzonitrile

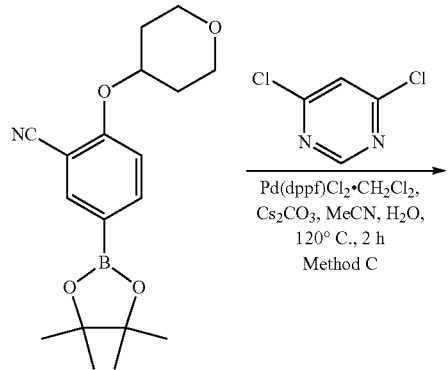

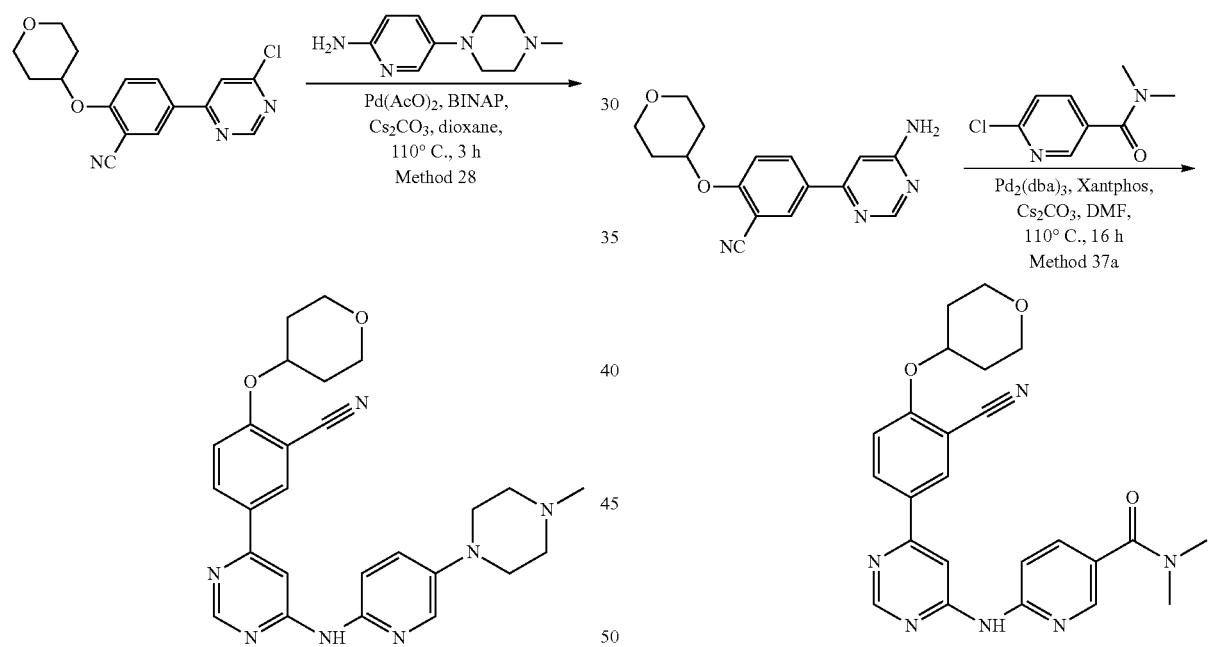

Method C 5-(6-[[5-(4-methylpiperazin-1-yl)pyridin-2-yl]amino]pyrimidin-4-yl)-2-(oxan-4-yloxy)benzonitrile: To a solution of 2-(oxan-4-yloxy)-5-(tetramethyl-1,3,2-dioxaborolan-2-yl)benzonitrile (183 mg, 0.56 mmol) in MeCN (12 mL) was added 4,6-dichloropyrimidine (172 mg, 1.15 mmol), Pd(dppf)Cl$_2$·CH$_2$Cl$_2$ (24 mg, 0.03 mmol), a solution of Cs$_2$CO$_3$ (396 mg, 1.15 mmol) in 4 mL water at room temperature. The resulting mixture was stirred for 2 h at 120° C. When the reaction was done, the reaction mixture was concentrated under reduced pressure and the residue was purified by flash chromatography eluting with EtOAc in hexane (0% to 100% gradient) to yield 5-(6-chloropyrimidin-4-yl)-2-(oxan-4-yloxy)benzonitrile as off-white solid (180 mg, crude). MS: m/z=316.1 [M+H]$^+$.

5-(6-[[5-(4-methylpiperazin-1-yl)pyridin-2-yl]amino]pyrimidin-4-yl)-2-(oxan-4-yloxy)benzonitrile: 5-(6-[[5-(4-methylpiperazin-1-yl)pyridin-2-yl]amino]pyrimidin-4-yl)-2-(oxan-4-yloxy)benzonitrile was prepared from 5-(6-chloropyrimidin-4-yl)-2-(oxan-4-yloxy)benzonitrile and 5-(4-methylpiperazin-1-yl)pyridin-2-amine using Method 28. The final product was purified by prep-HPLC under the following conditions: column, XBridge Prep C18 OBD Column, 150×19 mm, 5 um; mobile phase, acetonitrile in water (with 0.05% NH$_3$.H$_2$O), 30% to 60% gradient in 8 min; detector, UV 254 nm. 5-(6-[[5-(4-methylpiperazin-1-yl)pyridin-2-yl]amino]pyrimidin-4-yl)-2-(oxan-4-yloxy)benzonitrile was obtained as light yellow solid (59 mg, 44% for 2 steps). HPLC: 98.1% purity, RT=2.51 min. MS: m/z=472.3 [M+H]$^+$. $^1$H NMR (400 MHz, DMSO-d$_6$) δ 10.01 (s, 1H), 8.69 (s, 1H), 8.34-8.21 (m, 2H), 8.04-8.01 (m, 2H), 7.99 (s, 1H), 7.70-7.63 (m, 1H), 7.55-7.48 (m, 1H), 7.48-7.40 (m, 1H), 4.96-4.85 (m, 1H), 3.91-3.81 (m, 2H), 3.59-3.48 (m, 2H), 3.15-3.08 (m, 4H), 2.49-2.41 (m, 4H), 2.21 (s, 3H), 2.10-1.95 (m, 2H), 1.74-1.61 (m, 2H).

Example 30: 6-([6-[3-cyano-4-(oxan-4-yloxy)phenyl]pyrimidin-4-yl]amino)-N,N-dimethylpyridine-3-carboxamide The title compound was prepared from 5-(6-aminopyrimidin-4-yl)-2-(oxan-4-yloxy)benzonitrile and 6-chloro-N,N-dimethylpyridine-3-carboxamide using Method 37a. The final product was purified by prep-HPLC under the following conditions: column, XBridge Prep C18 OBD Column, 150×19 mm, 5 um; mobile phase, acetonitrile in water (with 0.05% NH$_3$.H$_2$O), 35% to 65% gradient in 8 min; detector, UV 254 nm. 6-([6-[3-cyano-4-(oxan-4-yloxy)phenyl]pyrimidin-4-yl]amino)-N,N-dimethylpyridine-3-carboxamide was obtained as white solid (30 mg, 70%). HPLC: 99.5% purity, RT=1.51 min. MS: m/z=445.2 [M+H]$^+$. $^1$H NMR (400 MHz, DMSO-d$_6$) δ 10.51 (s, 1H), 8.82 (s, 1H), 8.48-8.42 (m, 1H), 8.39-8.27 (m, 2H), 8.21 (s, 1H), 7.91-7.81 (m, 2H), 7.55 (d, J=9.1 Hz, 1H), 4.99-4.88 (m, 1H), 3.93-3.83 (m, 2H), 3.61-3.50 (m, 2H), 3.01 (s, 6H), 2.10-2.00 (m, 2H), 1.76-1.63 (m, 2H).

Example 31: 6-([6-[3-cyano-4-(oxan-4-yloxy)phenyl]pyrimidin-4-yl]amino)-4-methoxy-N,N-dimethylpyridine-3-carboxamide

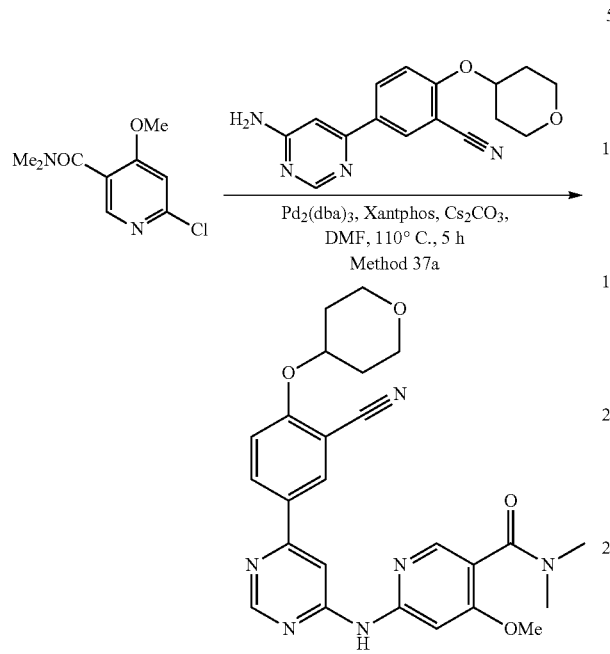

6-([6-[3-cyano-4-(oxan-4-yloxy)phenyl]pyrimidin-4-yl]amino)-4-methoxy-N,N-dimethylpyridine-3-carboxamide: 6-([6-[3-cyano-4-(oxan-4-yloxy)phenyl]pyrimidin-4-yl]amino)-4-methoxy-N,N-dimethylpyridine-3-carboxamide was prepared from 6-chloro-4-methoxy-N,N-dimethylpyridine-3-carboxamide and 5-(6-aminopyrimidin-4-yl)-2-(oxan-4-yloxy)benzonitrile using Method 37a. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 33% to 37% gradient in 7 min; detector, UV 254 nm. 6-([6-[3-cyano-4-(oxan-4-yloxy)phenyl]pyrimidin-4-yl]amino)-4-methoxy-N,N-dimethylpyridine-3-carboxamide was obtained as white solid (23 mg, 16%). HPLC: 99.8% purity, RT=1.51 min. MS: m/z=475.3 [M+H]$^+$. $^1$H NMR (300 MHz, DMSO-d$_6$) δ 10.34 (s, 1H), 8.82 (s, 1H), 8.39-8.24 (m, 2H), 8.22 (s, 1H), 8.07 (s, 1H), 7.59-7.50 (m, 2H), 4.99-4.87 (m, 1H), 3.89 (s, 3H), 3.89-3.82 (m, 2H), 3.63-3.48 (m, 2H), 2.98 (s, 3H), 2.83 (s, 3H), 2.10-1.99 (m, 2H), 1.78-1.60 (m, 2H).

Example 32: 5-([6-[3-cyano-4-(oxan-4-yloxy)phenyl]pyrimidin-4-yl]amino)-3-methoxy-N,N-dimethylpyridine-2-carboxamide

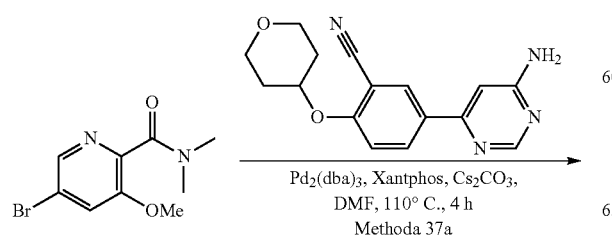

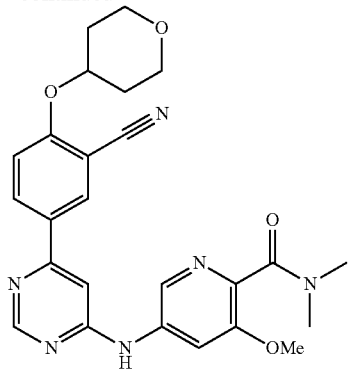

The title compound was prepared from 5-bromo-3-methoxy-N,N-dimethylpyridine-2-carboxamide and 5-(6-aminopyrimidin-4-yl)-2-(oxan-4-yloxy)benzonitrile using Method 37a. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 42% gradient in 7 min; detector, UV 254 nm. 5-([6-[3-cyano-4-(oxan-4-yloxy)phenyl]pyrimidin-4-yl]amino)-3-methoxy-N,N-dimethylpyridine-2-carboxamide was obtained as off-white solid (40 mg, 31%). HPLC: 99.3% purity, RT=0.95 min. MS: m/z=475.1 [M+H]$^+$. $^1$H NMR (300 MHz, DMSO-d$_6$) δ 10.02 (s, 1H), 8.79 (s, 1H), 8.48-8.36 (m, 2H), 8.35-8.27 (m, 1H), 8.08-8.00 (m, 1H), 7.59-7.50 (m, 1H), 7.30 (s, 1H), 4.99-4.87 (m, 1H), 3.93-3.86 (m, 2H), 3.85 (s, 3H), 3.63-3.48 (m, 2H), 2.98 (s, 3H), 2.76 (s, 3H), 2.10-1.98 (m, 2H), 1.78-1.60 (m, 2H).

Example 33: 5-(6-[[4-methoxy-5-(4-methylpiperazin-1-yl)pyridin-2-yl]amino]pyrimidin-4-yl)-2-(oxan-4-yloxy)benzonitrile

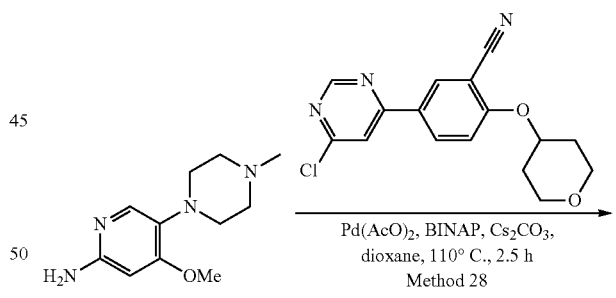

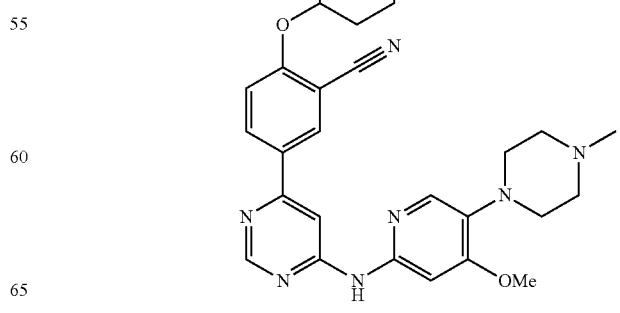

The title compound was prepared from 5-(6-chloropyrimidin-4-yl)-2-(oxan-4-yloxy)benzonitrile and 4-methoxy-5-(4-methylpiperazin-1-yl)pyridin-2-amine using Method 28. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 25% to 45% gradient in 7 min; detector, UV 254 nm. 5-(6-[[4-methoxy-5-(4-methylpiperazin-1-yl)pyridin-2-yl]amino]pyrimidin-4-yl)-2-(oxan-4-yloxy)benzonitrile was obtained as light yellow solid (13 mg, 32%). HPLC: 99.5% purity, RT=3.96 min. MS: m/z=502.2 [M+H]⁺. ¹H NMR (300 MHz, DMSO-d₆) δ 10.01 (s, 1H), 8.73 (s, 1H), 8.40-8.22 (m, 3H), 7.81 (s, 1H), 7.58-7.48 (m, 1H), 7.37 (s, 1H), 4.98-4.86 (m, 1H), 3.93-3.87 (m, 2H), 3.86 (s, 3H), 3.63-3.48 (m, 2H), 3.02-2.95 (m, 4H), 2.48-2.42 (m, 4H), 2.22 (s, 3H), 2.10-1.99 (m, 2H), 1.78-1.60 (m, 2H).

Example 34: 5-(6-[[5-methoxy-6-(4-methylpiperazin-1-yl)pyridin-3-yl]amino]pyrimidin-4-yl)-2-(oxan-4-yloxy)benzonitrile

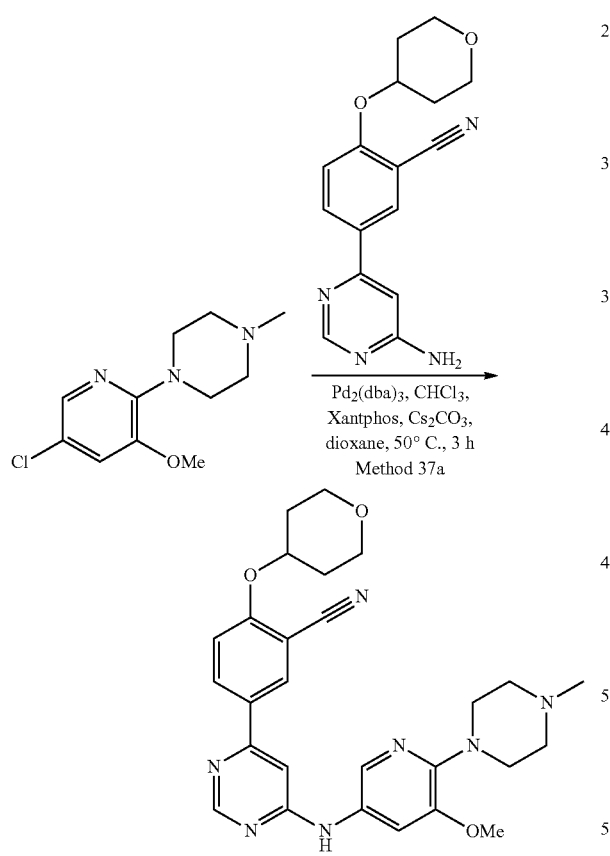

The title compound was prepared from 5-(6-chloropyrimidin-4-yl)-2-(oxan-4-yloxy)benzonitrile and 5-methoxy-6-(4-methylpiperazin-1-yl)pyridin-3-amine using Method 37a. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 30% to 44% gradient in 7 min; detector, UV 254 nm. 5-(6-[[5-methoxy-6-(4-methylpiperazin-1-yl)pyridin-3-yl]amino]pyrimidin-4-yl)-2-(oxan-4-yloxy)benzonitrile was obtained as yellow solid (39 mg, 27%). HPLC: 97.9% purity, RT=5.33 min. MS: m/z=502.2 [M+H]⁺. ¹H NMR (300 MHz, DMSO-d₆) δ 9.57 (s, 1H), 8.64 (s, 1H), 8.39-8.22 (m, 2H), 8.09-8.02 (m, 1H), 7.65-7.57 (m, 1H), 7.56-7.46 (m, 1H), 7.16 (s, 1H), 4.97-4.85 (m, 1H), 3.94-3.80 (m, 2H), 3.81 (s, 3H), 3.62-3.48 (m, 2H), 3.27-3.19 (m, 4H), 2.48-2.38 (m, 4H), 2.21 (s, 3H), 2.09-1.98 (m, 2H), 1.77-1.59 (m, 2H).

Example 35: 5-(6-[[5-methoxy-6-(1-methylpiperidin-4-yl)pyridin-3-yl]amino]pyrimidin-4-yl)-2-(oxan-4-yloxy)benzonitrile

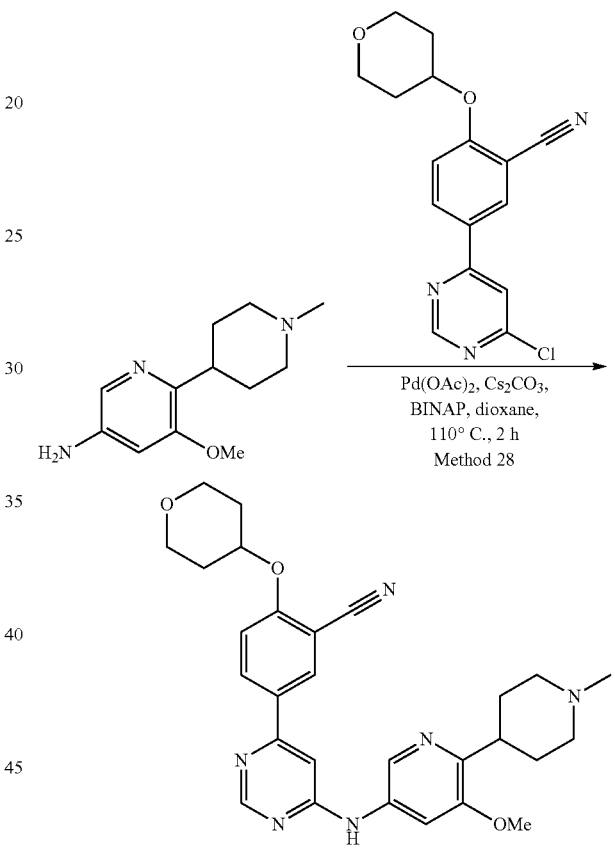

The title compound was prepared from 5-(6-chloropyrimidin-4-yl)-2-(oxan-4-yloxy)benzonitrile and 5-methoxy-6-(1-methylpiperidin-4-yl)pyridin-3-amine using Method 28. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 25% to 40% gradient in 7 min; detector, UV 254 nm. 5-(6-[[5-methoxy-6-(1-methylpiperidin-4-yl)pyridin-3-yl]amino]pyrimidin-4-yl)-2-(oxan-4-yloxy)benzonitrile was obtained as white solid (27 mg, 14%). HPLC: 98.8% purity, RT=2.63 min. MS: m/z=501.5 [M+H]⁺. ¹H NMR (400 MHz, DMSO-d₆) δ 9.77 (s, 1H), 8.71 (s, 1H), 8.39-8.32 (m, 2H), 8.32-8.25 (m, 1H), 7.84-7.78 (m, 1H), 7.56-7.49 (m, 1H), 7.25 (s, 1H), 4.98-4.87 (m, 1H), 3.93-3.82 (m, 2H), 3.83 (s, 3H), 3.61-3.50 (m, 2H), 3.00-2.77 (m, 3H), 2.19 (s, 3H), 2.10-1.90 (m, 4H), 1.86-1.59 (m, 6H).

Example 36: 5-(6-[[4-methoxy-5-(1-methylpiperidin-4-yl)pyridin-2-yl]amino]pyrimidin-4-yl)-2-(oxan-4-yloxy)benzonitrile

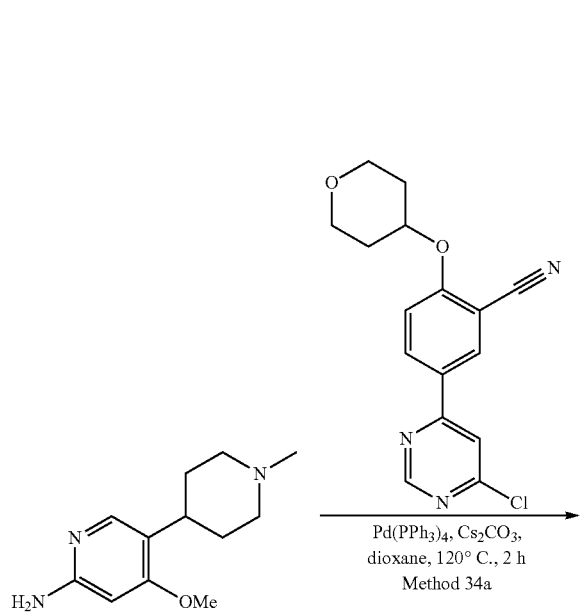

The title compound was prepared from 5-(6-chloropyrimidin-4-yl)-2-(oxan-4-yloxy)benzonitrile and 4-methoxy-5-(1-methylpiperidin-4-yl)pyridin-2-amine using Method 34a. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3 \cdot H_2O$), 35% to 47% gradient in 7 min; detector, UV 254 nm. 5-(6-[[4-methoxy-5-(1-methylpiperidin-4-yl)pyridin-2-yl]amino]pyrimidin-4-yl)-2-(oxan-4-yloxy)benzonitrile was obtained as white solid (34 mg, 22%). HPLC: 99.3% purity, RT=2.42 min. MS: m/z=501.5 [M+H]$^+$. $^1$H NMR (400 MHz, Methanol-d$_4$) δ 8.70 (s, 1H), 8.33-8.23 (m, 2H), 8.07-7.99 (m, 2H), 7.41-7.34 (m, 2H), 4.95-4.85 (m, 1H), 4.05-3.95 (m, 2H), 3.93 (s, 3H), 3.72-3.61 (m, 2H), 3.08-3.00 (m, 2H), 2.88-2.77 (m, 1H), 2.36 (s, 3H), 2.27-2.06 (m, 4H), 1.95-1.78 (m, 6H).

Example 37: 6-[(6-[3-cyano-4-[(1-methylazetidin-3-yl)oxy]phenyl]pyrimidin-4-yl)amino]-2-methoxy-N,N-dimethylpyridine-3-carboxamide

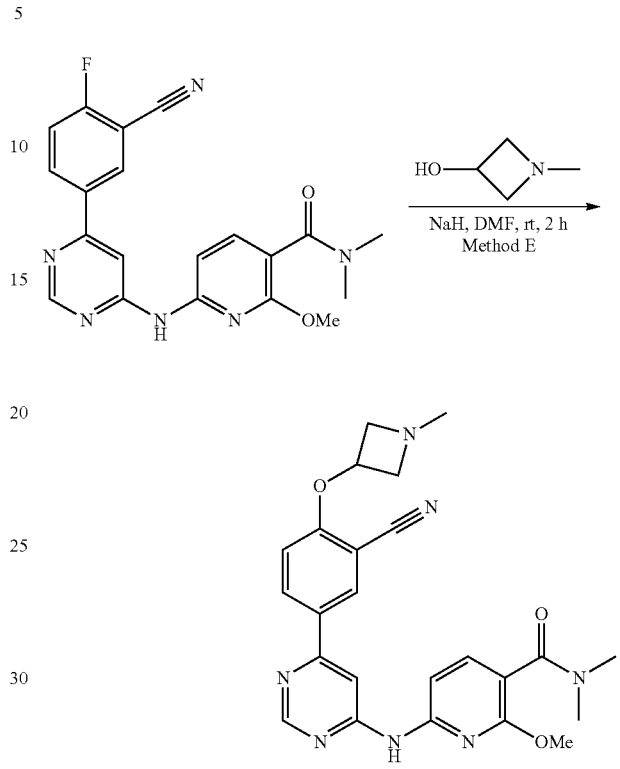

Method E

6-[(6-[3-cyano-4-[(1-methylazetidin-3-yl)oxy]phenyl]pyrimidin-4-yl)amino]-2-methoxy-N,N-dimethylpyridine-3-carboxamide: To a solution of 1-methylazetidin-3-ol (19 mg, 0.22 mmol) in N,N-dimethylformamide (6 mL) was added sodium hydride (11 mg, 0.44 mmol) at 0° C. The resulting mixture was stirred for 30 min, and then was added to 6-[[6-(3-cyano-4-fluorophenyl)pyrimidin-4-yl]amino]-2-methoxy-N,N-dimethylpyridine-3-carboxamide (29 mg, 0.07 mmol) at 0° C. The reaction mixture was stirred for 2 h at room temperature. When the reaction was done, it was quenched by ice water (5 mL) and the resulting mixture was extracted with ethyl acetate (20 mL×3). The organic phases were combined, washed with brine and dried over $Na_2SO_4$. The solvent was removed under reduced pressure and the residue was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3 \cdot H_2O$), 30% to 42% gradient in 10 min; detector, UV 254 nm. 6-[(6-[3-cyano-4-[(1-methylazetidin-3-yl)oxy]phenyl]pyrimidin-4-yl)amino]-2-methoxy-N,N-dimethylpyridine-3-carboxamide was obtained as yellow solid (26 mg, 76%). HPLC: 99.6% purity, RT=2.36 min. MS: m/z=460.3 [M+H]$^+$. $^1$H NMR (300 MHz, DMSO-d$_6$) δ 10.39 (s, 1H), 8.81 (s, 1H), 8.44-8.36 (m, 2H), 8.34-8.23 (m, 1H), 7.68-7.59 (m, 1H), 7.28-7.15 (m, 2H), 5.08-4.94 (m, 1H), 4.01 (s, 3H), 3.84-3.72 (m, 2H), 3.13-3.02 (m, 2H), 2.97 (s, 3H), 2.84 (s, 3H), 2.31 (s, 3H).

Example 38: 5-(6-[[6-methoxy-5-(4-methylpiperazin-1-yl)pyridin-2-yl]amino]pyrimidin-4-yl)-2-[(1-methylazetidin-3-yl)oxy]benzonitrile

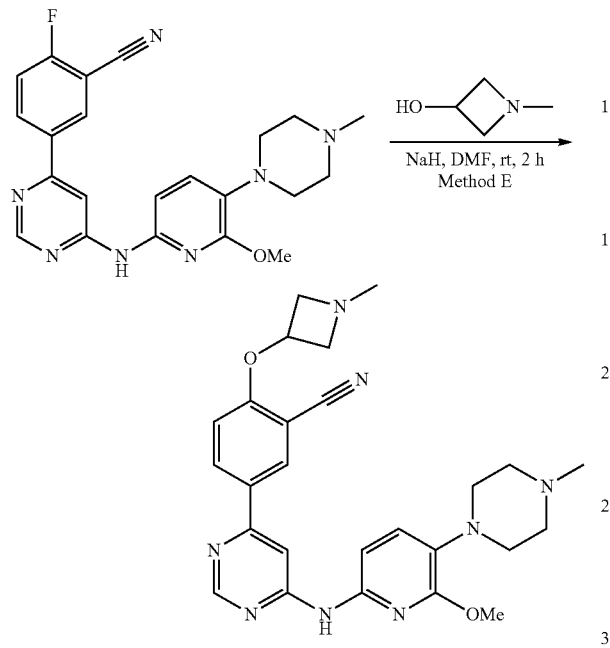

The title compound was prepared from 1-methylazetidin-3-ol and 2-fluoro-5-(6-[[6-methoxy-5-(4-methylpiperazin-1-yl)pyridin-2-yl]amino]pyrimidin-4-yl)benzonitrile using Method E. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 25% to 55% gradient in 7 min; detector, UV 254 nm. 5-(6-[[6-methoxy-5-(4-methylpiperazin-1-yl)pyridin-2-yl]amino]pyrimidin-4-yl)-2-[(1-methylazetidin-3-yl)oxy]benzonitrile was obtained as yellow solid (25 mg, 25%). HPLC: 99.0% purity, RT=3.64 min. MS: m/z=487.1 $[M+H]^+$. $^1H$ NMR (400 MHz, DMSO-$d_6$) δ 9.95 (s, 1H), 8.71 (s, 1H), 8.38-8.33 (m, 1H), 8.29-8.22 (m, 1H), 8.17 (br s, 1H), 7.31-7.24 (m, 1H), 7.22-7.15 (m, 2H), 5.06-4.96 (m, 1H), 3.98 (s, 3H), 3.83-3.74 (m, 2H), 3.13-3.04 (m, 2H), 2.98-2.93 (m, 4H), 2.48-2.43 (m, 4H), 2.32 (s, 3H), 2.23 (s, 3H).

Example 39: 6-[(6-[3-cyano-4-[(1-methylpyrrolidin-3-yl)oxy]phenyl]pyrimidin-4-yl)amino]-2-methoxy-N,N-dimethylpyridine-3-carboxamide

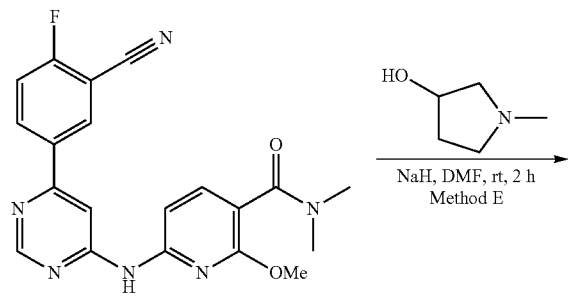

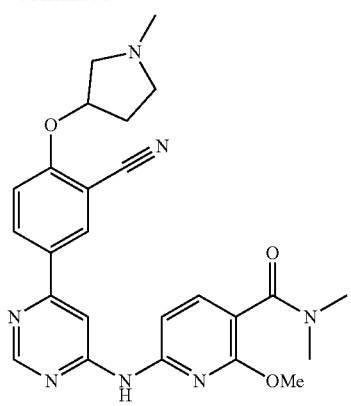

The title compound was prepared from 1-methylpyrrolidin-3-ol and 6-[[6-(3-cyano-4-fluorophenyl)pyrimidin-4-yl]amino]-2-methoxy-N,N-dimethylpyridine-3-carboxamide using Method E. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 32% to 34% gradient in 7 min; detector, UV 254 nm. 6-[(6-[3-cyano-4-[(1-methylpyrrolidin-3-yl)oxy]phenyl]pyrimidin-4-yl)amino]-2-methoxy-N,N-dimethylpyridine-3-carboxamide was obtained as yellow solid (25 mg, 35%). HPLC: 93.5% purity, RT=2.39 min. MS: m/z=474.2 $[M+H]^+$. $^1H$ NMR (300 MHz, DMSO-$d_6$) δ 10.38 (s, 1H), 8.81 (s, 1H), 8.45-8.25 (m, 3H), 7.68-7.59 (m, 1H), 7.41-7.32 (m, 1H), 7.29-7.19 (m, 1H), 5.15-5.08 (m, 1H), 4.02 (s, 3H), 2.97 (s, 3H), 2.84 (s, 3H), 2.82-2.77 (m, 1H), 2.77-2.68 (m, 2H), 2.43-2.31 (m, 2H), 2.29 (s, 3H), 1.93-1.75 (m, 1H).

Example 40: 5-(6-[[5-(4-methylpiperazin-1-yl)pyridin-2-yl]amino]pyrimidin-4-yl)-2-[(1-methylpyrrolidin-3-yl)oxy]benzonitrile

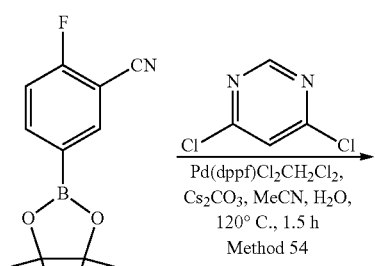

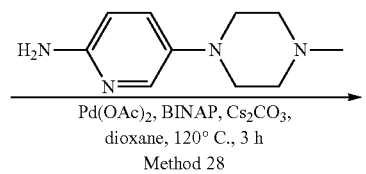

129

-continued

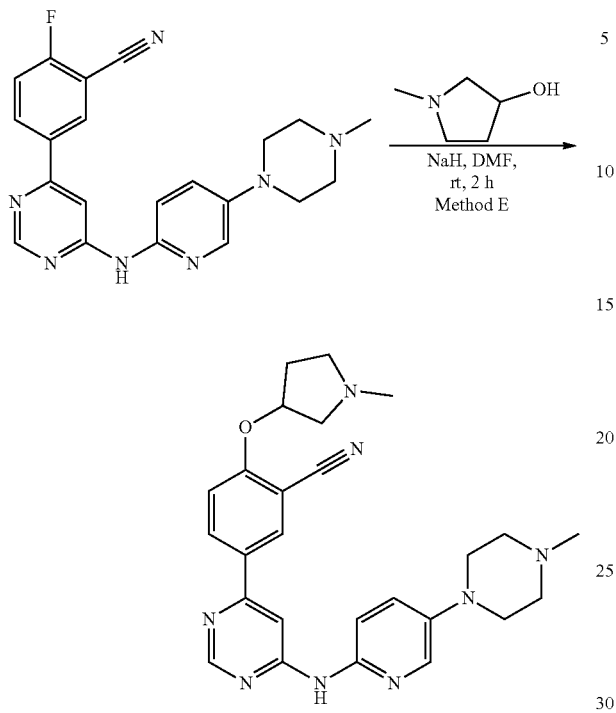

Method 54

5-(6-chloropyrimidin-4-yl)-2-fluorobenzonitrile: To a solution of 2-fluoro-5-(tetramethyl-1,3,2-dioxaborolan-2-yl) benzonitrile (1.90 g, 7.69 mmol) in MeCN (60 mL) was added 4,6-dichloropyrimidine (2.28 g, 15.30 mmol), Pd(dppf)Cl$_2$.CH$_2$Cl$_2$ (313 mg, 0.38 mmol), CS$_2$CO$_3$ solution (4.94 g in 20 mL water, 15.16 mmol) at room temperature. The resulting mixture was stirred for 1.5 h at 120° C. When the reaction was done, the reaction mixture was concentrated under reduced pressure and the residue was purified by flash chromatography eluting with EtOAc in hexane (0% to 50% gradient) to yield 5-(6-chloropyrimidin-4-yl)-2-fluorobenzonitrile as off-white solid (1.15 g, 64%). MS: m/z=234.0 [M+H]$^+$.

5-(6-[[5-(4-methylpiperazin-1-yl)pyridin-2-yl]amino]pyrimidin-4-yl)-2-[(1-methylpyrrolidin-3-yl)oxy]benzonitrile: The title compound was prepared from 5-(6-chloropyrimidin-4-yl)-2-fluorobenzonitrile, 5-(4-methylpiperazin-1-yl) pyridin-2-amine and 1-methylpyrrolidin-3-ol using Method 28 and E. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 41% gradient in 7 min; detector, UV 254 nm. 5-(6-[[5-(4-methylpiperazin-1-yl)pyridin-2-yl]amino]pyrimidin-4-yl)-2-[(1-methylpyrrolidin-3-yl)oxy]benzonitrile was obtained as yellow solid (23 mg, 6.7% for 2 steps). HPLC: 97.3% purity, RT=0.77 min. MS: m/z=471.2 [M+H]$^+$. $^1$H NMR (300 MHz, DMSO-d$_6$) δ 10.02 (s, 1H), 8.70 (s, 1H), 8.34-8.20 (m, 2H), 8.08-7.97 (m, 2H), 7.72-7.62 (m, 1H), 7.51-7.40 (m, 1H), 7.39-7.29 (m, 1H), 5.16-5.07 (m, 1H), 3.18-3.08 (m, 4H), 2.87-2.65 (m, 3H), 2.51-2.39 (m, 4H), 2.44-2.31 (m, 2H), 2.28 (s, 3H), 2.22 (s, 3H), 1.92-1.75 (m, 1H).

130

Example 41: 6-[(6-[3-cyano-4-[(1-methylpiperidin-4-yl)oxy]phenyl]pyrimidin-4-yl)amino]-2-methoxy-N,N-dimethylpyridine-3-carboxamide

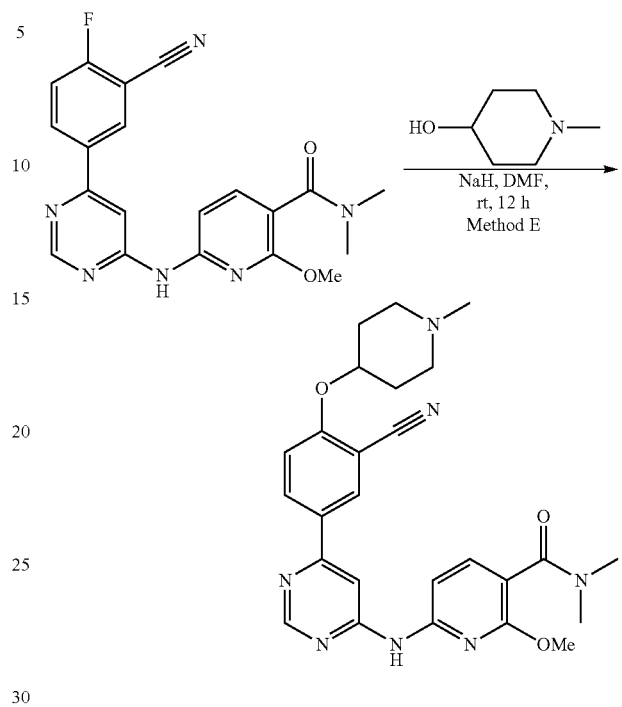

The title compound was prepared from 1-methylpiperidin-4-ol and 6-[[6-(3-cyano-4-fluorophenyl)pyrimidin-4-yl] amino]-2-methoxy-N,N-dimethylpyridine-3-carboxamide using Method E. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 30% to 43% gradient in 7 min; detector, UV 254 nm. 6-[(6-[3-cyano-4-[(1-methylpiperidin-4-yl)oxy]phenyl] pyrimidin-4-yl)amino]-2-methoxy-N,N-dimethylpyridine-3-carboxamide was obtained as off-white solid (24 mg, 25%). HPLC: 99.5% purity, RT=2.49 min. MS: m/z=488.4 [M+H]$^+$. $^1$H NMR (300 MHz, DMSO-d$_6$) δ 10.39 (s, 1H), 8.81 (s, 1H), 8.42 (s, 1H), 8.40-8.24 (m, 2H), 7.68-7.59 (m, 1H), 7.55-7.45 (m, 1H), 7.28-7.18 (m, 1H), 4.78-4.69 (m, 1H), 4.02 (s, 3H), 2.97 (s, 3H), 2.84 (s, 3H), 2.65-2.55 (m, 2H), 2.35-2.22 (m, 2H), 2.19 (s, 3H), 2.04-1.88 (m, 2H), 1.83-1.67 (m, 2H).

Example 42: 6-[[6-(3-cyano-4-[[1-(2-hydroxyacetyl) piperidin-4-yl]oxy]phenyl)pyrimidin-4-yl]amino]-2-methoxy-N,N-dimethylpyridine-3-carboxamide

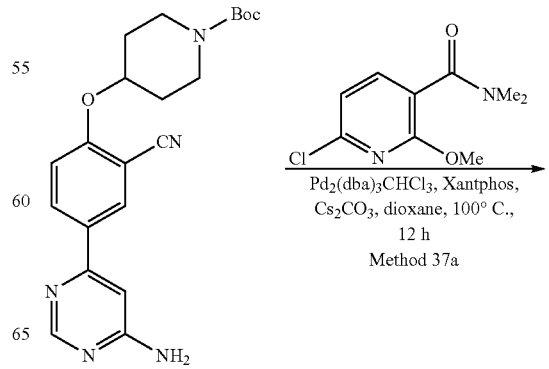

-continued

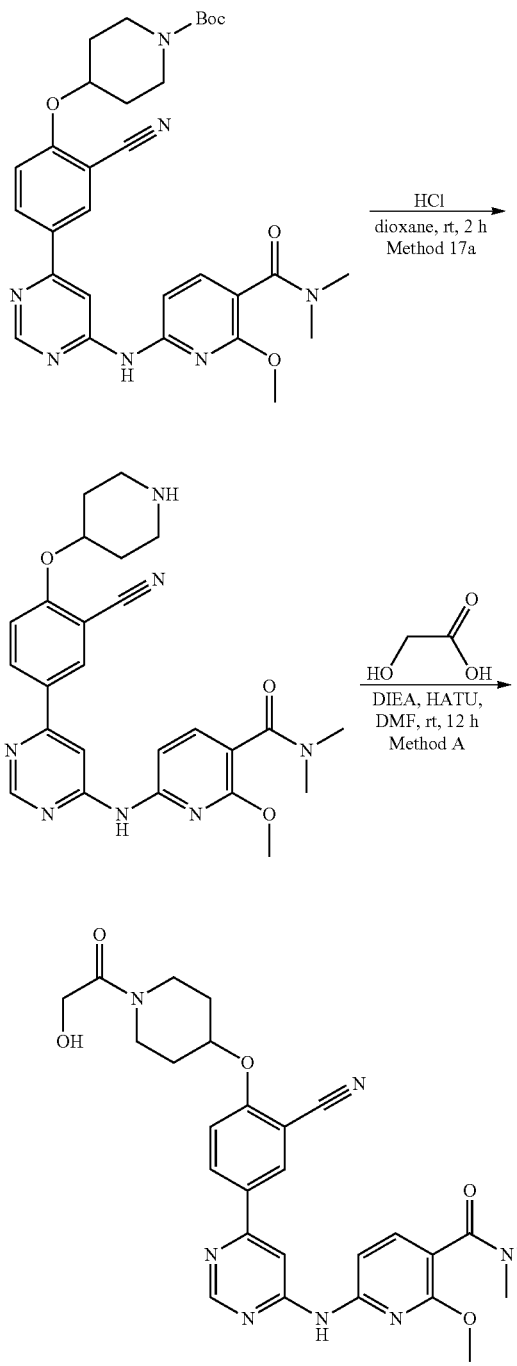

The title compound was prepared from tert-butyl 4-(4-(6-aminopyrimidin-4-yl)-2-cyanophenoxy)piperidine-1-carboxylate, 6-chloro-2-methoxy-N,N-dimethylnicotinamide and 2-hydroxyacetic acid using Method 37a, 17a and A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 22% to 34% gradient in 10 min; detector, UV 254 nm. 6-[[6-(3-cyano-4-[[1-(2-hydroxyacetyl)piperidin-4-yl]oxy]phenyl)pyrimidin-4-yl]amino]-2-methoxy-N,N-dimethylpyridine-3-carboxamide was obtained as off-white solid (24 mg, 16% for 3 steps). HPLC: 99.3% purity, RT=4.56 min. MS: m/z=532.2 [M+H]$^+$. $^1$H NMR (300 MHz, DMSO-d$_6$) δ 10.36 (s, 1H), 8.78 (s, 1H), 8.43-8.31 (m, 2H), 8.33-8.23 (m, 1H), 7.65-7.47 (m, 2H), 7.24-7.14 (m, 1H), 5.00-4.92 (m, 1H), 4.57-4.47 (m, 1H), 4.09 (d, J=5.4 Hz, 2H), 3.99 (s, 3H), 3.80-3.29 (m, 4H), 2.93 (s, 3H), 2.80 (s, 3H), 1.99-1.92 (m, 2H), 1.70-1.63 (m, 2H).

Example 43: 6-([6-[3-cyano-4-([1-[(1,3-oxazol-5-yl)carbonyl]piperidin-4-yl]oxy)phenyl]pyrimidin-4-yl]amino)-2-methoxy-N,N-dimethylpyridine-3-carboxamide

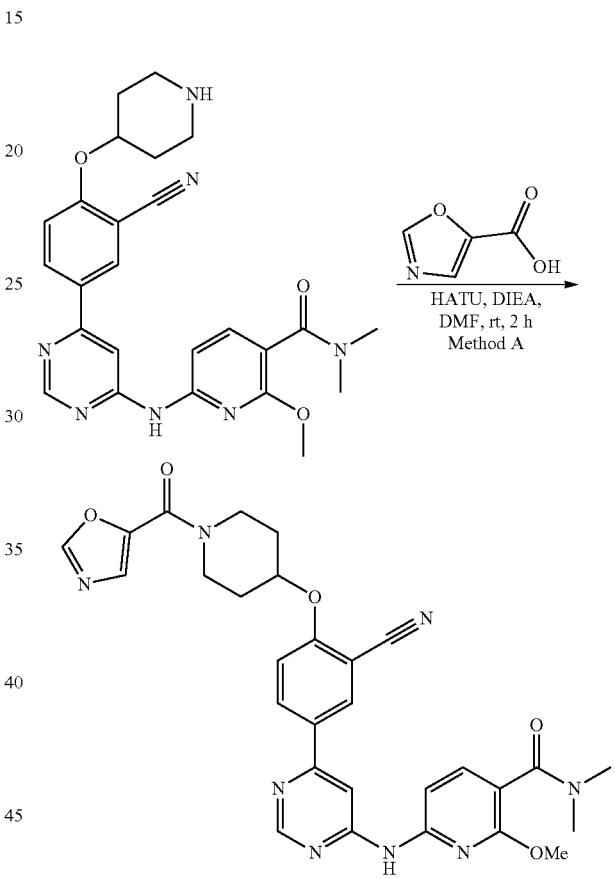

The title compound was prepared from 6-([6-[3-cyano-4-(piperidin-4-yloxy)phenyl]pyrimidin-4-yl]amino)-2-methoxy-N,N-dimethylpyridine-3-carboxamide and 1,3-oxazole-5-carboxylic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 20% to 44% gradient in 7 min; detector, UV 254 nm. 6-([6-[3-cyano-4-([1-[(1,3-oxazol-5-yl)carbonyl]piperidin-4-yl]oxy)phenyl]pyrimidin-4-yl]amino)-2-methoxy-N,N-dimethylpyridine-3-carboxamide was obtained as off-white solid (26 mg, 23%). HPLC: 99.3% purity, RT=4.97 min. MS: m/z=569.2 [M+H]$^+$. $^1$H NMR (300 MHz, DMSO-d$_6$) δ 10.40 (s, 1H), 8.82 (s, 1H), 8.56 (s, 1H), 8.47-8.36 (m, 2H), 8.38-8.28 (m, 1H), 7.75 (s, 1H), 7.69-7.53 (m, 2H), 7.27-7.18 (m, 1H), 5.09-5.02 (m, 1H), 4.02 (s, 3H), 3.97-3.55 (m, 4H), 2.97 (s, 3H), 2.84 (s, 3H), 2.15-1.99 (m, 2H), 1.90-1.68 (m, 2H).

Example 44: 6-([6-[3-cyano-4-([1-[(1,3-oxazol-4-yl)carbonyl]piperidin-4-yl]oxy)phenyl]pyrimidin-4-yl]amino)-2-methoxy-N,N-dimethylpyridine-3-carboxamide Example 45: 6-([6-[3-cyano-4-([1-[(5-methyl-1H-1,2,4-triazol-3-yl)carbonyl]piperidin-4-yl]oxy)phenyl]pyrimidin-4-yl]amino)-2-methoxy-N,N-dimethylpyridine-3-carboxamide

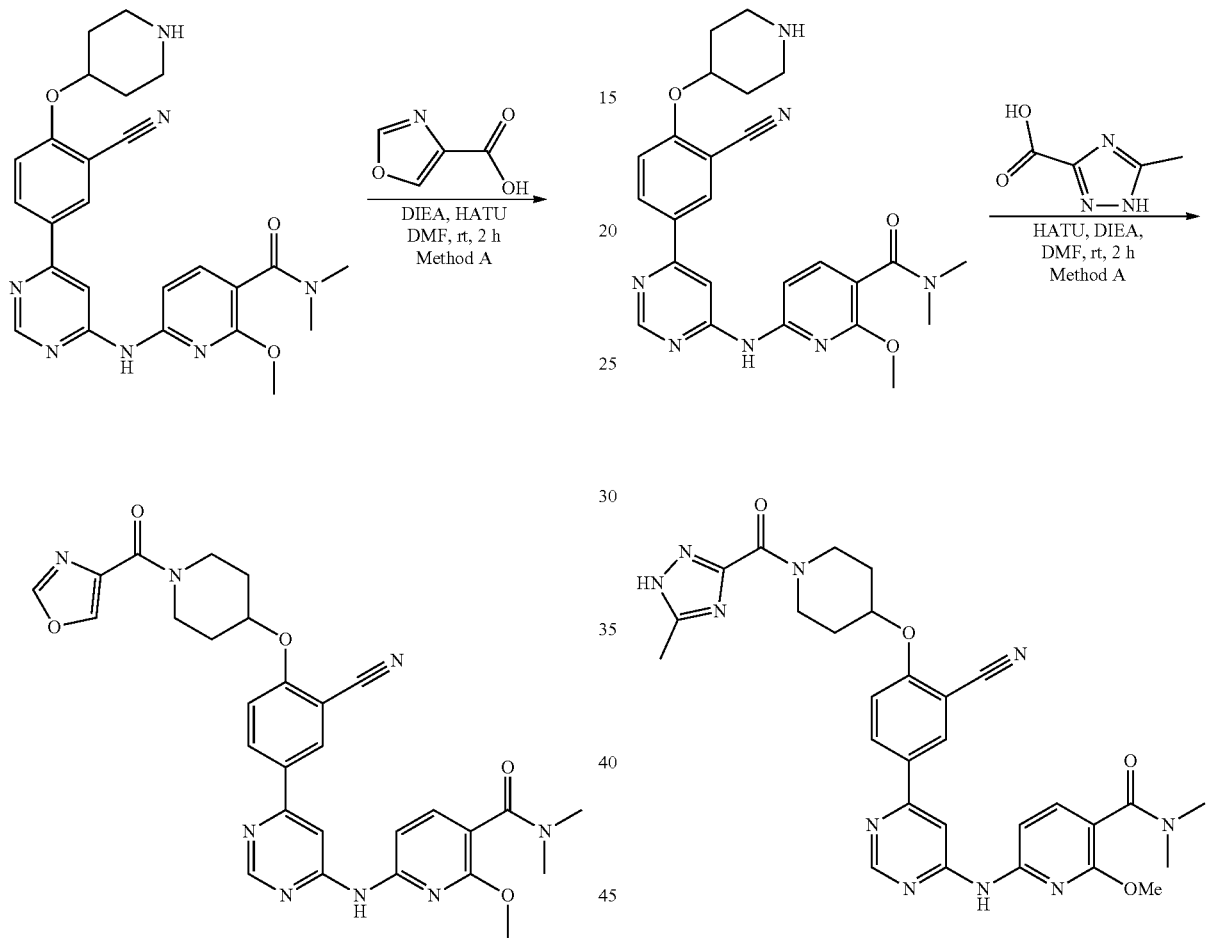

The title compound was prepared from 6-([6-[3-cyano-4-(piperidin-4-yloxy)phenyl]pyrimidin-4-yl]amino)-2-methoxy-N,N-dimethylpyridine-3-carboxamide and 1,3-oxazole-4-carboxylic acid using Method A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 20% to 44% gradient in 10 min; detector, UV 254 nm. 6-([6-[3-cyano-4-([1-[(1,3-oxazol-4-yl)carbonyl]piperidin-4-yl]oxy)phenyl]pyrimidin-4-yl]amino)-2-methoxy-N,N-dimethylpyridine-3-carboxamide was obtained as off-white solid (29 mg, 26%). HPLC: 98.2% purity, RT=5.07 min. MS: m/z=569.2 [M+H]+. $^1$H NMR (300 MHz, DMSO-$d_6$) δ 10.40 (s, 1H), 8.81 (s, 1H), 8.60 (s, 1H), 8.52 (s, 1H), 8.47-8.36 (m, 2H), 8.38-8.27 (m, 1H), 7.69-7.52 (m, 2H), 7.27-7.18 (m, 1H), 5.07-5.01 (m, 1H), 4.20-3.42 (m, 7H), 2.97 (s, 3H), 2.84 (s, 3H), 2.09-2.02 (m, 2H), 1.81-1.74 (m, 2H).

The title compound was prepared from 6-([6-[3-cyano-4-(piperidin-4-yloxy)phenyl]pyrimidin-4-yl]amino)-2-methoxy-N,N-dimethylpyridine-3-carboxamide and 5-methyl-1H-1,2,4-triazole-3-carboxylic acid using Method A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 20% to 35% gradient in 7 min; detector, UV 254 nm. 6-([6-[3-cyano-4-([1-[(5-methyl-1H-1,2,4-triazol-3-yl)carbonyl]piperidin-4-yl]oxy)phenyl]pyrimidin-4-yl]amino)-2-methoxy-N,N-dimethylpyridine-3-carboxamide was obtained as white solid (30 mg, 25%). HPLC: 99.3% purity, RT=4.48 min. MS: m/z=583.3 [M+H]+. $^1$H NMR (300 MHz, DMSO-$d_6$) δ 14.04 (br s, 1H), 10.40 (s, 1H), 8.81 (s, 1H), 8.49-8.25 (m, 3H), 7.68-7.51 (m, 2H), 7.27-7.18 (m, 1H), 5.07-5.01 (m, 1H), 4.02 (s, 3H), 3.97-3.55 (m, 4H), 2.97 (s, 3H), 2.84 (s, 3H), 2.37 (s, 3H), 2.08-2.01 (m, 2H), 1.81-1.71 (m, 2H).

Example 46: 6-[[6-(3-cyano-4-[[(3R,4S)-3-fluoropiperidin-4-yl]oxy]phenyl)pyrimidin-4-yl]amino]-2-methoxy-N,N-dimethylpyridine-3-carboxamide

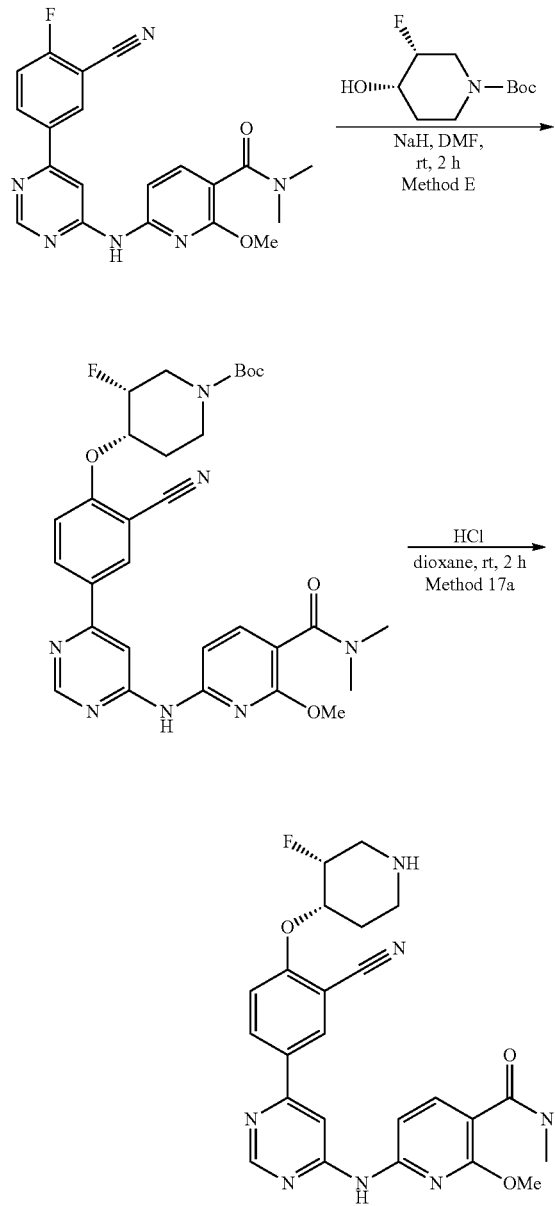

The title compound was prepared from tert-butyl (3R,4S)-3-fluoro-4-hydroxypiperidine-1-carboxylate and 6-[[6-(3-cyano-4-fluorophenyl)pyrimidin-4-yl]amino]-2-methoxy-N,N-dimethylpyridine-3-carboxamide using Method K and 17a. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 20% to 42% gradient in 7 min; detector, UV 254 nm. 6-[[6-(3-cyano-4-[[(3R,4S)-3-fluoropiperidin-4-yl]oxy]phenyl)pyrimidin-4-yl]amino]-2-methoxy-N,N-dimethylpyridine-3-carboxamide was obtained as white solid (32 mg, 34% for 2 steps). HPLC: 99.1% purity, RT=3.00 min. MS: m/z=492.2 [M+H]$^+$. $^1$H NMR (300 MHz, DMSO-d$_6$) δ 10.40 (s, 1H), 8.81 (s, 1H), 8.49-8.24 (m, 3H), 7.70-7.50 (m, 2H), 7.29-7.14 (m, 1H), 5.10-4.96 (m, 1H), 4.94-4.66 (m, 1H), 4.02 (s, 3H), 3.20-3.05 (m, 1H), 2.97 (s, 3H), 2.89-2.56 (m, 6H), 2.02-1.74 (m, 2H).

Example 47: 6-[[6-(3-cyano-4-[[(3R,4S)-3-fluoro-1-(2-hydroxyacetyl)piperidin-4-yl]oxy]phenyl)pyrimidin-4-yl]amino]-2-methoxy-N,N-dimethylpyridine-3-carboxamide

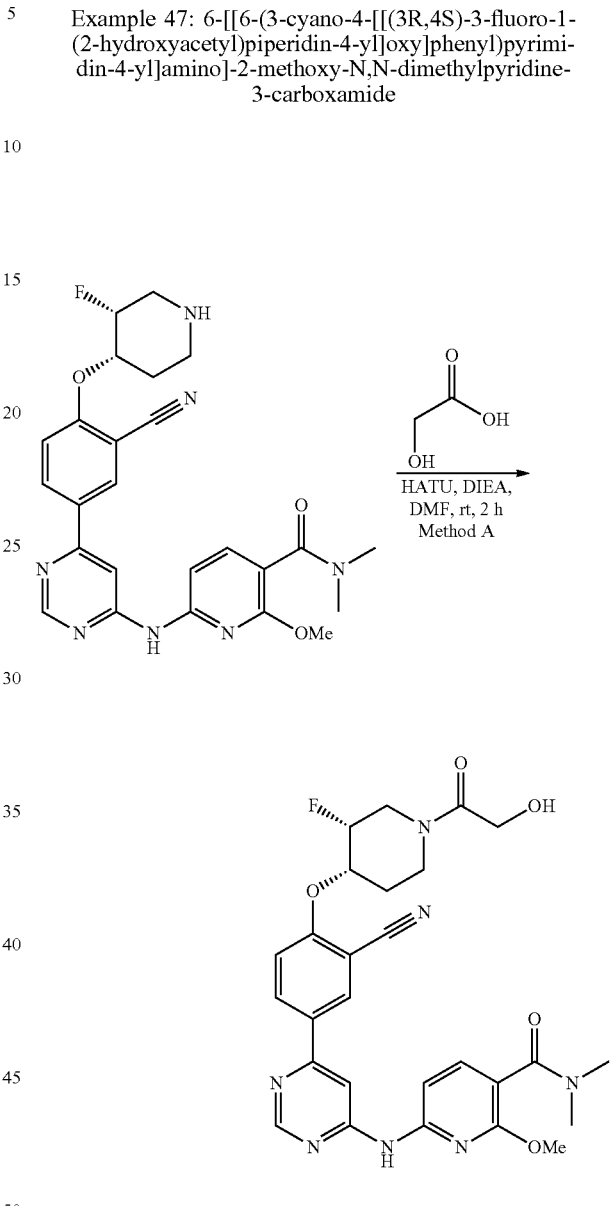

The title compound was prepared from 6-[[6-(3-cyano-4-[[(3R,4S)-3-fluoropiperidin-4-yl]oxy]phenyl)pyrimidin-4-yl]amino]-2-methoxy-N,N-dimethylpyridine-3-carboxamide and 2-hydroxyacetic acid using Method A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 22% to 33% gradient in 7 min; detector, UV 254 nm. 6-[[6-(3-cyano-4-[[(3R,4S)-3-fluoro-1-(2-hydroxyacetyl)piperidin-4-yl]oxy]phenyl)pyrimidin-4-yl]amino]-2-methoxy-N,N-dimethylpyridine-3-carboxamide was obtained as off-white solid (29 mg, 57%). HPLC: 92.9% purity, RT=3.12 min. MS: m/z=550.2 [M+H]$^+$. $^1$H NMR (300 MHz, DMSO-d$_6$) δ 10.41 (s, 1H), 8.82 (s, 1H), 8.53-8.24 (m, 3H), 7.74-7.55 (m, 2H), 7.31-7.16 (m, 1H), 5.22-4.89 (m, 2H), 4.69 (br s, 1H), 4.45-3.86 (m, 7H), 3.78-3.08 (m, 2H), 3.32 (s, 3H), 2.97 (s, 3H), 2.84 (s, 3H), 2.03-1.70 (m, 2H).

Example 48: 6-[(6-[3-cyano-4-[(3,3-difluoro-1-methylpiperidin-4-yl)oxy]phenyl]pyrimidin-4-yl)amino]-2-methoxy-N,N-dimethylpyridine-3-carboxamide

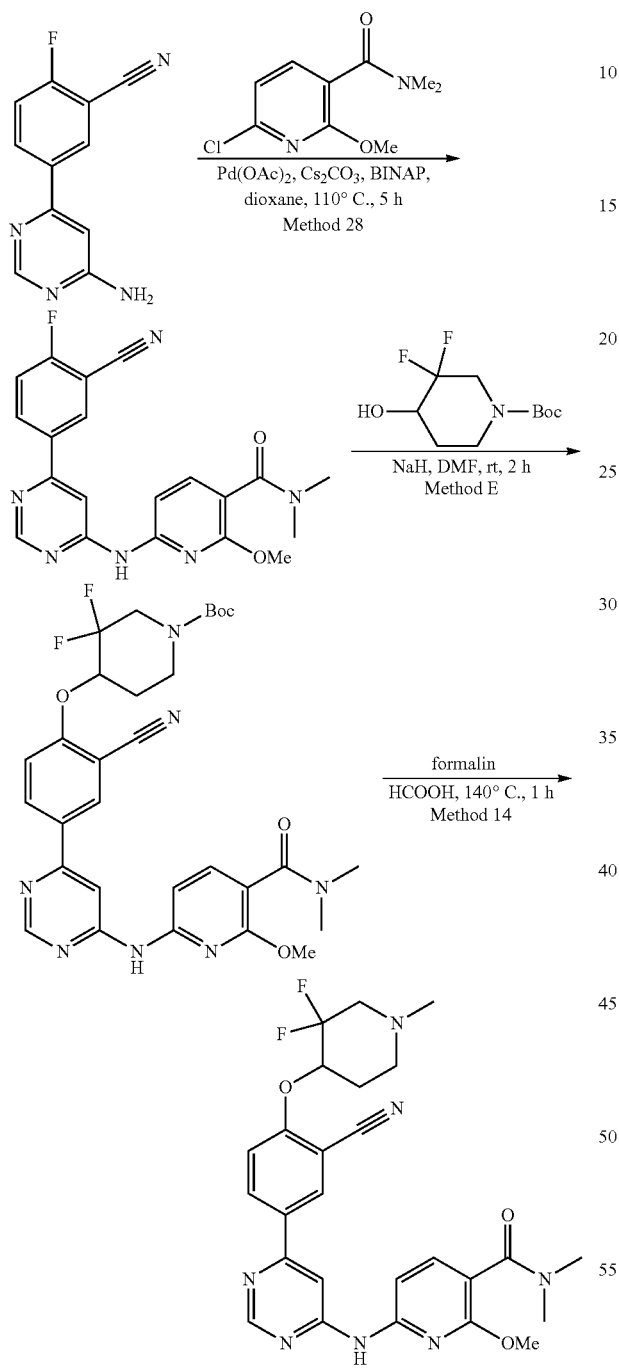

The title compound was prepared from 5-(6-aminopyrimidin-4-yl)-2-fluorobenzonitrile, 6-chloro-2-methoxy-N,N-dimethylnicotinamide, tert-butyl 3,3-difluoro-4-hydroxypiperidine-1-carboxylate, and formalin using Method 28, E and 14. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 30% to 49% gradient in 7 min; detector, UV 254 nm. 6-[(6-[3-cyano-4-[(3,3-difluoro-1-methylpiperidin-4-yl)oxy]phenyl]pyrimidin-4-yl)amino]-2-methoxy-N,N-dimethylpyridine-3-carboxamide was obtained as off-white solid (17 mg, 10% for 3 steps). HPLC: 98.4% purity, RT=2.60 min. MS: m/z=524.5 [M+H]$^+$. $^1$H NMR (300 MHz, DMSO-d$_6$) δ 10.42 (s, 1H), 8.82 (s, 1H), 8.48-8.37 (m, 2H), 8.40-8.28 (m, 1H), 7.69-7.59 (m, 2H), 7.26-7.17 (m, 1H), 5.26-4.99 (m, 1H), 4.02 (s, 3H), 2.97 (s, 3H), 2.95-2.86 (m, 1H), 2.84 (s, 3H), 2.81-2.64 (m, 3H), 2.28 (s, 3H), 2.16-1.84 (m, 2H).

Example 49: 6-[[6-(3-cyano-4-[[3,3-difluoro-1-(2-hydroxyacetyl)piperidin-4-yl]oxy]phenyl) pyrimidin-4-yl]amino]-2-methoxy-N,N-dimethylpyridine-3-carboxamide

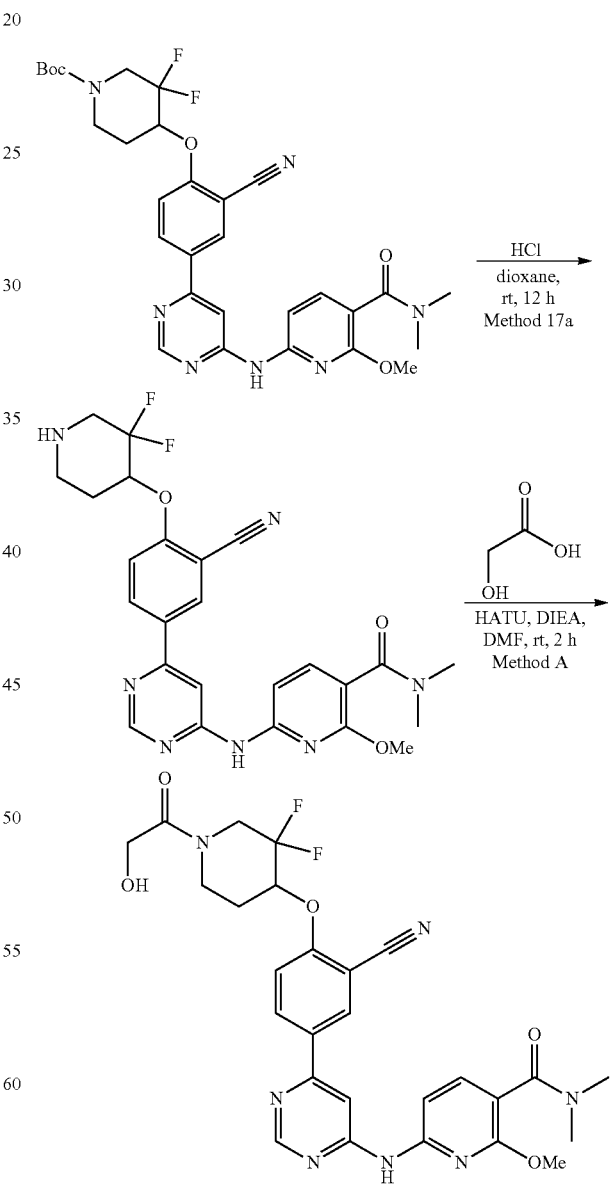

The title compound was prepared from tert-butyl 4-[2-cyano-4-(6-[[5-(dimethylcarbamoyl)-6-methoxypyridin-2- yl]amino]pyrimidin-4-yl)phenoxy]-3,3-difluoropiperidine-1-carboxylate and 2-hydroxyacetic acid using Method 17a and A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 35% gradient in 10 min; detector, UV 254 nm. 6-[[6-(3-cyano-4-[[3,3-difluoro-1-(2-hydroxyacetyl)piperidin-4-yl]oxy]phenyl)pyrimidin-4-yl]amino]-2-methoxy-N,N-dimethylpyridine-3-carboxamide was obtained as off-white solid (13 mg, 16% for 2 steps). HPLC: 99.1% purity, RT=3.28 min. MS: m/z=568.2 [M+H]$^+$. $^1$H NMR (300 MHz, DMSO-d$_6$) δ 10.43 (s, 1H), 8.83 (s, 1H), 8.55-8.31 (m, 3H), 7.71-7.59 (m, 2H), 7.26-7.17 (m, 1H), 5.42-5.29 (m, 1H), 4.93-4.84 (m, 1H), 4.24-3.76 (m, 7H), 3.70-3.39 (m, 2H), 2.97 (s, 3H), 2.84 (s, 3H), 2.25-1.76 (m, 2H).

Example 50: 5-(6-[[6-methoxy-5-(4-methylpiperazin-1-yl)pyridin-2-yl]amino]pyrimidin-4-yl)-2-(piperidin-4-yloxy)benzonitrile

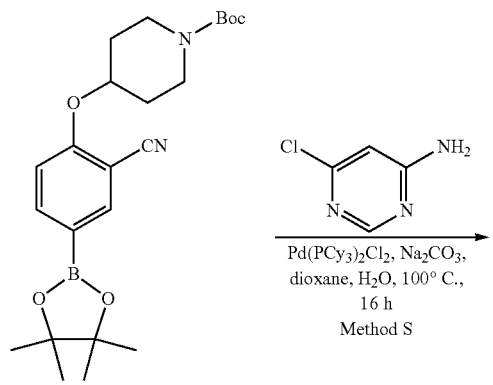

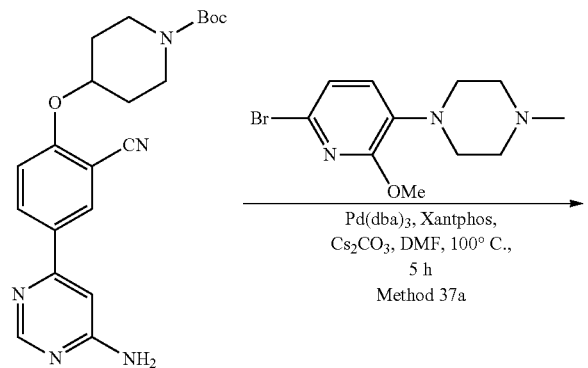

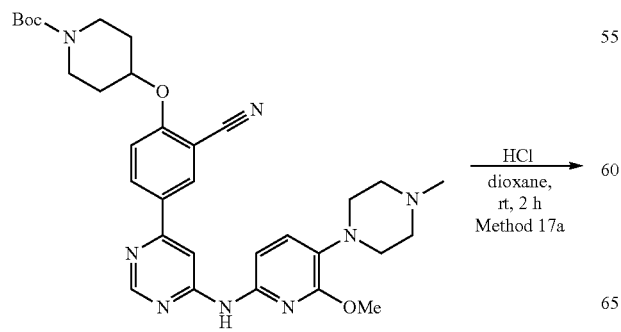

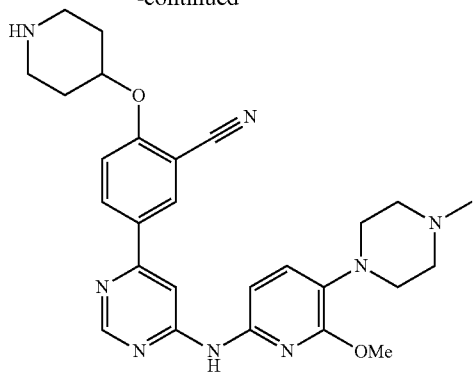

The title compound was prepared from tert-butyl 4-(2-cyano-4-(4,4,5,5-tetramethyl-1,3,2-dioxaborolan-2-yl)phenoxy)piperidine-1-carboxylate, 6-chloropyrimidin-4-amine, and 1-(6-bromo-2-methoxypyridin-3-yl)-4-methylpiperazine using Method S, 37a and 17a. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 22% to 42% gradient in 7 min; detector, UV 254 nm. 5-(6-[[6-methoxy-5-(4-methylpiperazin-1-yl)pyridin-2-yl]amino]pyrimidin-4-yl)-2-(piperidin-4-yloxy)benzonitrile was obtained as yellow solid (27 mg, 6.5% for 3 steps). HPLC: 99.5% purity, RT=2.60 min. MS: m/z=501.3 [M+H]$^+$. $^1$H NMR (300 MHz, DMSO-d$_6$) δ 9.95 (s, 1H), 8.71 (s, 1H), 8.36-8.21 (m, 2H), 8.18 (s, 1H), 7.53-7.43 (m, 1H), 7.32-7.23 (m, 1H), 7.22-7.13 (m, 1H), 4.81-4.69 (m, 1H), 3.98 (s, 3H), 2.98-2.91 (m, 6H), 2.67-2.53 (m, 3H), 2.48-2.42 (m, 4H), 2.22 (s, 3H), 2.00-1.89 (m, 2H), 1.64-1.47 (m, 2H).

Example 51: 5-(6-[[6-methoxy-5-(4-methylpiperazin-1-yl)pyridin-2-yl]amino]pyrimidin-4-yl)-2-[(1-methylpiperidin-4-yl)oxy]benzonitrile

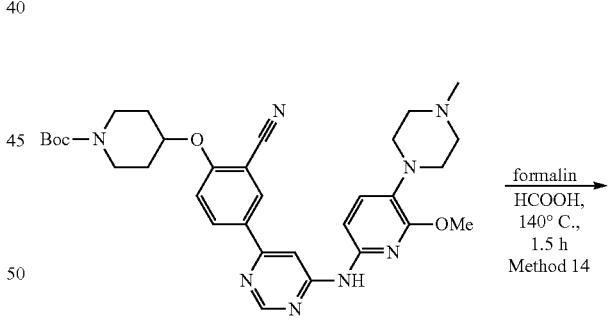

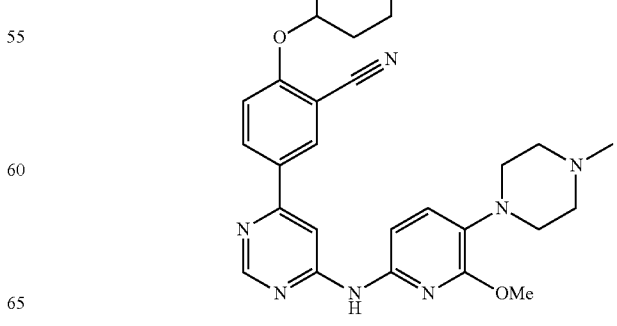

Method 14

To a solution of tert-butyl 4-[2-cyano-4-(6-[[6-methoxy-5-(4-methylpiperazin-1-yl)pyridin-2-yl]amino]pyrimidin-4-yl)phenoxy]piperidine-1-carboxylate (76 mg, 0.13 mmol) in HCOOH (10 mL) was added formalin (6 mL, 164 mmol) at room temperature. The resulting mixture was stirred for 1.5 h at 140° C. When the reaction was done, the solution was concentrated under reduced pressure and the residue was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 5% to 53% gradient in 10 min; detector, UV 254 nm. 5-(6-[[6-methoxy-5-(4-methylpiperazin-1-yl)pyridin-2-yl]amino]pyrimidin-4-yl)-2-[(1-methylpiperidin-4-yl)oxy]benzonitrile was obtained as yellow solid (20 mg, 31%). HPLC: 99.4% purity, RT=2.64 min. MS: m/z=515.2 [M+H]$^+$. $^1$H NMR (300 MHz, DMSO-$d_6$) δ 9.95 (s, 1H), 8.71 (s, 1H), 8.35-8.14 (m, 3H), 7.53-7.43 (m, 1H), 7.32-7.23 (m, 1H), 7.22-7.13 (m, 1H), 4.77-4.68 (m, 1H), 3.98 (s, 3H), 2.98-2.92 (m, 4H), 2.61-2.51 (m, 2H), 2.48-2.42 (m, 4H), 2.34-2.24 (m, 2H), 2.22 (s, 3H), 2.19 (s, 3H), 2.04-1.90 (m, 2H), 1.80-1.67 (m, 2H).

Example 52: 2-[[1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile

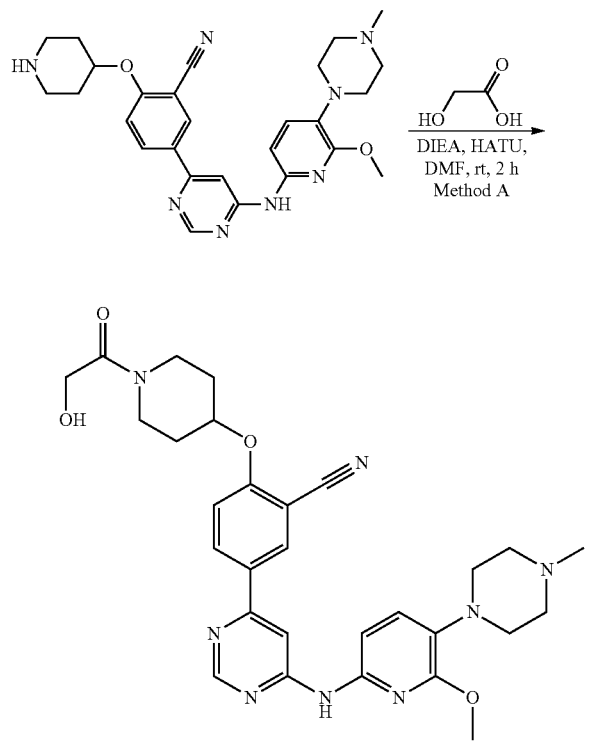

The title compound was prepared from 2-hydroxyacetic acid and 5-(6-[[6-methoxy-5-(4-methylpiperazin-1-yl)pyridin-2-yl]amino]pyrimidin-4-yl)-2-(piperidin-4-yloxy)benzonitrile using Method A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 30% to 42% gradient in 7 min; detector, UV 254 nm. 2-[[1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile was obtained as yellow solid (25 mg, 15%). HPLC: 99.4% purity, RT=1.16 min. MS: m/z=559.4 [M+H]$^+$. $^1$H NMR (300 MHz, DMSO-$d_6$) δ 9.97 (s, 1H), 8.72 (s, 1H), 8.39-8.24 (m, 2H), 8.20 (br s, 1H), 7.59-7.49 (m, 1H), 7.32-7.23 (m, 1H), 7.22-7.13 (m, 1H), 5.02-4.93 (m, 1H), 4.61-4.51 (m, 1H), 4.13 (d, J=5.4 Hz, 2H), 3.98 (s, 3H), 3.77-3.40 (m, 4H), 2.98-2.92 (m, 4H), 2.48-2.42 (m, 4H), 2.22 (s, 3H), 2.02-1.96 (m, 2H), 1.74-1.67 (m, 2H).

Example 53: 2-[[1-(2-hydroxypropanoyl)piperidin-4-yl]oxy]-5-(6-[[6-methoxy-5-(4-methylpiperazin-1-yl)pyridin-2-yl]amino]pyrimidin-4-yl)benzonitrile

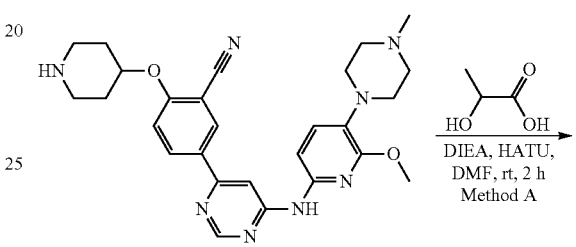

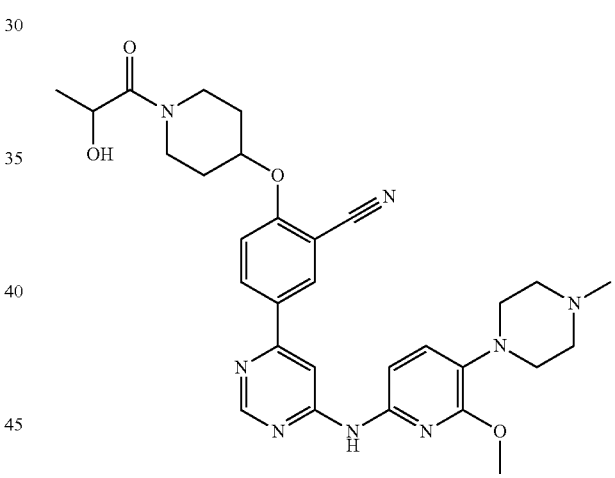

The title compound was prepared from 2-hydroxypropanoic acid and 5-(6-[[6-methoxy-5-(4-methylpiperazin-1-yl)pyridin-2-yl]amino]pyrimidin-4-yl)-2-(piperidin-4-yloxy)benzonitrile using Method A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3.H_2O$), 25% to 42% gradient in 7 min; detector, UV 254 nm. 2-[[1-(2-hydroxypropanoyl)piperidin-4-yl]oxy]-5-(6-[[6-methoxy-5-(4-methylpiperazin-1-yl)pyridin-2-yl]amino]pyrimidin-4-yl)benzonitrile was obtained as yellow solid (28 mg, 17%). HPLC: 98.6% purity, RT=1.18 min. MS: m/z=573.4 [M+H]$^+$. $^1$H NMR (300 MHz, DMSO-$d_6$) δ 9.97 (s, 1H), 8.72 (s, 1H), 8.39-8.24 (m, 2H), 8.20 (s, 1H), 7.59-7.49 (m, 1H), 7.33-7.23 (m, 1H), 7.22-7.13 (m, 1H), 4.98-4.90 (m, 2H), 4.54-4.39 (m, 1H), 3.98 (s, 3H), 3.81-3.75 (m, 2H), 3.55-3.48 (m, 2H), 2.98-2.92 (m, 4H), 2.48-2.42 (m, 4H), 2.22 (s, 3H), 2.11-1.85 (m, 2H), 1.83-1.56 (m, 2H), 1.20 (d, J=6.5 Hz, 3H).

Example 54: 5-(6-[[6-methoxy-5-(4-methylpiperazin-1-yl)pyridin-2-yl]amino]pyrimidin-4-yl)-2-([1-[(1,3-oxazol-4-yl)carbonyl]piperidin-4-yl]oxy)benzonitrile

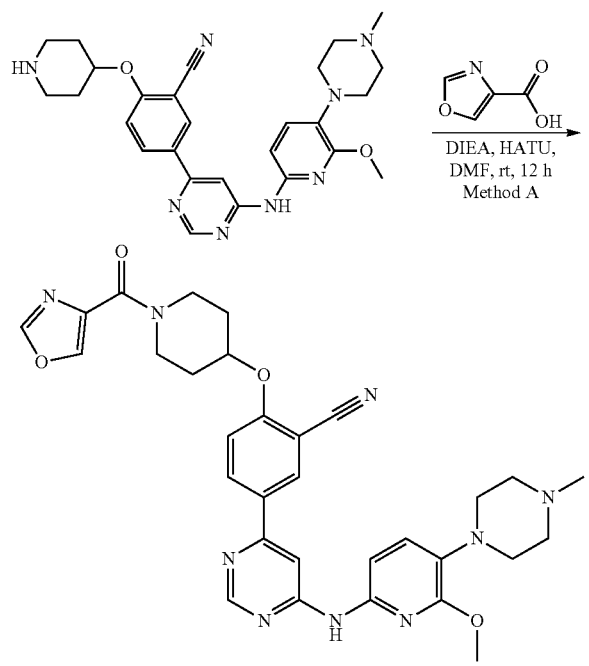

The title compound was prepared from 5-(6-[[6-methoxy-5-(4-methylpiperazin-1-yl)pyridin-2-yl]amino]pyrimidin-4-yl)-2-(piperidin-4-yloxy)benzonitrile and 1,3-oxazole-4-carboxylic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 30% to 40% gradient in 7 min; detector, UV 254 nm. 5-(6-[[6-methoxy-5-(4-methylpiperazin-1-yl)pyridin-2-yl]amino]pyrimidin-4-yl)-2-([1-[(1,3-oxazol-4-yl)carbonyl]piperidin-4-yl]oxy)benzonitrile was obtained as yellow solid (27 mg, 16%). HPLC: 98.8% purity, RT=1.23 min. MS: m/z=596.4 [M+H]$^+$. $^1$H NMR (300 MHz, DMSO-d$_6$) δ 9.97 (s, 1H), 8.72 (s, 1H), 8.63-8.56 (m, 1H), 8.55-8.48 (m, 1H), 8.39-8.24 (m, 2H), 8.20 (s, 1H), 7.60-7.51 (m, 1H), 7.33-7.23 (m, 1H), 7.22-7.13 (m, 1H), 5.07-5.00 (m, 1H), 4.16-3.82 (m, 8H), 3.66-3.59 (m, 1H), 2.98-2.92 (m, 4H), 2.48-2.40 (m, 4H), 2.22 (s, 3H), 2.16-1.99 (m, 2H), 1.90-1.66 (m, 2H).

Example 55: 5-(6-[[6-methoxy-5-(4-methylpiperazin-1-yl)pyridin-2-yl]amino]pyrimidin-4-yl)-2-([1-[(5-methyl-1H-1,2,4-triazol-3-yl)carbonyl]piperidin-4-yl]oxy)benzonitrile

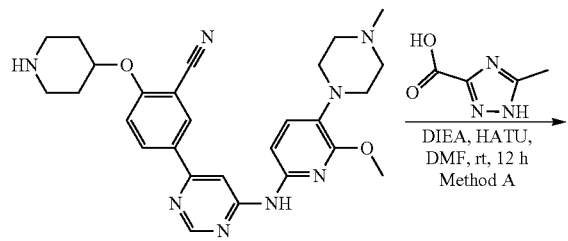

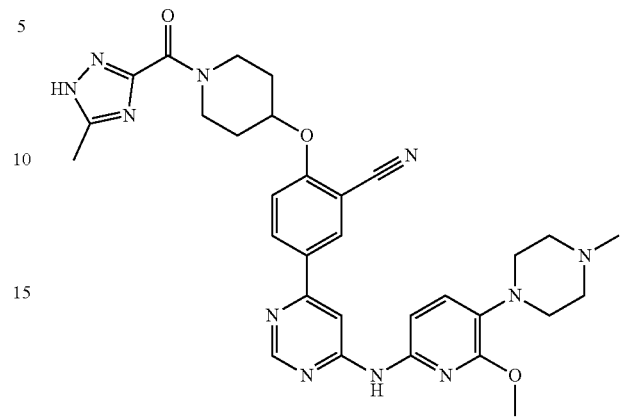

The title compound was prepared from 5-(6-[[6-methoxy-5-(4-methylpiperazin-1-yl)pyridin-2-yl]amino]pyrimidin-4-yl)-2-(piperidin-4-yloxy)benzonitrile and 5-methyl-1H-1,2,4-triazole-3-carboxylic acid using Method A. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 35% to 65% gradient in 7 min; detector, UV 254 nm. 5-(6-[[6-methoxy-5-(4-methylpiperazin-1-yl)pyridin-2-yl]amino]pyrimidin-4-yl)-2-([1-[(5-methyl-1H-1,2,4-triazol-3-yl)carbonyl]piperidin-4-yl]oxy)benzonitrile was obtained as yellow solid (25 mg, 14%). HPLC: 99.5% purity, RT=1.16 min. MS: m/z=610.4 [M+H]$^+$. $^1$H NMR (300 MHz, DMSO-d$_6$) δ 14.06 (br s, 1H), 9.97 (s, 1H), 8.72 (s, 1H), 8.39-8.24 (m, 2H), 8.20 (s, 1H), 7.60-7.50 (m, 1H), 7.33-7.23 (m, 1H), 7.22-7.13 (m, 1H), 5.07-5.00 (m, 1H), 3.98 (s, 3H), 3.91-3.84 (m, 2H), 3.72-3.62 (m, 2H), 2.98-2.92 (m, 4H), 2.49-2.42 (m, 4H), 2.37 (s, 3H), 2.22 (s, 3H), 2.08-2.02 (m, 2H), 1.80-1.74 (m, 2H).

Example 56: 5-(6-[[6-methoxy-5-(4-methylpiperazin-1-yl)pyridin-2-yl]amino]pyrimidin-4-yl)-2-([1-[(1,3-oxazol-5-yl)carbonyl]piperidin-4-yl]oxy)benzonitrile

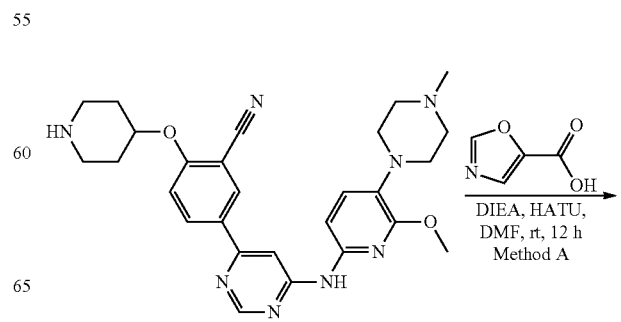

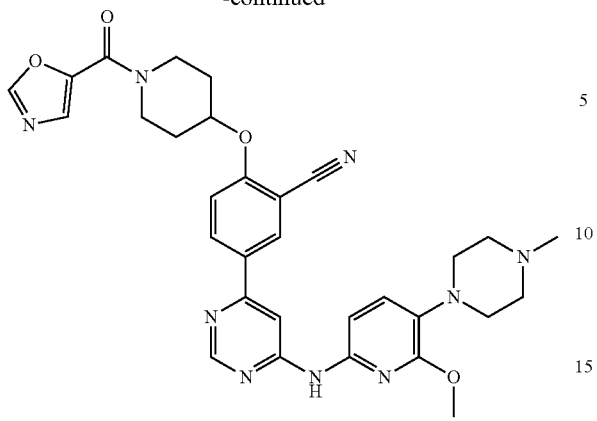

The title compound was prepared from 5-(6-[[6-methoxy-5-(4-methylpiperazin-1-yl)pyridin-2-yl]amino]pyrimidin-4-yl)-2-(piperidin-4-yloxy)benzonitrile and 1,3-oxazole-5-carboxylic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 40% gradient in 7 min; detector, UV 254 nm. 5-(6-[[6-methoxy-5-(4-methylpiperazin-1-yl)pyridin-2-yl]amino]pyrimidin-4-yl)-2-([1-[(1,3-oxazol-5-yl)carbonyl]piperidin-4-yl]oxy)benzonitrile was obtained as yellow solid (29 mg, 17%). HPLC: 98.5% purity, RT=2.44 min. MS: m/z=596.2 [M+H]$^+$. $^1$H NMR (300 MHz, Methanol-d$_4$) δ 8.70-8.63 (m, 1H), 8.35 (s, 1H), 8.33-8.23 (m, 2H), 8.07 (s, 1H), 7.69 (s, 1H), 7.48-7.38 (m, 1H), 7.36-7.27 (m, 1H), 7.27-7.17 (m, 1H), 5.08-4.99 (m, 1H), 4.06 (s, 3H), 3.96-3.89 (m, 4H), 3.11-3.04 (m, 4H), 2.68-2.62 (m, 4H), 2.36 (s, 3H), 2.17-2.10 (m, 2H), 2.08-1.93 (m, 2H).

Example 57: 2-[[(3R,4S)-3-fluoro-1-[(1H-1,2,3-triazol-5-yl)carbonyl]piperidin-4-yl]oxy]-5-(6-[[6-methoxy-5-(4-methylpiperazin-1-yl)pyridin-2-yl]amino]pyrimidin-4-yl)benzonitrile

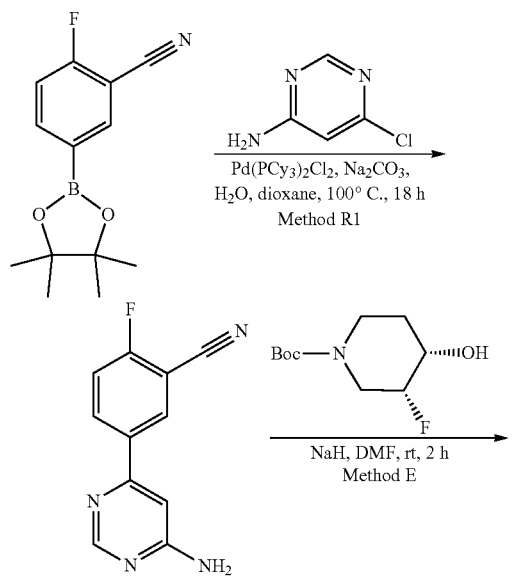

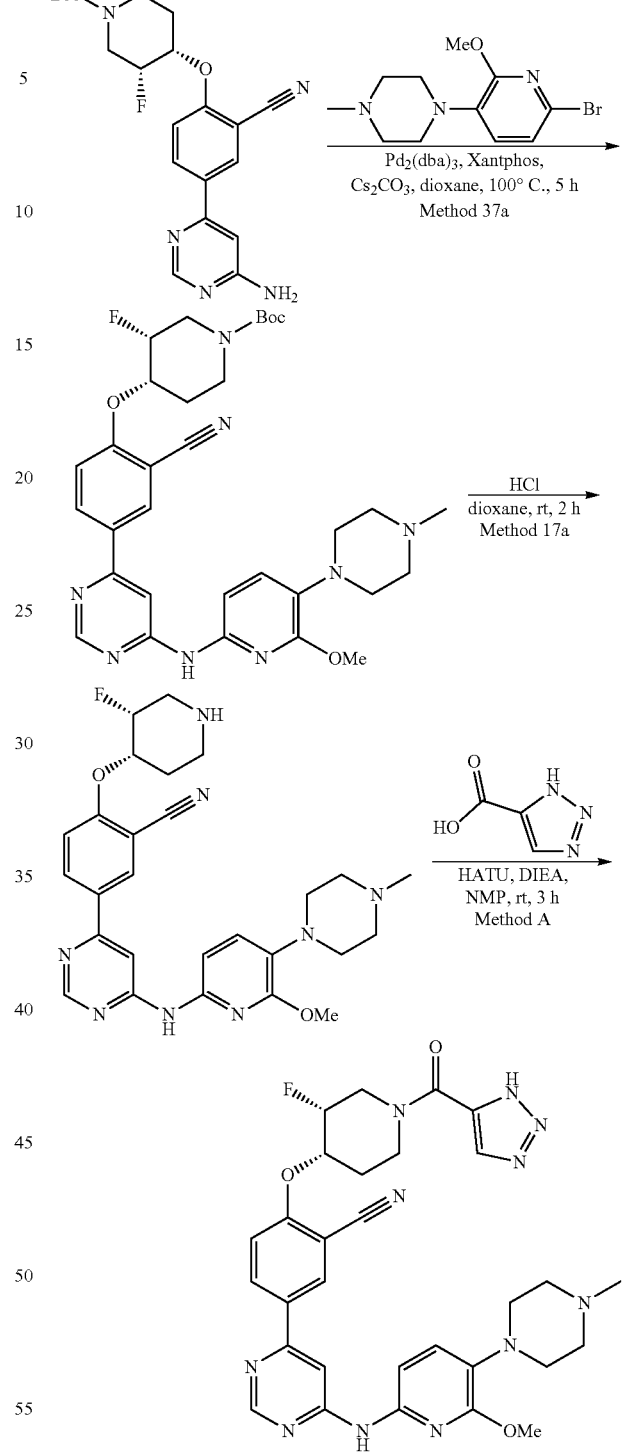

Method R1

5-(6-aminopyrimidin-4-yl)-2-fluorobenzonitrile: To a solution of 2-fluoro-5-(tetramethyl-1,3,2-dioxaborolan-2-yl)benzonitrile (570 mg, 2.31 mmol) in 1,4-dioxane (120 mL) was added 6-chloropyrimidin-4-amine (302 mg, 2.33 mmol), Pd(Pcy$_3$)$_2$Cl$_2$ (170 mg, 0.23 mmol) and a solution of sodium carbonate in water (10 M, 4.6 mL, 46 mmol) at the room temperature. The resulting solution was stirred for 18 h at 100° C. When the reaction was done, the solids in the reaction mixture were filtered out and the filtrate was concentrated under reduced pressure. The residue was purified by flash chromatography eluting with EtOAc in hexane (0% to 80% gradient) to yield 5-(6-aminopyrimidin-4-yl)-2-fluorobenzonitrile as yellow solid (441 mg, 89%). MS: m/z=215.0 [M+H]$^+$.

2-[[(3R,4S)-3-fluoro-1-[(1H-1,2,3-triazol-5-yl)carbonyl]piperidin-4-yl]oxy]-5-(6-[[6-methoxy-5-(4-methylpiperazin-1-yl)pyridin-2-yl]amino]pyrimidin-4-yl)benzonitrile: 2-[[(3R,4S)-3-fluoro-1-[(1H-1,2,3-triazol-5-yl)carbonyl]piperidin-4-yl]oxy]-5-(6-[[6-methoxy-5-(4-methylpiperazin-1-yl)pyridin-2-yl]amino]pyrimidin-4-yl)benzonitrile was prepared from 5-(6-aminopyrimidin-4-yl)-2-fluorobenzonitrile, (3R,4S)-tert-butyl 3-fluoro-4-hydroxypiperidine-1-carboxylate, 1-(6-bromo-2-methoxypyridin-3-yl)-4-methylpiperazine and 3H-1,2,3-triazole-4-carboxylic acid using Method E, 37a, 17a and A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 5% to 47% gradient in 8 min; detector, UV 254 nm. 2-[[(3R,4S)-3-fluoro-1-[(1H-1,2,3-triazol-5-yl)carbonyl]piperidin-4-yl]oxy]-5-(6-[[6-methoxy-5-(4-methylpiperazin-1-yl)pyridin-2-yl]amino]pyrimidin-4-yl)benzonitrile was obtained as yellow solid (18 mg, 1.1% for 4 steps). HPLC: 98.9% purity, RT=1.02 min. MS: m/z=307.5 [M+H]$^+$. $^1$H NMR (400 MHz, DMSO-d$_6$) δ 9.97 (s, 1H), 8.73 (s, 1H), 8.41-8.27 (m, 3H), 8.23 (s, 1H), 7.66-7.58 (m, 1H), 7.32-7.23 (m, 1H), 7.23-7.15 (m, 1H), 5.26-4.86 (m, 2.5H), 4.62-4.28 (m, 1.5H), 3.98 (s, 3H), 3.96-3.14 (m, 2H), 3.04-2.89 (m, 4H), 2.48-2.38 (m, 4H), 2.22 (s, 3H), 2.12-1.83 (m, 2H).

Example 58: 2-[(3,3-difluoro-1-methylpiperidin-4-yl)oxy]-5-(6-[[6-methoxy-5-(4-methylpiperazin-1-yl)pyridin-2-yl]amino]pyrimidin-4-yl)benzonitrile

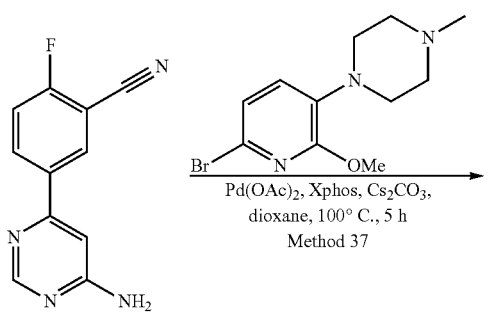

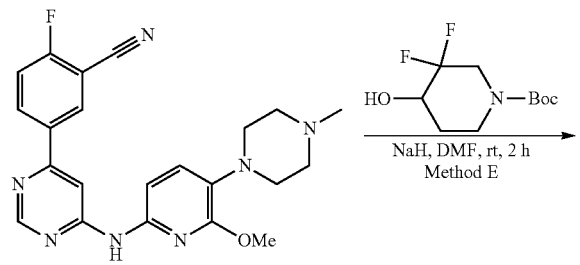

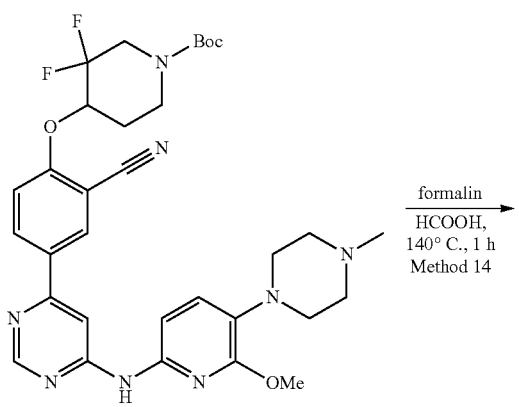

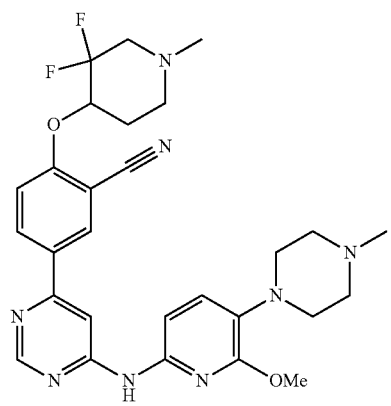

The title compound was prepared from 5-(6-aminopyrimidin-4-yl)-2-fluorobenzonitrile, 1-(6-bromo-2-methoxypyridin-3-yl)-4-methylpiperazine, tert-butyl 3,3-difluoro-4-hydroxypiperidine-1-carboxylate and formalin using Method 37, E and 14. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 5% to 38% gradient in 7 min; detector, UV 254 nm. 2-[(3,3-difluoro-1-methylpiperidin-4-yl)oxy]-5-(6-[[6-methoxy-5-(4-methylpiperazin-1-yl)pyridin-2-yl]amino]pyrimidin-4-yl)benzonitrile was obtained as yellow solid (15 mg, 9% for 3 steps). HPLC: 96.4% purity, RT=1.93 min. MS: m/z=551.3 [M+H]$^+$. $^1$H NMR (300 MHz, DMSO-d$_6$) δ 9.98 (s, 1H), 8.72 (s, 1H), 8.40-8.25 (m, 2H), 8.21 (s, 1H), 7.67-7.58 (m, 1H), 7.32-7.23 (m, 1H), 7.21-7.12 (m, 1H), 5.15-5.07 (m, 1H), 3.98 (s, 3H), 3.03-2.82 (m, 5H), 2.81-2.55 (m, 2H), 2.48-2.42 (m, 5H), 2.28 (s, 3H), 2.22 (s, 3H), 2.16-1.84 (m, 2H).

Example 59: 2-[[3,3-difluoro-1-(2-hydroxyacetyl)
piperidin-4-yl]oxy]-5-(6-[[6-methoxy-5-(4-methylpiperazin-1-yl)pyridin-2-yl]amino]pyrimidin-4-yl)benzonitrile

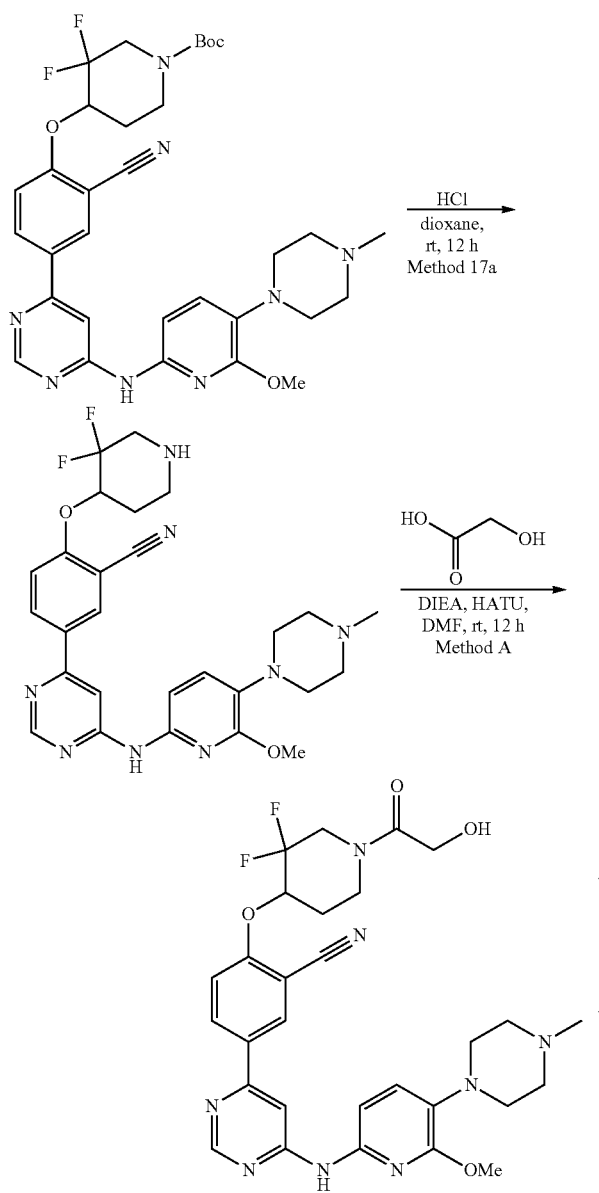

The title compound was prepared from tert-butyl 4-(2-cyano-4-(6-(6-methoxy-5-(4-methylpiperazin-1-yl)pyridin-2-ylamino)pyrimidin-4-yl)phenoxy)-3,3-difluoropiperidine-1-carboxylate and 2-hydroxyacetic acid using Method 17a and A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 47% gradient in 7 min; detector, UV 254 nm. 2-[[3,3-difluoro-1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile was obtained as yellow solid (15 mg, 6% for 2 steps). HPLC: 98.0% purity, RT=9.06 min. MS: m/z=595.1 [M+H]$^+$. $^1$H NMR (300 MHz, DMSO-d$_6$) δ 10.00 (s, 1H), 8.73 (s, 1H), 8.42-8.28 (m, 2H), 8.23 (s, 1H), 7.69-7.59 (m, 1H), 7.33-7.23 (m, 1H), 7.21-7.12 (m, 1H), 5.40-5.31 (m, 1H), 4.93-4.85 (m, 1H), 4.24-3.42 (m, 9H), 2.98-2.92 (m, 4H), 2.49-2.42 (m, 4H), 2.22 (s, 3H), 2.17-1.78 (m, 2H).

Example 60 & 61: 2-[[(4S)-3,3-difluoro-1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile & 2-[[(4R)-3,3-difluoro-1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile

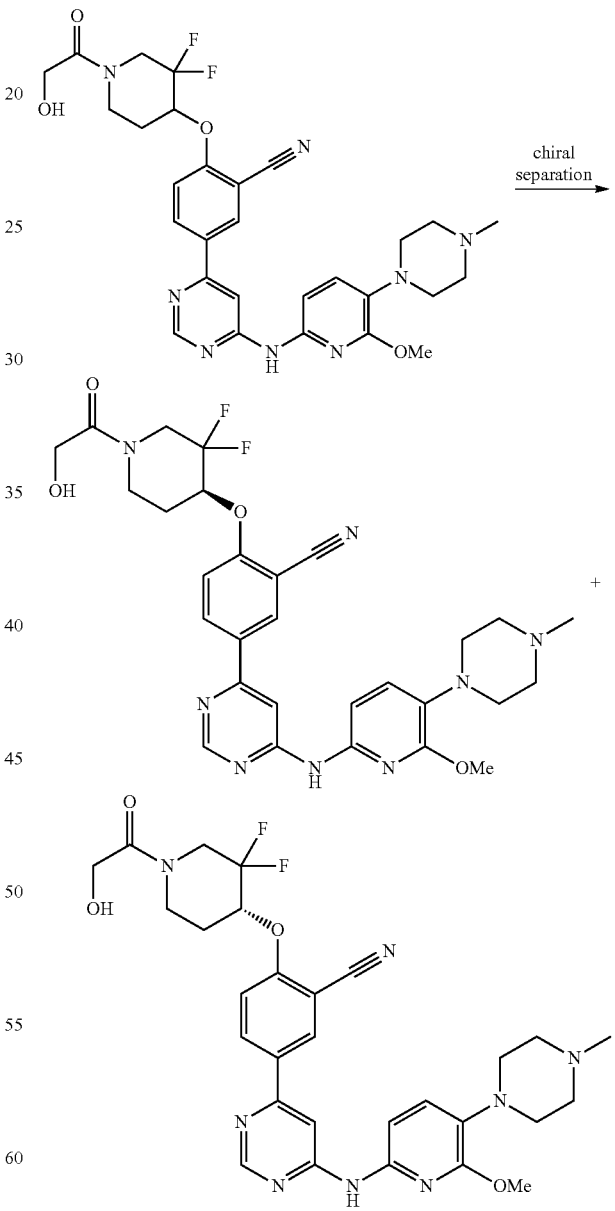

The two isomers were obtained by separation of 2-[[3,3-difluoro-1-(2-hydroxyacetyl)piperidin-4-yl]oxy]-5-(6-[[6-methoxy-5-(4-methylpiperazin-1-yl)pyridin-2-yl]amino]pyrimidin-4-yl)benzonitrile on chiral prep-HPLC under the following conditions: column, CHIRALPAK ID-3, 0.46×10 cm, 3 um; mobile phase, MtBE (with 0.1% DEA) in EtOH, 95% isocratic in 30 min; detector, UV 254 nm.

2-[[(4S)-3,3-difluoro-1-(2-hydroxyacetyl)piperidin-4-yl] oxy]-5-(6-[[6-methoxy-5-(4-methylpiperazin-1-yl)pyridin-2-yl]amino]pyrimidin-4-yl)benzonitrile: (100 mg, 67%, yellow solid) HPLC: 99.6% purity, RT=0.93 min. MS: m/z=595.3 [M+H]+. 1H NMR (300 MHz, DMSO-d6) δ 9.99 (s, 1H), 8.73 (s, 1H), 8.42-8.28 (m, 2H), 8.22 (s, 1H), 7.69-7.59 (m, 1H), 7.33-7.23 (m, 1H), 7.21-7.12 (m, 1H), 5.42-5.32 (m, 1H), 4.94-4.85 (m, 1H), 4.27-4.02 (m, 3H), 3.98 (s, 3H), 3.96-3.74 (m, 1H), 3.71-3.43 (m, 2H), 2.99-2.92 (m, 4H), 2.49-2.43 (m, 4H), 2.22 (s, 3H), 2.18-1.79 (m, 2H).

2-[[(4R)-3,3-difluoro-1-(2-hydroxyacetyl)piperidin-4-yl] oxy]-5-(6-[[6-methoxy-5-(4-methylpiperazin-1-yl)pyridin-2-yl]amino]pyrimidin-4-yl)benzonitrile: (98 mg, 68%, yellow solid) HPLC: 99.8% purity, RT=0.94 min. MS: m/z=595.3 [M+H]+. 1H NMR (300 MHz, DMSO-d6) δ 9.99 (s, 1H), 8.73 (s, 1H), 8.42-8.28 (m, 2H), 8.22 (s, 1H), 7.69-7.59 (m, 1H), 7.32-7.23 (m, 1H), 7.21-7.12 (m, 1H), 5.42-5.28 (m, 1H), 4.94-4.85 (m, 1H), 4.27-4.04 (m, 3H), 3.98 (s, 3H), 3.96-3.77 (m, 1H), 3.71-3.42 (m, 2H), 2.99-2.90 (m, 4H), 2.49-2.42 (m, 4H), 2.22 (s, 3H), 2.18-1.72 (m, 2H).

Example 62: 2-([3,3-difluoro-1-[(2S)-2-hydroxypropanoyl]piperidin-4-yl]oxy)-5-[6-([5-[(2S)-2,4-dimethylpiperazin-1-yl]-6-methoxypyridin-2-yl]amino) pyrimidin-4-yl]benzonitrile hydrochloride

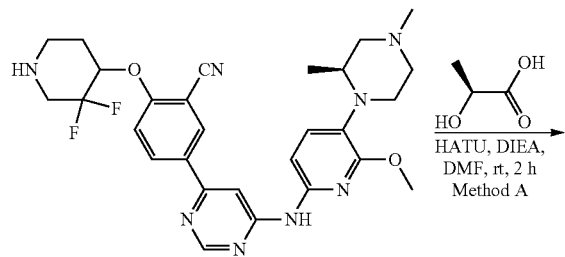

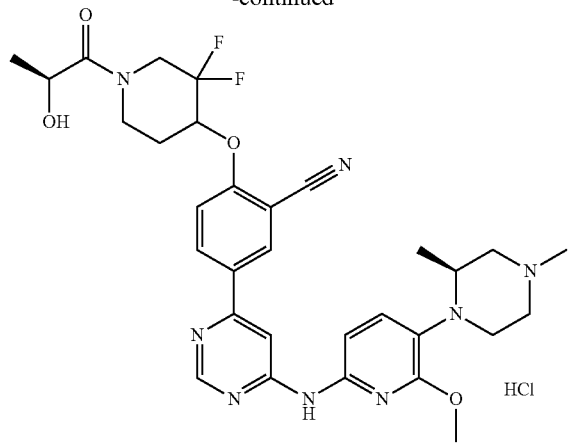

The title compound was prepared from 2-[(3,3-difluoropiperidin-4-yl)oxy]-5-[6-([5-[(2S)-2,4-dimethylpiperazin-1-yl]-6-methoxypyridin-2-yl]amino)pyrimidin-4-yl]benzonitrile and (S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 0.05% HCl), 18% to 40% gradient in 8 min; detector, UV 254 nm. 2-([3,3-difluoro-1-[(2S)-2-hydroxypropanoyl] piperidin-4-yl]oxy)-5-[6-([5-[(2S)-2,4-dimethylpiperazin-1-yl]-6-methoxypyridin-2-yl]amino)pyrimidin-4-yl]benzonitrile hydrochloride was obtained as orange solid (21 mg, 15%). HPLC: 96.4% purity, RT=8.70 min. MS: m/z=623.2 [M+H]+. 1H NMR (300 MHz, DMSO-d6) δ 9.06-8.96 (m, 1H), 8.55-8.47 (m, 1H), 8.42-8.32 (m, 1H), 7.84-7.70 (m, 2H), 7.47-7.38 (m, 1H), 7.26-7.17 (m, 1H), 5.52-5.45 (m, 1H), 4.53-4.42 (m, 1H), 4.26-4.14 (m, 1H), 3.98 (s, 3H), 3.85-3.79 (m, 3H), 3.72-2.89 (m, 7H), 2.79 (s, 3H), 2.23-1.70 (m, 2H), 1.20 (d, J=6.5 Hz, 3H), 1.12 (d, J=6.9 Hz, 1H), 0.90 (d, J=6.0 Hz, 2H).

Example 63: 2-([3,3-difluoro-1-[(2R)-2-hydroxypropanoyl]piperidin-4-yl]oxy)-5-[6-([5-[(2S)-2,4-dimethylpiperazin-1-yl]-6-methoxypyridin-2-yl]amino) pyrimidin-4-yl]benzonitrile hydrochloride

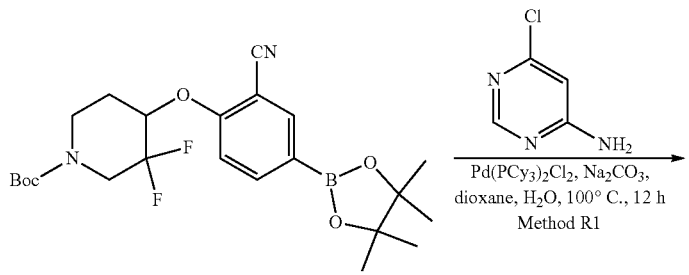

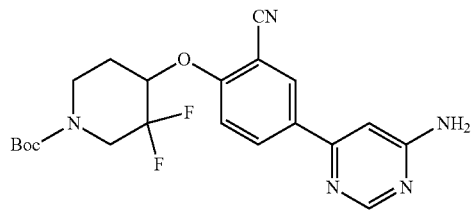

-continued
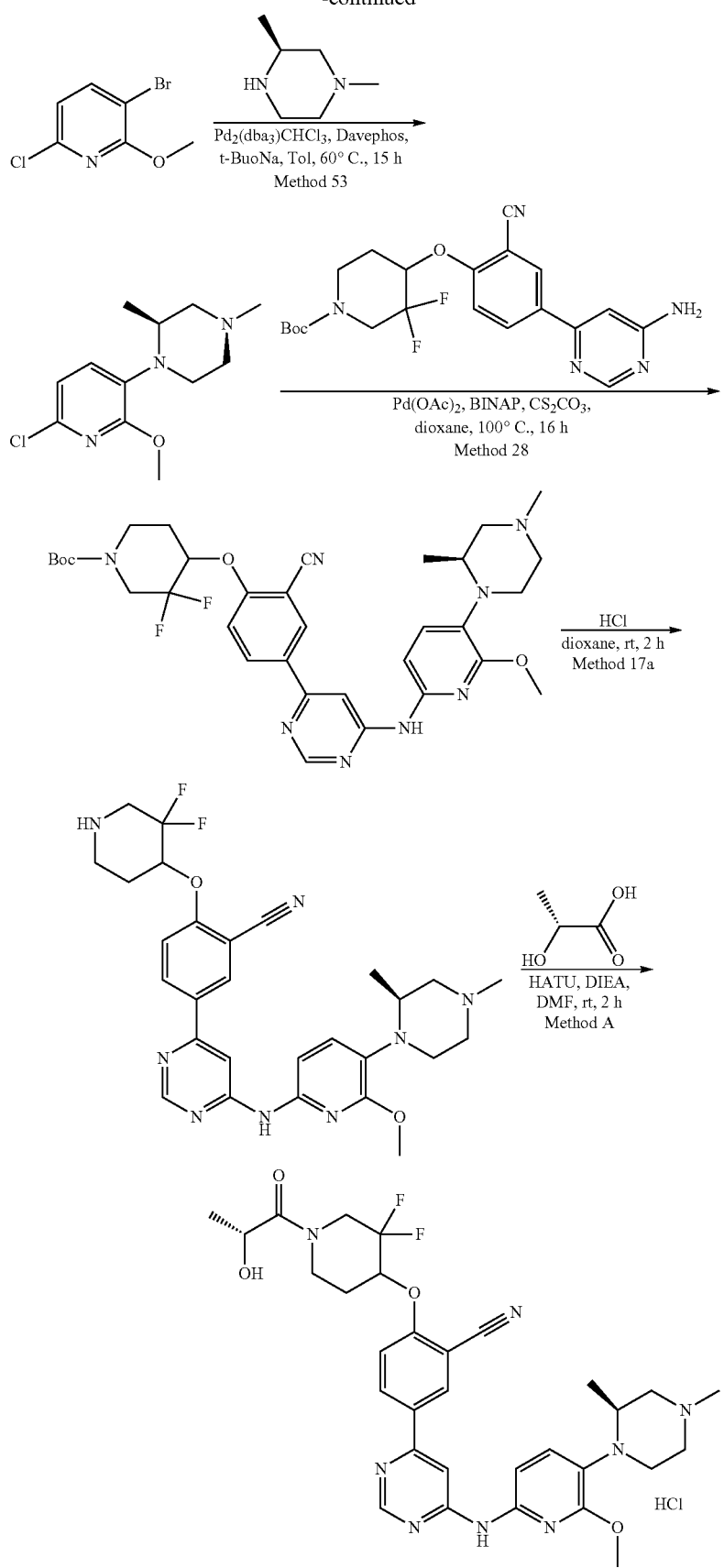

Method 53

(2S)-1-(6-chloro-2-methoxypyridin-3-yl)-2,4-dimethylpiperazine: To a solution of 3-bromo-6-chloro-2-methoxypyridine (1.47 g, 6.62 mmol) in toluene (20 mL) was added (3S)-1,3-dimethylpiperazine (760 mg, 6.66 mmol), Pd$_2$(dba)$_3$CHCl$_3$ (345 mg, 0.33 mmol), Davephos (393 mg, 1.00 mmol) and t-BuONa (960 mg, 9.98 mmol) at room temperature. The resulting mixture was stirred for 5 h at 60° C. When the reaction was done, the reaction mixture was concentrated under reduced pressure and the residue was purified by flash chromatography eluting with EtOAc in petroleum ether (0% to 85% gradient) to yield (2S)-1-(6-chloro-2-methoxypyridin-3-yl)-2,4-dimethylpiperazine as yellow oil (129 mg, 8%). MS: m/z=256.3 [M+H]$^+$.

2-([3,3-difluoro-1-[(2R)-2-hydroxypropanoyl]piperidin-4-yl]oxy)-5-[6-([5-[(2S)-2,4-dimethylpiperazin-1-yl]-6-methoxypyridin-2-yl]amino)pyrimidin-4-yl]benzonitrile hydrochloride: 2-([3,3-difluoro-1-[(2R)-2-hydroxypropanoyl]piperidin-4-yl]oxy)-5-[6-([5-[(2S)-2,4-dimethylpiperazin-1-yl]-6-methoxypyridin-2-yl]amino)pyrimidin-4-yl]benzonitrile hydrochloride was prepared from tert-butyl 4-(2-cyano-4-(4,4,5,5-tetramethyl-1,3,2-dioxaborolan-2-yl)phenoxy)-3,3-difluoropiperidine-1-carboxylate, 6-chloropyrimidin-4-amine, (2S)-1-(6-chloro-2-methoxypyridin-3-yl)-2,4-dimethylpiperazine and (R)-2-hydroxypropanoic acid using Method R1, 28, 17a and A. The final product was purified by prep-HPLC under the following conditions: column, XBridge Shield RP18 OBD Column, 150×19 mm, 5 um; mobile phase, acetonitrile in water (with 0.05% HCl), 18% to 40% gradient in 8 min; detector, UV 254 nm. 2-([3,3-difluoro-1-[(2R)-2-hydroxypropanoyl]piperidin-4-yl]oxy)-5-[6-([5-[(2S)-2,4-dimethylpiperazin-1-yl]-6-methoxypyridin-2-yl]amino)pyrimidin-4-yl]benzonitrile hydrochloride was obtained as orange solid (14 mg, 5% 4 steps). HPLC: 95.0% purity, RT=8.96 min. MS: m/z=623.1 [M+H]$^+$. $^1$H NMR (300 MHz, DMSO-d$_6$) δ 10.83 (s, 1H), 8.89 (s, 1H), 8.49-8.32 (m, 3H), 7.82-7.36 (m, 2H), 7.29-7.15 (m, 1H), 5.43 (s, 1H), 4.56-4.47 (m, 1H), 4.35-3.73 (m, 6H), 3.71-3.03 (m, 7H), 2.87-2.77 (m, 4H), 2.28-1.76 (m, 2H), 1.24 (d, J=6.5 Hz, 3H), 1.10 (d, J=6.3 Hz, 0.6H), 0.85 (d, J=6.3 Hz, 2.4H).

Example 64: 2-[(3,3-difluoropiperidin-4-yl)oxy]-5-[6-({5-[(2R)-2,4-dimethylpiperazin-1-yl]-6-methoxypyridin-2-yl}amino)pyrimidin-4-yl]benzonitrile

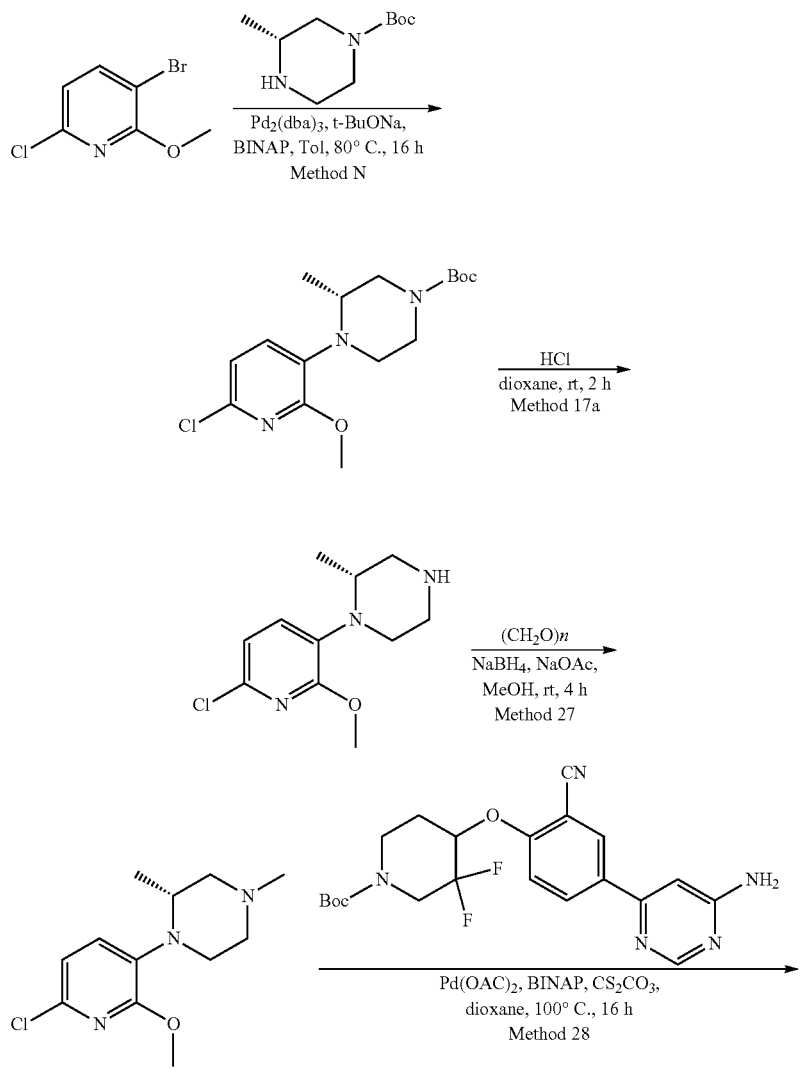

-continued

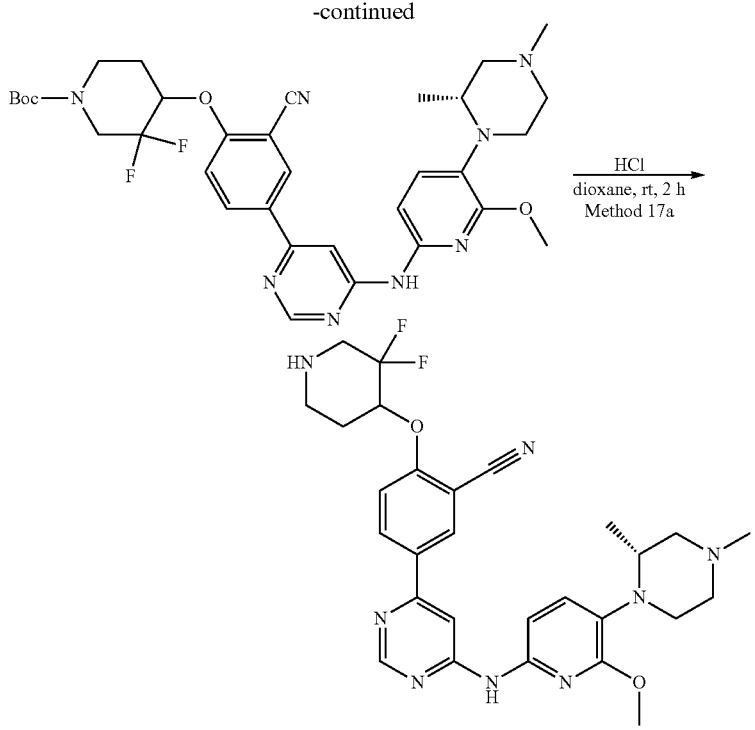

Method N tert-butyl (3R)-4-(6-chloro-2-methoxypyridin-3-yl)-3-methylpiperazine-1-carboxylate: To a solution of 3-bromo-6-chloro-2-methoxypyridine (3.80 g, 17.08 mmol) in toluene (40 mL) was added tert-butyl (3R)-3-methylpiperazine-1-carboxylate (3.42 g, 17.08 mmol), $Pd_2(dba)_3$ (319 mg, 0.35 mmol), BINAP (426 mg, 0.68 mmol), t-BuONa (2.84 g, 29.58 mmol) at room temperature. The resulting mixture was stirred for 16 h at 80° C. When the reaction was done, the solvent was concentrated under reduced pressure and the residue was purified by flash chromatography eluting with EtOAc in petroleum ether (0% to 12% gradient) to yield tert-butyl (3R)-4-(6-chloro-2-methoxypyridin-3-yl)-3-methylpiperazine-1-carboxylate as yellow oil (326 mg, 6%). MS: m/z=342.2 [M+H]+.

2-[(3,3-difluoropiperidin-4-yl)oxy]-5-[6-([5-[(2R)-2,4-dimethylpiperazin-1-yl]-6-methoxypyridin-2-yl]amino)pyrimidin-4-yl]benzonitrile: 2-[(3,3-difluoropiperidin-4-yl)oxy]-5-[6-([5-[(2R)-2,4-dimethylpiperazin-1-yl]-6-methoxypyridin-2-yl]amino)pyrimidin-4-yl]benzonitrile was prepared from (R)-tert-butyl 4-(6-chloro-2-methoxypyridin-3-yl)-3-methylpiperazine-1-carboxylate, $(HCHO)_n$, tert-butyl 4-(4-(6-aminopyrimidin-4-yl)-2-cyanophenoxy)-3,3-difluoropiperidine-1-carboxylate using Method 17a, 27, 28, 17a. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 30% to 60% gradient in 8 min; detector, UV 254 nm. 2-[(3,3-difluoropiperidin-4-yl)oxy]-5-[6-([5-[(2R)-2,4-dimethylpiperazin-1-yl]-6-methoxypyridin-2-yl]amino)pyrimidin-4-yl]benzonitrile was obtained as yellow solid (7 mg, 9.3% for 4 steps). HPLC: 99.4% purity, RT=3.44 min. MS: m/z=551.1 [M+H]+. 1H NMR (300 MHz, DMSO-$d_6$) δ 10.05 (s, 1H), 8.73 (s, 1H), 8.45-8.25 (m, 3H), 7.66-7.56 (m, 1H), 7.41-7.31 (m, 1H), 7.19-7.10 (m, 1H), 5.24-5.10 (m, 1H), 3.97 (s, 3H), 3.49-3.43 (m, 1H), 3.23-2.54 (m, 8H), 2.45-2.25 (m, 2H), 2.18 (s, 3H), 2.12-1.97 (m, 2H), 1.88-1.78 (m, 1H), 0.81 (d, J=6.3 Hz, 3H).

Example 65: 2-([3,3-difluoro-1-[(2S)-2-hydroxypropanoyl]piperidin-4-yl]oxy)-5-[6-([5-[(2R)-2,4-dimethylpiperazin-1-yl]-6-methoxypyridin-2-yl]amino)pyrimidin-4-yl]benzonitrile hydrochloride

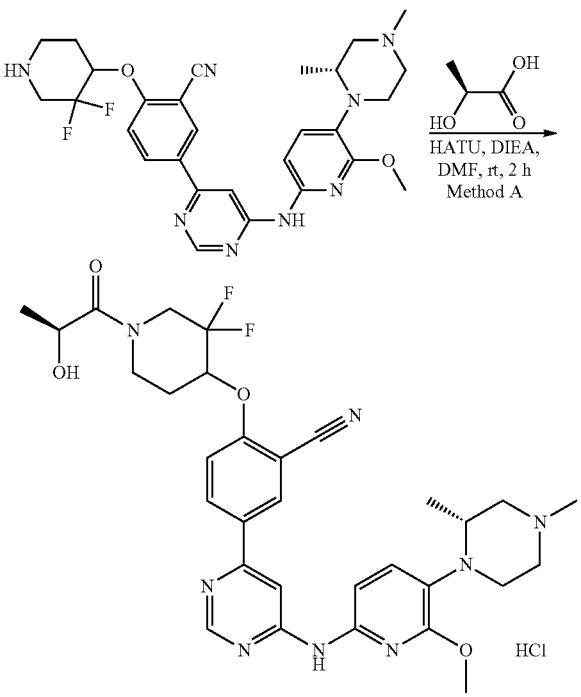

The title compound was prepared from 2-[(3,3-difluoropiperidin-4-yl)oxy]-5-[6-([5-[(2R)-2,4-dimethylpiperazin-1-yl]-6-methoxypyridin-2-yl]amino)pyrimidin-4-yl]benzonitrile and (S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 0.05% HCl), 30% to 65% gradient in 8 min; detector, UV 254 nm. 2-([3,3-difluoro-1-[(2S)-2-hydroxypropanoyl]piperidin-4-yl]oxy)-5-[6-([5-[(2R)-2,4-dimethylpiperazin-1-yl]-6-methoxypyridin-2-yl]amino)pyrimidin-4-yl]benzonitrile hydrochloride was obtained as orange solid (30 mg, 46%). HPLC: 96.2% purity, RT=3.57 min. MS: m/z=623.1 [M+H]$^+$. $^1$H NMR (300 MHz, DMSO-d$_6$) δ 9.09-8.99 (m, 1H), 8.58-8.49 (m, 2H), 8.45-8.35 (m, 1H), 7.94-7.38 (m, 2H), 7.30-7.21 (m, 1H), 5.55-5.49 (m, 1H), 4.58-4.45 (m, 1H), 4.37-3.83 (m, 7H), 3.73-2.91 (m, 7H), 2.82 (s, 3H), 2.34-1.75 (m, 2H), 1.23 (d, J=6.4 Hz, 3H), 1.12 (d, J=6.5 Hz, 1H), 0.89 (d, J=6.0 Hz, 2H).

Example 66: 2-([3,3-difluoro-1-[(2R)-2-hydroxypropanoyl]piperidin-4-yl]oxy)-5-[6-([5-[(2R)-2,4-dimethylpiperazin-1-yl]-6-methoxypyridin-2-yl]amino)pyrimidin-4-yl]benzonitrile hydrochloride

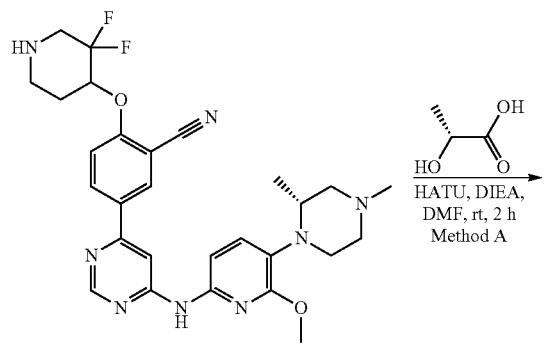

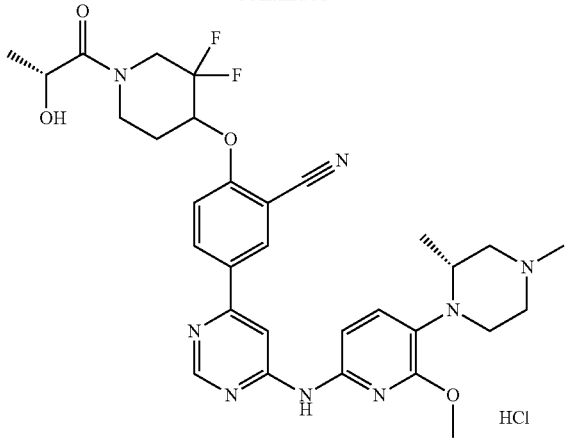

The title compound was prepared from 2-[(3,3-difluoropiperidin-4-yl)oxy]-5-[6-({5-[(2R)-2,4-dimethylpiperazin-1-yl]-6-methoxypyridin-2-yl}amino)pyrimidin-4-yl]benzonitrile, and (R)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 0.05% HCl), 30% to 60% gradient in 8 min; detector, UV 254 nm. 2-([3,3-difluoro-1-[(2R)-2-hydroxypropanoyl]piperidin-4-yl]oxy)-5-[6-([5-[(2R)-2,4-dimethylpiperazin-1-yl]-6-methoxypyridin-2-yl]amino)pyrimidin-4-yl]benzonitrile hydrochloride was obtained as orange solid (30 mg, 5% 5 steps). HPLC: 95.7% purity, RT=3.56 min. MS: m/z=623.1 [M+H]$^+$. 1H NMR (300 MHz, DMSO-d6) δ 9.05-8.96 (m, 1H), 8.55-8.45 (m, 2H), 8.43-8.31 (m, 1H), 7.89-7.76 (m, 2H), 7.46-7.17 (m, 1H), 5.52-5.46 (m, 1H), 4.55-4.42 (m, 1H), 4.36-3.70 (m, 7H), 3.68-2.88 (m, 7H), 2.79 (s, 3H), 2.30-1.68 (m, 2H), 1.20 (d, J=6.4 Hz, 3H), 1.12 (d, J=6.9 Hz, 1H), 0.89 (d, J=6.0 Hz, 2H).

Example 67: 2-[(3,3-difluoropiperidin-4-yl)oxy]-5-[6-({6-methoxy-5-[(2S)-2-methyl-4-(oxetan-3-yl)piperazin-1-yl]pyridin-2-yl}amino)pyrimidin-4-yl]benzonitrile

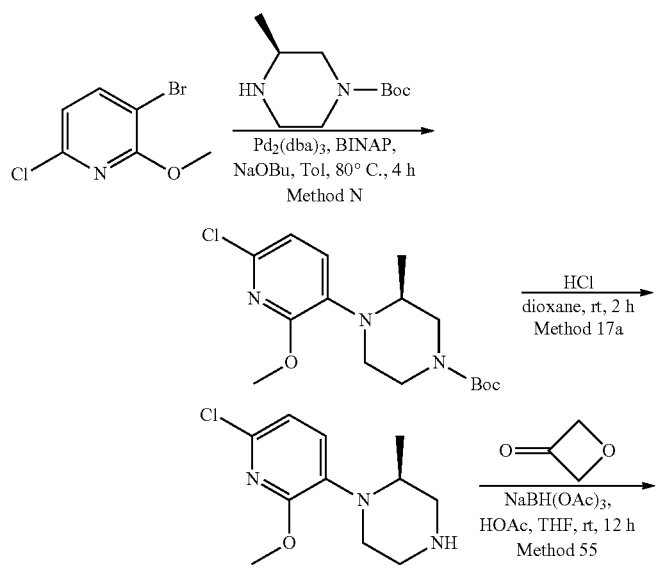

-continued

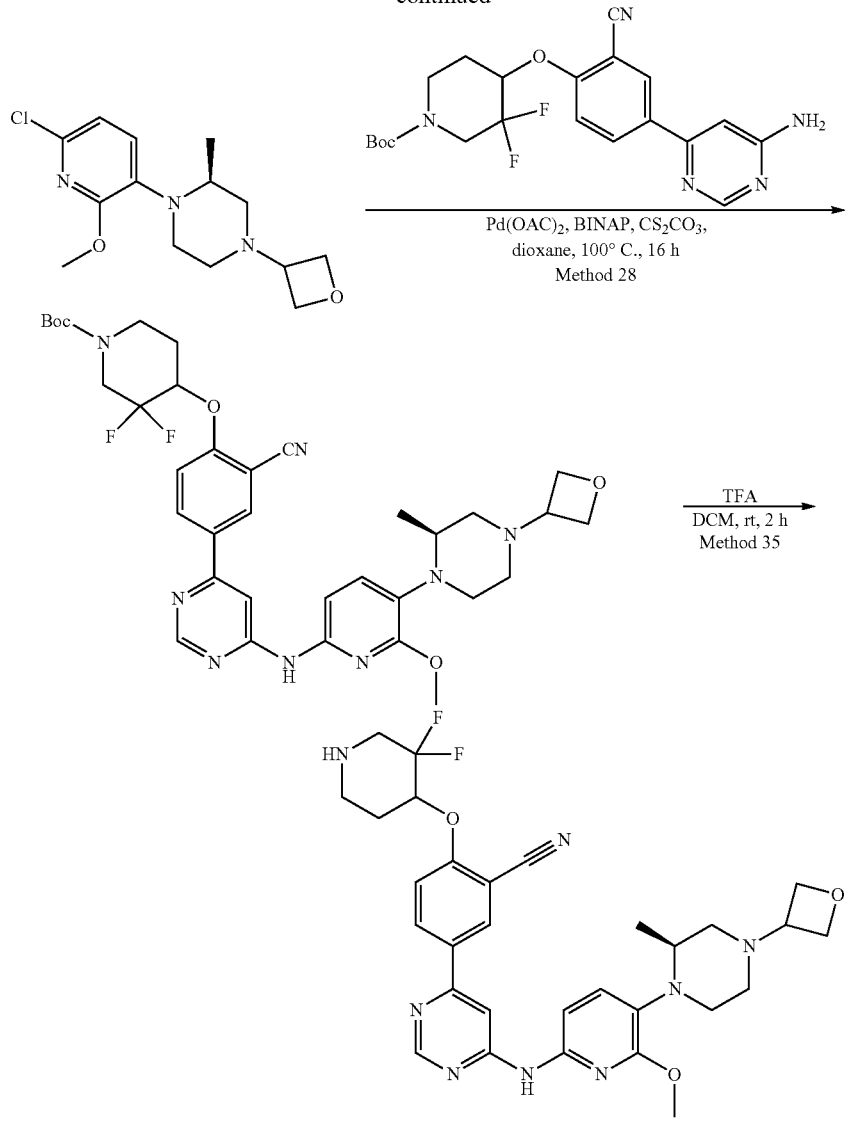

(2S)-1-(6-chloro-2-methoxypyridin-3-yl)-2-methylpiperazine: The title compound was prepared from 3-bromo-6-chloro-2-methoxypyridine and (S)-tert-butyl 3-methylpiperazine-1-carboxylate using Method N and 17a. (2S)-1-(6-chloro-2-methoxypyridin-3-yl)-2-methylpiperazine were obtained as an yellow oil (92 mg, 4.3% for 2 steps). MS: m/z=242.2 [M+H]$^+$.

Method 55

(2S)-1-(6-chloro-2-methoxypyridin-3-yl)-2-methyl-4-(oxetan-3-yl)piperazine: To a solution of (2S)-1-(6-chloro-2-methoxypyridin-3-yl)-2-methylpiperazine (92 mg, 0.38 mmol) in tetrahydrofuran (3 mL) was added oxetan-3-one (101 mg, 1.41 mmol), AcOH (0.1 mL) and NaBH(OAc)$_3$ (298 mg, 1.41 mmol) at room temperature. The resulting mixture was stirred for 12 h at room temperature. When the reaction was done, it was quenched by water. The pH value of the resulting mixture was adjusted to 8 with sat. sodium bicarbonate solution. The mixture was extracted with ethyl acetate (20 mL×3). The organic phases were combined, washed with brine and dried over Na$_2$SO$_4$. The solvent was removed under reduced pressure to yield (2S)-1-(6-chloro-2-methoxypyridin-3-yl)-2-methyl-4-(oxetan-3-yl)piperazine as yellow oil (160 mg, crude). MS: m/z=242.2 [M+H]$^+$.

2-[(3,3-difluoropiperidin-4-yl)oxy]-5-[6-({6-methoxy-5-[(2S)-2-methyl-4-(oxetan-3-yl)piperazin-1-yl]pyridin-2-yl}amino)pyrimidin-4-yl]benzonitrile: The title compound was prepared from (S)-1-(6-chloro-2-methoxypyridin-3-yl)-2-methyl-4-(oxetan-3-yl)piperazine, and tert-butyl 4-(4-(6-aminopyrimidin-4-yl)-2-cyanophenoxy)-3,3-difluoropiperidine-1-carboxylate using Method 28, 35. The final product was purified by prep-HPLC under the following conditions: column, XBridge Prep OBD C18 Column, 150×19 mm, 5 um; mobile phase, acetonitrile in water (with 10 mmol/L NH$_4$HCO$_3$ and 0.1% NH$_3$.H$_2$O), 30% to 60% gradient in 8 min; detector, UV 254 nm. 2-[(3,3-difluoropiperidin-4-yl)oxy]-5-[6-([6-methoxy-5-[(2S)-2-methyl-4-(oxetan-3-yl)piperazin-1-yl]pyridin-2-yl]amino)pyrimidin-4-yl]benzonitrile was obtained as yellow solid (4.8 mg, 1.3% for 3 steps). HPLC: 96.0% purity, RT=3.44 min. MS: m/z=593.1 [M+H]$^+$. $^1$H NMR (300 MHz, DMSO-d$_6$) δ 10.07 (s, 1H), 8.74 (s, 1H), 8.46-8.24 (m, 3H), 7.69-7.55 (m, 1H), 7.45-7.34 (m, 1H), 7.23-7.06 (m, 1H), 5.35-5.04 (m, 1H), 4.63-

4.40 (m, 4H), 3.97 (s, 3H), 3.53-3.36 (m, 2H), 3.25-2.54 (m, 8H), 2.48-2.40 (m, 1H), 2.31-2.20 (m, 1H), 2.13-1.70 (m, 3H), 0.82 (d, J=6.2 Hz, 3H).

Example 68: 2-([3,3-difluoro-1-[(2R)-2-hydroxypropanoyl]piperidin-4-yl]oxy)-5-[6-([6-methoxy-5-[(2S)-2-methyl-4-(oxetan-3-yl)piperazin-1-yl]pyridin-2-yl]amino)pyrimidin-4-yl]benzonitrile

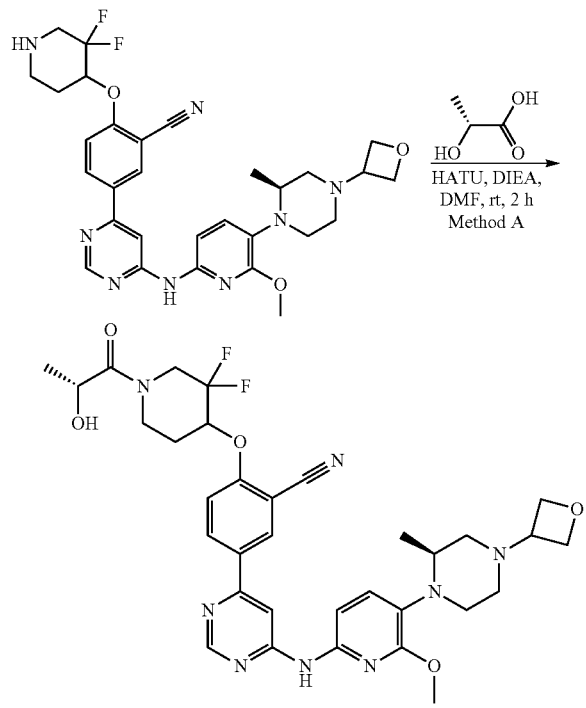

2-([3,3-difluoro-1-[(2R)-2-hydroxypropanoyl]piperidin-4-yl]oxy)-5-[6-([6-methoxy-5-[(2S)-2-methyl-4-(oxetan-3-yl)piperazin-1-yl]pyridin-2-yl]amino)pyrimidin-4-yl]benzonitrile: The title compound was prepared from 2-[(3,3-difluoropiperidin-4-yl)oxy]-5-[6-({6-methoxy-5-[(2S)-2-methyl-4-(oxetan-3-yl)piperazin-1-yl]pyridin-2-yl}amino)pyrimidin-4-yl]benzonitrile and (R)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 35% to 65% gradient in 8 min; detector, UV 254 nm. 2-([3,3-difluoro-1-[(2R)-2-hydroxypropanoyl]piperidin-4-yl]oxy)-5-[6-([6-methoxy-5-[(2S)-2-methyl-4-(oxetan-3-yl)piperazin-1-yl]pyridin-2-yl]amino)pyrimidin-4-yl]benzonitrile was obtained as yellow solid (16 mg, 0.03% for 3 steps). HPLC: 90.2% purity, RT=4.12 min. MS: m/z=665.2 [M+H]$^+$. $^1$H NMR (300 MHz, DMSO-$d_6$) δ 10.09 (s, 1H), 8.75 (s, 1H), 8.44-8.29 (m, 2H), 7.70-7.60 (m, 1H), 7.45-7.35 (m, 1H), 7.20-7.11 (m, 1H), 5.39-5.33 (m, 1H), 5.28-5.19 (m, 1H), 4.62-4.38 (m, 5H), 4.34-4.03 (m, 2H), 3.98 (s, 3H), 3.94-3.38 (m, 4H), 3.08-2.99 (m, 1H), 2.84-2.73 (m, 1H), 2.64-2.40 (m, 2H), 2.37-1.75 (m, 4H), 1.22 (d, J=6.5 Hz, 3H), 0.83 (d, J=6.2 Hz, 3H).

Example 69: 2-[(3,3-difluoropiperidin-4-yl)oxy]-5-[6-({6-methoxy-5-[(2R)-2-methyl-4-(oxetan-3-yl)piperazin-1-yl]pyridin-2-yl}amino)pyrimidin-4-yl]benzonitrile

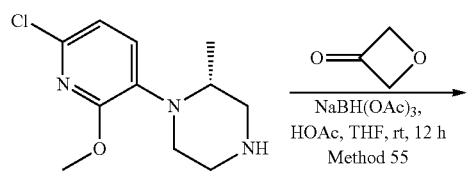

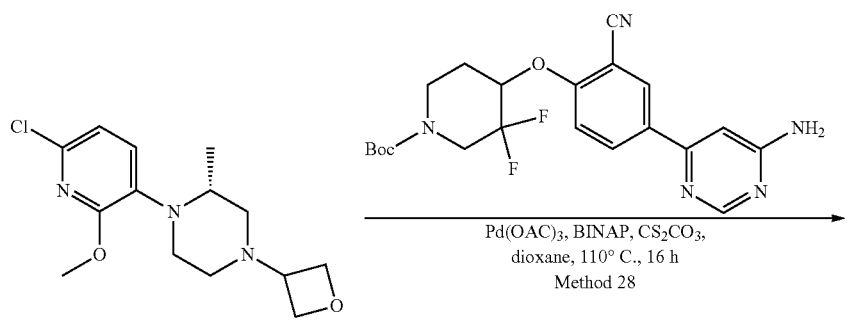

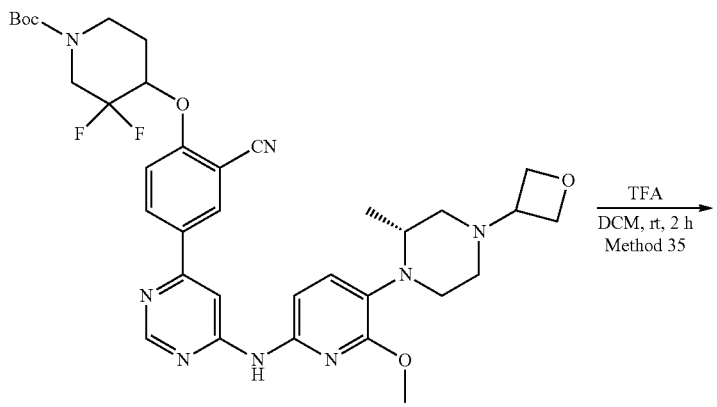

The title compound was prepared from (R)-1-(6-chloro-2-methoxypyridin-3-yl)-2-methylpiperazine, oxetan-3-one, tert-butyl 4-(4-(6-aminopyrimidin-4-yl)-2-cyanophenoxy)-3,3-difluoropiperidine-1-carboxylate and (R)-2-hydroxypropanoic acid using Method 55, 28, 35. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 20% to 50% gradient in 8 min; detector, UV 254 nm. 2-[(3,3-difluoropiperidin-4-yl)oxy]-5-[6-([6-methoxy-5-[(2R)-2-methyl-4-(oxetan-3-yl)piperazin-1-yl]pyridin-2-yl]amino)pyrimidin-4-yl]benzonitrile was obtained as yellow solid (5 mg, 5.5% for 3 steps). HPLC: 92.0% purity, RT=3.13 min. MS: m/z=593.1 [M+H]$^+$. $^1$H NMR (300 MHz, DMSO-d$_6$) δ 10.08 (s, 1H), 8.74 (s, 1H), 8.42-8.26 (m, 3H), 7.66-7.57 (m, 1H), 7.44-7.35 (m, 1H), 7.21-7.11 (m, 1H), 5.22-5.16 (m, 1H), 4.62-4.38 (m, 4H), 3.98 (s, 3H), 3.60-3.36 (m, 2H), 3.26-2.52 (m, 8H), 2.46-2.42 (m, 1H), 2.30-2.24 (m, 1H), 2.08-1.94 (m, 2H), 1.88-1.81 (m, 1H), 0.83 (d, J=6.2 Hz, 3H).

Example 70: 2-([3,3-difluoro-1-[(2R)-2-hydroxypropanoyl]piperidin-4-yl]oxy)-5-[6-([6-methoxy-5-[(2R)-2-methyl-4-(oxetan-3-yl)piperazin-1-yl]pyridin-2-yl]amino)pyrimidin-4-yl]benzonitrile

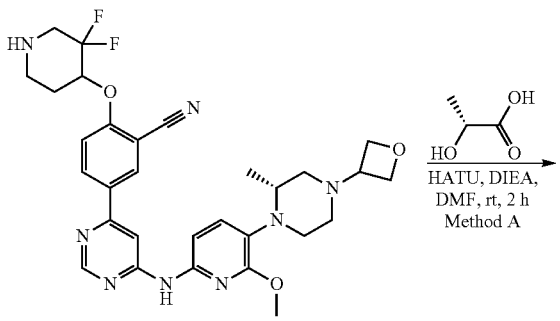

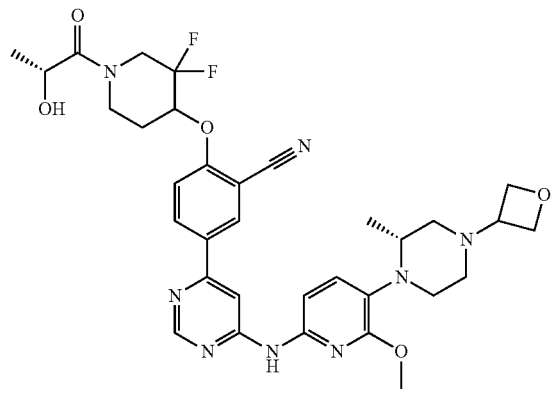

2-([3,3-difluoro-1-[(2R)-2-hydroxypropanoyl]piperidin-4-yl]oxy)-5-[6-([6-methoxy-5-[(2R)-2-methyl-4-(oxetan-3-yl)piperazin-1-yl]pyridin-2-yl]amino)pyrimidin-4-yl]benzonitrile was prepared from 2-[(3,3-difluoropiperidin-4-yl)oxy]-5-[6-([6-methoxy-5-[(2R)-2-methyl-4-(oxetan-3-yl)piperazin-1-yl]pyridin-2-yl]amino)pyrimidin-4-yl]benzonitrile and (R)-2-hydroxypropanoic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 28% to 38% gradient in 8 min; detector, UV 254 nm. 2-([3,3-difluoro-1-[(2R)-2-hydroxypropanoyl]piperidin-4-yl]oxy)-5-[6-([6-methoxy-5-[(2R)-2-methyl-4-(oxetan-3-yl)piperazin-1-yl]pyridin-2-yl]amino)pyrimidin-4-yl]benzonitrile was obtained as yellow solid (17 mg, 14%). HPLC: 95.6% purity, RT=3.82 min. MS: m/z=665.1 [M+H]$^+$. $^1$H NMR (300 MHz, DMSO-d$_6$) δ 10.09 (s, 1H), 8.75 (s, 1H), 8.44-8.29 (m, 3H), 7.70-7.60 (m, 1H), 7.45-7.35 (m, 1H), 7.20-7.11 (m, 1H), 5.40-5.33 (m, 1H), 5.28-5.19 (m, 1H), 4.60-4.38 (m, 5H), 4.32-4.02 (m, 1H), 3.98 (s, 3H), 3.91-3.54 (m, 3H), 3.50-3.37 (m, 2H), 3.17-2.56 (m, 3H), 2.46-1.81 (m, 5H), 1.22 (d, J=6.6 Hz, 3H), 0.83 (d, J=6.2 Hz, 3H).

Example 71: 2-([3,3-difluoro-1-[(2S)-2-hydroxypropanoyl]piperidin-4-yl]oxy)-5-[6-([6-methoxy-5-[(2R)-2-methyl-4-(oxetan-3-yl)piperazin-1-yl]pyridin-2-yl]amino)pyrimidin-4-yl]benzonitrile

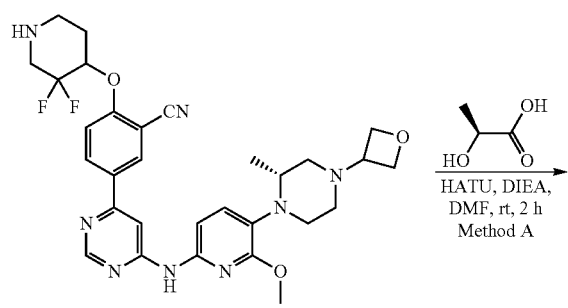

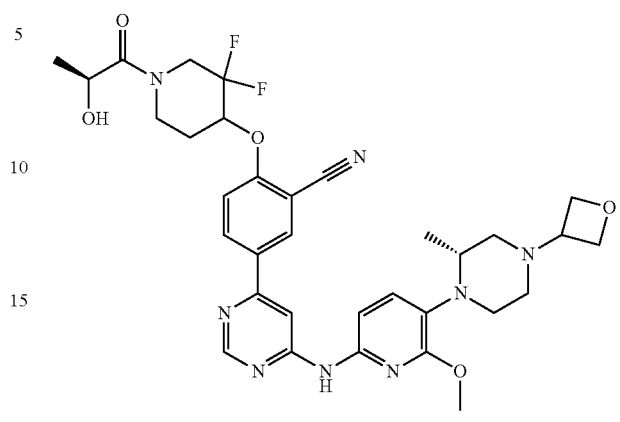

The title compound was prepared from 2-[(3,3-difluoropiperidin-4-yl)oxy]-5-[6-([6-methoxy-5-[(2R)-2-methyl-4-(oxetan-3-yl)piperazin-1-yl]pyridin-2-yl]amino)pyrimidin-4-yl]benzonitrile and (2S)-2-hydroxypropanoic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 25% to 50% gradient in 8 min; detector, UV 254 nm. 2-([3,3-difluoro-1-[(2S)-2-hydroxypropanoyl]piperidin-4-yl]oxy)-5-[6-([6-methoxy-5-[(2R)-2-methyl-4-(oxetan-3-yl)piperazin-1-yl]pyridin-2-yl]amino)pyrimidin-4-yl]benzonitrile was obtained as yellow solid (16 mg, 14%). HPLC: 94.1% purity, RT=3.82 min. MS: m/z=665.1 [M+H]$^+$. $^1$H NMR (300 MHz, DMSO-d$_6$) δ 10.09 (s, 1H), 8.75 (s, 1H), 8.50-8.28 (m, 3H), 7.75-7.60 (m, 1H), 7.47-7.35 (m, 1H), 7.24-7.08 (m, 1H), 5.44-5.28 (m, 1H), 5.27-5.19 (m, 1H), 4.66-4.37 (m, 5H), 4.34-3.36 (m, 9H), 3.14-3.00 (m, 1H), 2.80-2.69 (m, 1H), 2.55-2.37 (m, 2H), 2.27-1.79 (m, 4H), 1.22 (d, J=6.3 Hz, 3H), 0.82 (d, J=6.3 Hz, 3H).

Example 72: 2-([3,3-difluoro-1-[(2S)-2-hydroxypropanoyl]piperidin-4-yl]oxy)-5-[6-([6-methoxy-5-[(2S)-2-methyl-4-(oxetan-3-yl)piperazin-1-yl]pyridin-2-yl]amino)pyrimidin-4-yl]benzonitrile

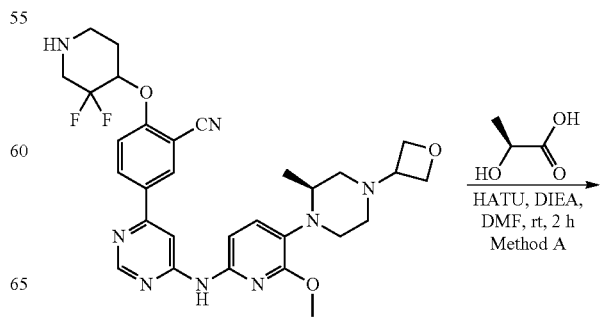

169

-continued

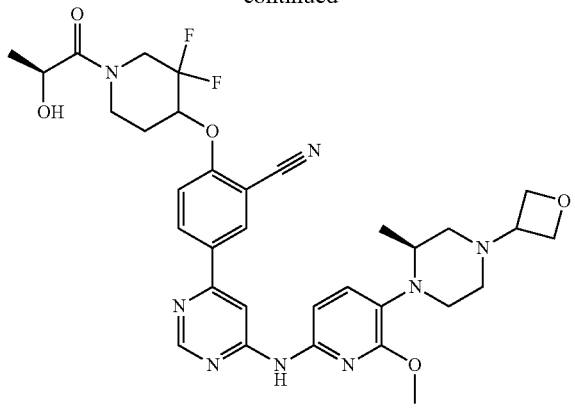

The title compound was prepared from 2-[(3,3-difluoropiperidin-4-yl)oxy]-5-[6-([6-methoxy-5-[(2S)-2-methyl-4-(oxetan-3-yl)piperazin-1-yl]pyridin-2-yl]amino)pyrimidin-4-yl]benzonitrile and (2S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 30% to 60% gradient in 8 min; detector, UV 254 nm. 2-([3,3-difluoro-1-[(2S)-2-hydroxypropanoyl]piperidin-4-yl]oxy)-5-[6-([6-methoxy-5-[(2S)-2-methyl-4-(oxetan-3-yl)piperazin-1-yl]pyridin-2-yl]amino)pyrimidin-4-yl]benzonitrile was obtained as yellow solid (23 mg, 33%). HPLC: 93.4% purity, RT=4.11 min. MS: m/z=665.1 [M+H]$^+$. $^1$H NMR (300 MHz, DMSO-d$_6$) δ 10.09 (s, 1H), 8.75 (s, 1H), 8.43-8.28 (m, 3H), 7.69-7.59 (m, 1H), 7.44-7.35 (m, 1H), 7.19-7.10 (m, 1H), 5.39-5.32 (m, 1H), 5.27-5.18 (m, 1H), 4.61-4.41 (m, 5H), 4.29-3.56 (m, 9H), 3.12-3.02 (m, 1H), 2.80-2.72 (m, 1H), 2.58-2.39 (m, 2H), 2.30-1.81 (m, 4H), 1.22 (d, J=6.5 Hz, 3H), 0.82 (d, J=6.2 Hz, 3H).

Example 73: 2-[(3,3-difluoropiperidin-4-yl)oxy]-5-[6-({5-[(3R)-3,4-dimethylpiperazin-1-yl]-6-methoxypyridin-2-yl}amino)pyrimidin-4-yl]benzonitrile

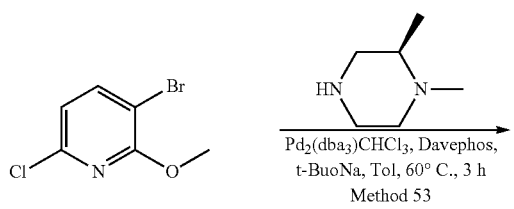

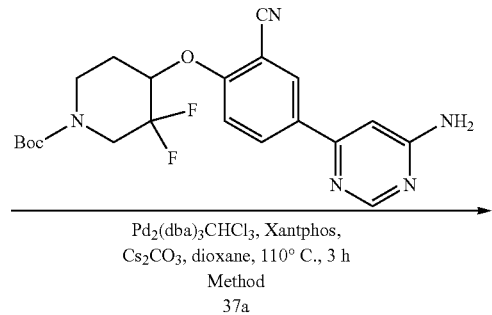

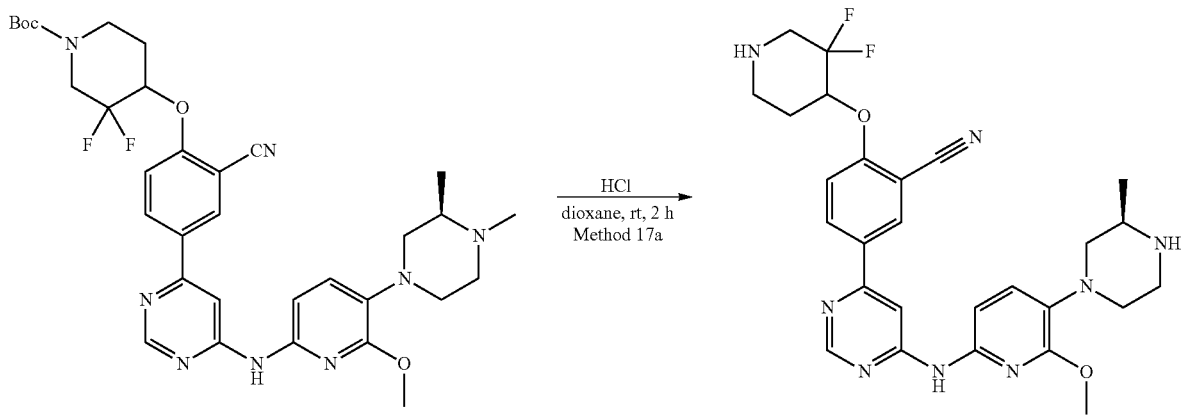

The title compound was prepared from 3-bromo-6-chloro-2-methoxypyridine, (R)-1,2-dimethylpiperazine and tert-butyl 4-(4-(6-aminopyrimidin-4-yl)-2-cyanophenoxy)-3,3-difluoropiperidine-1-carboxylate using Method 53, 37a and 17a. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 30% to 50% gradient in 8 min; detector, UV 254 nm. 2-[(3,3-difluoropiperidin-4-yl)oxy]-5-[6-([5-[(3R)-3,4-dimethylpiperazin-1-yl]-6-methoxypyridin-2-yl]amino)pyrimidin-4-yl]benzonitrile was obtained as light yellow solid (8 mg, 6.2% for 3 steps). HPLC: 92.0% purity, RT=3.13 min. MS: m/z=593.1 [M+H]$^+$. $^1$H NMR (300 MHz, DMSO-d$_6$) δ 9.97 (s, 1H), 8.71 (s, 1H), 8.42-8.11 (m, 3H), 7.65-7.55 (m, 1H), 7.29-7.21 (m, 1H), 7.21-7.08 (m, 1H), 5.24-5.09 (m, 1H), 3.97 (s, 3H), 3.27-3.06 (m, 3H), 3.03-2.52 (m, 6H), 2.40-2.22 (m, 2H), 2.20 (s, 3H), 2.18-2.12 (m, 1H), 2.10-1.99 (m, 1H), 1.88-1.79 (m, 1H), 1.00 (d, J=6.1 Hz, 3H).

Example 74: 2-([3,3-difluoro-1-[(2S)-2-hydroxypropanoyl]piperidin-4-yl]oxy)-5-[6-([5-[(3R)-3,4-dimethylpiperazin-1-yl]-6-methoxypyridin-2-yl]amino)pyrimidin-4-yl]benzonitrile hydrochloride

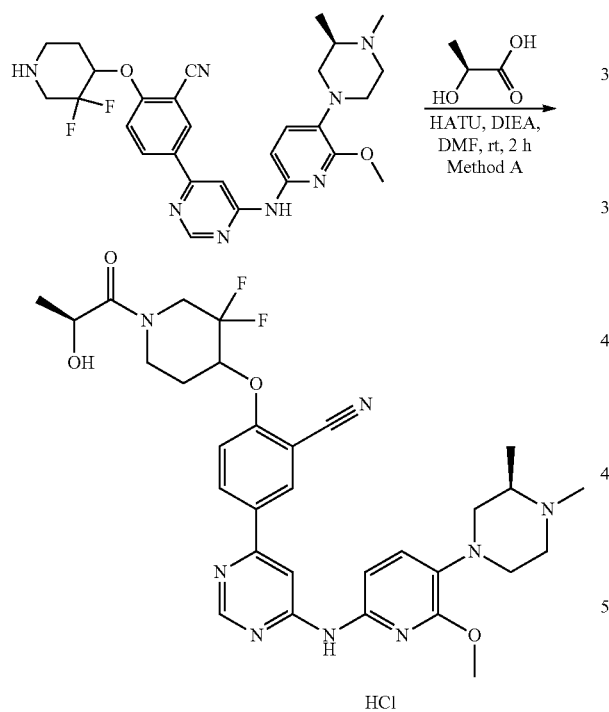

The title compound was prepared from 2-[(3,3-difluoropiperidin-4-yl)oxy]-5-[6-([5-[(3R)-3,4-dimethylpiperazin-1-yl]-6-methoxypyridin-2-yl]amino)pyrimidin-4-yl]benzonitrile and (S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 0.05% HCl), 18% to 45% gradient in 8 min; detector, UV 254 nm. 2-([3,3-difluoro-1-[(2S)-2-hydroxypropanoyl]piperidin-4-yl]oxy)-5-[6-([5-[(3R)-3,4-dimethylpiperazin-1-yl]-6-methoxypyridin-2-yl]amino)pyrimidin-4-yl]benzonitrile hydrochloride was obtained as orange solid (9 mg, 11%). HPLC: 94.8% purity, RT=10.05 min. MS: m/z=623.2 [M+H]$^+$. $^1$H NMR (300 MHz, DMSO-d$_6$) δ 9.02 (s, 1H), 8.52 (s, 2H), 8.46-8.26 (m, 1H), 7.97-7.76 (m, 1H), 7.58-7.38 (m, 1H), 7.23 (br s, 1H), 5.51-5.42 (m, 1H), 4.70-4.40 (m, 1H), 4.41-4.15 (m, 1H), 4.00 (s, 3H), 3.96-2.89 (m, 10H), 2.83 (s, 3H), 2.33-1.68 (m, 2H), 1.39 (d, J=6.6 Hz, 3H), 1.23 (d, J=6.4 Hz, 3H).

Example 75: 2-([3,3-difluoro-1-[(2R)-2-hydroxypropanoyl]piperidin-4-yl]oxy)-5-[6-([5-[(3R)-3,4-dimethylpiperazin-1-yl]-6-methoxypyridin-2-yl]amino)pyrimidin-4-yl]benzonitrile hydrochloride

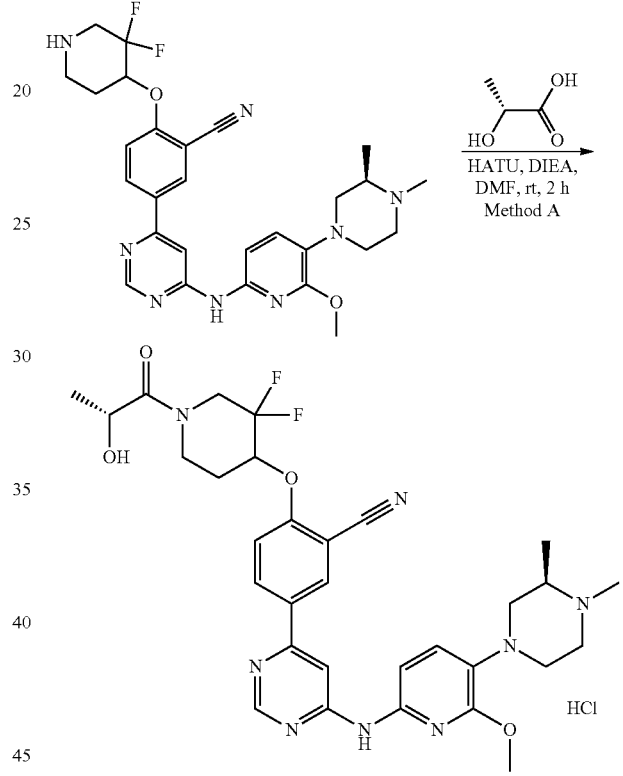

The title compound was prepared from 2-[(3,3-difluoropiperidin-4-yl)oxy]-5-[6-([5-[(3R)-3,4-dimethylpiperazin-1-yl]-6-methoxypyridin-2-yl]amino)pyrimidin-4-yl]benzonitrile and (R)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 0.05% HCl), 18% to 45% gradient in 8 min; detector, UV 254 nm. 2-([3,3-difluoro-1-[(2R)-2-hydroxypropanoyl]piperidin-4-yl]oxy)-5-[6-([5-[(3R)-3,4-dimethylpiperazin-1-yl]-6-methoxypyridin-2-yl]amino)pyrimidin-4-yl]benzonitrile hydrochloride was obtained as orange solid (11 mg, 2.7% 4 steps). HPLC: 92.3% purity, RT=10.04 min. MS: m/z=623.0 [M+H]$^+$. $^1$H NMR (300 MHz, DMSO-d$_6$) δ 8.99 (s, 1H), 8.56-8.46 (m, 1H), 8.41-8.31 (m, 2H), 7.86-7.76 (m, 1H), 7.51-7.41 (m, 1H), 7.19 (br s, 1H), 5.59-5.41 (m, 2H), 4.58-4.41 (m, 1H), 4.34-4.06 (m, 1H), 3.97 (s, 3H), 3.93-2.82 (m, 10H), 2.79 (s, 3H), 2.22-1.72 (m, 2H), 1.36 (d, J=6.4 Hz, 3H), 1.20 (d, J=6.6 Hz, 3H).

Example 76: 2-[(3,3-difluoropiperidin-4-yl)oxy]-5-[6-({6-methoxy-5-[4-(oxetan-3-yl)piperazin-1-yl]pyridin-2-yl}amino)pyrimidin-4-yl]benzonitrile

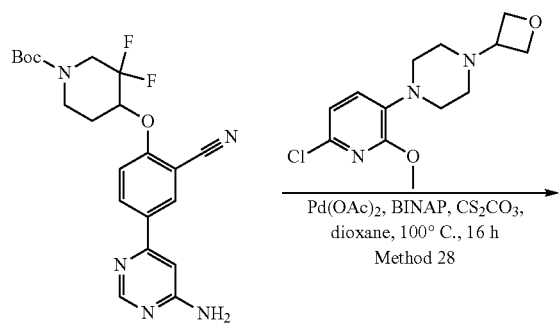

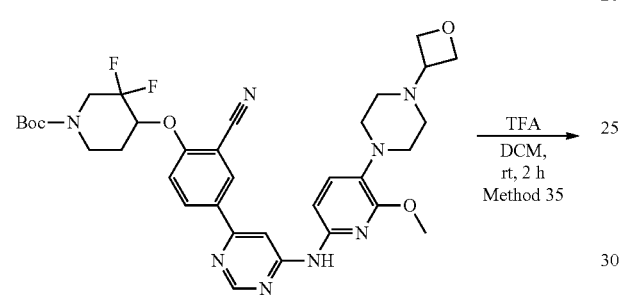

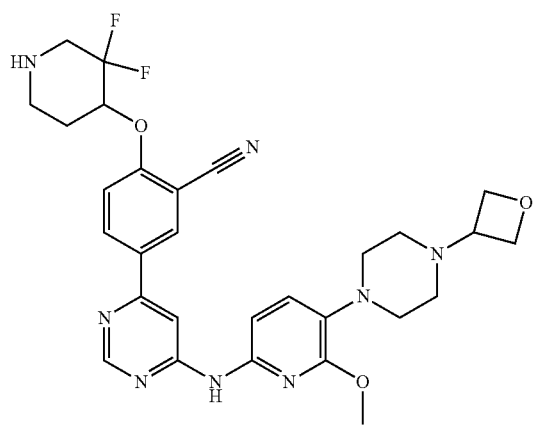

The title compound was prepared from tert-butyl 4-(4-(6-aminopyrimidin-4-yl)-2-cyanophenoxy)-3,3-difluoropiperidine-1-carboxylate, 1-(6-chloro-2-methoxypyridin-3-yl)-4-(oxetan-3-yl)piperazine and (R)-2-hydroxypropanoic acid using Method 28, 35. The final product was purified by prep-HPLC under the following conditions: column, Atlantis HILIC OBD Column, 150×19 mm, 5 um; mobile phase, acetonitrile in water (with 10 mmol/L NH$_4$HCO$_3$ and 0.1% NH$_3$.H$_2$O), 35% to 55% gradient in 8 min; detector, UV 254 nm. 2-[(3,3-difluoropiperidin-4-yl)oxy]-5-[6-([6-methoxy-5-[4-(oxetan-3-yl)piperazin-1-yl]pyridin-2-yl]amino)pyrimidin-4-yl]benzonitrile as a yellow solid (5 mg, 8.9% for 2 steps). HPLC: 99.2% purity, RT=3.21 min. MS: m/z=579.3 [M+H]$^+$. $^1$H NMR (300 MHz, DMSO-d$_6$) δ 9.98 (s, 1H), 8.71 (s, 1H), 8.39-8.23 (m, 2H), 8.20 (br s, 1H), 7.64-7.55 (m, 1H), 7.33-7.23 (m, 1H), 7.21-7.11 (m, 1H), 5.21-5.09 (m, 1H), 4.61-4.38 (m, 4H), 3.96 (s, 3H), 3.53-3.38 (m, 1H), 3.24-2.51 (m, 9H), 2.42-2.36 (m, 4H), 2.10-1.73 (m, 2H).

Example 77: 2-([3,3-difluoro-1-[(2R)-2-hydroxypropanoyl]piperidin-4-yl]oxy)-5-[6-([6-methoxy-5-[4-(oxetan-3-yl)piperazin-1-yl]pyridin-2-yl]amino)pyrimidin-4-yl]benzonitrile

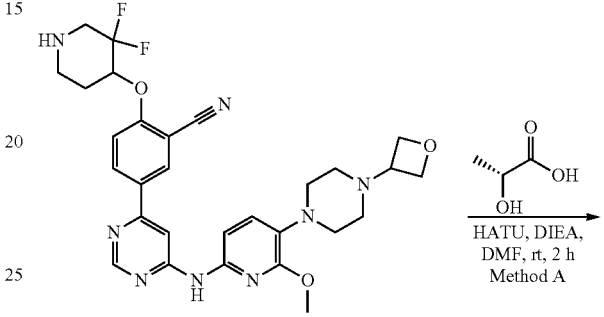

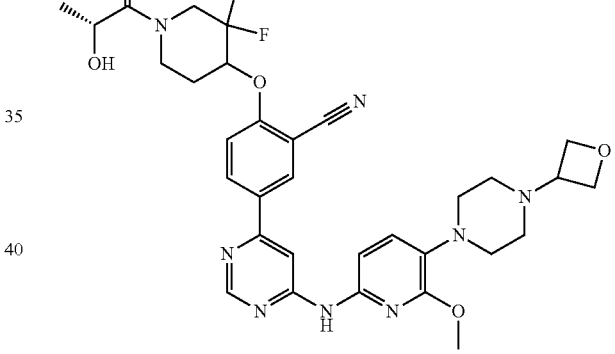

The title compound was prepared from 2-[(3,3-difluoropiperidin-4-yl)oxy]-5-[6-({6-methoxy-5-[4-(oxetan-3-yl)piperazin-1-yl]pyridin-2-yl}amino)pyrimidin-4-yl]benzonitrile and (R)-2-hydroxypropanoic acid using Method A. The final product was purified by prep-HPLC under the following conditions: column, XBridge Prep OBD C18 Column, 150× 19 mm, 5 um; mobile phase, acetonitrile in water (with 10 mmol/L NH$_4$HCO$_3$ and 0.1% NH$_3$.H$_2$O), 25% to 45% gradient in 8 min; detector, UV 254 nm. 2-([3,3-difluoro-1-[(2R)-2-hydroxypropanoyl]piperidin-4-yl]oxy)-5-[6-([6-methoxy-5-[4-(oxetan-3-yl)piperazin-1-yl]pyridin-2-yl]amino)pyrimidin-4-yl]benzonitrile was obtained as yellow solid (29 mg, 2.1% for 3 steps). HPLC: 99.6% purity, RT=3.61 min. MS: m/z=651.4 [M+H]$^+$. $^1$H NMR (300 MHz, DMSO-d$_6$) δ 10.01 (s, 1H), 8.73 (s, 1H), 8.43-8.28 (m, 2H), 8.23 (s, 1H), 7.69-7.60 (m, 1H), 7.35-7.25 (m, 1H), 7.22-7.12 (m, 1H), 5.40-5.33 (m, 1H), 5.27-5.20 (m, 1H), 4.62-4.38 (m, 5H), 4.32-3.41 (m, 8H), 3.01-2.95 (m, 4H), 2.44-2.37 (m, 4H), 2.24-1.72 (m, 2H), 1.22 (d, J=6.5 Hz, 3H).

Example 78: 2-([3,3-difluoro-1-[(2S)-2-hydroxypropanoyl]piperidin-4-yl]oxy)-5-[6-([6-methoxy-5-[4-(oxetan-3-yl)piperazin-1-yl]pyridin-2-yl]amino)pyrimidin-4-yl]benzonitrile

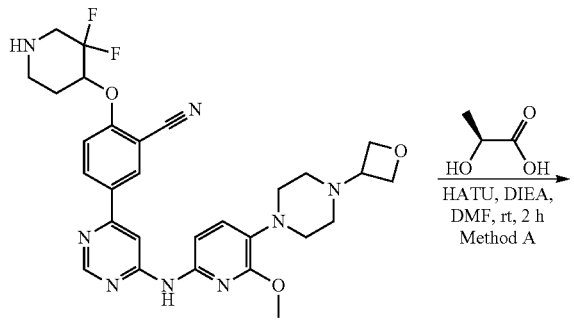

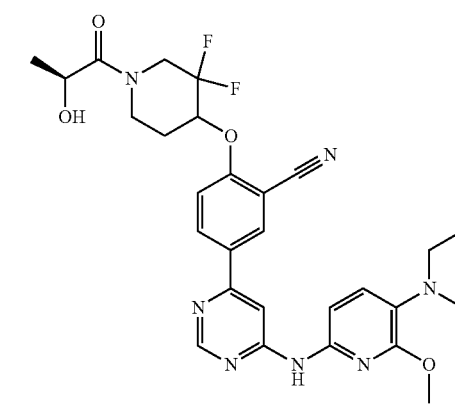

The title compound was prepared from 2-[(3,3-difluoropiperidin-4-yl)oxy]-5-[6-([6-methoxy-5-[4-(oxetan-3-yl)piperazin-1-yl]pyridin-2-yl]amino)pyrimidin-4-yl]benzonitrile and (S)-2-hydroxypropanoic acid using Method A. The final product was purified by prep-HPLC under the following conditions: column, XBridge Shield RP18 OBD C18 Column, 150×19 mm, 5 um; mobile phase, acetonitrile in water (with 10 mmol/L NH$_4$HCO$_3$ and 0.1% NH$_3$·H$_2$O), 25% to 45% gradient in 8 min; detector, UV 254 nm. 2-([3,3-difluoro-1-[(2S)-2-hydroxypropanoyl]piperidin-4-yl]oxy)-5-[6-([6-methoxy-5-[4-(oxetan-3-yl)piperazin-1-yl]pyridin-2-yl]amino)pyrimidin-4-yl]benzonitrile was obtained as yellow solid (25 mg, 21%). HPLC: 99.5% purity, RT=3.60 min. MS: m/z=651.5 [M+H]$^+$. $^1$H NMR (300 MHz, DMSO-d$_6$) δ 10.00 (s, 1H), 8.72 (s, 1H), 8.41-8.26 (m, 2H), 8.22 (s, 1H), 7.68-7.58 (m, 1H), 7.33-7.23 (m, 1H), 7.20-7.11 (m, 1H), 5.37-5.31 (m, 1H), 5.27-5.18 (m, 1H), 4.60-4.39 (m, 5H), 4.23-3.40 (m, 8H), 3.00-2.93 (m, 4H), 2.42-2.36 (m, 4H), 2.24-1.73 (m, 2H), 1.21 (d, J=6.5 Hz, 3H).

Example 79: 2-[[(3R,4S)-3-fluoro-1-[(1H-1,2,3-triazol-5-yl)carbonyl]piperidin-4-yl]oxy]-5-[6-([6-methoxy-5-[4-(oxetan-3-yl)piperazin-1-yl]pyridin-2-yl]amino)pyrimidin-4-yl]benzonitrile

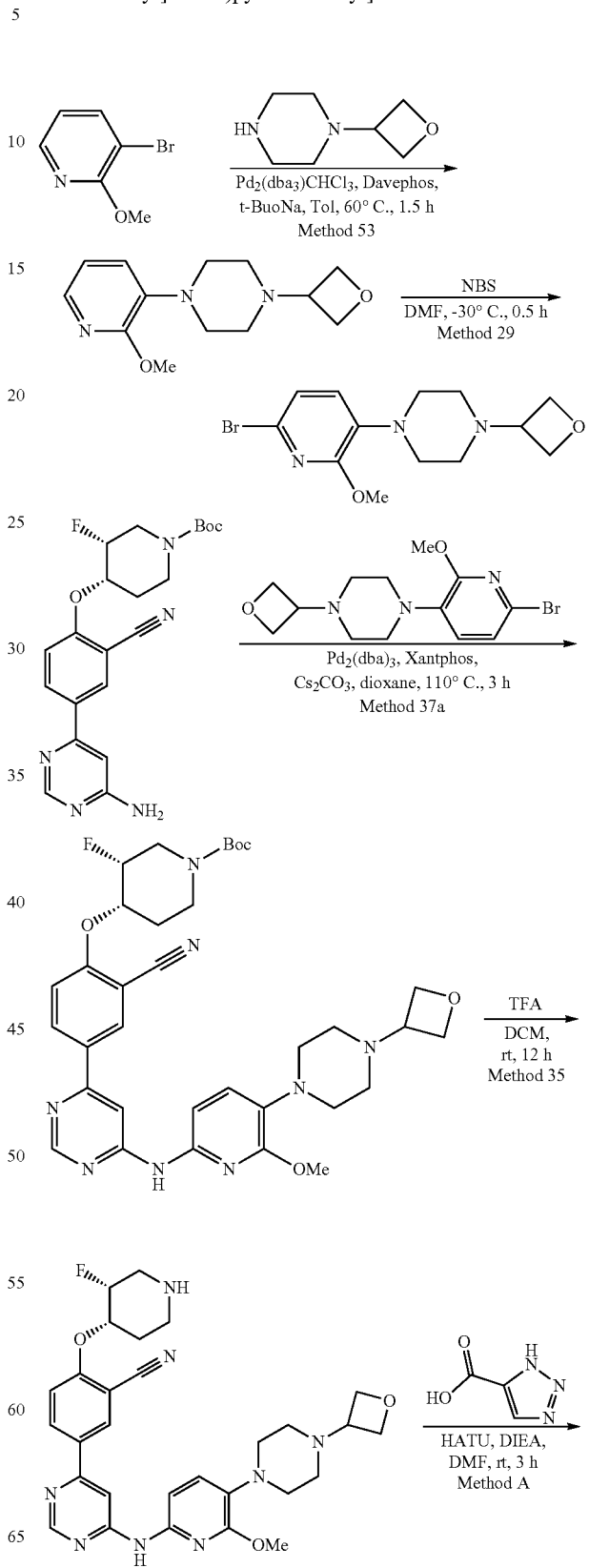

-continued

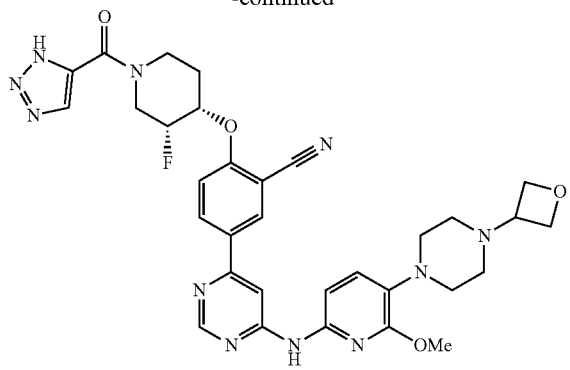

Method 53

1-(2-methoxypyridin-3-yl)-4-(oxetan-3-yl)piperazine: To a solution of 3-bromo-2-methoxypyridine (1.81 g, 9.59 mmol) in toluene (50 mL) was added 1-(oxetan-3-yl)piperazine (1.86 g, 13.06 mmol), $Pd_2(dba)_3 \cdot CHCl_3$ (479 mg, 0.46 mmol), DavePhos (578 mg, 1.47 mmol) and t-BuONa (1.41 g, 14.64 mmol) at room temperature. The resulting mixture was stirred for 1.5 h at 60° C. After the reaction was done, the solids in the reaction mixture were filtered out and the filtrate was concentrated under reduced pressure. The residue was purified by flash chromatography eluting with EtOAc in hexane (0% to 70% gradient) to yield 1-(2-methoxypyridin-3-yl)-4-(oxetan-3-yl)piperazine as brown oil (1.28 g, 54%). MS: m/z=250.1 $[M+H]^+$.

2-[[(3R,4S)-3-fluoro-1-[(1H-1,2,3-triazol-5-yl)carbonyl]piperidin-4-yl]oxy]-5-[6-([6-methoxy-5-[4-(oxetan-3-yl)piperazin-1-yl]pyridin-2-yl]amino)pyrimidin-4-yl]benzonitrile: The title compound was prepared from 1-(2-methoxypyridin-3-yl)-4-(oxetan-3-yl)piperazine, NBS, (3R,4S)-tert-butyl 4-(4-(6-aminopyrimidin-4-yl)-2-cyanophenoxy)-3-fluoropiperidine-1-carboxylate and 3H-1,2,3-triazole-4-carboxylic acid using Method 29, 37a, 35 and A. The final product was purified by prep-HPLC under the following conditions: column, XBridge Prep C18 OBD Column, 150×19 mm, 5 um; mobile phase, acetonitrile in water (with 10 mmol/L $NH_4HCO_3$ and 0.1% $NH_3 \cdot H_2O$), 20% to 32% gradient in 8 min; detector, UV 254 nm. 2-[[(3R,4S)-3-fluoro-1-[(1H-1,2,3-triazol-5-yl)carbonyl]piperidin-4-yl]oxy]-5-[6-([6-methoxy-5-[4-(oxetan-3-yl)piperazin-1-yl]pyridin-2-yl]amino)pyrimidin-4-yl]benzonitrile was obtained as yellow solid (26 mg, 8.4% for 4 steps). HPLC: 97.7% purity, RT=2.38 min. MS: m/z=656.6 $[M+H]^+$. $^1$H NMR (300 MHz, DMSO-$d_6$) δ 9.99 (s, 1H), 8.73 (s, 1H), 8.40-8.26 (m, 2H), 8.25-8.16 (m, 2H), 7.67-7.57 (m, 1H), 7.34-7.25 (m, 1H), 7.23-7.13 (m, 1H), 5.26-4.90 (m, 2.5H), 4.63-4.26 (m, 5.5H), 3.98 (s, 3H), 3.81-3.14 (m, 3H), 3.02-2.93 (m, 4H), 2.44-2.37 (m, 4H), 2.12-1.86 (m, 2H).

Example 80: 2-[(3,3-difluoropiperidin-4-yl)oxy]-5-[6-({5-[(3S)-3,4-dimethylpiperazin-1-yl]-6-methoxypyridin-2-yl}amino)pyrimidin-4-yl]benzonitrile

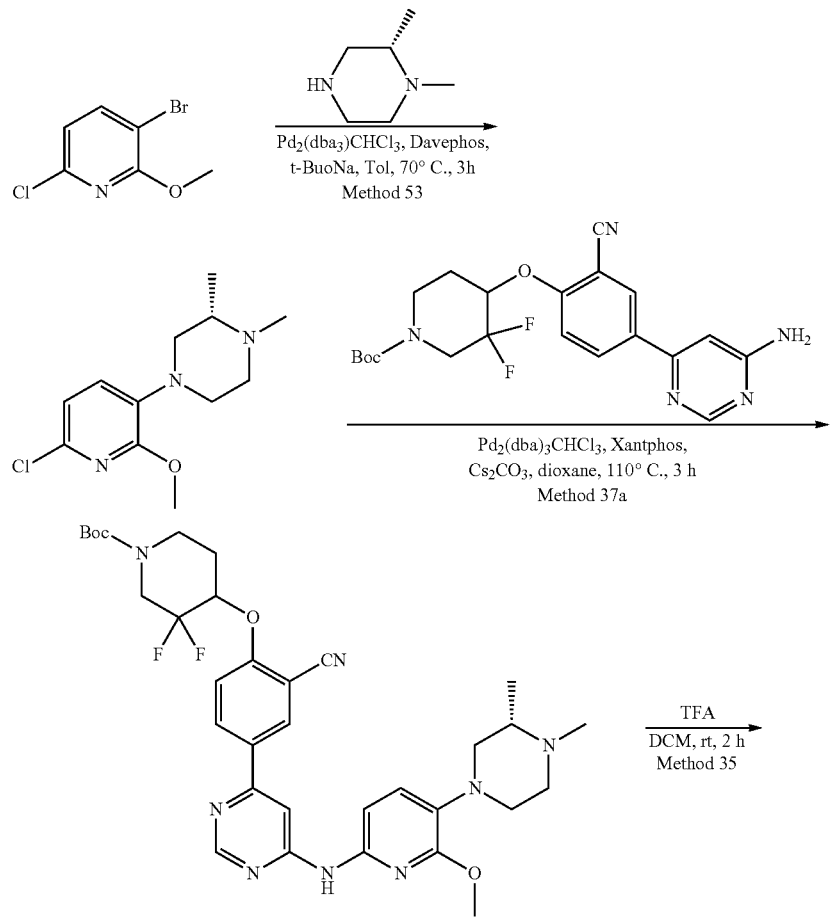

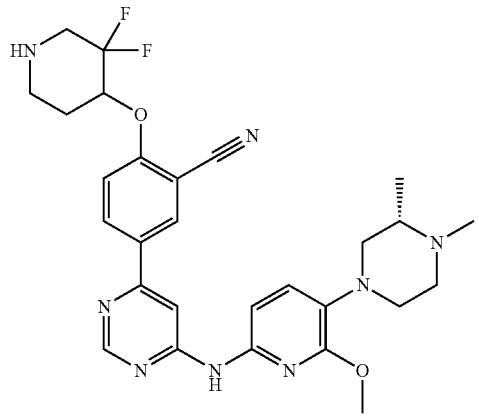

The title compound was prepared from 3-bromo-6-chloro-2-methoxypyridine, (S)-1,2-dimethylpiperazine and tert-butyl 4-(4-(6-aminopyrimidin-4-yl)-2-cyanophenoxy)-3,3-difluoropiperidine-1-carboxylate using Method 53, 37a and 35. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 25% to 55% gradient in 8 min; detector, UV 254 nm. 2-[(3,3-difluoropiperidin-4-yl)oxy]-5-[6-([5-[(3S)-3,4-dimethylpiperazin-1-yl]-6-methoxypyridin-2-yl]amino)pyrimidin-4-yl]benzonitrile was obtained as light yellow solid (8 mg, 4.1% for 3 steps). HPLC: 99.3% purity, RT=4.38 min. MS: m/z=551.1 [M+H]⁺. ¹H NMR (300 MHz, DMSO-d₆) δ 9.97 (s, 1H), 8.71 (s, 1H), 8.39-8.24 (m, 2H), 8.20 (br s, 1H), 7.65-7.56 (m, 1H), 7.30-7.20 (m, 1H), 7.20-7.11 (m, 1H), 5.23-5.10 (m, 1H), 3.97 (s, 3H), 3.27-2.52 (m, 9H), 2.40-2.20 (m, 2H), 2.20 (s, 3H), 2.20-2.11 (m, 1H), 2.06-1.99 (m, 1H), 1.88-1.78 (m, 1H), 1.01 (d, J=6.1 Hz, 3H).

Example 81: 2-([3,3-difluoro-1-[(2R)-2-hydroxypropanoyl]piperidin-4-yl]oxy)-5-[6-([5-[(3S)-3,4-dimethylpiperazin-1-yl]-6-methoxypyridin-2-yl]amino)pyrimidin-4-yl]benzonitrile

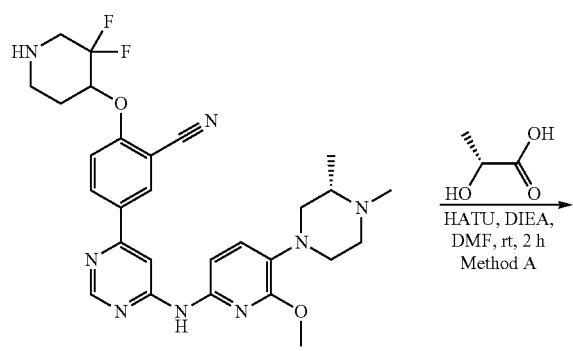

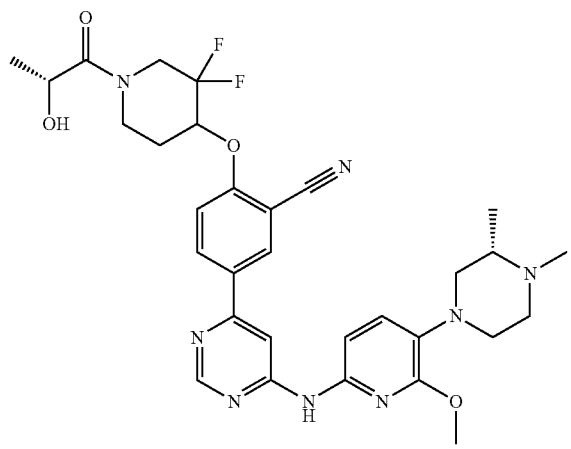

The title compound was prepared from 2-[(3,3-difluoropiperidin-4-yl)oxy]-5-[6-({5-[(3S)-3,4-dimethylpiperazin-1-yl]-6-methoxypyridin-2-yl}amino)pyrimidin-4-yl]benzonitrile and (R)-2-hydroxypropanoic acid using Method A. The final product was purified by prep-HPLC under the following conditions: column, XBridge Prep C18 OBD Column, 150×19 mm, 5 um; mobile phase, acetonitrile in water (with 10 mmol/L NH₄HCO₃ and 0.1% NH₃.H₂O), 25% to 55% gradient in 8 min; detector, UV 254 nm. 2-([3,3-difluoro-1-[(2R)-2-hydroxypropanoyl]piperidin-4-yl]oxy)-5-[6-([5-[(3S)-3,4-dimethylpiperazin-1-yl]-6-methoxypyridin-2-yl]amino)pyrimidin-4-yl]benzonitrile was obtained as light yellow solid (29 mg, 0.8% 4 steps). HPLC: 99.0% purity, RT=5.34 min. MS: m/z=623.1 [M+H]⁺. ¹H NMR (300 MHz, DMSO-d₆) δ 9.99 (s, 1H), 8.73 (s, 1H), 8.42-8.28 (m, 2H), 8.23 (s, 1H), 7.70-7.60 (m, 1H), 7.31-7.22 (m, 1H), 7.20-7.11 (m, 1H), 5.39-5.33 (m, 1H), 5.28-5.18 (m, 1H), 4.56-4.45 (m, 1H), 4.31-3.40 (m, 7H), 3.28-3.12 (m, 2H), 2.82-2.61 (m, 2H), 2.41-2.10 (m, 7H), 2.08-1.81 (m, 1H), 1.22 (d, J=6.5 Hz, 3H), 1.01 (d, J=6.1 Hz, 3H).

Example 82: 2-([3,3-difluoro-1-[(2S)-2-hydroxypropanoyl]piperidin-4-yl]oxy)-5-[6-([5-[(3S)-3,4-dimethylpiperazin-1-yl]-6-methoxypyridin-2-yl]amino)pyrimidin-4-yl]benzonitrile

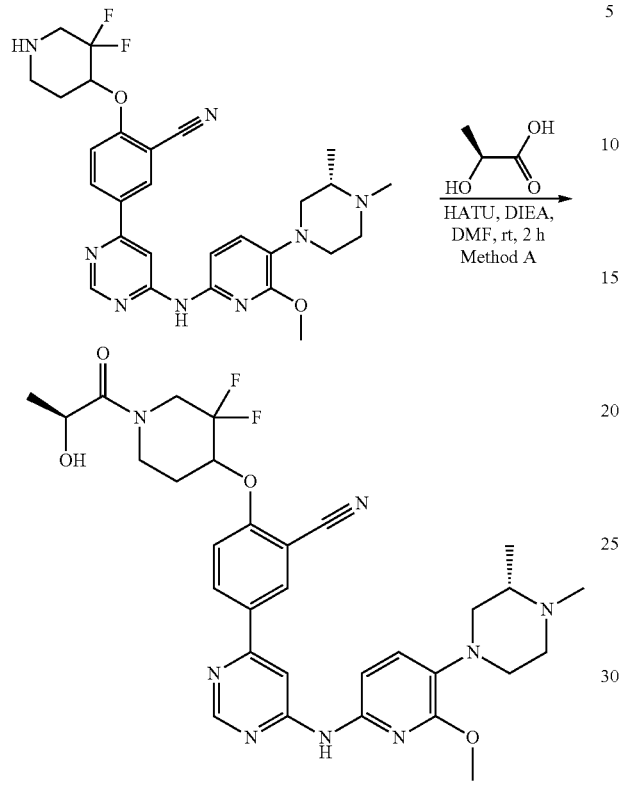

The title compound was prepared from 2-[(3,3-difluoropiperidin-4-yl)oxy]-5-[6-([5-[(3S)-3,4-dimethylpiperazin-1-yl]-6-methoxypyridin-2-yl]amino)pyrimidin-4-yl]benzonitrile and (S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 10 mmol/L $NH_4HCO_3$ and 0.1% $NH_3.H_2O$), 25% to 55% gradient in 8 min; detector, UV 254 nm. 2-([3,3-difluoro-1-[(2S)-2-hydroxypropanoyl]piperidin-4-yl]oxy)-5-[6-([5-[(3S)-3,4-dimethylpiperazin-1-yl]-6-methoxypyridin-2-yl]amino)pyrimidin-4-yl]benzonitrile was obtained as light yellow solid (30 mg, 27%). HPLC: 98.00% purity, RT=5.33 min. MS: m/z=623.1 [M+H]$^+$. $^1$H NMR (300 MHz, DMSO-$d_6$) δ 9.98 (s, 1H), 8.72 (s, 1H), 8.42-8.27 (m, 2H), 8.22 (s, 1H), 7.69-7.59 (m, 1H), 7.30-7.21 (m, 1H), 7.20-7.10 (m, 1H), 5.39-5.30 (m, 1H), 5.27-5.19 (m, 1H), 4.55-4.44 (m, 1H), 4.32-3.52 (m, 7H), 3.27-3.11 (m, 2H), 2.81-2.60 (m, 2H), 2.40-1.71 (m, 8H), 1.22 (d, J=6.5 Hz, 3H), 1.01 (d, J=6.1 Hz, 3H).

Example 83: 2-[(3,3-difluoropiperidin-4-yl)oxy]-5-[6-({6-methoxy-5-[1-(oxetan-3-yl)piperidin-4-yl]pyridin-2-yl}oxy)pyrimidin-4-yl]benzonitrile

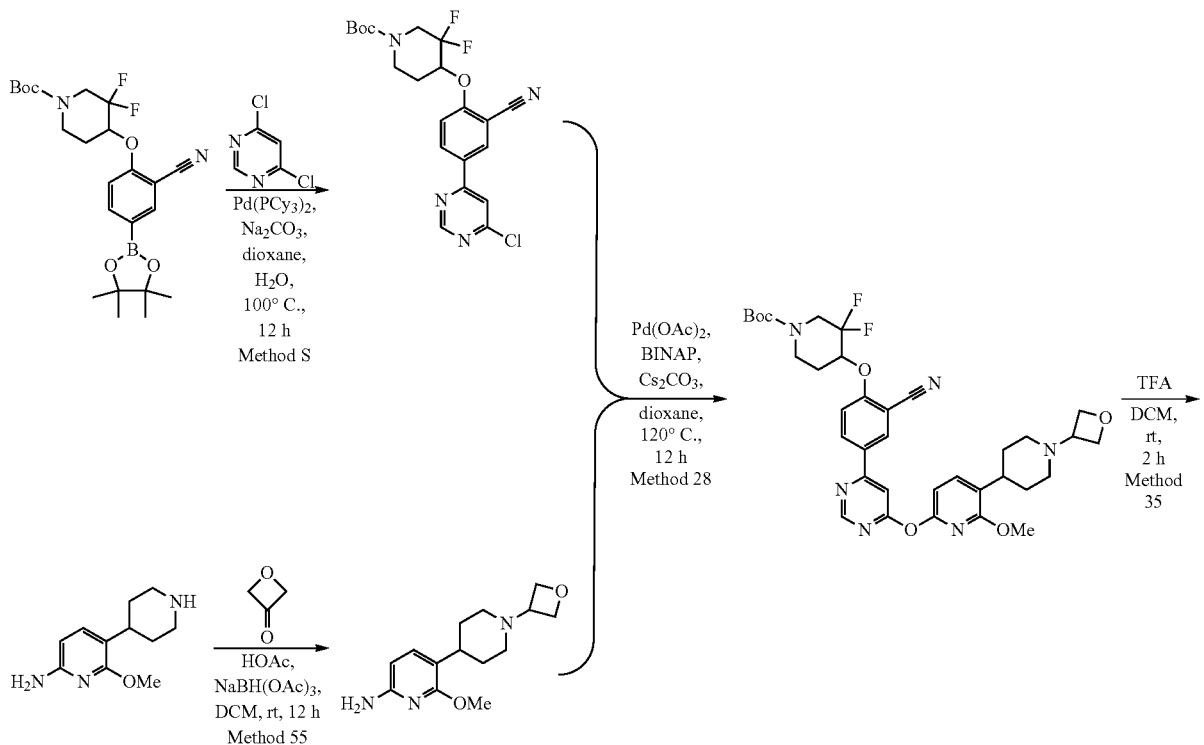

-continued

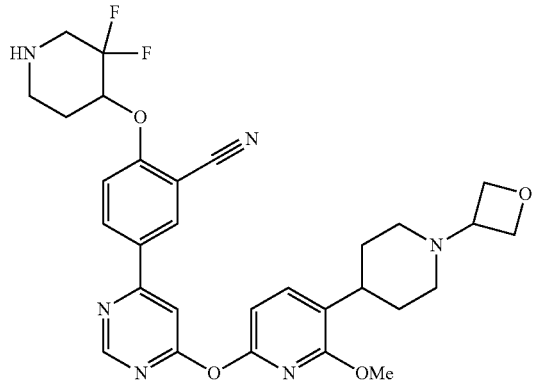

The title compound was prepared from 6-methoxy-5-(piperidin-4-yl)pyridin-2-amine, oxetan-3-one, tert-butyl 4-(4-(6-chloropyrimidin-4-yl)-2-cyanophenoxy)-3,3-difluoropiperidine-1-carboxylate using Method S, 55, 28 and 35. The final product was purified by prep-HPLC under the following conditions: column, Atlantis HILIC OBD Column, 150×19 mm, 5 um; mobile phase, acetonitrile in water (with 10 mmol/L NH$_4$HCO$_3$ and 0.1% NH$_3$.H$_2$O), 35% to 65% gradient in 8 min; detector, UV 254 nm. 2-[(3,3-difluoropiperidin-4-yl)oxy]-5-[6-([6-methoxy-5-[1-(oxetan-3-yl)piperidin-4-yl]pyridin-2-yl]amino)pyrimidin-4-yl]benzonitrile was obtained as white solid (8 mg, 2.5% for 4 steps). HPLC: 99.2% purity, RT=3.49 min. MS: m/z=578.4 [M+H]$^+$. $^1$H NMR (300 MHz, DMSO-d$_6$) δHPLC: 99.2% purity, RT=3.49 min. MS: m/z=578.4 [M+H]+. $^1$H NMR (300 MHz, DMSO-d$_6$) δ 10.13 (s, 1H), 8.76 (s, 1H), 8.42-8.26 (m, 3H), 7.69-7.52 (m, 2H), 7.20-7.10 (m, 1H), 5.23-5.14 (m, 1H), 4.59-4.38 (m, 4H), 3.99 (s, 3H), 3.46-3.35 (m, 1H), 3.24-2.64 (m, 7H), 2.55-2.50 (m, 1H), 2.07-2.01 (m, 1H), 1.92-1.78 (m, 3H), 1.76-1.60 (m, 4H).

Example 84: 2-([3,3-difluoro-1-[(2S)-2-hydroxypropanoyl]piperidin-4-yl]oxy)-5-[6-([6-methoxy-5-[1-(oxetan-3-yl)piperidin-4-yl]pyridin-2-yl]amino)pyrimidin-4-yl]benzonitrile

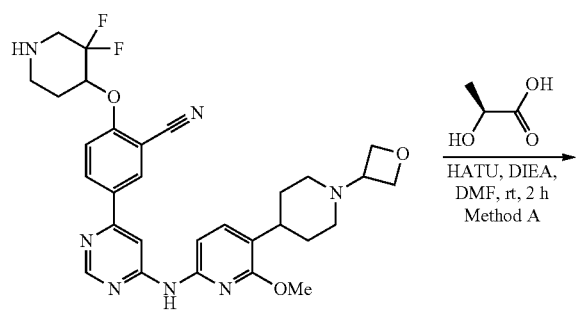

-continued

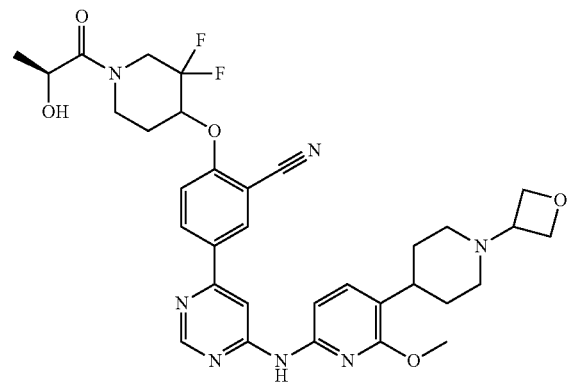

The title compound was prepared from 2-[(3,3-difluoropiperidin-4-yl)oxy]-5-[6-({6-methoxy-5-[1-(oxetan-3-yl)piperidin-4-yl]pyridin-2-yl}oxy)pyrimidin-4-yl]benzonitrile and (S)-2-hydroxypropanoic acid using Method A. The final product was purified by prep-HPLC under the following conditions: column, XBridge Shield RP18 OBD Column, 150×19 mm, 5 um; mobile phase, acetonitrile in water (with 10 mmol/L NH$_4$HCO$_3$ and 0.1% NH$_3$.H$_2$O), 55% to 85% gradient in 8 min; detector, UV 254 nm. 2-([3,3-difluoro-1-[(2S)-2-hydroxypropanoyl]piperidin-4-yl]oxy)-5-[6-([6-methoxy-5-[1-(oxetan-3-yl)piperidin-4-yl]pyridin-2-yl]amino)pyrimidin-4-yl]benzonitrile was obtained as white solid (11 mg, 1.6% for 5 steps). HPLC: 99.8% purity, RT=4.21 min. MS: m/z=650.5 [M+H]$^+$. $^1$H NMR (300 MHz, DMSO-d$_6$) δ 10.15 (s, 1H), 8.77 (s, 1H), 8.44-8.29 (m, 3H), 7.70-7.55 (m, 2H), 7.19-7.10 (m, 1H), 5.40-5.33 (m, 1H), 5.28-5.20 (m, 1H), 4.60-4.39 (m, 5H), 4.21-3.48 (m, 7H), 3.46-3.37 (m, 1H), 2.85-2.65 (m, 3H), 2.30-1.91 (m, 2H), 1.91-1.56 (m, 6H), 1.22 (d, J=6.5 Hz, 3H).

Example 85: 2-([3,3-difluoro-1-[(2S)-2-hydroxypropanoyl]piperidin-4-yl]oxy)-5-[6-([4-[4-(oxetan-3-yl)piperazin-1-yl]phenyl]amino)pyrimidin-4-yl]benzonitrile
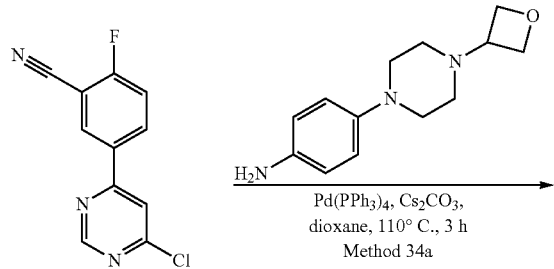
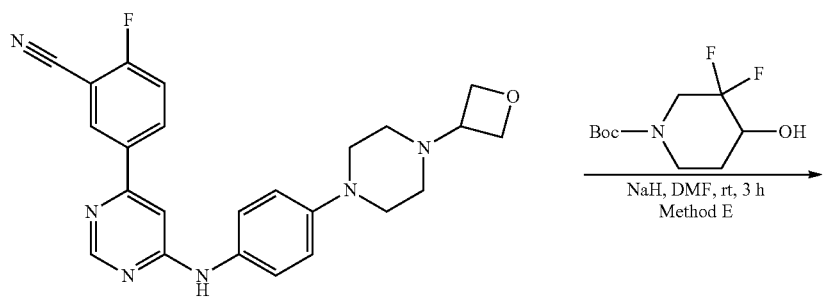
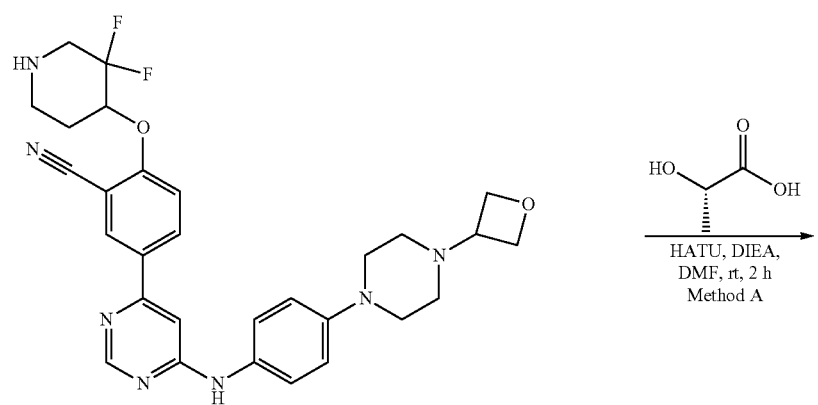

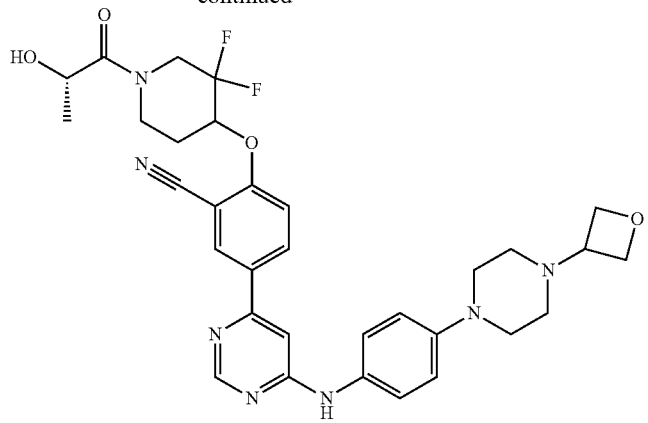

The title compound was prepared from 5-(6-chloropyrimidin-4-yl)-2-fluorobenzonitrile, 4-(4-(oxetan-3-yl)piperazin-1-yl)benzenamine, tert-butyl 3,3-difluoro-4-hydroxypiperidine-1-carboxylate and (S)-2-hydroxypropanoic acid using Method 34a, E, 35 and A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 27% to 32% gradient in 8 min; detector, UV 254 nm. 5-[6-([5-[(2R,6S)-2,6-dimethylmorpholin-4-yl]-6-methoxypyridin-2-yl]amino)pyrimidin-4-yl]-2-(oxan-4-yloxy)benzonitrile was obtained as off-white solid (27 mg, 3.1% for 4 steps). HPLC: 97.6% purity, RT=6.25 min. MS: m/z=620.2 [M+H]$^+$. $^1$H NMR (300 MHz, DMSO-d$_6$) δ 9.47 (s, 1H), 8.63 (s, 1H), 8.40-8.26 (m, 2H), 7.69-7.59 (m, 1H), 7.55-7.45 (m, 2H), 7.14 (s, 1H), 7.01-6.92 (m, 2H), 5.39-5.32 (m, 1H), 5.29-5.19 (m, 1H), 4.64-4.44 (m, 5H), 4.35-3.39 (m, 5H), 3.19-3.09 (m, 4H), 2.48-2.38 (m, 4H), 2.27-1.77 (m, 2H), 1.24 (d, J=6.5 Hz, 3H).

Example 86: 2-([3,3-difluoro-1-[(2R)-2-hydroxypropanoyl]piperidin-4-yl]oxy)-5-[6-([4-[4-(oxetan-3-yl)piperazin-1-yl]phenyl]amino)pyrimidin-4-yl]benzonitrile

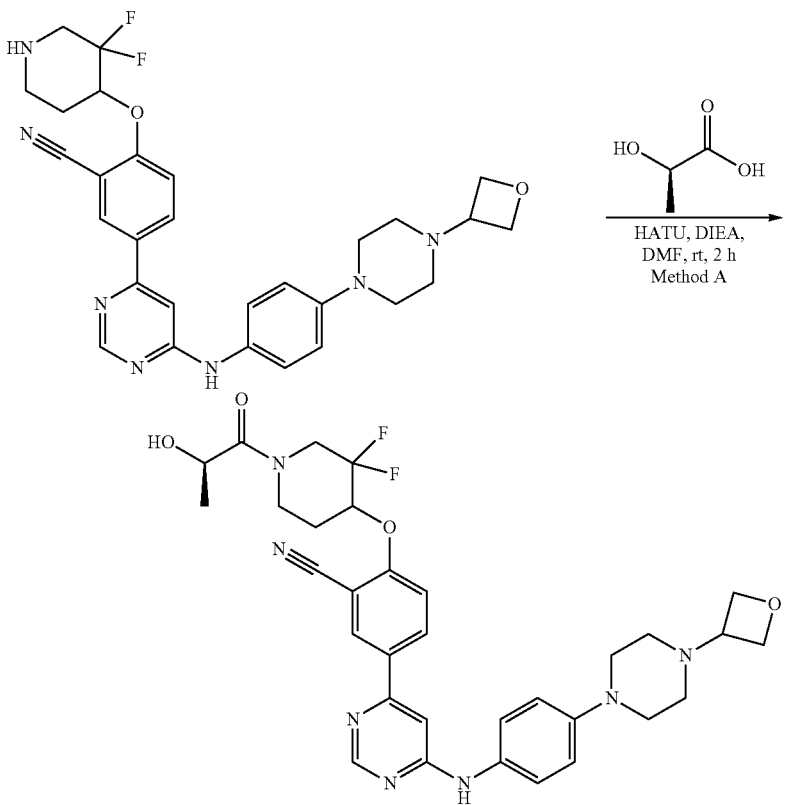

The title compound was prepared from 2-[(3,3-difluoropiperidin-4-yl)oxy]-5-[6-([4-[4-(oxetan-3-yl)piperazin-1-yl]

phenyl]amino)pyrimidin-4-yl]benzonitrile and (R)-2-hydroxypropanoic acid using Method A. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 27% to 32% gradient in 8 min; detector, UV 254 nm. 2-([3,3-difluoro-1-[(2R)-2-hydroxypropanoyl]piperidin-4-yl]oxy)-5-[6-([4-[4-(oxetan-3-yl)piperazin-1-yl]phenyl]amino)pyrimidin-4-yl]benzonitrile was obtained as yellow solid (20 mg, 28%). HPLC: 98.6% purity, RT=3.21 min. MS: m/z=620.2 [M+H]$^+$. $^1$H NMR (300 MHz, DMSO-d$_6$) δ 9.45 (s, 1H), 8.62 (s, 1H), 8.39-8.25 (m, 2H), 7.67-7.58 (m, 1H), 7.53-7.43 (m, 2H), 7.13 (s, 1H), 7.00-6.90 (m, 2H), 5.38-5.31 (m, 1H), 5.27-5.18 (m, 1H), 4.63-4.42 (m, 5H), 4.35-3.38 (m, 5H), 3.18-3.08 (m, 4H), 2.46-2.36 (m, 4H), 2.23-1.75 (m, 2H), 1.22 (d, J=6.5 Hz, 3H).

Example 87: 6-[(6-[3-cyano-4-[(oxan-4-yl)amino]phenyl]pyrimidin-4-yl)amino]-2-methoxy-N,N-dimethylpyridine-3-carboxamide The title compound was prepared from 2-(tetrahydro-2H-pyran-4-ylamino)-5-(4,4,5,5-tetramethyl-1,3,2-dioxaborolan-2-yl)benzonitrile, 6-chloropyrimidin-4-amine, and 6-chloro-2-methoxy-N,N-dimethylnicotinamide using Method S and 34a. The final product was purified by prep-HPLC under the following conditions: column, XBridge Prep C18 OBD Column, 150×19 mm, 5 um; mobile phase, acetonitrile in water (with 10 mmol/L NH$_4$HCO$_3$ and 0.1% NH$_3$.H$_2$O), 20% to 53% gradient in 7 min; detector, UV 254 nm. 6-[(6-[3-cyano-4-[(oxan-4-yl)amino]phenyl]pyrimidin-4-yl)amino]-2-methoxy-N,N-dimethylpyridine-3-carboxamide was obtained as off-white solid (25 mg, 17% for 2 steps). HPLC: 98.1% purity, RT=0.98 min. MS: m/z=474.1 [M+H]$^+$. $^1$H NMR (300 MHz, DMSO-d$_6$) δ 10.28 (s, 1H), 8.73 (s, 1H), 8.32 (s, 1H), 8.18 (s, 1H), 8.14-8.03 (m, 1H), 7.67-7.57 (m, 1H), 7.27-7.17 (m, 1H), 7.12-7.02 (m, 1H), 6.37-6.28 (m, 1H), 4.02 (s, 3H), 3.95-3.85 (m, 2H), 3.80-3.71 (m, 1H), 3.50-3.35 (m, 2H), 2.97 (s, 3H), 2.84 (s, 3H), 1.90-1.79 (m, 2H), 1.74-1.54 (m, 2H).

Example 88: 6-([6-[3-cyano-4-(oxan-4-yloxy)phenyl]pyrimidin-4-yl]amino)-N-(2-hydroxyethyl)-2-methoxypyridine-3-carboxamide

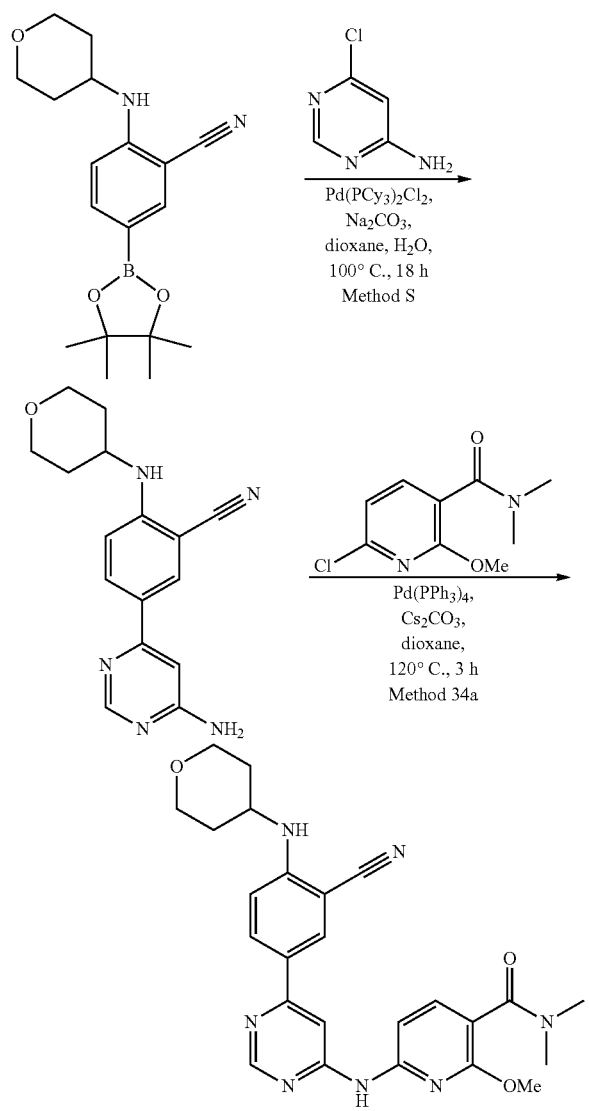

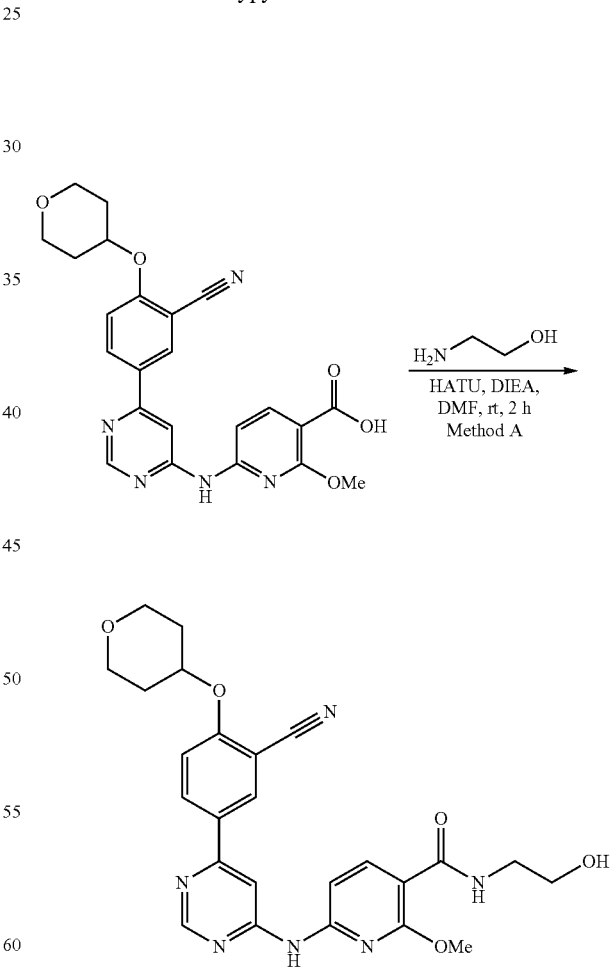

The title compound was prepared from 6-([6-[3-cyano-4-(oxan-4-yloxy)phenyl]pyrimidin-4-yl]amino)-2-methoxypyridine-3-carboxylic acid and 2-aminoethan-1-ol using Method A. The final product was purified by prep-HPLC under the following conditions: column, Atlantis HILIC OBD Column, 150×19 mm, 5 um; mobile phase, acetonitrile in water (with 10 mmol/L $NH_4HCO_3$ and 0.1% $NH_3.H_2O$), 20% to 47% gradient in 8 min; detector, UV 254 nm. 6-([6-[3-cyano-4-(oxan-4-yloxy)phenyl]pyrimidin-4-yl]amino)-N-(2-hydroxyethyl)-2-methoxypyridine-3-carboxamide was obtained as a white solid (28 mg, 20%). HPLC: 96.8% purity, RT=4.92 min. MS: m/z=491.0 [M+H]$^+$. $^1$H NMR (300 MHz, DMSO-d$_6$) δ 10.57 (s, 1H), 8.83 (s, 1H), 8.47 (s, 1H), 8.42-8.27 (m, 2H), 8.29-8.11 (m, 2H), 7.54 (d, J=9.1 Hz, 1H), 7.23 (d, J=8.4 Hz, 1H), 4.97-4.90 (m, 1H), 4.85-4.78 (m, 1H), 4.13 (s, 3H), 3.95-3.81 (m, 2H), 3.63-3.47 (m, 4H), 3.44-3.34 (m, 2H), 2.10-1.99 (m, 2H), 1.78-1.61 (m, 2H).

Example 89: 6-((6-(3-cyano-4-((tetrahydro-2H-pyran-4-yl)oxy)phenyl)pyrimidin-4-yl)amino)-2-methoxy-N-(quinuclidin-3-yl)nicotinamide

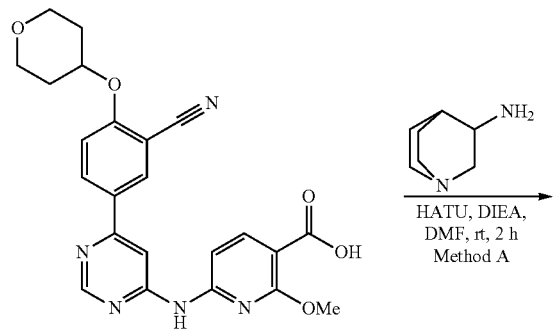

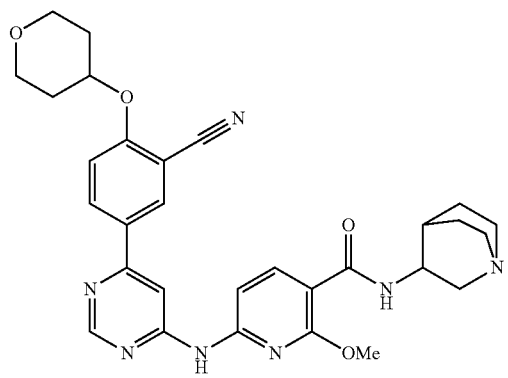

The title compound was prepared from 6-([6-[3-cyano-4-(oxan-4-yloxy)phenyl]pyrimidin-4-yl]amino)-2-methoxypyridine-3-carboxylic acid and 1-azabicyclo[2.2.2]octan-3-amine using Method A. The final product was purified by prep-HPLC under the following conditions: column, XBridge Prep OBD C18 Column, 150×19 mm, 5 um; mobile phase, acetonitrile in water (with 10 mmol/L $NH_4HCO_3$ and 0.1% $NH_3.H_2O$), 25% to 55% gradient in 8 min; detector, UV 254 nm. 6-((6-(3-cyano-4-((tetrahydro-2H-pyran-4-yl)oxy)phenyl)pyrimidin-4-yl)amino)-2-methoxy-N-(quinuclidin-3-yl)nicotinamide was obtained as a white solid (25 mg, 19%). HPLC: 97.7% purity, RT=4.64 min. MS: m/z=556.1 [M+H]$^+$. $^1$H NMR (300 MHz, DMSO-d$_6$) δ 10.56 (s, 1H), 8.83 (s, 1H), 8.48 (s, 1H), 8.42-8.28 (m, 2H), 8.19-8.02 (m, 2H), 7.59-7.50 (m, 1H), 7.27-7.18 (m, 1H), 4.96-4.89 (m, 1H), 4.14 (s, 3H), 4.02-3.80 (m, 3H), 3.62-3.49 (m, 2H), 3.24-3.10 (m, 1H), 2.80-2.65 (m, 4H), 2.58-2.51 (m, 1H), 2.10-1.99 (m, 2H), 1.91-1.84 (m, 1H), 1.77-1.45 (m, 5H), 1.44-1.37 (m, 1H).

Example 90: 5-(6-[[6-methoxy-5-([3-oxa-9-azabicyclo[3.3.1]nonan-9-yl]carbonyl)pyridin-2-yl]amino]pyrimidin-4-yl)-2-(oxan-4-yloxy)benzonitrile

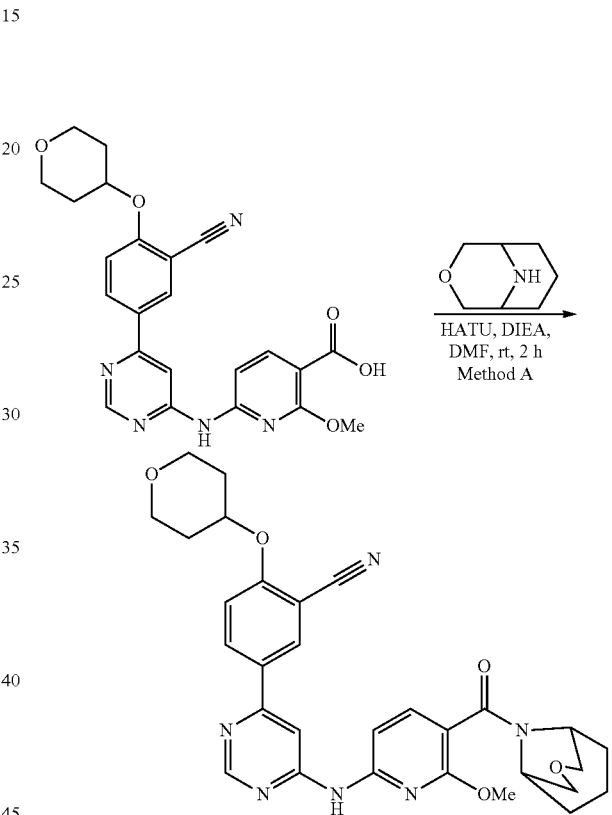

The title compound was prepared from 6-([6-[3-cyano-4-(oxan-4-yloxy)phenyl]pyrimidin-4-yl]amino)-2-methoxypyridine-3-carboxylic acid and 3-oxa-9-azabicyclo[3.3.1]nonane using Method A. The final product was purified by prep-HPLC under the following conditions: column, XBridge Prep OBD C18 Column, 150×19 mm, 5 um; mobile phase, acetonitrile in water (with 10 mmol/L $NH_4HCO_3$ and 0.1% $NH_3.H_2O$), 20% to 50% gradient in 8 min; detector, UV 254 nm. 5-(6-[[6-methoxy-5-([3-oxa-9-azabicyclo[3.3.1]nonan-9-yl]carbonyl)pyridin-2-yl]amino]pyrimidin-4-yl)-2-(oxan-4-yloxy)benzonitrile was obtained as a light yellow solid (23 mg, 33%). HPLC: 93.8% purity, RT=5.78 min. MS: m/z=557.1 [M+H]$^+$. $^1$H NMR (300 MHz, DMSO-d$_6$) δ 10.43 (s, 1H), 8.85-8.78 (m, 1H), 8.44 (s, 1H), 8.42-8.26 (m, 2H), 7.75-7.65 (m, 1H), 7.60-7.50 (m, 1H), 7.23 (d, J=8.0 Hz, 1H), 4.99-4.87 (m, 1H), 4.41 (br s, 1H), 4.02 (s, 3H), 3.99-3.76 (m, 4H), 3.74-3.49 (m, 4H), 2.51-2.40 (m, 1H), 2.15-1.96 (m, 2H), 1.93-1.47 (m, 8H).

Example 91: 2-[[(4S)-3,3-difluoro-1-[(2S)-2-hydroxypropanoyl]piperidin-4-yl]oxy]-5-[6-([6-methoxy-5-[4-(oxetan-3-yl)piperazin-1-yl]pyridin-2-yl]amino)pyrimidin-4-yl]benzonitrile & Example 92: 2-[[(4R)-3,3-difluoro-1-[(2S)-2-hydroxypropanoyl]piperidin-4-yl]oxy]-5-[6-([6-methoxy-5-[4-(oxetan-3-yl)piperazin-1-yl]pyridin-2-yl]amino)pyrimidin-4-yl]benzonitrile

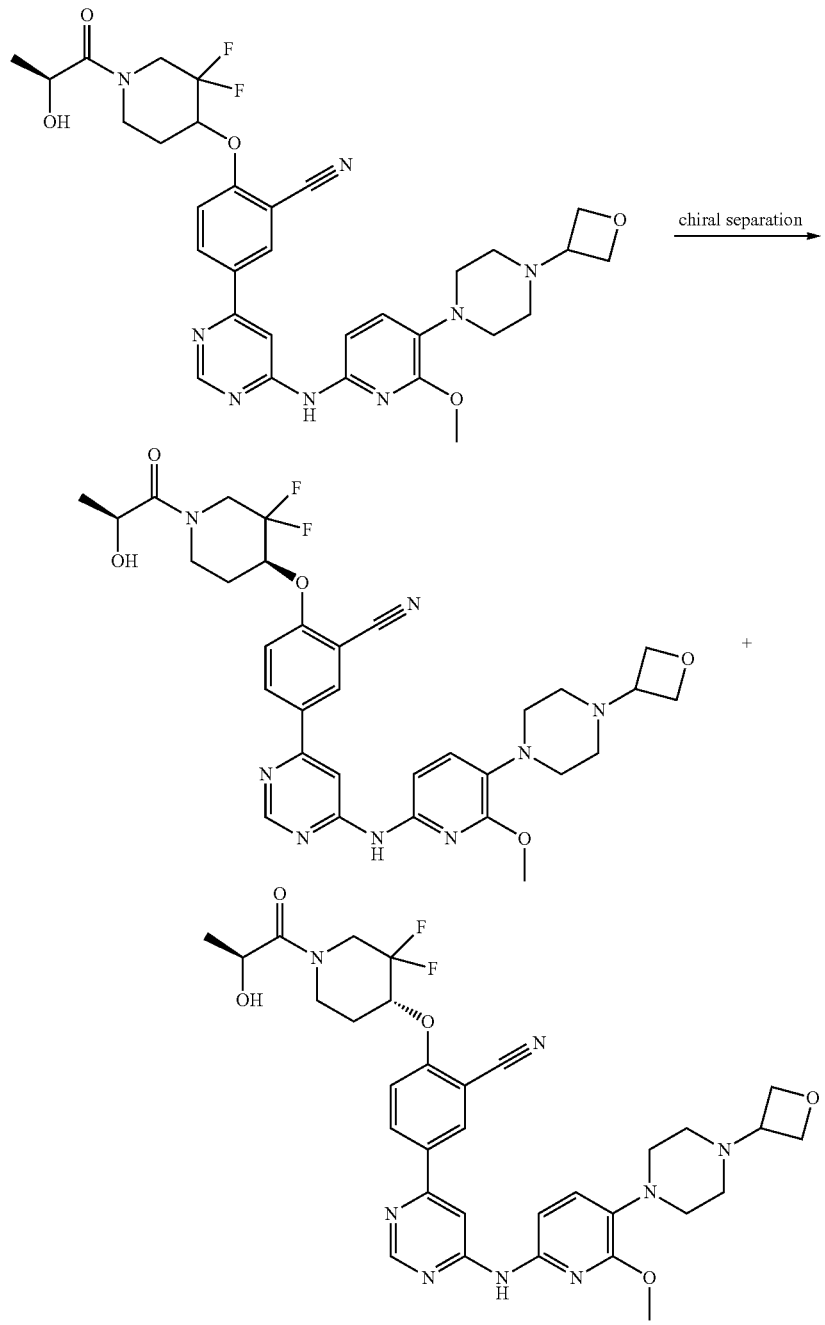

The two diastereomers were obtained by separation on chiral prep-HPLC under the following condition: column, CHIRALPAK IA-3, 0.46×5 cm, 3 um; mobile phase, hexane:DCM:EtOH=5:1:6 (with 0.1% DEA), isocratic for 30 min; detector, UV 254 nm.

Example 91: (101 mg, 26%, light yellow solid) HPLC: 95.9% purity, RT=3.93 min. MS: m/z=651.1 [M+H]$^+$. $^1$H NMR (400 MHz, DMSO-d$_6$, ppm) δ 9.97 (s, 1H), 8.70 (s, 1H), 8.40-8.28 (m, 2H), 8.19-8.04 (m, 1H), 7.66-7.58 (m, 1H), 7.31-7.23 (m, 1H), 7.23-7.14 (m, 1H), 5.38-5.23 (m, 2H), 4.60-4.41 (m, 5H), 4.30-4.00 (m, 1H), 3.95 (s, 3H), 3.89-3.69 (m, 3H), 3.49-3.26 (m, 1H), 3.03-2.90 (m, 4H), 2.45-2.33 (m, 4H), 2.25-1.75 (m, 2H), 1.21 (d, J=6.1 Hz, 3H).

Example 92: (105 mg, 27%, yellow solid) HPLC: 97.5% purity, RT=3.93 min. MS: m/z=651.1 [M+H]+. 1H NMR (400 MHz, DMSO-d6, ppm) δ 10.00 (s, 1H), 8.73 (s, 1H), 8.41-8.29 (m, 2H), 8.23 (s, 1H), 7.68-7.61 (m, 1H), 7.33-7.26 (m, 1H), 7.21-7.14 (m, 1H), 5.44-5.19 (m, 2H), 4.61-4.41 (m, 5H), 4.27-4.02 (m, 1H), 3.98 (s, 3H), 3.94-3.41 (m, 4H), 3.01-2.94 (m, 4H), 2.43-2.38 (m, 4H), 2.25-1.83 (m, 2H), 1.23 (d, J=6.5 Hz, 3H).

2-[[(4S)-3,3-difluoro-1-[(2S)-2-hydroxypropanoyl] piperidin-4-yl]oxy]-5-[6-([6-methoxy-5-[1-(oxetan-3-yl)piperidin-4-yl]pyridin-2-yl]amino)pyrimidin-4-yl]benzonitrile & 2-[[(4R)-3,3-difluoro-1-[(2S)-2-hydroxypropanoyl]piperidin-4-yl]oxy]-5-[6-([6-methoxy-5-[1-(oxetan-3-yl)piperidin-4-yl]pyridin-2-yl]amino)pyrimidin-4-yl]benzonitrile

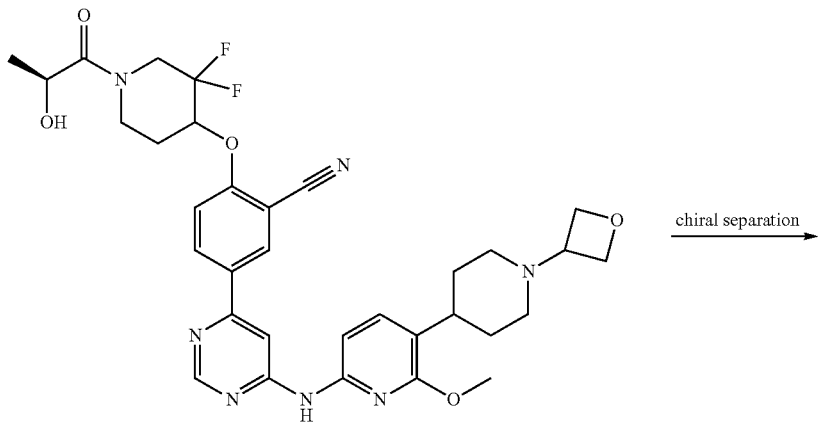

chiral separation →

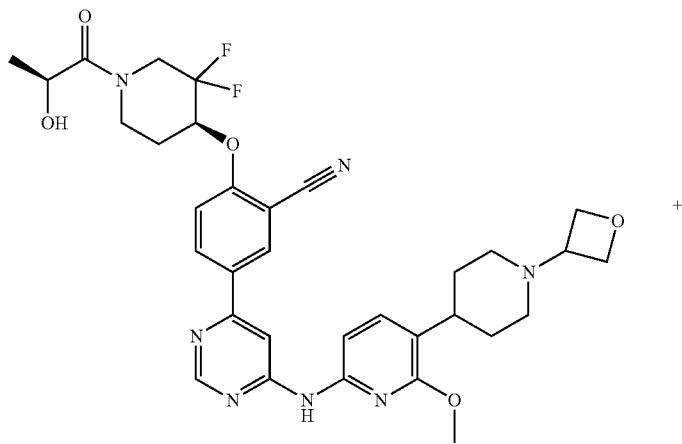

+

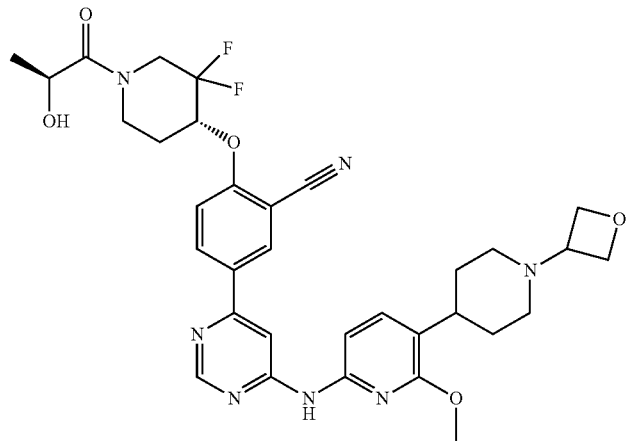

Example 93: 2-[[(4S)-3,3-difluoro-1-[(2S)-2-hydroxypropanoyl]piperidin-4-yl]oxy]-5-[6-([6-methoxy-5-[1-(oxetan-3-yl)piperidin-4-yl]pyridin-2-yl]amino)pyrimidin-4-yl]benzonitrile & Example 94: 2-[[(4R)-3,3-difluoro-1-[(2S)-2-hydroxypropanoyl]piperidin-4-yl]oxy]-5-[6-([6-methoxy-5-[1-(oxetan-3-yl)piperidin-4-yl]pyridin-2-yl]amino)pyrimidin-4-yl]benzonitrile The two diastereomers were obtained by separation on chiral prep-HPLC under the following condition: column, CHIRALPAK ID-3, 0.46×10 cm, 3 um; mobile phase, MtBE (with 0.1% DEA):MeOH=95:5, isocratic for 25 min; detector, UV 254 nm.

Example 93: (72 mg, 23%, white solid) HPLC: 94.5% purity, RT=4.20 min. MS: m/z=650.1 [M+H]⁺. ¹H NMR (400 MHz, DMSO-$d_6$, ppm) δ 10.13 (s, 1H), 8.77 (s, 1H), 8.45-8.29 (m, 3H), 7.68-7.56 (m, 2H), 7.18-7.11 (m, 1H), 5.38-5.33 (m, 1H), 5.26-5.19 (m, 1H), 4.60-4.39 (m, 5H), 4.28-3.51 (m, 7H), 3.45-3.38 (m, 1H), 2.86-2.67 (m, 3H), 2.25-1.91 (m, 2H), 1.90-1.80 (m, 2H), 1.73-1.53 (m, 4H), 1.22 (d, J=6.4 Hz, 3H).

Example 94: (82 mg, 26%, white solid) HPLC: 96.5% purity, RT=4.20 min. MS: m/z=650.2 [M+H]⁺. 1H NMR (400 MHz, DMSO-d6, ppm) δ 10.13 (s, 1H), 8.77 (s, 1H), 8.43-8.30 (m, 3H), 7.69-7.56 (m, 2H), 7.18-7.11 (m, 1H), 5.38-5.33 (m, 1H), 5.24-5.18 (m, 1H), 4.61-4.36 (m, 5H), 4.28-3.51 (m, 7H), 3.46-3.36 (m, 1H), 2.87-2.63 (m, 3H), 2.23-1.94 (m, 2H), 1.93-1.79 (m, 2H), 1.75-1.54 (m, 4H), 1.23 (d, J=6.5 Hz, 3H).

Example 95: 2-[[(4S)-3,3-difluoro-1-[(2R)-2-hydroxypropanoyl]piperidin-4-yl]oxy]-5-[6-([6-methoxy-5-[4-(oxetan-3-yl)piperazin-1-yl]pyridin-2-yl]amino)pyrimidin-4-yl]benzonitrile & Example 96: 2-[[(4S)-3,3-difluoro-1-[(2R)-2-hydroxypropanoyl]piperidin-4-yl]oxy]-5-[6-([6-methoxy-5-[4-(oxetan-3-yl)piperazin-1-yl]pyridin-2-yl]amino)pyrimidin-4-yl]benzonitrile

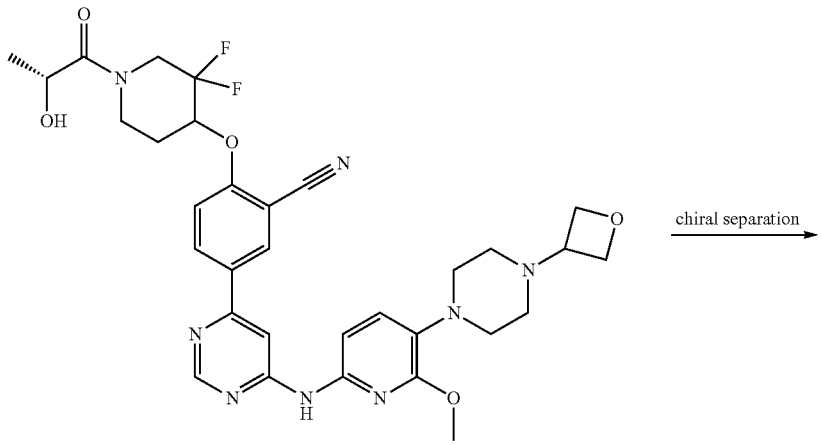

chiral separation

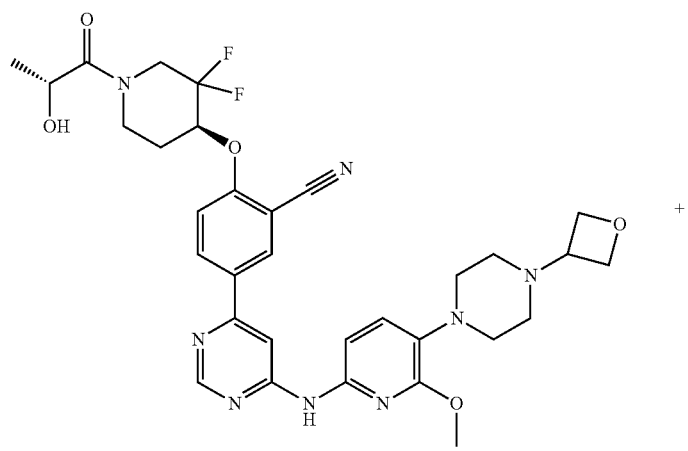

+

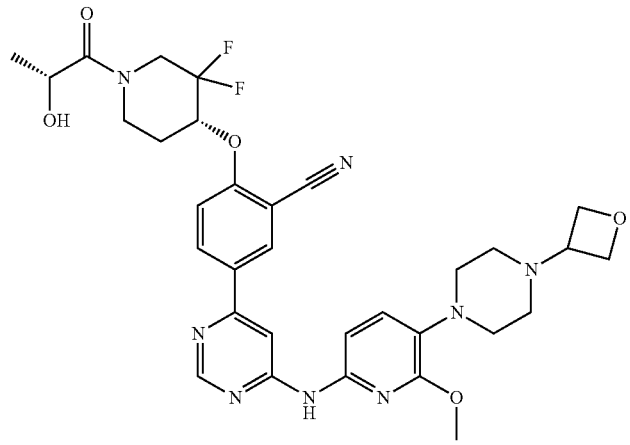

The two diastereomers were obtained by separation on chiral prep-HPLC under the following condition: column, CHIRAL Cellulose-SB, 0.46×10 cm, 3 um; mobile phase, Hexane (with 20 mM NH₃H₂O):EtOH=50:50, isocratic for 25 min; detector, UV 254 nm.

Example 95: (92 mg, 31%, white solid) HPLC: 96.1% purity, RT=4.00 min. MS: m/z=651.3 [M+H]⁺. ¹H NMR (300 MHz, DMSO-d₆, ppm) δ 9.98 (s, 1H), 8.71 (s, 1H), 8.42-8.27 (m, 2H), 8.21 (s, 1H), 7.67-7.58 (m, 1H), 7.32-7.23 (m, 1H), 7.20-7.11 (m, 1H), 5.36-5.30 (m, 1H), 5.25-5.16 (m, 1H), 4.60-4.39 (m, 5H), 4.30-3.42 (m, 8H), 2.99-2.93 (m, 4H), 2.42-2.35 (m, 4H), 2.24-1.76 (m, 2H), 1.20 (d, J=6.5 Hz, 3H).

Example 96: (96 mg, 32%, white solid) HPLC: 99.4% purity, RT=3.93 min. MS: m/z=651.5 [M+H]⁺. ¹H NMR (300 MHz, DMSO-d₆, ppm) δ 9.98 (s, 1H), 8.70 (s, 1H), 8.40-8.26 (m, 2H), 8.19 (s, 1H), 7.66-7.56 (m, 1H), 7.32-7.22 (m, 1H), 7.20-7.10 (m, 1H), 5.36-5.30 (m, 1H), 5.27-5.18 (m, 1H), 4.61-4.38 (m, 5H), 4.23-3.41 (m, 8H), 2.99-2.92 (m, 4H), 2.41-2.35 (m, 4H), 2.21-1.69 (m, 2H), 1.20 (d, J=6.4 Hz, 3H).

Example 97: 2-([3,3-difluoro-1-[(2R)-2-hydroxypropanoyl]piperidin-4-yl]oxy)-5-[6-([6-methoxy-5-[1-(oxetan-3-yl)piperidin-4-yl]pyridin-2-yl]amino)pyrimidin-4-yl]benzonitrile

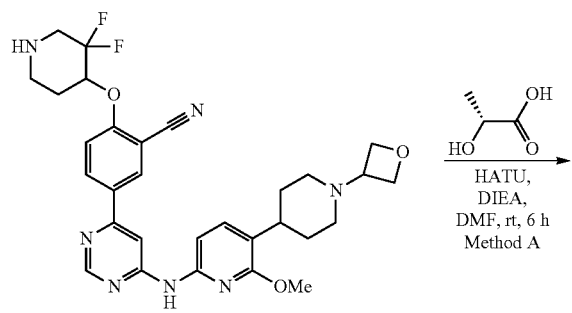

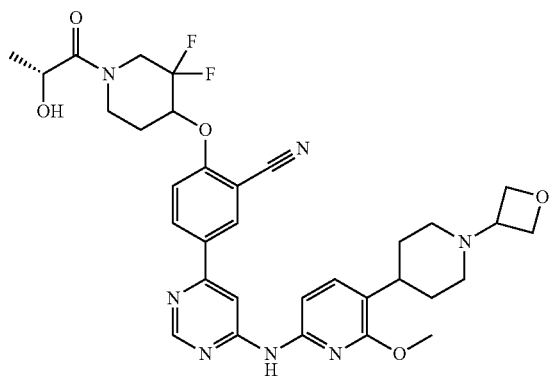

The title compound was prepared from 2-[(3,3-difluoropiperidin-4-yl)oxy]-5-[6-([6-methoxy-5-[1-(oxetan-3-yl)piperidin-4-yl]pyridin-2-yl]amino)pyrimidin-4-yl]benzonitrile and (2R)-2-hydroxypropanoic acid using Method A. The final product was purified by prep-HPLC under the following condition: column, XBridge Prep OBD C18 Column, 150×30 mm, 5 um; mobile phase, acetonitrile in water (with 10 mmol/L NH₄HCO₃ and 0.1% NH₃.H₂O), 30% to 45% gradient in 8 min; detector, UV 254 nm. 2-([3,3-difluoro-1-[(2R)-2-hydroxypropanoyl]piperidin-4-yl]oxy)-5-[6-([6-methoxy-5-[1-(oxetan-3-yl)piperidin-4-yl]pyridin-2-yl]amino)pyrimidin-4-yl]benzonitrile was obtained as a white solid (26 mg, 33%). HPLC: 97.9% purity, RT=3.16 min. MS: m/z=650.1[M+H]⁺. ¹H NMR (400 MHz, DMSO-d₆, ppm) δ 10.14 (s, 1H), 8.79-8.74 (m, 1H), 8.43-8.30 (m, 3H), 7.69-7.56 (m, 2H), 7.18-7.11 (m, 1H), 5.38-5.34 (m, 1H), 5.27-5.18 (m, 1H), 4.58-4.40 (m, 5H), 4.27-4.03 (m, 1H), 3.99 (s, 3H), 3.93-3.52 (m, 2H), 3.46-3.35 (m, 1H), 2.83-2.67 (m, 3H), 2.24-1.94 (m, 2H), 1.90-1.80 (m, 2H), 1.75-1.58 (m, 4H), 1.22 (d, J=6.5 Hz, 3H).

Example 98: 2-((R)-3,3-difluoro-1-((R)-2-hydroxy-propanoyl)piperidin-4-yloxy)-5-(6-(6-methoxy-5-((S)-2-methyl-4-(oxetan-3-yl)piperazin-1-yl)pyridin-2-ylamino)pyrimidin-4-yl)benzonitrile & Example 99: 2-((S)-3,3-difluoro-1-((R)-2-hydroxypropanoyl)piperidin-4-yloxy)-5-(6-(6-methoxy-5-((S)-2-methyl-4-(oxetan-3-yl)piperazin-1-yl)pyridin-2-ylamino)pyrimidin-4-yl)benzonitrile
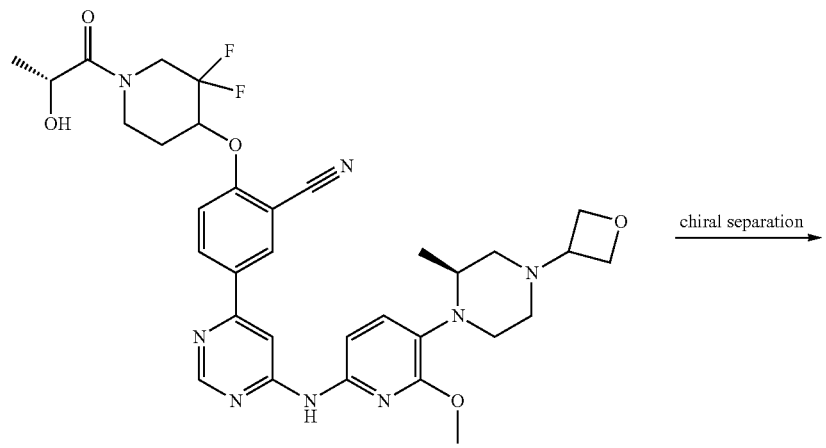
chiral separation
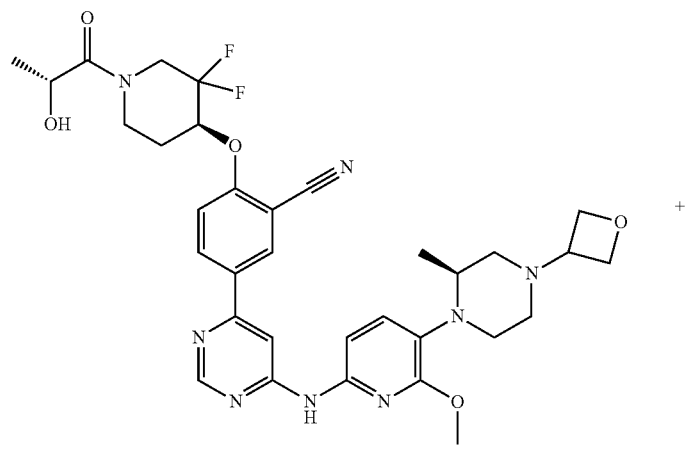
+
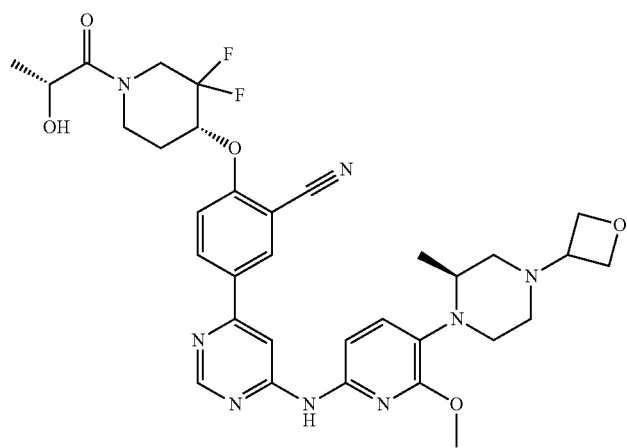

The title compounds were obtained by separation on chiral prep-HPLC under the following condition: column, CHIRAL Cellulose-SB, 0.46×10 cm, 3 um; mobile phase, 70% hexane (with 20 mM NH$_3$H$_2$O) in EtOH, isocratic for 25 min; detector, UV 254 nm.

Example 98: (99 mg, 45%, yellow solid) HPLC: 99.4% purity, RT=4.20 min. MS: m/z=665.0 [M+H]$^+$. $^1$H NMR (300 MHz, DMSO-d$_6$, ppm) δ 10.08 (s, 1H), 8.73 (s, 1H), 8.42-8.27 (m, 3H), 7.68-7.58 (m, 1H), 7.43-7.33 (m, 1H), 7.18-7.08 (m, 1H), 5.36-5.33 (m, 1H), 5.27-5.18 (m, 1H), 4.58-4.36 (m, 5H), 4.18-3.34 (m, 9H), 3.07-3.00 (m, 1H), 2.82-2.75 (m, 1H), 2.59-2.53 (m, 2H), 2.31-1.88 (m, 4H), 1.20 (d, J=6.3 Hz, 3H), 0.81 (d, J=6.2 Hz, 3H).

Example 99: (99 mg, 45%, light yellow solid) HPLC: 99.4% purity, RT=4.20 min. MS: m/z=665.0 [M+H]$^+$. $^1$H NMR (300 MHz, DMSO-d$_6$, ppm) δ 10.08 (s, 1H), 8.73 (s, 1H), 8.42-8.27 (m, 3H), 7.68-7.58 (m, 1H), 7.43-7.33 (m, 1H), 7.18-7.09 (m, 1H), 5.36-5.33 (m, 1H), 5.25-5.16 (m, 1H), 4.60-4.36 (m, 5H), 4.18-3.34 (m, 9H), 3.06-3.00 (m, 1H), 2.82-2.75 (m, 1H), 2.59-2.53 (m, 2H), 2.33-1.69 (m, 4H), 1.20 (d, J=6.5 Hz, 3H), 0.81 (d, J=6.2 Hz, 3H).

Example 100: 5-[6-({6-methoxy-5-[4-(oxetan-3-yl)piperazin-1-yl]pyridin-2-yl}amino)pyrimidin-4-yl]-2-(oxan-4-yloxy)benzonitrile

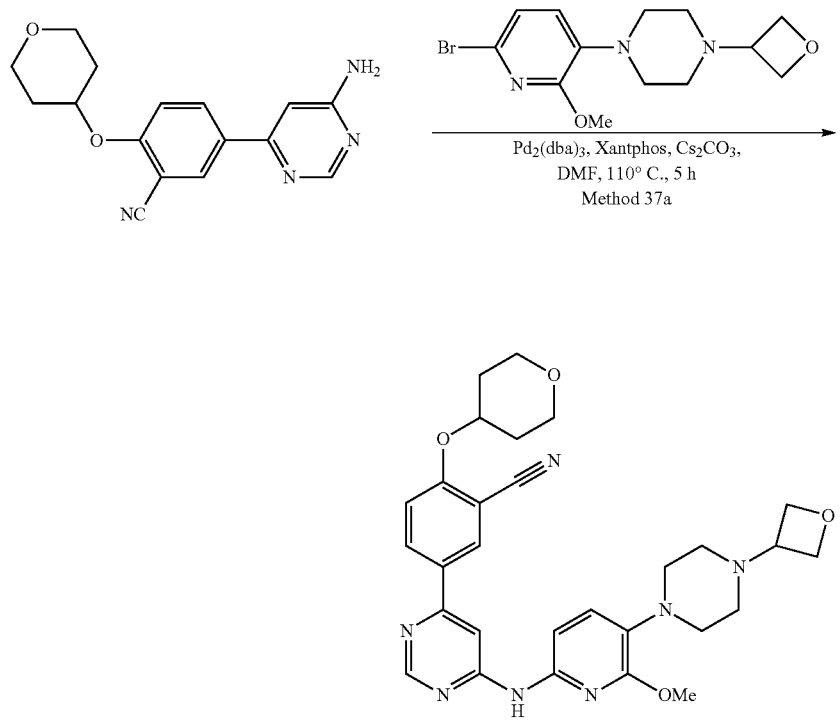

The title compound was prepared (250 mg, 54%) as in Example 1 using 5-(6-Amino-pyrimidin-4-yl)-2-(tetrahydro-pyran-4-yloxy)-benzonitrile (250.00 mg; 0.84 mmol; 1.00 eq.), 1-(6-Bromo-2-methoxy-pyridin-3-yl)-4-oxetan-3-yl-piperazine (276.90 mg; 0.84 mmol; 1.00 eq.), Xantphos (184.32 mg; 0.28 mmol; 0.33 eq.), Cs$_2$CO$_3$ (578.71 mg; 1.69 mmol; 2.00 eq.) and Pd2(dba)3CHCl3 (101.12 mg; 0.09 mmol; 0.11 eq.) in N,N-Dimethyl-formamide (20.00 ml). HPLC: 100% purity, RT=1.97 min. MS: m/z=544.9 [M+H]$^+$; $^1$H NMR (400 MHz, Chloroform-d) δ 8.77 (s, 1H), 8.27 (d, J=7.3 Hz, 2H), 8.09 (s, 1H), 7.83-7.77 (m, 1H), 7.24 (d, J=8.1 Hz, 1H), 7.09 (d, J=9.1 Hz, 1H), 6.92 (d, J=8.1 Hz, 1H), 4.72 (m, J=6.4 Hz, 5H), 4.12-4.00 (m, 4H), 4.04 (s, 3H) 3.73-3.59 (m, 5H), 3.14 (br s, 2H), 2.59 (br s, 2H), 2.17-2.04 (m, 2H), 1.94 (m, 2H).

Example 101: 2-[[(4S)-3,3-difluoro-1-[(2S)-2-hydroxypropanoyl]piperidin-4-yl]oxy]-5-[6-([6-methoxy-5-[(2S)-2-methyl-4-(oxetan-3-yl)piperazin-1-yl]pyridin-2-yl]amino)pyrimidin-4-yl]benzonitrile & Example 102: 2-[[(4R)-3,3-difluoro-1-[(2S)-2-hydroxypropanoyl]piperidin-4-yl]oxy]-5-[6-([6-methoxy-5-[(2S)-2-methyl-4-(oxetan-3-yl)piperazin-1-yl]pyridin-2-yl]amino)pyrimidin-4-yl]benzonitrile

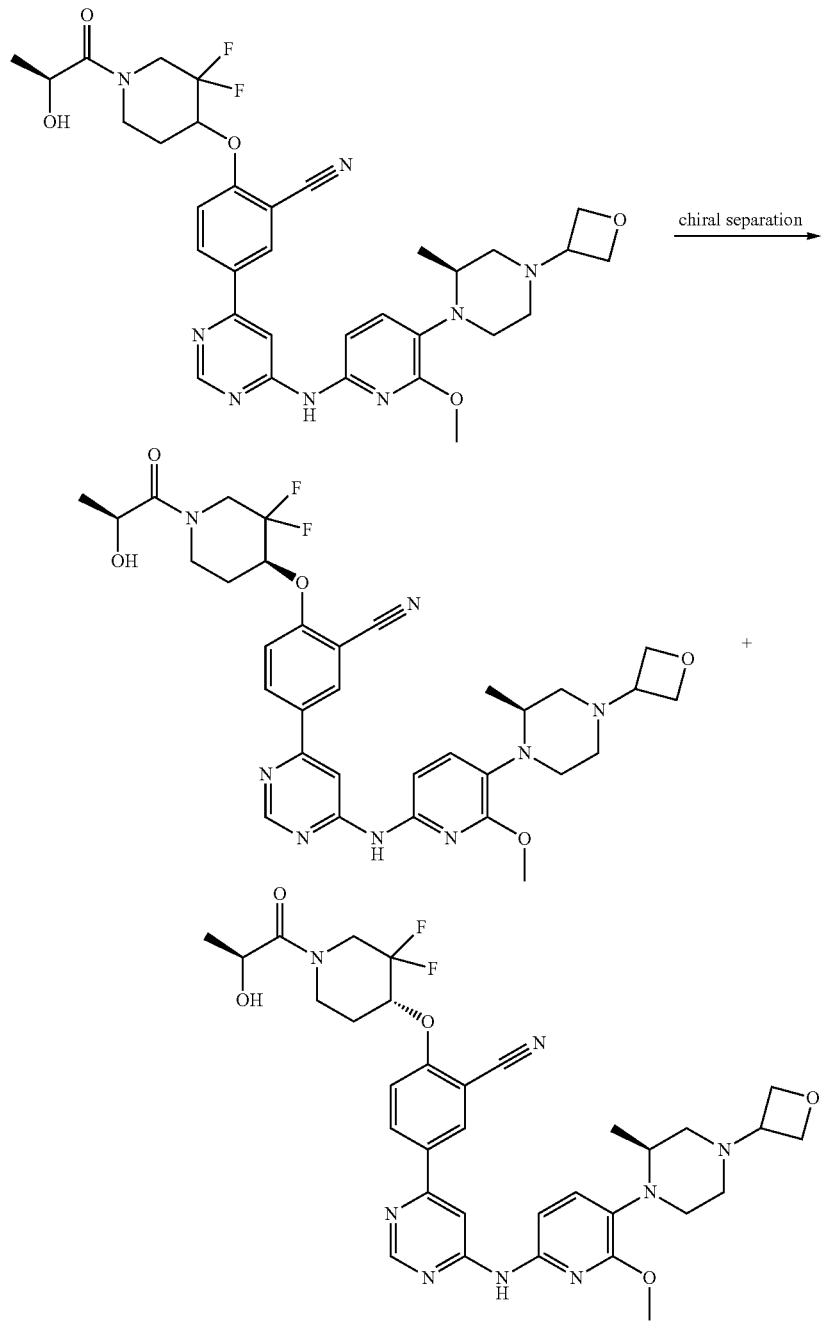

The title compounds were obtained by separation on chiral prep-HPLC under the following condition: column, ChiraPAK ID-3, 0.46×5 cm, 3 um; mobile phase, hexane: DCM:EtOH=5:1:6, isocratic for 25 min; detector, UV 254 nm.

Example 101: (110 mg, 20%, light yellow solid) HPLC: 96.0% purity, RT=4.18 min. MS: m/z=665.2 [M+H]$^+$. $^1$H NMR (300 MHz, DMSO-d$_6$, ppm) δ 10.09 (s, 1H), 8.84-8.72 (m, 1H), 8.49-8.29 (m, 3H), 7.72-7.60 (m, 1H), 7.47-7.33 (m, 1H), 7.25-7.12 (m, 1H), 5.40-5.36 (m, 1H), 5.29-

5.18 (m, 1H), 4.68-4.36 (m, 5H), 4.23-3.35 (m, 9H), 3.17-2.99 (m, 1H), 2.89-2.70 (m, 1H), 2.64-2.39 (m, 2H), 2.36-1.82 (m, 4H), 1.24 (d, J=6.4 Hz, 3H), 0.84 (d, J=6.2 Hz, 3H).

Example 102: (110 mg, 20%, light yellow solid) HPLC: 96.9% purity, RT=4.19 min. MS: m/z=665.2 [M+H]+. 1H NMR (400 MHz, DMSO-$d_6$, ppm) δ 10.08 (s, 1H), 8.75-8.73 (m, 1H), 8.43-8.29 (m, 3H), 7.69-7.61 (m, 1H), 7.43-7.36 (m, 1H), 7.19-7.12 (m, 1H), 5.40-5.36 (m, 1H), 5.24-5.17 (m, 1H), 4.60-4.40 (m, 5H), 4.23-3.35 (m, 9H), 3.10-3.02 (m, 1H), 2.86-2.76 (m, 1H), 2.60-2.42 (m, 2H), 2.37-1.73 (m, 4H), 1.23 (d, J=6.4 Hz, 3H), 0.83 (d, J=6.2 Hz, 3H).

Example 103: 2-[[(4S)-3,3-difluoro-1-[(2S)-2-hydroxypropanoyl]piperidin-4-yl]oxy]-5-[6-([6-methoxy-5-[(2R)-2-methyl-4-(oxetan-3-yl)piperazin-1-yl]pyridin-2-yl]amino)pyrimidin-4-yl]benzonitrile & Example 104: 2-[[(4R)-3,3-difluoro-1-[(2S)-2-hydroxypropanoyl]piperidin-4-yl]oxy]-5-[6-([6-methoxy-5-[(2R)-2-methyl-4-(oxetan-3-yl)piperazin-1-yl]pyridin-2-yl]amino)pyrimidin-4-yl]benzonitrile

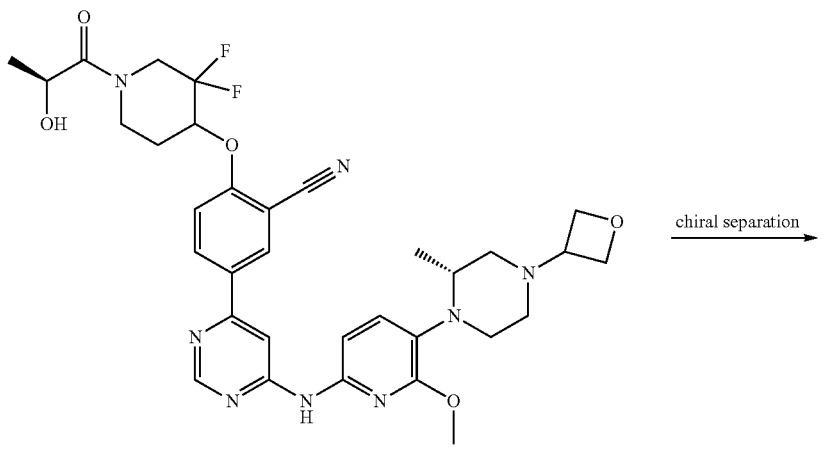

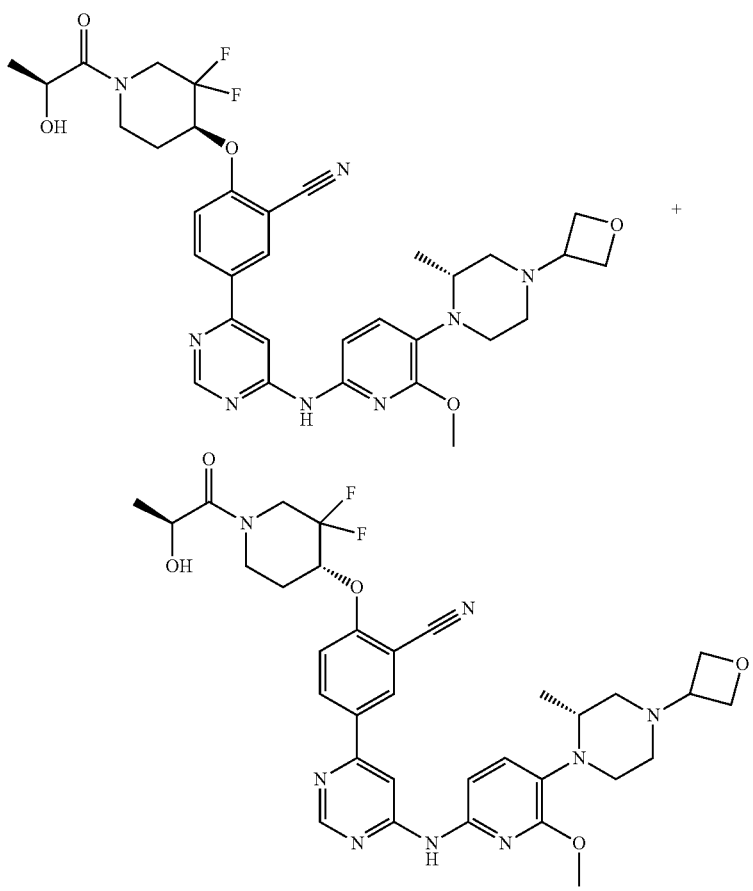

The title compounds were obtained by separation on chiral prep-HPLC under the following condition: column, CHIRALPAK AD-3, 3×100 cm, 3 um; mobile phase, CO$_2$: IPA (0.1% DEA)=60:40, isocratic for 15 min; detector, UV 254 nm.

Example 103: (126 mg, 50%, yellow solid) HPLC: 97.3% purity, RT=4.14 min. MS: m/z=665.1 [M+H]$^+$. $^1$H NMR (300 MHz, DMSO-d$_6$, ppm) δ 10.07 (s, 1H), 8.73 (s, 1H), 8.43-8.25 (m, 3H), 7.67-7.58 (m, 1H), 7.42-7.33 (m, 1H), 7.18-7.09 (m, 1H), 5.37-5.31 (m, 1H), 5.22 (d, J=6.9 Hz, 1H), 4.59-4.36 (m, 5H), 4.19-4.13 (m, 1H), 3.96 (s, 3H), 3.90-3.35 (m, 5H), 3.06-3.00 (m, 1H), 2.82-2.76 (m, 1H), 2.60-2.50 (m, 1H), 2.45-2.36 (m, 1H), 2.33-1.75 (m, 4H), 1.20 (d, J=6.3 Hz, 3H), 0.81 (d, J=6.2 Hz, 3H).

Example 104: (114 mg, 31%, yellow solid) HPLC: 95.6% purity, RT=4.08 min. MS: m/z=665.3 [M+H]$^+$. $^1$H NMR (300 MHz, DMSO-d$_6$, ppm) δ 10.07 (s, 1H), 8.73 (s, 1H), 8.41-8.20 (m, 3H), 7.68-7.59 (m, 1H), 7.42-7.33 (m, 1H), 7.18-7.09 (m, 1H), 5.41-5.26 (m, 1H), 5.20 (d, J=6.8 Hz, 1H), 4.60-4.36 (m, 5H), 4.26-3.53 (m, 7H), 3.51-3.35 (m, 2H), 3.09-2.99 (m, 1H), 2.82-2.76 (m, 1H), 2.59-2.50 (m, 1H), 2.45-2.39 (m, 1H), 2.33-1.75 (m, 4H), 1.21 (d, J=6.5 Hz, 3H), 0.81 (d, J=6.2 Hz, 3H).

Example 105: 6-([6-[3-cyano-4-([1-[(2S)-2-hydroxypropanoyl]piperidin-4-yl]oxy)phenyl]pyrimidin-4-yl]amino)-2-methoxy-N,N-dimethylpyridine-3-carboxamide

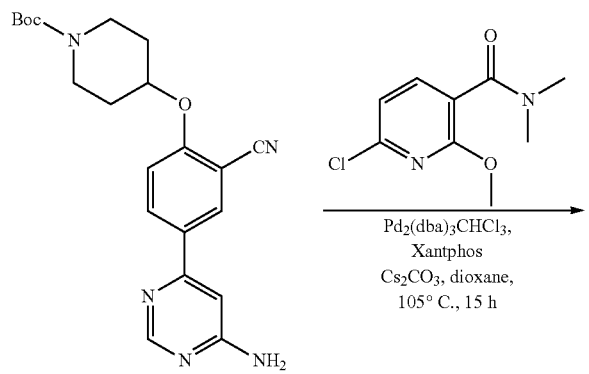

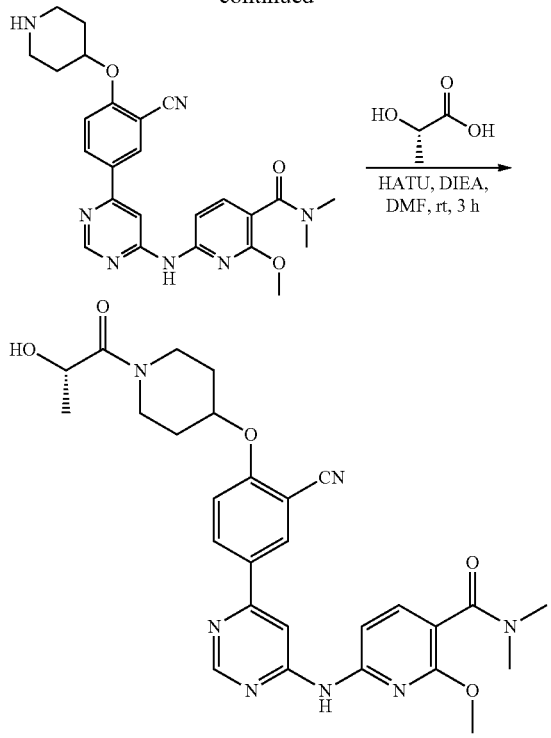

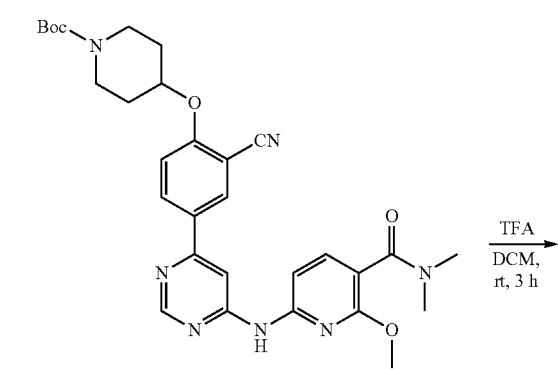

The title compound was prepared from tert-butyl 4-(4-(6-aminopyrimidin-4-yl)-2-cyanophenoxy)piperidine-1-carboxylate, 6-chloro-2-methoxy-N,N-dimethylnicotinamide and (S)-2-hydroxypropanoic acid using Methods 37, 35 and A. The final product was purified by prep-HPLC under the following conditions: column, XBridge Prep OBD C18 Column, 150×19 mm, 5 um; mobile phase, acetonitrile in water (with 10 mmol/L NH$_4$HCO$_3$), 18% to 29% gradient in 8 min; detector, UV 254 nm. 6-([6-[3-cyano-4-([1-[(2S)-2-hydroxypropanoyl]piperidin-4-yl]oxy)phenyl]pyrimidin-4-yl]amino)-2-methoxy-N,N-dimethylpyridine-3-carboxamide was obtained as an yellow solid (16 mg, 12% for 3 steps). HPLC: 96.8% purity, RT=3.63 min. MS: m/z=546.2 [M+H]$^+$. $^1$H NMR (300 MHz, DMSO-d6, ppm) δ 10.39 (s, 1H), 8.80 (s, 1H), 8.51-8.21 (m, 3H), 7.62 (d, J=8.1 Hz, 1H), 7.54 (d, J=9.1 Hz, 1H), 7.21 (d, J=8.1 Hz, 1H), 5.08-4.82 (m, 2H), 4.50-4.40 (m, 1H), 3.98 (s, 3H), 3.79-3.73 (m, 2H), 3.53-3.47 (m, 2H), 2.95 (s, 3H), 2.82 (s, 3H), 2.10-1.84 (m, 2H), 1.73-1.67 (m, 2H), 1.19 (d, J=6.5 Hz, 3H).

Example 106: TBK Biochemical Assay

Test compounds were transferred into Labcyte polypropylene 384 well plates (P055-25) and diluted to 3 mM using DMSO. 3 mM test compounds were dispensed using Labcyte ECHO dose response module into Greiner 784075 plates (columns 3-12 and 13-22, 10 point 1:4) so that high concentration was 30 uM final. 100 uM of a reference compound (1 uM final high concentration). Backfilling was performed if necessary so that all wells contain 1% DMSO final:
 add 75 nl DMSO/well into columns 1, 2 and 24 using Labcyte Echo.
 add 75 nl 1.0 mM staurosporine/well into column 23 using Labcyte Echo (10 uM final)
 add 4.5 ul enzyme/well using multidrop dispenser
 add 3 ul substrate/well using multidrop dispenser incubate at 25° C. in Heidolph incubator for 90 min.
add 7.5 ul 2× stop buffer using multidrop dispenser
read on labchip ez reader II using TBK1.job Raw data files were opened in the Caliper LabChip Reviewer program (Version 3.0.265.0 SP2) and peak assignments were adjusted to reflect "substrate first" with the software's post-run analysis options. A spline-fit baseline was applied using the software's analysis algorithm.

IKKe Biochemical Assay

Test compounds were transferred into Labcyte polypropylene 384 well plates (P055-25) and diluted to 3 mM using DMSO. 3 mM test compounds were dispensed using Labcyte ECHO dose response module into Greiner 784075 plates (columns 3-12 and 13-22, 10 point 1:4) so that high concentration was 30 uM final. 100 uM of a reference compound (1 uM final high concentration). Backfilling was performed if necessary so that all wells contain 1% DMSO final:

add 75 nl DMSO/well into columns 1, 2 and 24 using Labcyte Echo.
add 75 nl 1.0 mM staurosporine/well into column 23 using Labcyte Echo (10 uM final)
add 4.5 ul enzyme/well using multidrop dispenser
add 3 ul substrate/well using multidrop dispenser
incubate at 25° C. for 90 min.
add 7.5 ul 2× stop buffer
read on labchip ez reader II using IKKε. job Raw data files were opened in the Caliper LabChip Reviewer program (Version 3.0.265.0 SP2) and peak assignments were adjusted to reflect "substrate first" with the software's post-run analysis options. A spline-fit baseline was applied using the software's analysis algorithm.

The purpose of the pIRF3 immunocytochemistry cell based assay was to identify small molecules which modulates TBK/IKKe kinase activity through on target substrate phosphorylation of the IRF-3 protein. On the first day of the experiment, MDA-MB-468 cells were plated in 384 well, black, clear-bottom, Poly D lysine coated plates at a density of 5000 cells/well in 45 ul of complete DMEM and allowed to adhere overnight. On the second day compounds were added to cells at a starting concentration of 10 uM with a serial dilution of 3-fold for a total of 10 points. The cells were incubated for 1 hr at 37° C. Cells were then stimulated with Poly(I:C) at a final concentration of 10 ug/ml, and were incubated for 2 hr at 37° C. Following the incubation, media was removed from the wells and the cells were fixed with 4% PFA for 15 min at RT. Cells were washed at least 3 times with PBS, and then permeabilized with ice-cold methanol for 10 min at RT. The washing step was repeated and the cells were then blocked using 10% goat serum/1% BSA, made up in PBS and allowed to incubate at RT for 1 hr. The cells were washed again and then treated with an anti-pIRF3 antibody at 4° C. overnight (1:250 dilution of Abcam ab76493 in PBS containing 1% BSA). On the third day the primary antibody was washed off and pIRF3 was detected by adding the secondary antibody conjugated to AlexaFluor488 (1:200 dilution of secondary antibody in PBS containing 1% BSA) for 1 hr at RT. Cells were washed and then counterstained with PI/RNase staining buffer for 15 min at RT and read on the Acumen Explorer laser scanning cytometer. The percentage of phosphorylation of the IRF-3 protein was calculated using the following algorithm, a modified version of the mean half width intensity (pIRF3 staining)/(PI staining or # of cells)×100%). IC50 curves were generated using the Genedata software.

Results are given in the following table.
D $IC_{50} > 5$ μM
C $IC_{50}$ ranges from 1 μM-5 μM
B $IC_{50}$ ranges from 100 nM-1.0 μM
A $IC_{50} < 100$ nM

| Example | TBK1 IC50 | IKKe IC50 |
|---|---|---|
| 1 | A | A |
| 2 | A | A |
| 3 | A | A |
| 4 | A | A |
| 5 | A | A |
| 6 | A | A |
| 7 | A | A |
| 8 | C | C |
| 9 | A | A |
| 10 | A | A |
| 11 | A | A |
| 12 | A | A |
| 13 | A | A |
| 14 | A | A |
| 15 | A | A |
| 16 | A | A |
| 17 | A | A |
| 18 | A | A |
| 19 | A | A |
| 20 | A | A |
| 21 | A | A |
| 22 | B | B |
| 23 | A | A |
| 24 | A | A |
| 25 | C | C |
| 26 | A | A |
| 27 | B | B |
| 28 | A | A |
| 29 | A | A |
| 30 | A | A |
| 31 | A | A |
| 32 | C | C |
| 33 | A | A |
| 34 | B | B |
| 35 | B | B |
| 36 | A | A |
| 37 | B | B |
| 38 | A | A |
| 39 | B | B |
| 40 | B | B |
| 41 | C | C |
| 42 | A | A |
| 43 | A | A |
| 44 | A | A |
| 45 | A | A |
| 46 | B | B |
| 47 | A | A |
| 48 | A | A |
| 49 | A | A |
| 50 | A | A |
| 51 | B | B |
| 52 | A | A |
| 53 | A | A |
| 54 | A | A |
| 55 | A | A |
| 56 | A | A |
| 57 | A | A |
| 58 | A | A |
| 59 | A | A |
| 60 | A | A |
| 61 | A | N/A |
| 62 | A | A |
| 63 | A | A |
| 64 | A | A |
| 65 | A | A |
| 66 | A | A |
| 67 | A | A |
| 68 | A | A |
| 69 | A | A |
| 70 | A | A |
| 71 | A | A |
| 72 | A | A |

-continued

| Example | TBK1 IC50 | IKKe IC50 |
|---|---|---|
| 73 | A | A |
| 74 | A | A |
| 75 | A | A |
| 76 | A | A |
| 77 | A | A |
| 78 | A | A |
| 79 | A | A |
| 80 | A | A |
| 81 | A | A |
| 82 | A | A |
| 83 | A | A |
| 84 | A | A |
| 85 | A | A |
| 86 | A | B |
| 87 | A | B |
| 88 | A | A |
| 89 | A | A |
| 90 | A | A |
| 91 | A | A |
| 92 | A | A |
| 93 | A | A |
| 94 | A | A |
| 95 | A | A |
| 96 | A | A |
| 97 | A | A |
| 98 | A | A |
| 99 | A | A |
| 100 | A | A |
| 101 | A | A |
| 102 | A | A |
| 103 | A | A |
| 104 | A | A |
| 105 | A | A |

Example 89. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2 H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

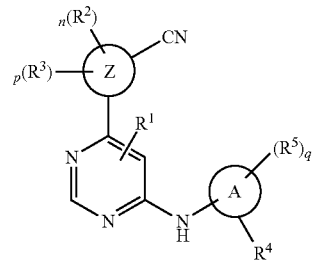

or a pharmaceutically acceptable salt thereof; wherein
$R^1$ is hydrogen, optionally substituted $C_{1-6}$ aliphatic, —OR, or halogen;
Ring Z is phenyl or a 5-6-membered heteroaryl having 1, 2, or 3 nitrogens;
each $R^2$ is independently

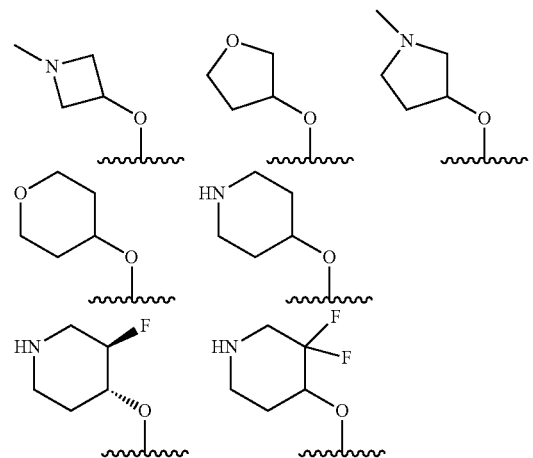

215
-continued
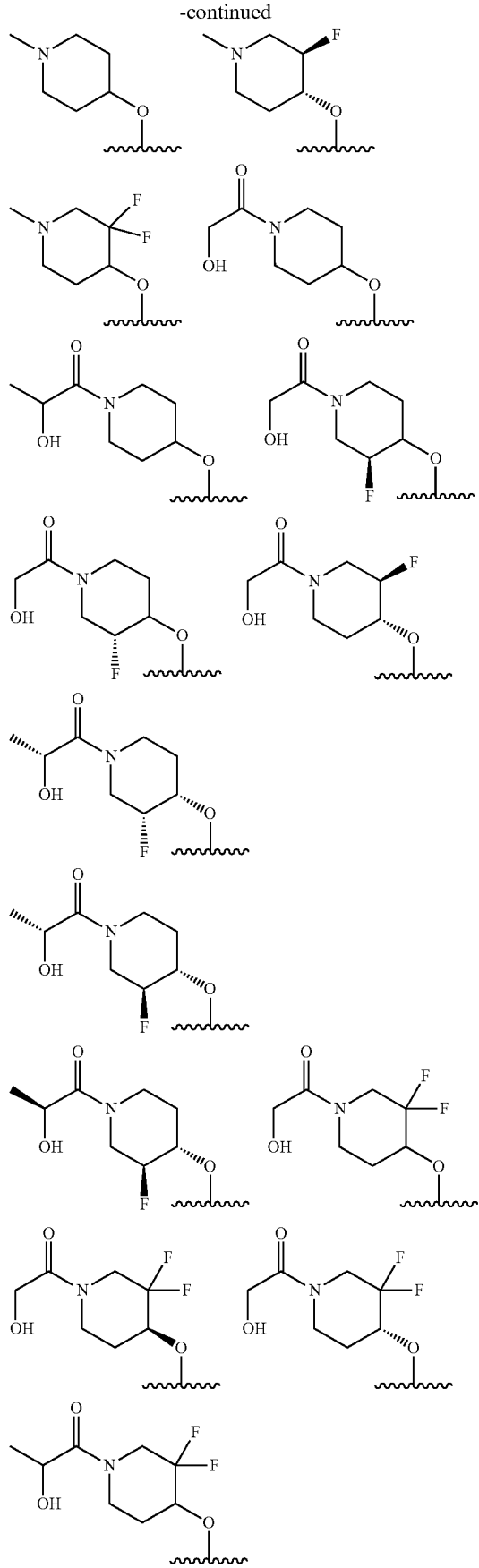
216
-continued
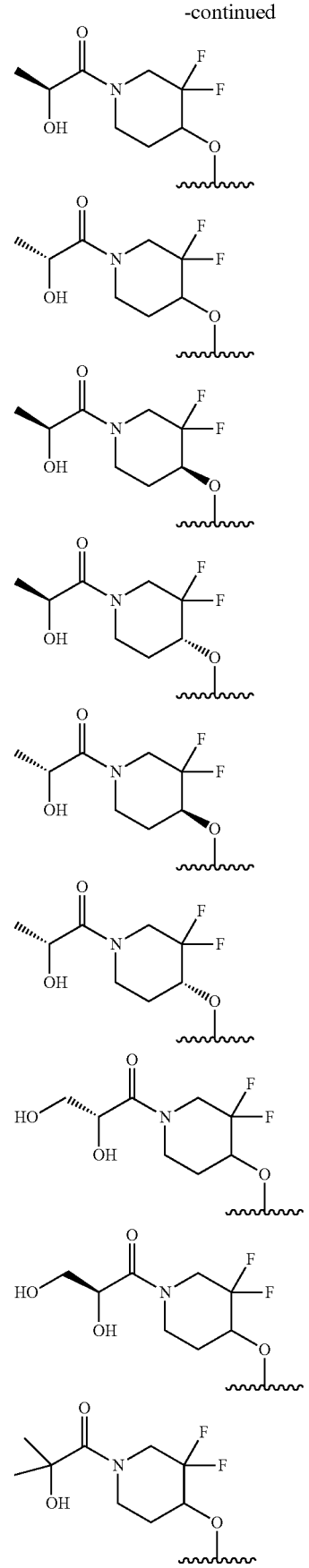

-continued

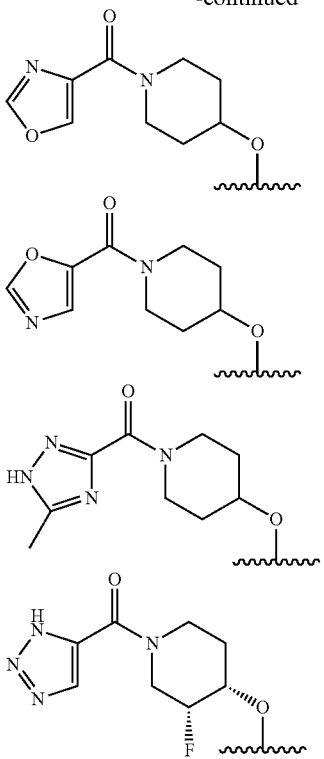

each R³ is independently —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;
Ring A is phenyl or a 5-6-membered heteroaryl having 1, 2, or 3 nitrogens;
R⁴ is —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;
each R⁵ is independently —R, halogen, —OR, —SR, —SO₂R, —SOR, —C(O)R, —CO₂R, —C(O)N(R)₂, —NRC(O)R, —NRC(O)N(R)₂, —NRSO₂R, or —N(R)₂;
each R is independently hydrogen, C₁₋₆ aliphatic, C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur; or a 6-12 membered spiro, fused, or bridged bicyclic carbocyclic or heterocyclic ring having 1-4 heteroatoms independently selected from nitrogen, oxygen, or sulfur; each of which is optionally substituted; or
two R groups on the same atom are taken together with the atom to which they are attached to form a C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
n is 1 or 2;
p is 0, 1, or 2; and
q is 0, 1, or 2.

2. The compound of claim 1, wherein R¹ is H.
3. The compound of claim 1, wherein Ring Z is phenyl, pyridine, or pyrimidine.
4. The compound of claim 1, wherein Ring Z is

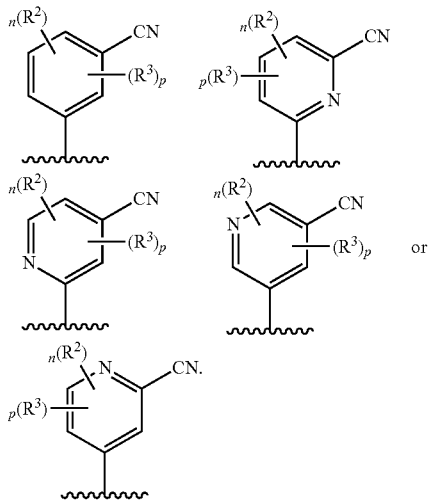

5. The compound of claim 1, wherein each R² is independently —R, halogen, —OR, or —N(R)₂.
6. The compound of claim 1, wherein each R³ is independently —R, halogen, —OR, or —N(R)₂.
7. The compound of claim 1, wherein Ring A is phenyl or pyridyl.
8. The compound of claim 1, wherein Ring A is

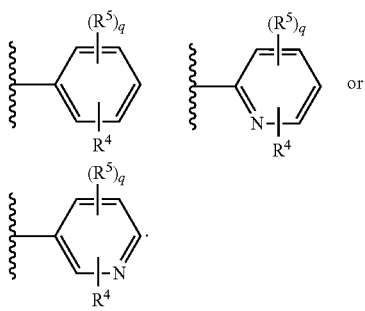

9. The compound of claim 1, wherein R⁴ is —R or —OR.
10. The compound of claim 1, wherein each R⁵ is independently —R, —C(O)R, —CO₂R, —C(O)N(R)₂, —NRC(O)R, or —N(R)₂.
11. The compound of claim 1, wherein each R⁵ is independently

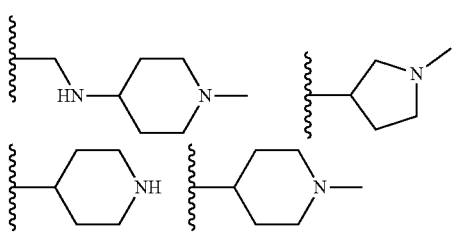

-continued
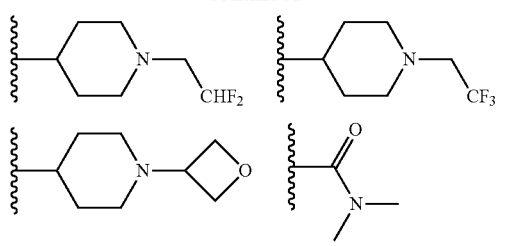
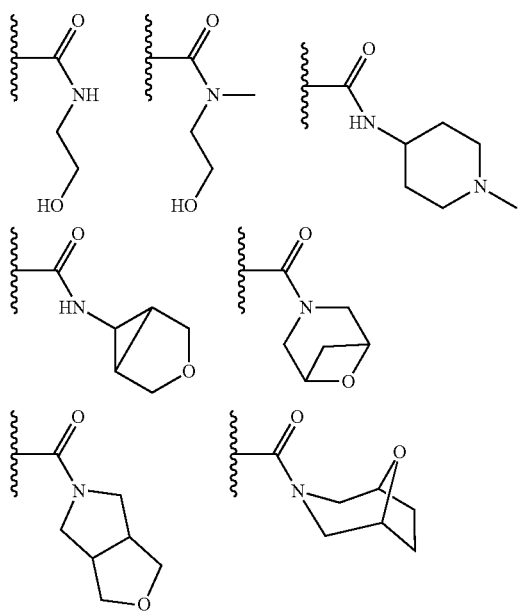
-continued
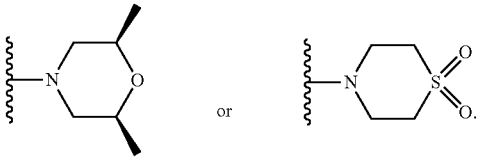
12. The compound of claim 1, of formula II,
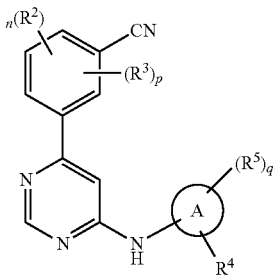
II
or a pharmaceutically acceptable salt thereof.
13. The compound of claim 1, of formula VI,
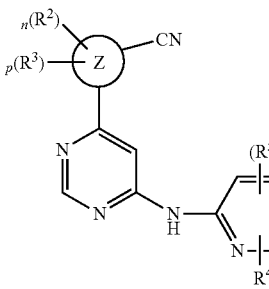
VI
or a pharmaceutically acceptable salt thereof.
14. The compound of claim 1, selected from
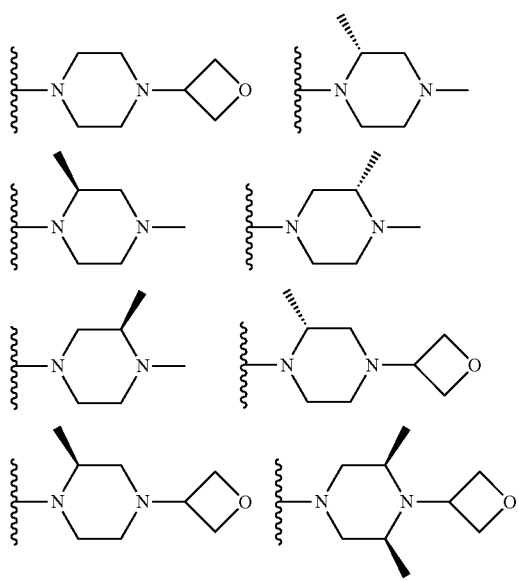
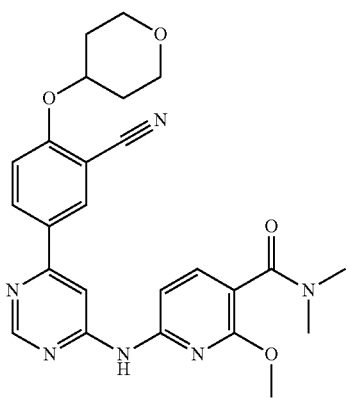
1

-continued
2
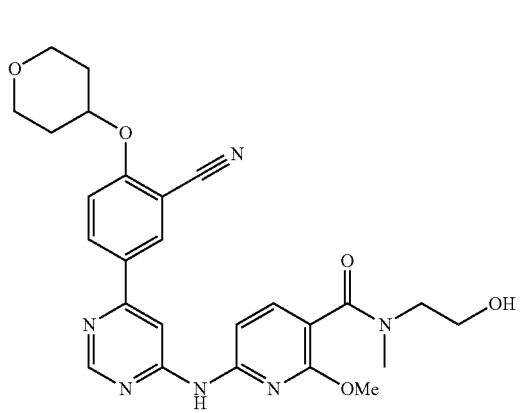
3
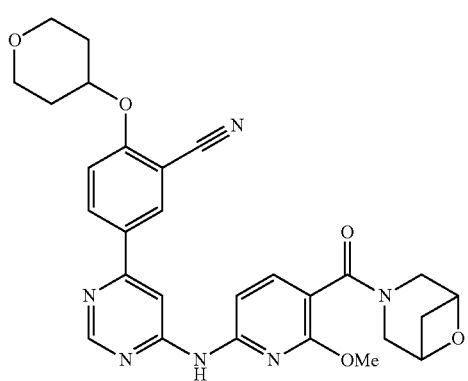
4
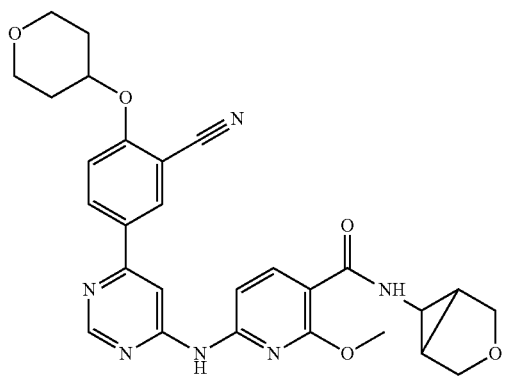
5
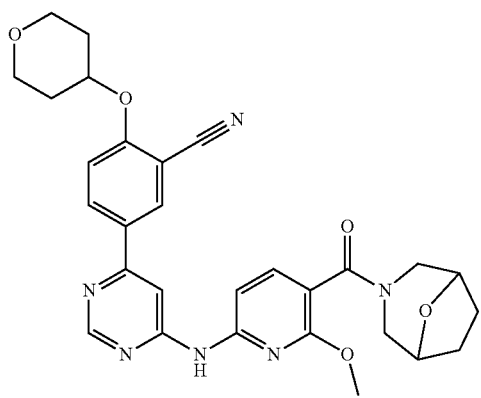
-continued
6
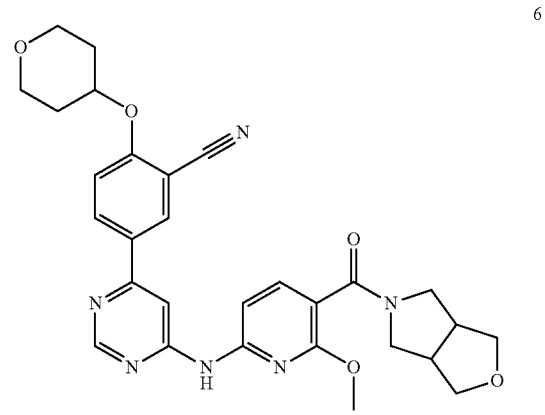
7
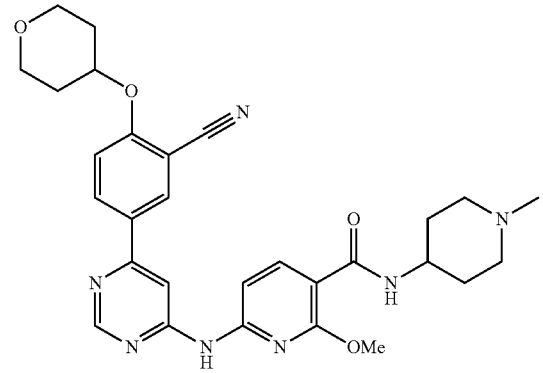
8
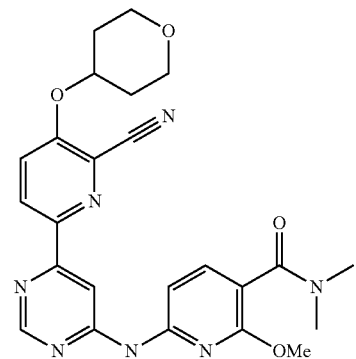
9
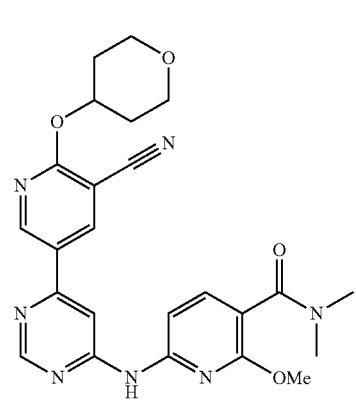

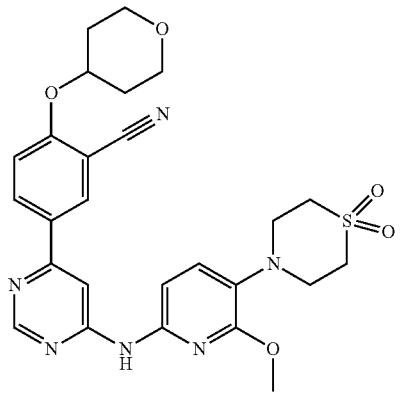
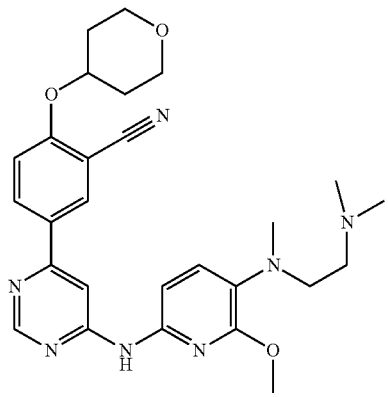
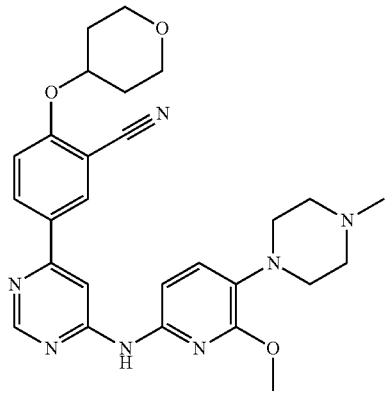
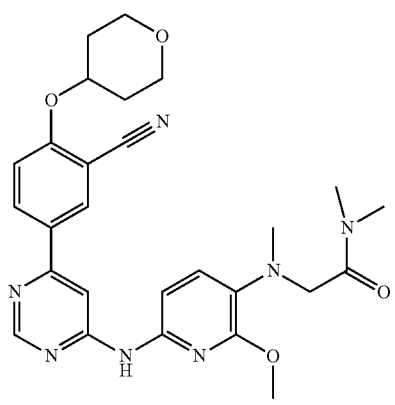
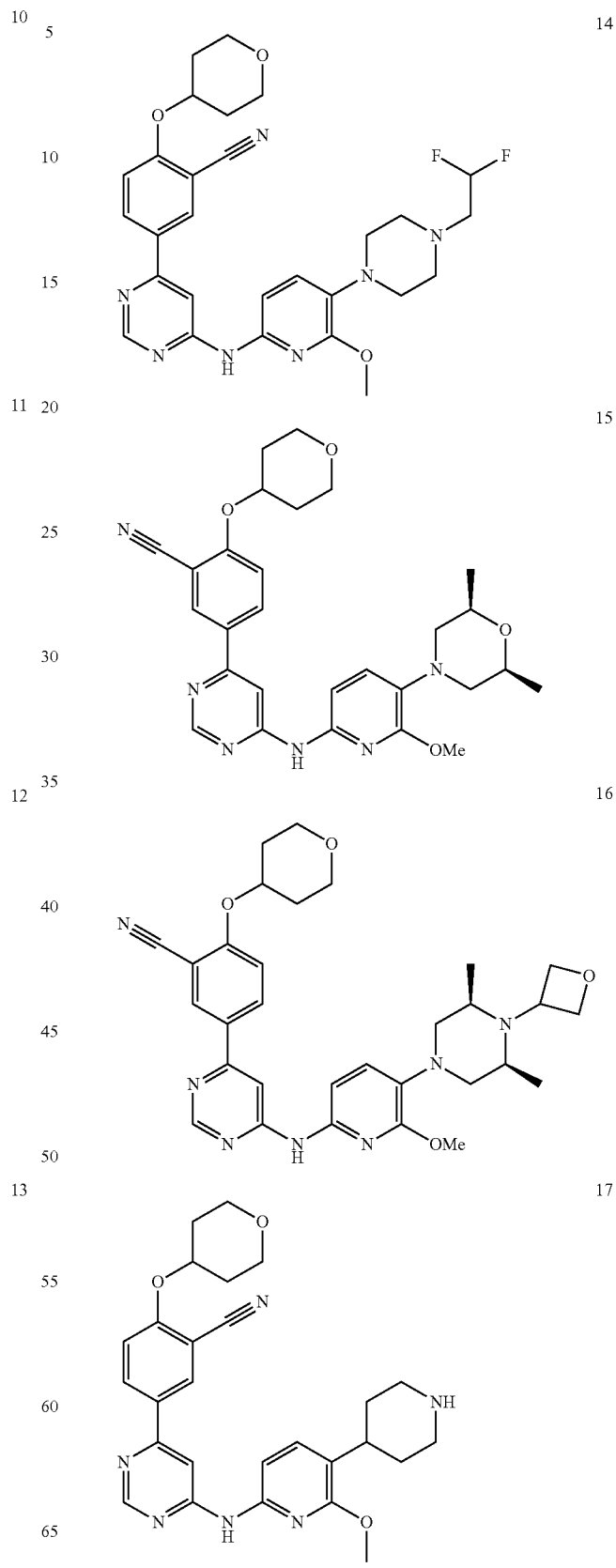

225
-continued
18
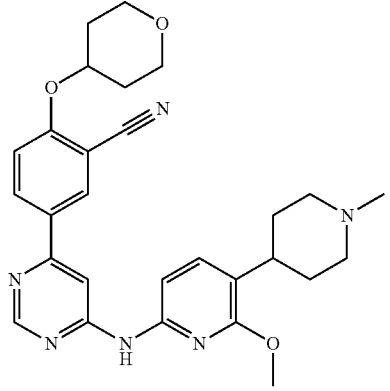
19
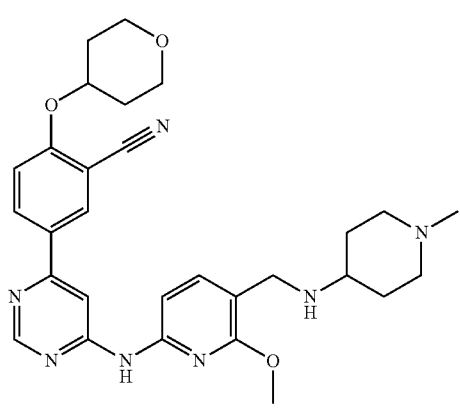
20
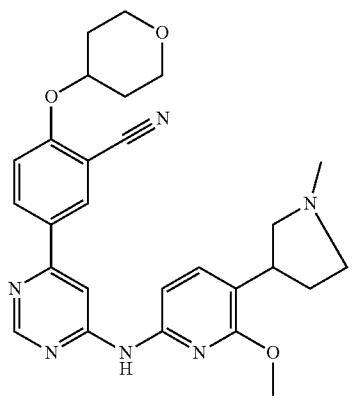
21
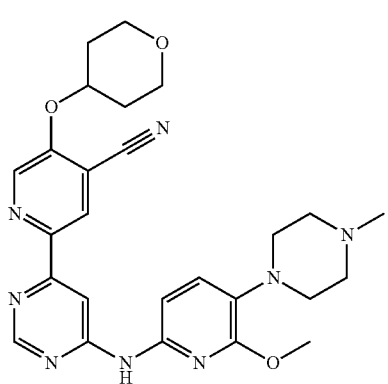
226
-continued
22
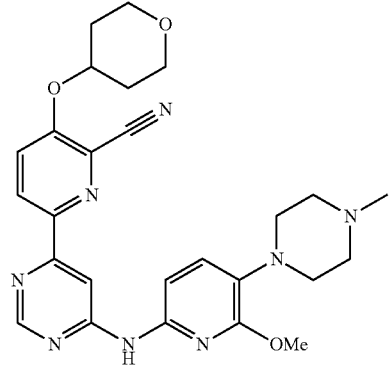
23
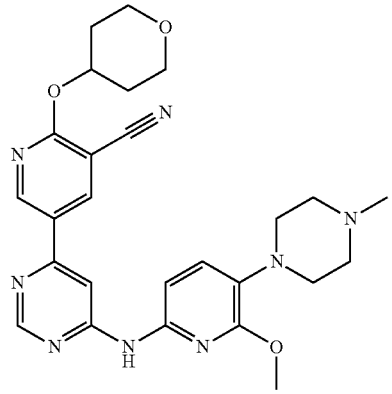
24
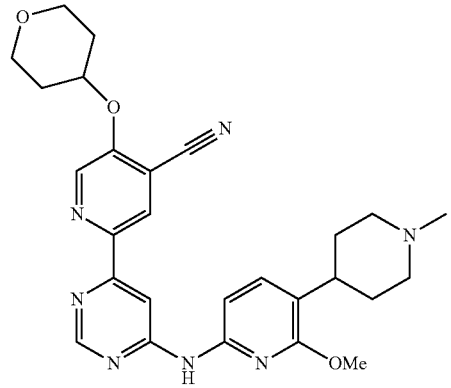
25
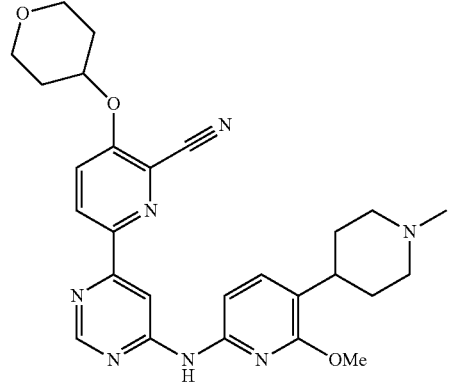

26 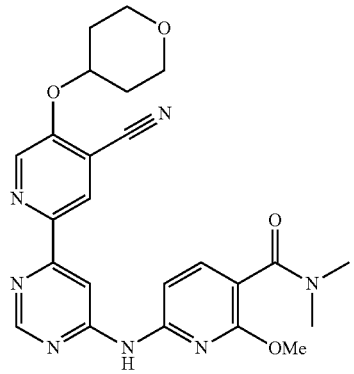
27 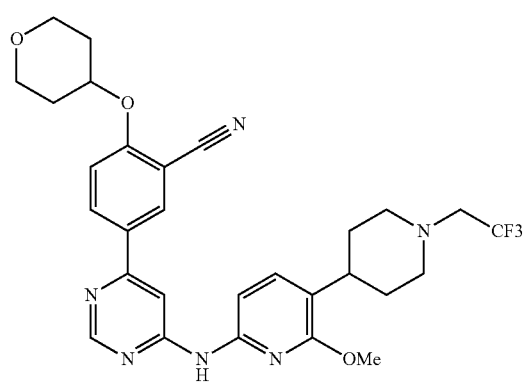
28 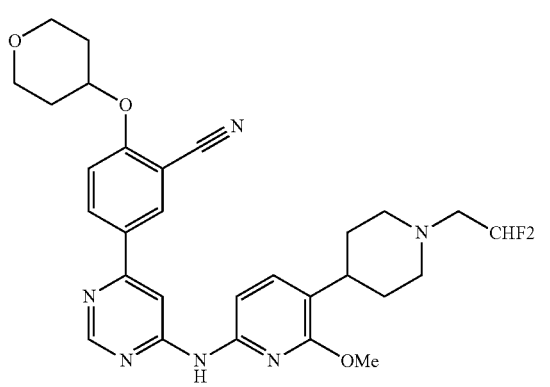
29 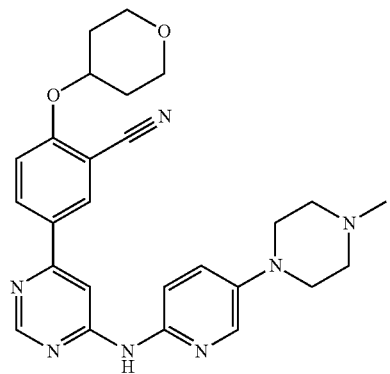
30 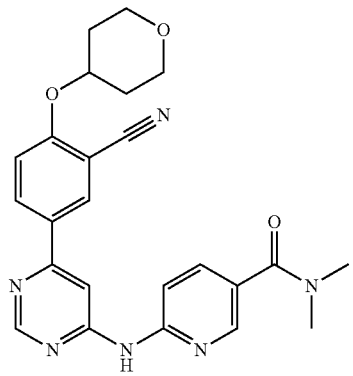
31 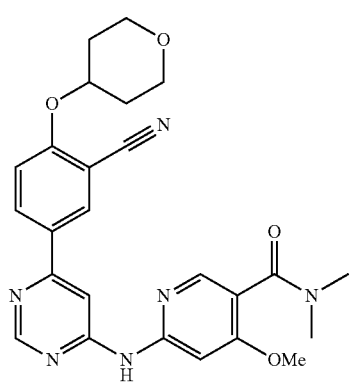
32 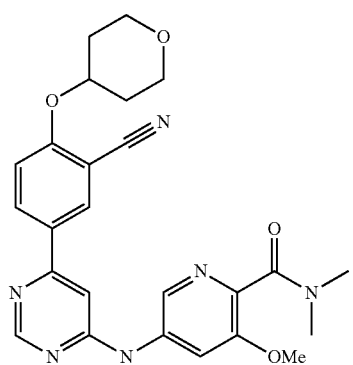
33 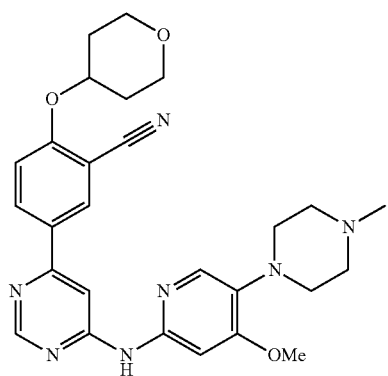

34
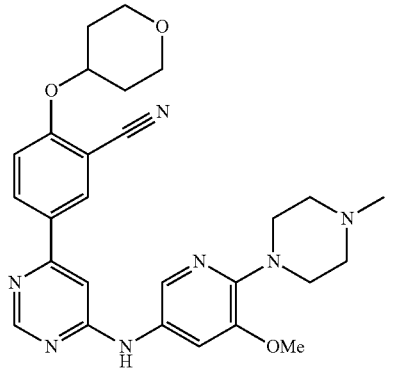
35
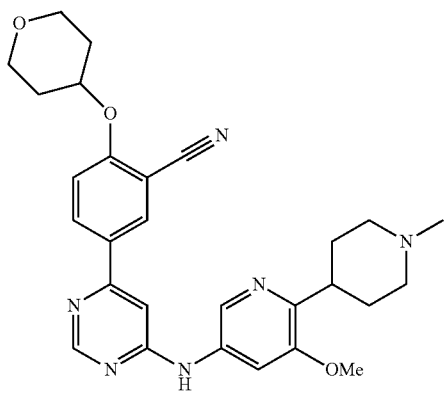
36
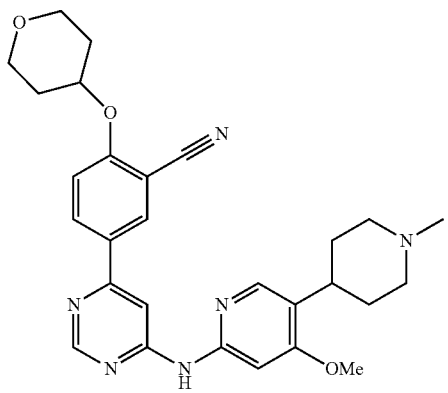
37
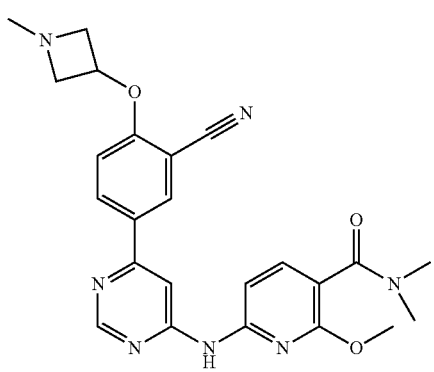
38
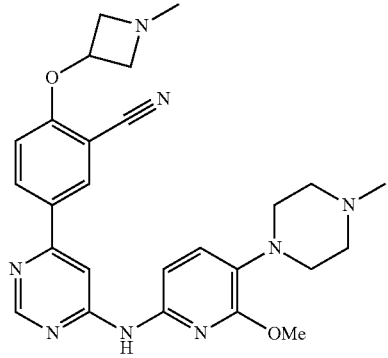
39
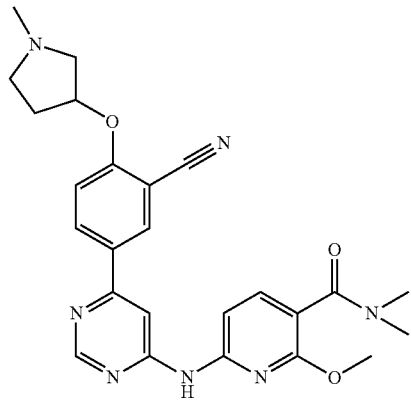
40
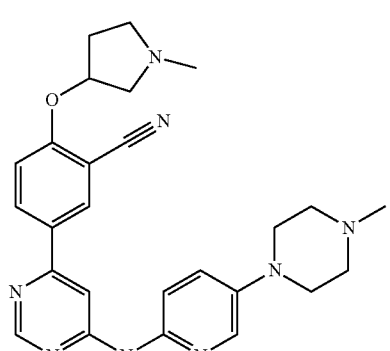
41
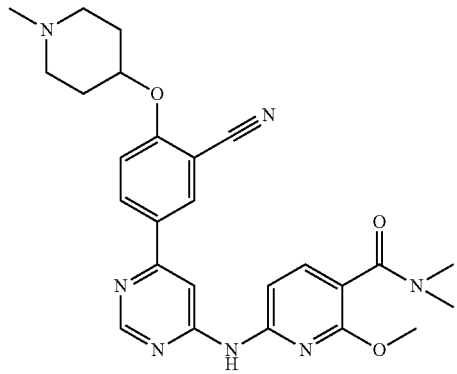

231
-continued
42
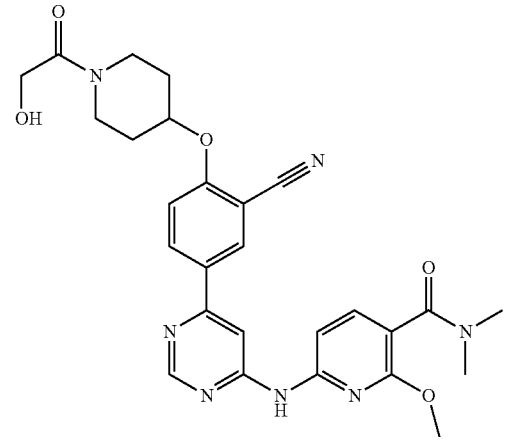
43
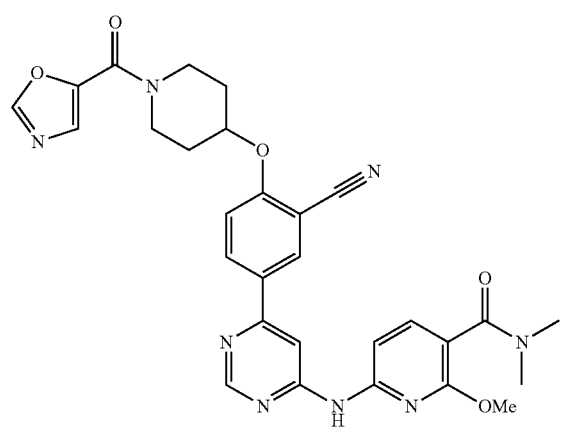
44
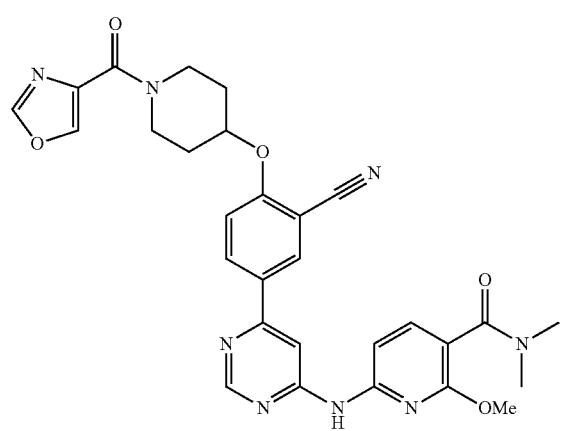
232
-continued
45
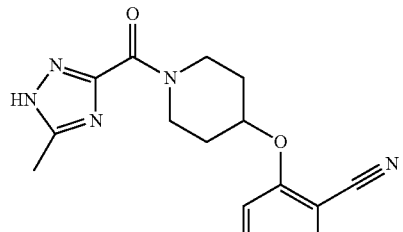
46
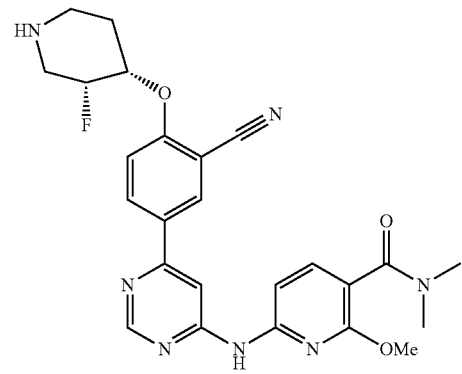
47
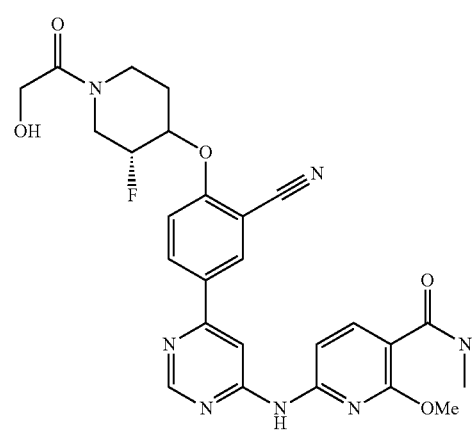
48
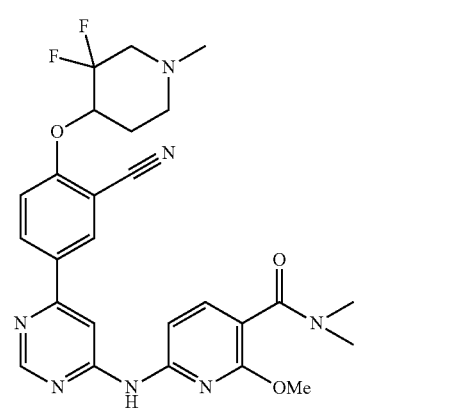

49
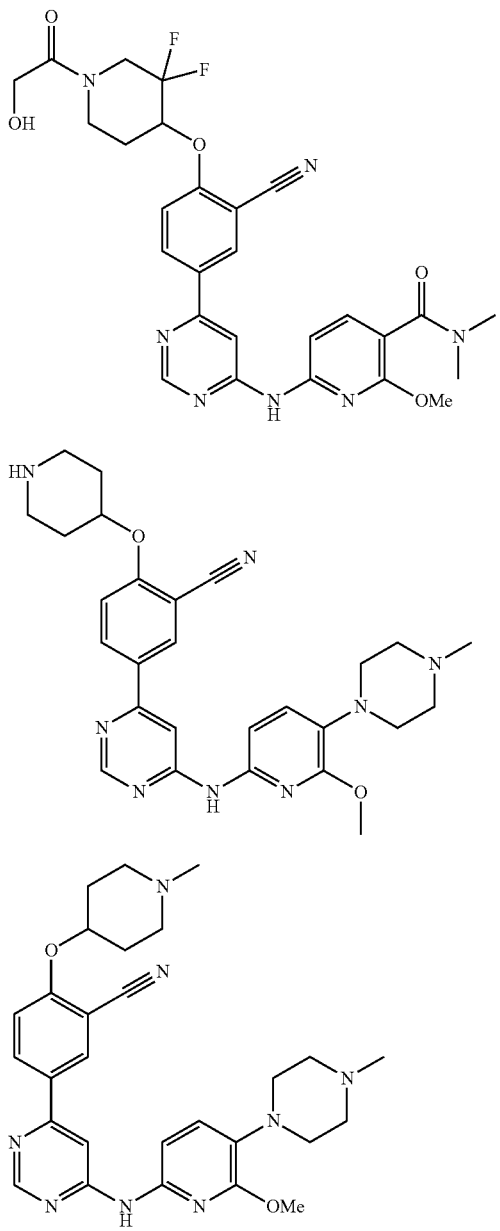
50
51
52
53
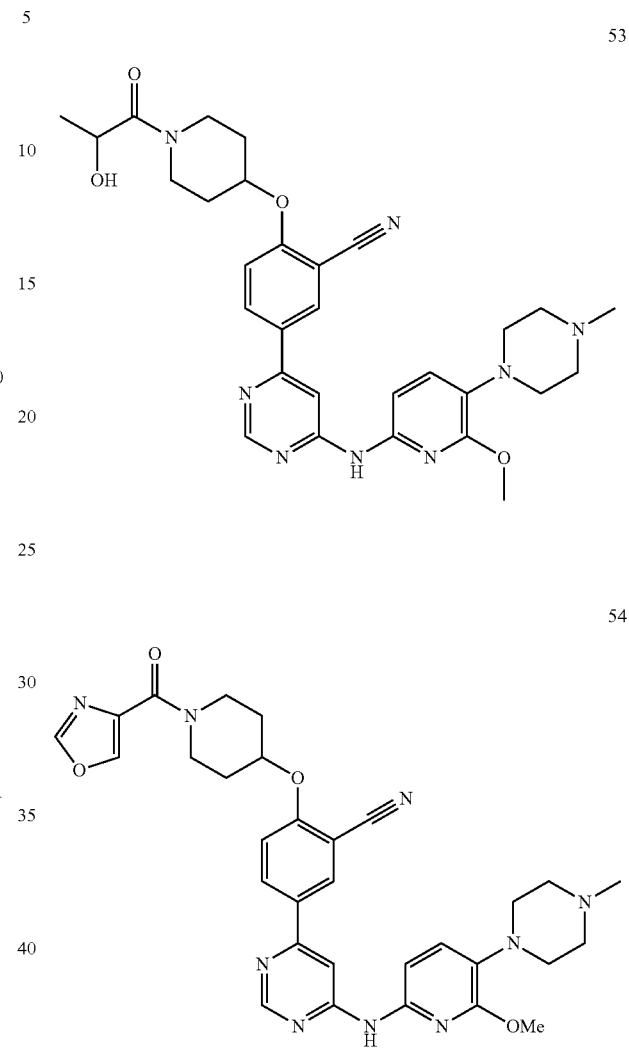
54
55
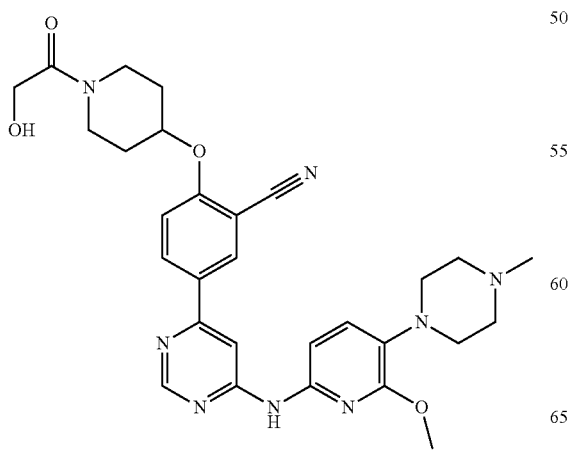
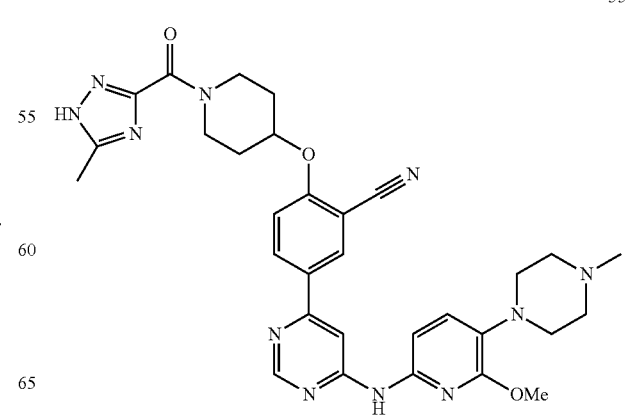

56
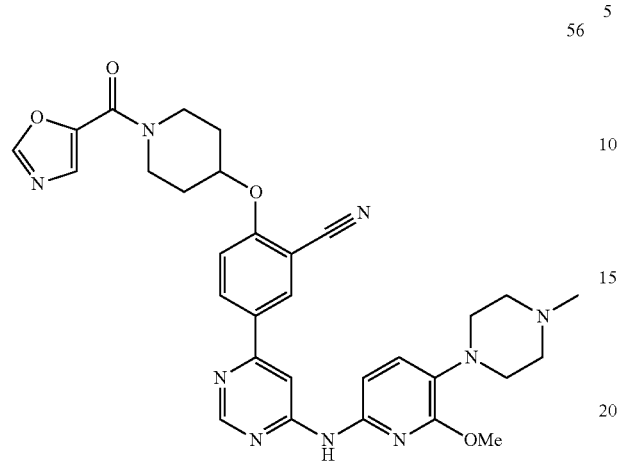
57
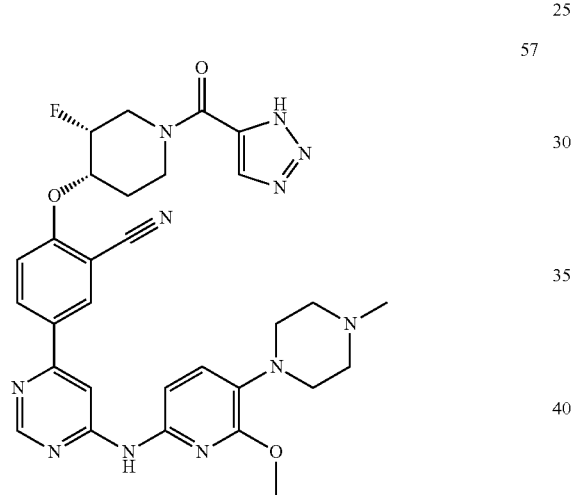
58
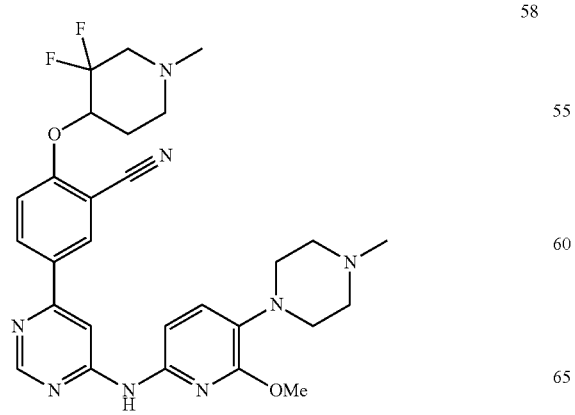
59
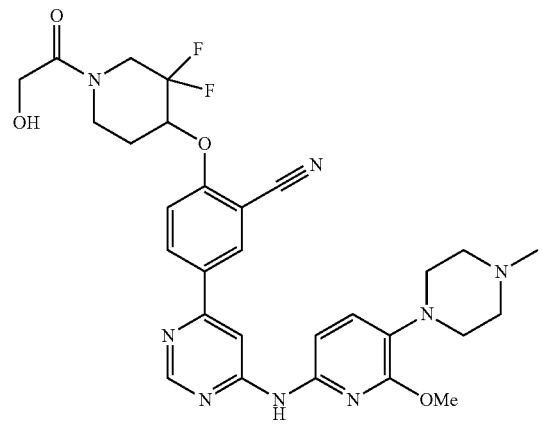
60
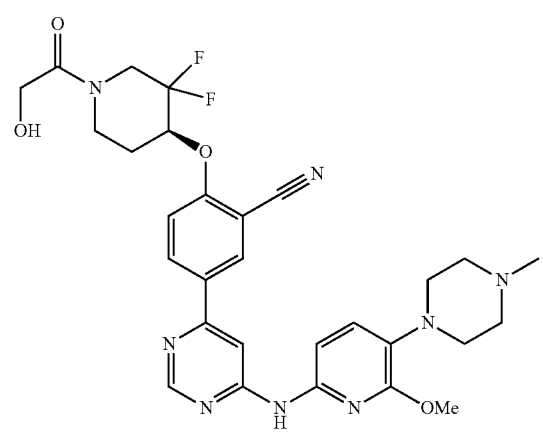
61
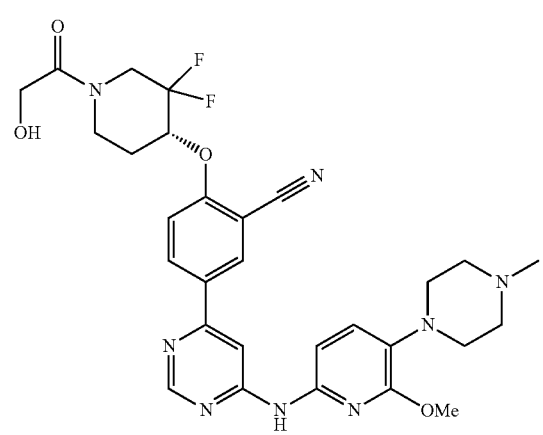

62
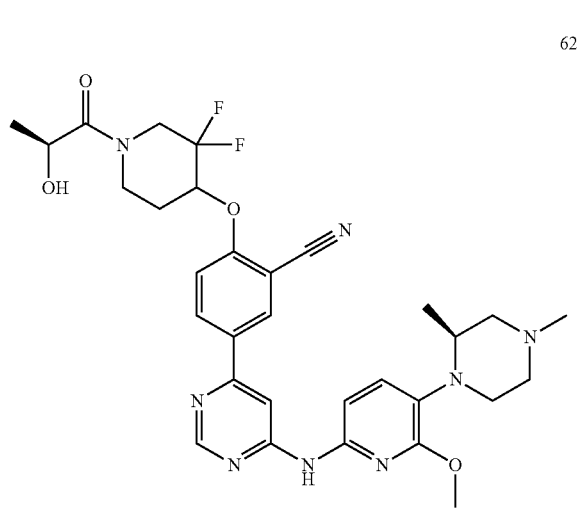
63
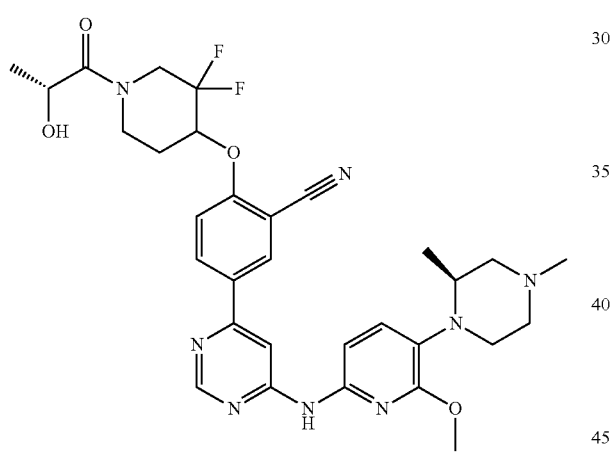
64
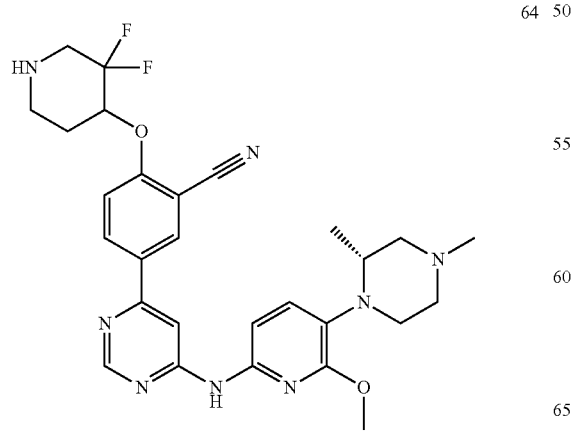
65
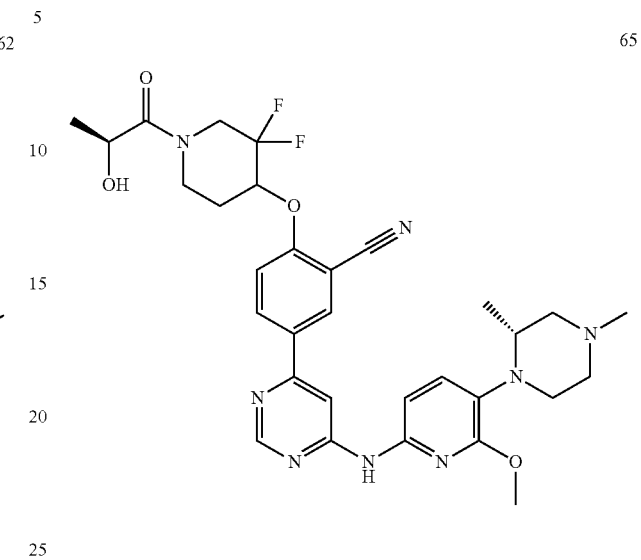
66
67
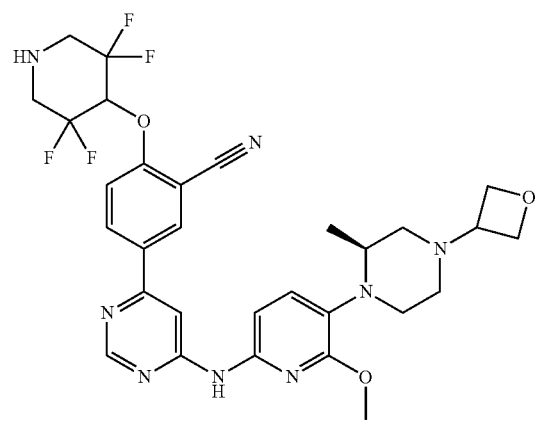

239
-continued
68
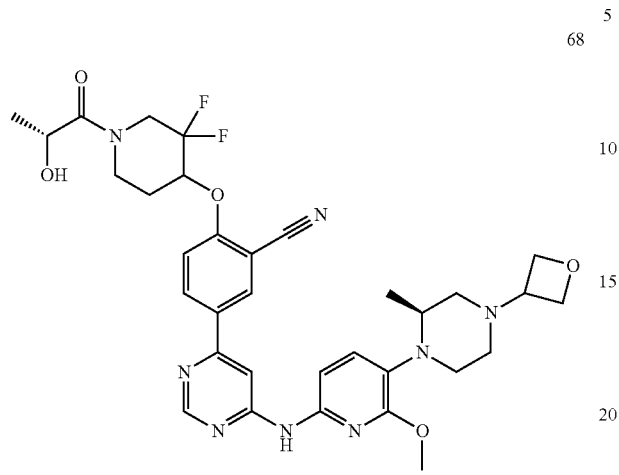
70
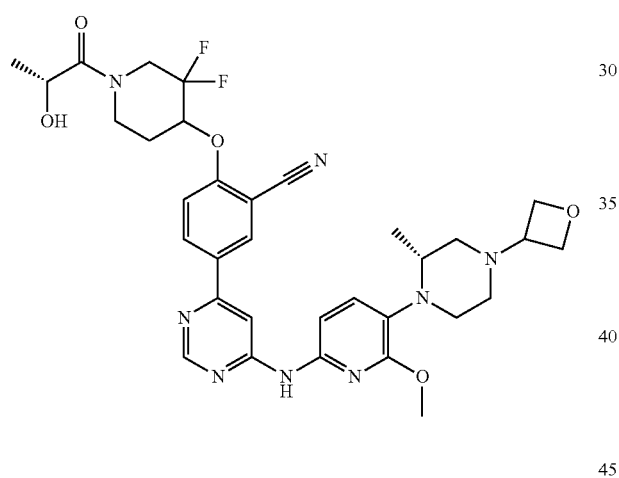
72
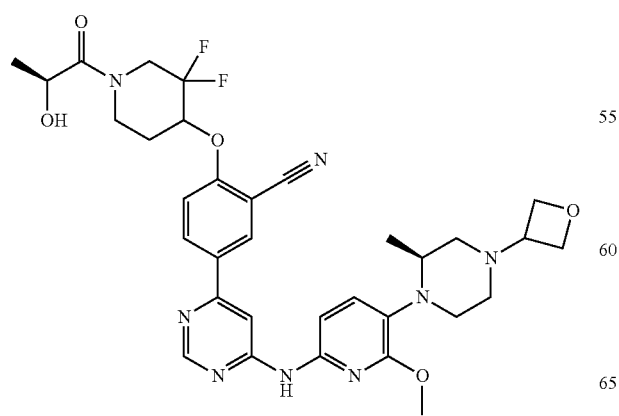
240
-continued
69
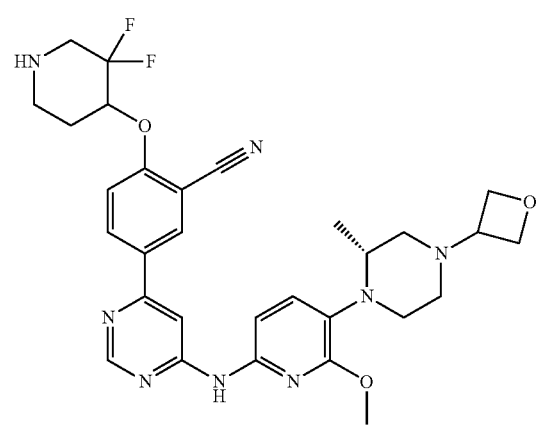
71
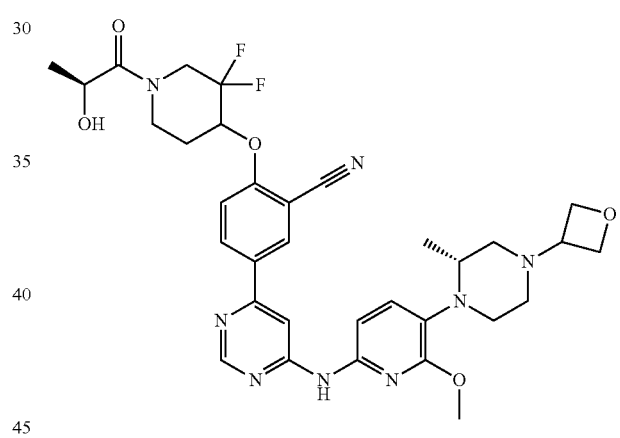
73
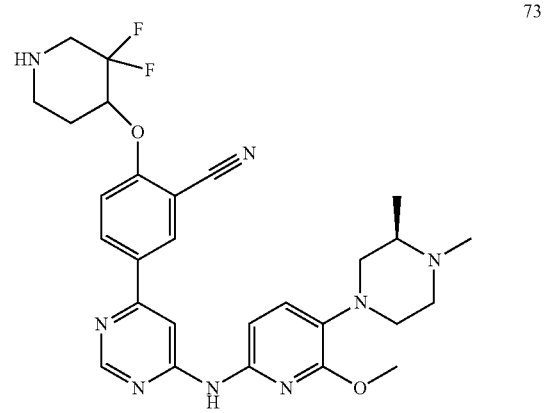

241
-continued
74
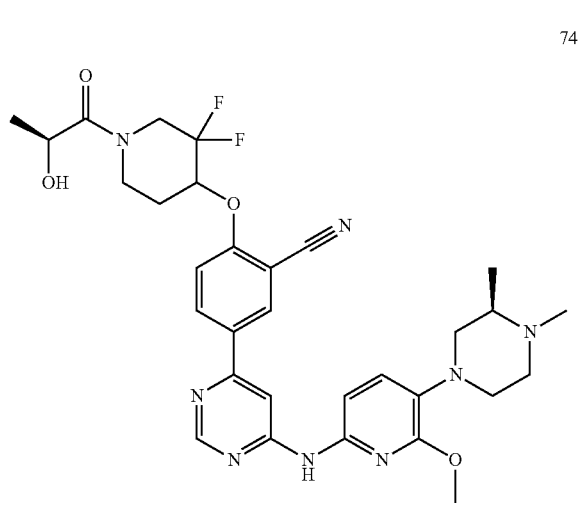
75
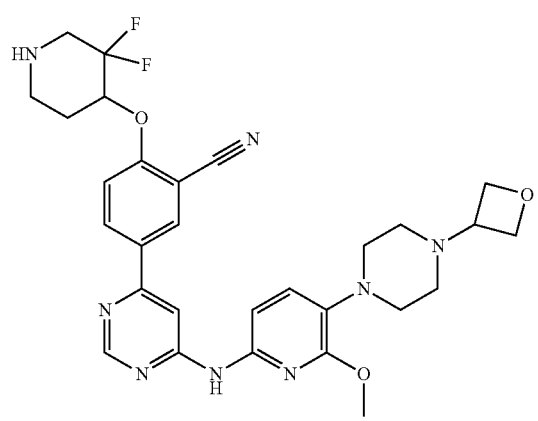
242
-continued
77
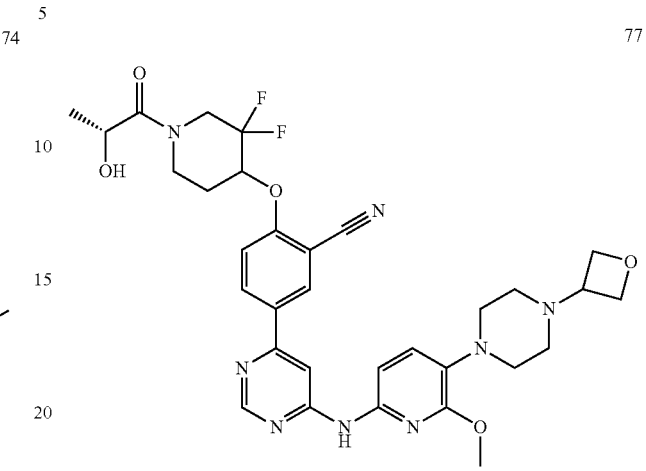
78
76
79
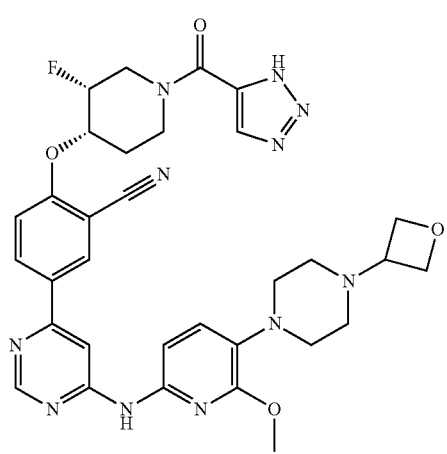

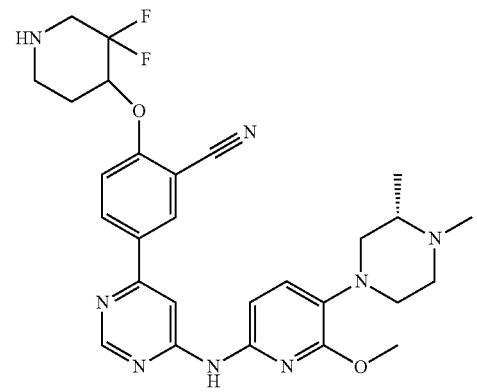
80
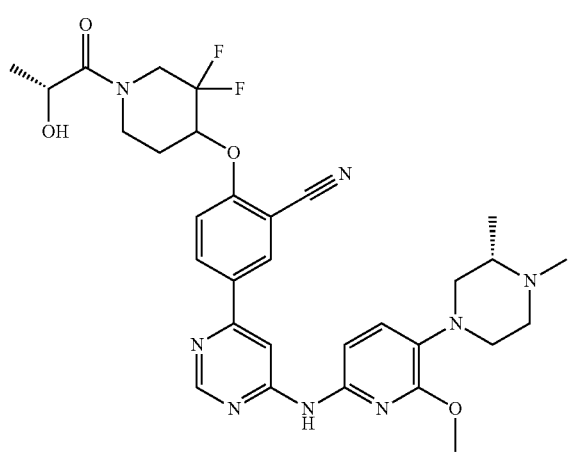
81
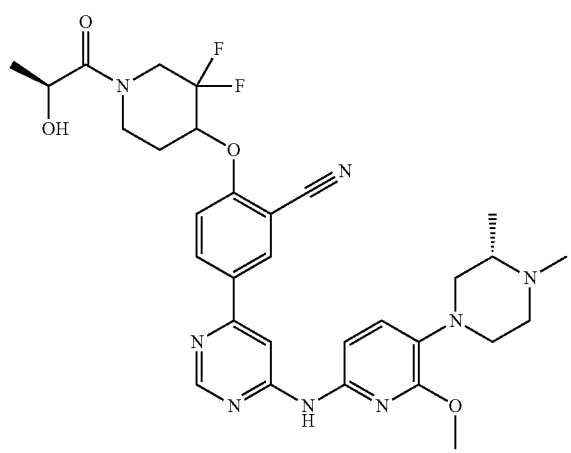
82
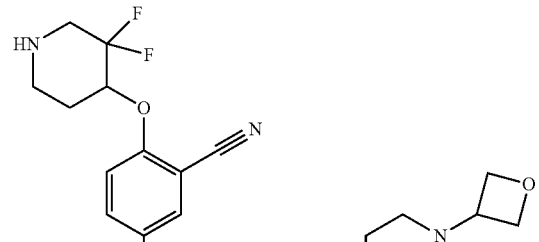
83
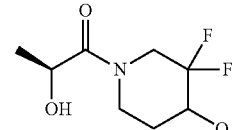
84
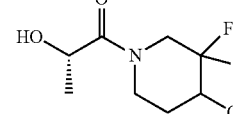
85
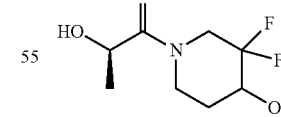
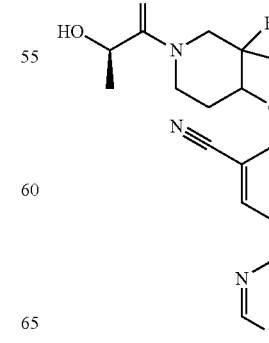
86

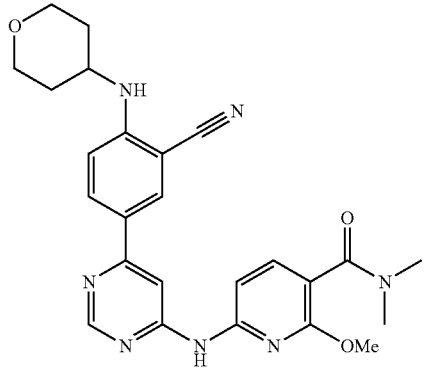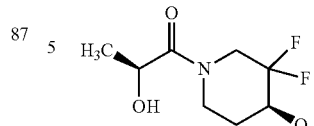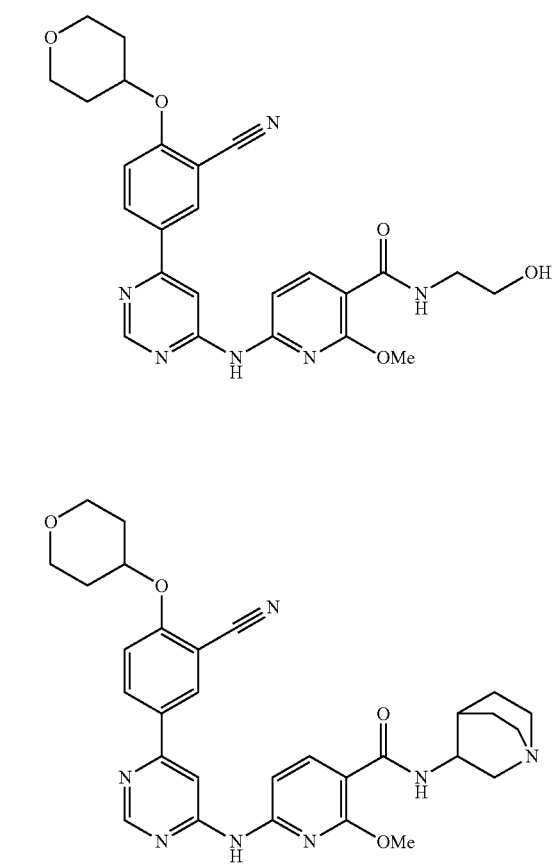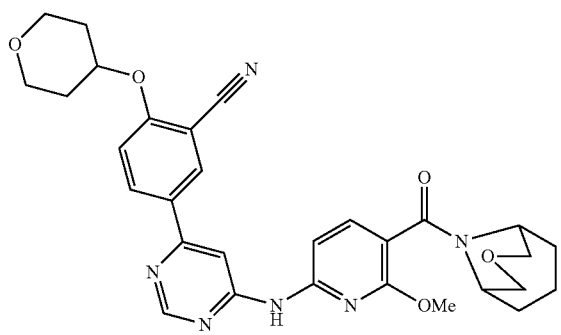

95
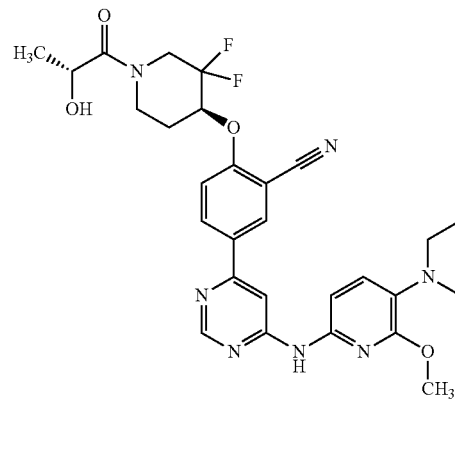
96
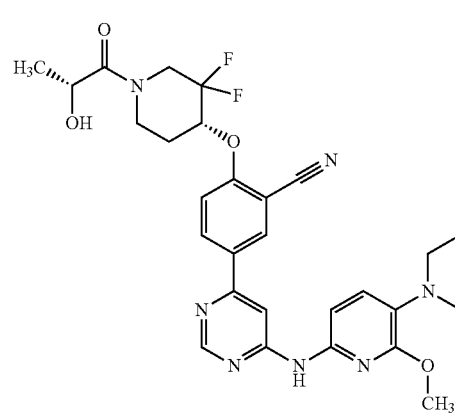
97
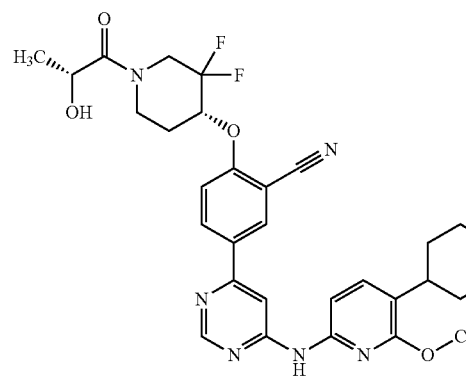
98
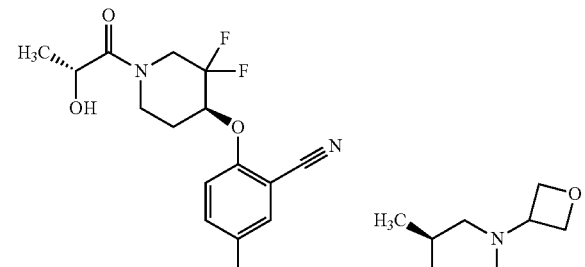
99
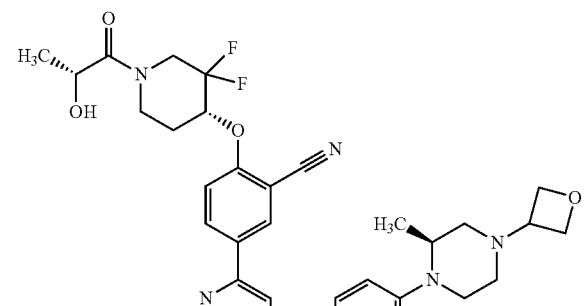
100
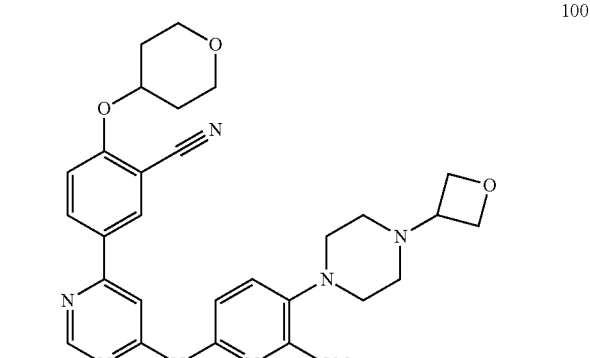
101
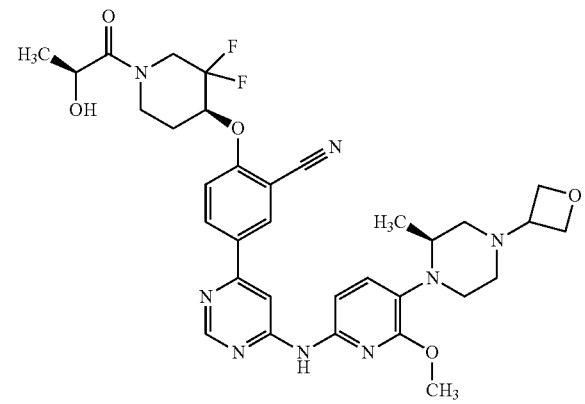

102

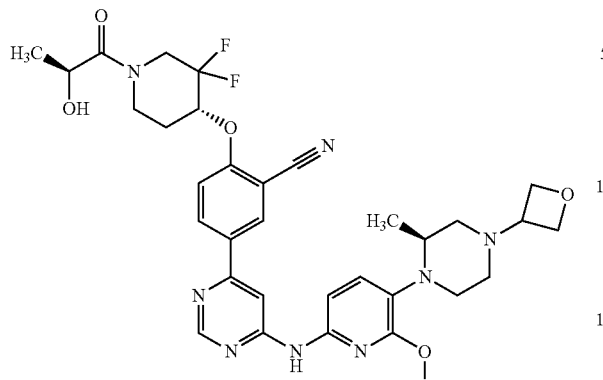

103

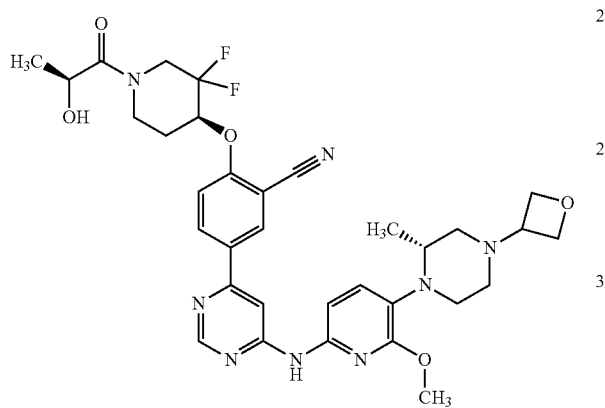

104

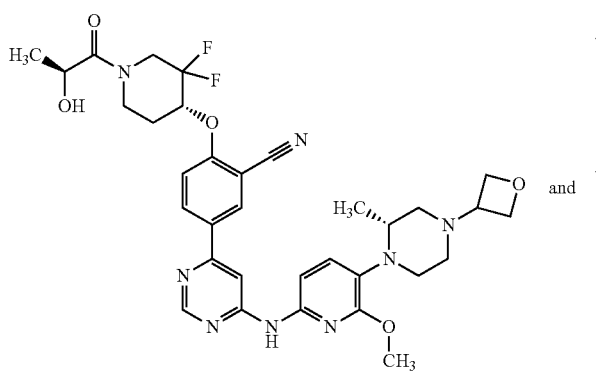

and

105

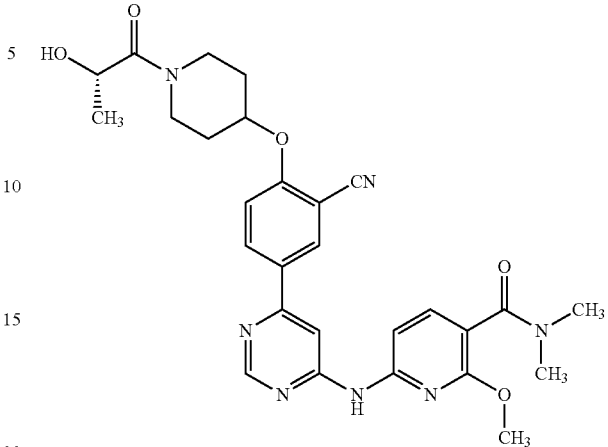

or a pharmaceutically acceptable salt thereof.

15. A pharmaceutical composition comprising a compound of claim 1, or a pharmaceutically acceptable salt thereof, and a pharmaceutically acceptable adjuvant, carrier, or vehicle.

16. A method for inhibiting TBK and IKKε activity in a patient, comprising a step of administering to said patient an effective amount of a compound of claim 1, or a pharmaceutically acceptable salt thereof.

17. A method for treating a TBK/IKKε related disorder in a patient in need thereof, comprising the step of administering to said patient an effective amount of a compound of claim 1, or a pharmaceutically acceptable salt thereof.

18. The method of claim 17, wherein the disorder is selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease, Crohn's Disease, Ulcerative Colitis, Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

19. A method for treating Systemic Lupus Erythematosus in a subject, comprising a step of administering to said subject an effective amount of a compound of claim 1, or a pharmaceutically acceptable salt thereof.

* * * * *